United States Patent
Keston-Smith et al.

(10) Patent No.: US 12,195,770 B2
(45) Date of Patent: Jan. 14, 2025

(54) CRISPR DNA AND RNA TARGETING ENZYMES AND SYSTEMS

(71) Applicant: ARBOR BIOTECHNOLOGIES, INC., Cambridge, MA (US)

(72) Inventors: Elise Keston-Smith, Cambridge, MA (US); David A. Scott, Cambridge, MA (US); David R. Cheng, Boston, MA (US); Winston X. Yan, Boston, MA (US); Pratyusha Hunnewell, Needham, MA (US); Jason Carte, Boston, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 1067 days.

(21) Appl. No.: 16/980,246

(22) PCT Filed: Mar. 14, 2019

(86) PCT No.: PCT/US2019/022376
§ 371 (c)(1),
(2) Date: Jan. 28, 2021

(87) PCT Pub. No.: WO2019/178428
PCT Pub. Date: Sep. 19, 2019

(65) Prior Publication Data
US 2023/0242891 A1    Aug. 3, 2023

Related U.S. Application Data

(60) Provisional application No. 62/775,874, filed on Dec. 5, 2018, provisional application No. 62/772,043, filed on Nov. 27, 2018, provisional application No. 62/746,539, filed on Oct. 16, 2018, provisional application No. 62/740,867, filed on Oct. 3, 2018, provisional application No. 62/729,393, filed on Sep. 10, 2018, provisional application No. 62/699,498, filed on Jul. 17, 2018, provisional application No. 62/672,489, filed on May 16, 2018, provisional application No. 62/666,397, filed on May 3, 2018, provisional application No. 62/642,919, filed on Mar. 14, 2018.

(51) Int. Cl.
*C12N 9/22* (2006.01)
*C12N 15/10* (2006.01)

(52) U.S. Cl.
CPC ............ *C12N 9/22* (2013.01); *C12N 15/102* (2013.01); *C12N 2310/20* (2017.05)

(58) Field of Classification Search
None
See application file for complete search history.

(56) References Cited

U.S. PATENT DOCUMENTS

| 10,808,245 B2 | 10/2020 | Chong et al. |
| 2017/0211142 A1 | 7/2017 | Smargon et al. |
| 2018/0371487 A1 | 12/2018 | Yang |

FOREIGN PATENT DOCUMENTS

| WO | 2012164565 A1 | 12/2012 |
| WO | 2016106236 A1 | 6/2016 |
| WO | 2017091630 A1 | 6/2017 |
| WO | 2017127807 A1 | 7/2017 |
| WO | 2017219027 A1 | 12/2017 |
| WO | 2018035250 A1 | 2/2018 |
| WO | 2018035388 A1 | 2/2018 |
| WO | 2019178427 A1 | 9/2019 |
| WO | 2019178428 A1 | 9/2019 |
| WO | 2020028823 A1 | 2/2020 |
| WO | 2020181101 A1 | 9/2020 |

OTHER PUBLICATIONS

Shmakov, S. et al. "Diversity and evolution of class 2 CRISPR-Cas systems". Nature Reviews | Microbiology, vol. 15, No. 3 (Mar. 2017), pp. 169-182. (Year: 2017).*
Peters, J.E. et al. "Recruitment of CRISPR-Cas systems by Tn7-like transposons". Proceedings of the National Academy of Sciences USA, vol. 114, No. 35 (Aug. 2017), pp: E7358-E7366. (Year: 2017).*
Karginov, F.V. et al."The CRISPR System: Small RNA-guided defense in bacteria and archaea". Molecular Cell, vol. 37 (Jan. 2010), pp. 7-19 (Year: 2010).*
Wang, H. et al. "CRISPR/Cas9 in genome editing and beyond", Annual Review in Biochemistry, vol. 85 (2016), pp. 227-264 (Year: 2016).*
Nelles, D.A. et al. "Programmable RNA tracking in live cells with CRISPR/Cas9". Cell, vol. 165 (Apr. 2016), pp. 488-496 (Year: 2016).*
Yan, W.X. et al."Functionally diverse type V CRISPR-Cas systems" Science, vol. 363 (Jan. 2019), pp. 88-91 (Year: 2019).*
Abudayyeh et al. "C2c2 is a single-component programmable RNA-guided RNA-targeting CRISPR effector" Science (2016) vol. 353, No. 6299, pp aaf5573-1-aaf5573-9.
Al-Shayeb et al., "Clades of huge phages from across Earth's ecosystems," Nature (2020) vol. 578, pp. 425-431 and Methods pages.
Chen et al., "CRISPR-Cas12a target binding unleashes indiscriminate single-stranded DNase activity," Science 360 (6387) 436-9 (Feb. 2018).

(Continued)

*Primary Examiner* — Joseph G. Dauner
*Assistant Examiner* — Alexandra Geraldine Dace Denito
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of nucleic acids such as DNA. Each system includes one or more protein components and one or more nucleic acid components that together target nucleic acids.

20 Claims, 56 Drawing Sheets

Specification includes a Sequence Listing.

(56) References Cited

OTHER PUBLICATIONS

Databse EMBL Online—Speth D.R. et al. "Candidatus Scalindua brodae Chat domain protein," retrieved from UNIPARC accession no. UPI0005442945, database Accession No. KHE91663, dated Dec. 14, 2014.
Dong et al., "The crystal structure of Cpf1 in complex with CRISPR RNA," Nature 532(7600): 522-6 (Apr. 2016).
Garrett et al., "CRISPR-based immune systems of the Sulfolobales: complexity and diversity," Biochem Soc Trans (2011) vol. 39, pp. 51-57.
Gaudelli et al., "Programmable base editing of A.T to G.C in genomic DNA without DNA cleavage," Nature 551 (7681): 464-71 (Oct. 2017).
International Search Report and Written Opinion for International Application No. PCT/US2019/022376 dated Jun. 17, 2019.
International Search Report for International Application No. PCT/US2019/022375, mailed Jun. 13, 2019 (6 pages).
International Search Report for PCT/US2019/032750, mailed Sep. 25, 2019.
Kim et al., "Efficient Transcriptional Gene Repression by Type V-A CRISPR-Cpf1 from Eubacterium eligens," ACS Synthetic Biology 6(7): 1273-82 (Apr. 2017).
Koonin et al., "Diversity, classification and evolution of CRISPR-Cas systems," Current Opinion in Microbiology 37: 67-78 (Jun. 2017).
Liu et al., "C2c1-sgRNA Complex Structure Reveals RNA-Guided DNA Cleavage Mechanism," Mol Cell. 65(2):310-22 (Dec. 2016).
Makarova et al., "An updated evolutionary classification of CRISPR-Cas systems," Nat. Rev. Microbiol. 13 (11):722-36 (Sep. 2015).
Makarova et al., "Annotation and Classification of CRISPR-Cas Systems," Methods Mol Biol (2015) vol. 1311, pp. 47-75.
Makarova et al., "Classification and Nomenclature of CRISPR-Cas Systems: Where from Here?" CRISPR J. 1 (5):325-36 (Oct. 2018).
Makarova et al., "Unification of Cas protein families and a simple scenario for the origin and evolution of CRISPR-Cas systems," Biology Direct (2011) vol. 6, Article 38, 27 pages.
Murugan et al., "The Revolution Continues: Newly Discovered Systems Expand the CRISPR-Cas Toolkit," Molecular Cell 68(1): 15-25 (Oct. 2017).
O'Connell et al. "Programmable RNA recognition and cleavage by CRISPR/Cas9" Nature (2014) vol. 516, No. 7530, pp. 263-266.
Pausch et al., "CRISPR-Cas-Phi from huge phages is a hypercompact genome editor," Science (2020) vol. 369, pp. 333-337.
Ran et al., "Double nicking by RNA-guided CRISPR Cas9 for enhanced genome editing specificity," Cell 154 (6):1380-9 (Aug. 2013).
Sequence Alignment of SEQ ID No. 5 with BGX25975, Search conducted on Jun. 5, 2020, 4 pages. (Year: 2020).
Sequence Alignment of SEQ ID No. 5 with BGX25978, Search conducted on Jun. 11, 2020, 7 pages. (Year: 2020).
Sequence Alignment of SEQ ID No. 5 with BGX25997, Search conducted on Jun. 11, 2020, 7 pages. (Year: 2020).
Shmakov et al., "Discovery and Functional Characterization of Diverse Class 2 CRISPR-Cas Systems," Molecular Cell 60(3): 385-97 (Oct. 2015).
Smargon et al. "Cas13b Is a Type VI-B CRISPR-Associated RNA-Guided RNase Differentially Regulated by Accessory Proteins Csx27 and Csx28" Molecular Cell (2017) vol. 65, No. 4, pp. 618-630.
Stella et al., "Class 2 CRISPR-Cas RNA-guided endonucleases: Swiss Army knives of genome editing," Nature Structural & Molecular Biology 24(11): 882-92 (Oct. 2017).
Strutt et al. "RNA-dependent RNA targeting by CRISPR-Cas9" eLIFE (2018) vol. 7, e 32724, pp. 1-17.
Tamulaitis et al., "Type III CRISPR-Cas Immunity: Major Differences Brushed Aside," Trends Microbiol (2017) vol. 25, No. 1, pp. 49-61.
Written Opinion of the International Searching Authority for International Application No. PCT/US2019/022375 (7 pages).
Wu et al., "Structural basis of stringent PAM recognition by CRISPR-C2c1 in complex with sgRNA," Cell Res. 27 (5):705-8 (Apr. 2017).
Yamano et al., "Crystal Structure of Cpf1 in Complex with Guide RNA and Target DNA," Cell 165(4):949-62 (Apr. 2016).
Yan et al., "Cas13d Is a Compact RNA-Targeting Type Vi Crispr Effector Positively Modulated by a WYL-Domain-Containing Accessory Protein," Mol. Cell 70(2)327-39.e5 (Mar. 2018).
Yan et al., "Functionally diverse type V CRISPR-Cas systems," Science 363(6422):88-91 (Dec. 2018).
Yang et al., "PAM-Dependent Target DNA Recognition and Cleavage by C2c1 CRISPR-Cas Endonuclease," Cell 167 (7):1814-28 (Dec. 2016).
Zetsche et al., "Cpf1 is a single RNA-guided endonuclease of a class 2 CRISPR-Cas system," Cell 163(3), 759-71 (Sep. 2015).

* cited by examiner

Type v-g Cas12g - Functional Domains

Cas12g (768 aa)

RuvC domain architecture:

FIG. 12 (SEQ ID NO. 250)

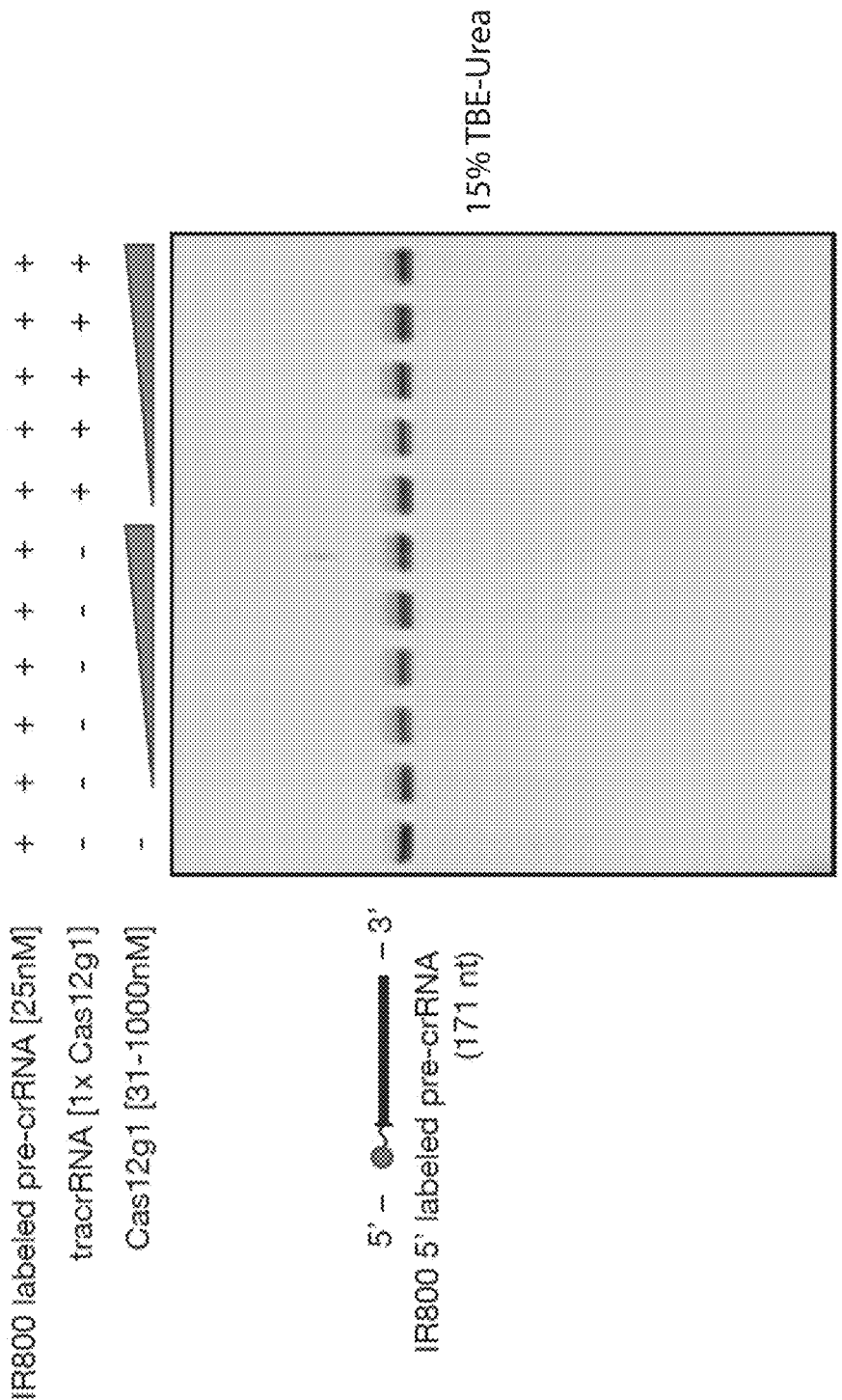

CRISPR DNA AND RNA TARGETING ENZYMES AND SYSTEMS

CROSS REFERENCE TO RELATED APPLICATIONS

This application is a U.S. National Phase Application under 35 U.S.C. § 371 of International Application No. PCT/US2019/022376, filed Mar. 14, 2019, which claims the benefit of priority of U.S. Application No. 62/642,919, filed Mar. 14, 2018; U.S. Application No. 62/666,397, filed May 3, 2018; U.S. Application No. 62/672,489, filed May 16, 2018; U.S. Application No. 62/699,498, filed Jul. 17, 2018; U.S. Application No. 62/729,393, filed Sep. 10, 2018; U.S. Application No. 62/740,867, filed Oct. 3, 2018; U.S. Application No. 62/746,539, filed Oct. 16, 2018; U.S. Application No. 62/772,043, filed Nov. 27, 2018; and U.S. Application No. 62/775,874, filed Dec. 5, 2018. The content of each of the foregoing applications is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 21, 2020, is named A2186-7013US_SL.txt and is 211,253 bytes in size.

FIELD OF THE INVENTION

The present disclosure relates to systems, methods, and compositions used for the control of gene expression involving sequence targeting and nucleic acid editing, which uses vector systems related to Clustered Regularly Interspaced Short Palindromic Repeats (CRISPR) and components thereof.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems, which are composed of multiple effector proteins that together form a complex around a crRNA, and Class 2 systems, which consist of a single effector protein that complexes with the RNA guide to target DNA or RNA substrates. The single-subunit effector composition of the Class 2 systems provides a simpler component set for engineering and application translation, and have thus far been an important source of programmable effectors. Thus, the discovery, engineering, and optimization of novel Class 2 systems may lead to widespread and powerful programmable technologies for genome engineering and beyond.

The characterization and engineering of Class 2 CRISPR-Cas systems, exemplified by CRISPR-Cas9, have paved the way for a diverse array of biotechnology applications in genome editing and beyond. For example, the effector proteins Cas12a (Cpf1) and Cas13a (C2c2) possess non-specific "collateral" single-stranded-nuclease cleavage activities, which may be harnessed to create novel diagnostics, methods, and other applications. Nevertheless, there remains a need for additional programmable effectors and systems for modifying nucleic acids and polynucleotides (i.e., DNA, RNA, or any hybrid, derivative, or modification) beyond the current CRISPR-Cas systems that enable novel applications through their unique properties.

Citation or identification of any document in this application is not an admission that such document is available as prior art to the present invention.

SUMMARY

This disclosure provides non-naturally-occurring, engineered systems and compositions for new single-effector Class 2 CRISPR-Cas systems, together with methods for computational identification from genomic databases, development of the natural loci into an engineered system, and experimental validation and application translation. These new effectors are divergent in sequence to orthologs and homologs of existing Class 2 CRISPR effectors, and also have unique domain organizations. They provide additional features that include, but are not limited to, 1) novel DNA/RNA editing properties and control mechanisms, 2) smaller size for greater versatility in delivery strategies, 3) genotype triggered cellular processes such as cell death, and 4) programmable RNA-guided DNA insertion, excision, and mobilization. Adding the novel DNA-targeting systems described herein to the toolbox of techniques for genome and epigenome manipulation enables broad applications for specific, programmed perturbations.

In general, this disclosure relates to new CRISPR-Cas systems including newly discovered enzymes and other components used to create minimal systems that can be used in non-natural environments, e.g., in bacteria other than those in which the system was initially discovered or mammalian cells.

In one aspect, the disclosure provides engineered, non-naturally occurring CRISPR-Cas systems that include: i) an RNA guide including or consisting of a direct repeat sequence and a spacer sequence capable of hybridizing to a target nucleic acid; and ii) a CLUST.019143 (Type V-G) CRISPR-Cas effector protein, wherein the effector protein includes or consists of an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence provided in Table 4 (e.g., SEQ ID NOs: 1-8, and 15-24); wherein the effector protein is capable of binding to the RNA guide and of targeting the target nucleic acid sequence complementary to the spacer sequence. In some embodiments, the CRISPR-associated protein has a RuvC domain.

As used herein, the Type V-G (CLUST.019143) CRISPR-Cas effector proteins are also referred to as Cas12g effector proteins, and these two terms are used interchangeably in this disclosure.

In some embodiments of any of the systems described herein, the Type V-G CRISPR-Cas effector protein includes the RuvC I domain $X_aX_bDX_bX_a$ (SEQ ID NO: 210), wherein $X_a$ is a small residue (A or G or S or T), and $X_b$ is a hydrophobic residue (C or F or I or L or M or P or V or W or Y). In some embodiments, the Type V-G CRISPR-Cas effector protein includes the RuvC II domain $X_bX_bX_bX_bE$ (SEQ ID NO: 211), wherein $X_b$ is a hydrophobic residue (C or F or I or L or M or P or V or W or Y). In some embodiments, the Type V-G CRISPR-Cas effector protein includes the RuvC III domain DXNAA (SEQ ID NO: 212), wherein X is any amino acid residue. In some embodiments, the Type V-G CRISPR-Cas effector protein includes more than one of the motifs in the set SEQ ID NO: 210, SEQ ID NO: 211, SEQ ID NO: 212.

In some embodiments of any of the systems described herein, the Type V-G CRISPR-Cas effector protein is the CLUST.019143 FLYL01000025 effector (Cas12g1) (SEQ ID NO: 6).

In some embodiments of any of the systems described herein, the Type V-G CRISPR-Cas effector protein includes or consists of at least one RuvC domain, e.g., a RuvC I, RuvC II, or RuvC III domain. In some embodiments, none, one, or more of the RuvC domains are catalytically inactivated.

In some embodiments of any of the systems described herein, the Type V-G CRISPR-Cas effector protein includes or consists of one or more amino acid substitutions within at least one of the RuvC domains. In some embodiments, the one or more amino acid substitutions include, e.g., an alanine substitution at an amino residue corresponding to D513 of SEQ ID NO: 6.

In some embodiments, the one or more amino acid substitutions result in a reduction of the nuclease activity of the Type V-G CRISPR-Cas effector protein as compared to the nuclease activity of the Type V-G CRISPR-Cas effector protein without the one or more amino acid substitutions.

In some embodiments of any of the systems described herein, the RNA guide includes a direct repeat sequence including or consisting of a nucleotide sequence or subsequence thereof provided in Table 5A (e.g., SEQ ID NOs: 9-13, 25-34). In some embodiments, the direct repeat sequence includes 5'-$X_1X_2X_3$GN$X_6$T$X_8X_9$GACACC-3' (SEQ ID NO: 200) proximal to its 3' end and adjacent to the spacer sequence, wherein $X_1$ is A or G, $X_2$ is A or C or G, $X_3$ is C or G, $X_6$ is A or C or T or U, N is any nucleic acid, $X_8$ is C or G or T or U, and $X_9$ is C or G or T or U. In some embodiments, the direct repeat sequence includes 5'-$X_1$G$X_3$GGT$X_7X_8$TTACA$X_{14}$C-3' (SEQ ID NO: 201) proximal to its 3' end and adjacent to the spacer sequence, wherein $X_1$ is C or G, $X_3$ is G or T or U, $X_7$ is A or T or U, $X_8$ is C or G, and $X_{14}$ is A or C.

In some embodiments, the Type V-G RNA guide includes or consists of a nucleotide sequence or subsequence thereof provided in Table 5B (e.g., SEQ ID Nos: 150-167), wherein the spacer sequence is denoted by contiguous Ns. In some embodiments, the Type V-G RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens column in Table 5B.

In some embodiments, the direct repeat of the RNA guide is truncated at the 5' end by between 1 to about 25 nucleotides (e.g., 16, 17, 18, 19, 20, 21, 22, 23, or 24 nucleotides). In some embodiments, the direct repeat of the RNA guide is truncated at the 5' end by 18 nucleotides. In some embodiments, the full length or truncated direct repeat of the RNA guide is linked at the 5' end to a full length or truncated tracrRNA.

In some embodiments of any of the systems described herein, the spacer sequence of the RNA guide includes or consists of between about 20 to about 38 nucleotides (e.g., 16, 17, 18, 19, 20, 21, 22, 23, or 24 nucleotides).

In some embodiments of any of the systems described herein, the RNA guide includes a tracrRNA sequence including a nucleotide sequence provided in Table 6 (e.g., SEQ ID NOs: 100-116). In some embodiments of any of the systems described herein, the RNA guide includes a tracrRNA encoded by a sequence (or fragment thereof) listed in Table 7 (e.g., SEQ ID NOs: 117-134). In some embodiments, the RNA guide includes a tracrRNA sequence that includes the sequence (SEQ ID NO: 250)
GAUGCUUACUUAGUCAUCUGGUUGGCAAACCUCCGCGGACCUUCGGGACC

AAUGGAGAGGAACCCAGCCGAGAAGCAUCGAGCCGGUAAAUGCCGGAAA.

In some embodiments of any of the systems provided herein, the target nucleic acid is a DNA. In some embodiments of any of the systems provided herein, the target nucleic acid is a single-stranded DNA. In some embodiments of any of the systems provided herein, the target nucleic acid is an RNA. In some embodiments of any of the systems provided herein, the target nucleic acid is a single-stranded RNA.

In certain embodiments of any of the systems provided herein, the targeting of the target nucleic acid by the CRISPR-associated protein and RNA guide results in a modification (e.g., a single-stranded or a double-stranded cleavage event) in the target nucleic acid. In some embodiments, the modification is a deletion event. In some embodiments, the modification is an insertion event. In some embodiments, the modification results in cell toxicity and/or cell death.

In some embodiments, the CRISPR associated protein has non-specific (i.e., "collateral") nuclease (e.g., DNase or RNase) activity. In certain embodiments of any of the systems provided herein, the system further includes a donor template nucleic acid (e.g., a DNA or a RNA).

In some embodiments of any of the systems provided herein, the system is within a cell (e.g., a eukaryotic cell (e.g., a mammalian cell) or a prokaryotic cell (e.g., a bacterial cell).

In some embodiments of any of the systems provided herein, the RNA guide includes a tracrRNA.

In another aspect, the disclosure provides methods of targeting and editing a target nucleic acid, wherein the methods include contacting the target nucleic acid with any of the systems described herein.

In another aspect, the disclosure provides methods of targeting the insertion of a payload nucleic acid at a site of a target nucleic acid, wherein the methods include contacting the target nucleic acid with any of the systems described herein.

In yet another aspect, the disclosure provides methods of targeting the excision of a payload nucleic acid from a site at a target nucleic acid, wherein the methods include contacting the target nucleic acid with any of the systems described herein.

In some embodiments of any of the methods described herein, the target nucleic acid is present at a transcriptionally-active site.

In another aspect, the disclosure provides methods of cleaving or non-specifically degrading single-stranded DNA upon recognition of a DNA or RNA target nucleic acid, wherein the methods include contacting the target nucleic acid with any of the systems described herein.

In another aspect, the disclosure provides methods of cleaving or non-specifically degrading single-stranded RNA upon recognition of a DNA or RNA target nucleic acid, wherein the methods include contacting the target nucleic acid with any of the systems described herein.

In some embodiments of the methods, the target nucleic acid does not have a protospacer adjacent motif (PAM) or protospacer flanking sequence (PFS).

In some embodiments of the system, the spacer sequence comprises 18-23 nucleotides.

In some embodiments, the methods occur at a temperature between about 42° C. to 60° C.

In some embodiments, the methods occur at a temperature of 42° C., 50° C., or 60° C.

In another aspect, the disclosure provides methods of cleaving and/or degrading single-stranded DNA, single-stranded RNA, or double-stranded RNA upon recognition of a RNA target nucleic acid, the method comprising contacting the target nucleic acid with any of the systems disclosed herein.

In another aspect the disclosure provides methods of inducing dormancy or death of a cell which include contacting the cell with a system described herein (and compositions for use in such methods), wherein the spacer sequence is complementary to at least 15 nucleotides of the target nucleic acid, wherein the Type V-G CRISPR effector protein associates with the RNA guide to form a complex, wherein the complex binds to a target nucleic acid sequence that is complementary to the at least 15 nucleotides of the spacer sequence, and wherein upon binding of the complex to the target nucleic acid sequence the Type V-G CRISPR-Cas effector protein cleaves a non-target nucleic acid within the cell, thereby inducing dormancy or death of the cell.

In some embodiments, the death is via apoptosis, necrosis, necroptosis, or a combination thereof.

In some embodiments of any of the methods described herein (and compositions for use in such methods), the target nucleic acid is an RNA selected from the group consisting of an mRNA, a tRNA, a ribosomal RNA, a non-coding RNA, a lncRNA, or a nuclear RNA. In some embodiments of any of the methods described herein, the target nucleic acid is a DNA selected from the group consisting of chromosomal DNA, mitochondrial DNA, single-stranded DNA, or plasmid DNA.

In some embodiments of any of the methods described herein (and compositions for use in such methods), upon binding of the complex to the target nucleic acid, the Type V-G CRISPR-Cas effector protein exhibits collateral RNase activity.

In some embodiments of any of the methods described herein (and compositions for use in such methods), the cell is a eukaryotic cell. In some embodiments, the cell is an animal cell. In some embodiments, the cell is a cancer cell (e.g., a tumor cell). In some embodiments, the cell is an infectious agent cell or a cell infected with an infectious agent. In some embodiments, the cell is a bacterial cell, a cell infected with a virus, a cell infected with a prion, a fungal cell, a protozoan, or a parasite cell.

In another aspect, the disclosure provides methods of treating a condition or disease in a subject in need thereof and compositions for use in such methods. The methods include administering to the subject a system described herein, wherein the spacer sequence is complementary to at least 15 nucleotides of a target nucleic acid associated with the condition or disease, wherein the Type V-G CRISPR-Cas effector protein associates with the RNA guide to form a complex, wherein the complex binds to a target nucleic acid sequence that is complementary to the at least 15 nucleotides of the spacer sequence, and wherein upon binding of the complex to the target nucleic acid sequence the Type V-G CRISPR-Cas effector protein cleaves or silences the target nucleic acid, thereby treating the condition or disease in the subject.

In some embodiments, the methods described here are used to treat a subject, e.g., a mammal, such as a human patient. The mammalian subject can also be a domesticated mammal, such as a dog, cat, horse, monkey, rabbit, rat, mouse, cow, goat, or sheep.

In some embodiments of the methods described herein (and compositions for use in such methods), the condition or disease is a cancer or an infectious disease. In some embodiments, the condition or disease is cancer, and wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In another aspect, the disclosure provides the use of a system described herein in a method selected from the group consisting of RNA sequence specific interference; RNA sequence-specific gene regulation; screening of RNA, RNA products, lncRNA, non-coding RNA, nuclear RNA, or mRNA; mutagenesis; inhibition of RNA splicing; fluorescence in situ hybridization; breeding; induction of cell dormancy; induction of cell cycle arrest; reduction of cell growth and/or cell proliferation; induction of cell anergy; induction of cell apoptosis; induction of cell necrosis; induction of cell death; or induction of programmed cell death.

In some embodiments of any of the systems described herein, the Type V-G CRISPR-Cas effector protein is fused to a base-editing domain, an RNA methyltransferase, an RNA demethylase, a splicing modifier, a localization factor, or a translation modification factor. In some embodiments of any of the systems described herein, the Type V-G CRISPR- Cas effector protein is fused to a base-editing domain (e.g., Adenosine Deaminase Acting on RNA (ADAR) 1 (ADAR1), ADAR2, apolipoprotein B mRNA editing enzyme, catalytic polypeptide-like (APOBEC)), and activation-induced cytidine deaminase (AID)), an RNA methyltransferase, an RNA demethylase, a splicing modifier, a localization factor, or a translation modification factor.

In some embodiments, the Type V-G CRISPR-Cas effector protein further includes a linker sequence. In some embodiments, the Type V-G CRISPR-Cas effector protein includes one or more mutations or amino acid substitutions that render the Type V-G CRISPR-Cas effector protein unable to cleave RNA.

In some embodiments, the systems described herein also include an RNA-binding fusion polypeptide that includes an RNA-binding domain (e.g. MS2) and a base-editing domain (e.g., ADAR1, ADAR2, APOBEC, and AID). In some embodiments, the RNA-binding domain is MS2, PP7, or Qbeta.

In another aspect, the disclosure provides method of modifying an RNA molecule, comprising contacting the RNA molecule with a system described herein. These methods can be carried out ex vivo or in vitro. In some embodiments, the methods described herein do not modify the germ line genetic identity of a human being.

In some embodiments, the Type V-G CRISPR-Cas effector protein includes or consist of at least one (e.g., two, three, four, five, six, or more) nuclear localization signal (NLS). In some embodiments, the Type V-G CRISPR-Cas effector protein includes or consist of at least one (e.g., two, three, four, five, six, or more) nuclear export signal (NES). In some embodiments, the Type V-G CRISPR-Cas effector protein includes at least one (e.g., two, three, four, five, six, or more) NLS and at least one (e.g., two, three, four, five, six, or more) NES.

In some embodiments, the systems described herein include a nucleic acid encoding one or more RNA guides. In some embodiments, the nucleic acid encoding the one or more RNA guides is operably linked to a promoter (e.g., a constitutive promoter or an inducible promoter).

In some embodiments, the systems described herein include a nucleic acid encoding a target nucleic acid (e.g., a target RNA). In some embodiments, the nucleic acid encoding the target nucleic acid is operably linked to a promoter (e.g., a constitutive promoter or an inducible promoter).

In some embodiments, the systems described herein include a nucleic acid encoding a Type V-G CRISPR-Cas effector protein in a vector. In some embodiments, the system further includes one or more nucleic acids encoding an RNA guide present in the vector.

In some embodiments, the vectors included in the systems are viral vectors (e.g., retroviral vectors, lentiviral vectors, adenoviral vectors, adeno-associated vectors, and herpes simplex vectors. In some embodiments, the vectors included in the system are phage vectors.

In some embodiments, the systems provided herein are in a delivery system. In some embodiments, the delivery system is a nanoparticle, a liposome, an exosome, a microvesicle, and a gene-gun.

The disclosure also provides a cell (e.g., a eukaryotic cell or a prokaryotice cell (e.g., a bacterial cell)) comprising a system described herein. In some embodiments, the eukaryotic cell is a mammalian cell (e.g., a human cell) or a plant cell. The disclosure also provides animal models (e.g., rodent, rabbit, dog, monkey, or ape models) and plant model that include the cells.

In yet another aspect, the disclosure provides methods of detecting a target nucleic acid (e.g., DNA or RNA) in a sample, the method including: (a) contacting the sample with any of the systems described herein and a labeled reporter nucleic acid, wherein hybridization of the effector:RNA guide to the target nucleic acid causes cleavage of the labeled reporter nucleic acid; and (b) measuring a detectable signal produced by cleavage of the labeled reporter nucleic acid, thereby detecting the presence of the target nucleic acid in the sample.

In some embodiments, the methods of detecting a target nucleic acid can also include comparing a level of the detectable signal with a reference signal level, and determining an amount of target nucleic acid in the sample based on the level of the detectable signal.

In some embodiments, the methods of detecting a target nucleic acid can also include the usage of an RNA reporter nucleic acid and a DNA reporter nucleic acid on a different channel (e.g. fluorescent color), and determining the level of a detectable signal by measuring the signal level of both RNA and DNA reporters, and determining an amount of target nucleic acid in the sample based on combining (e.g. using the minimum or multiplicative product) the levels of the detectable signals.

In some embodiments, the measuring is performed using gold nanoparticle detection, fluorescence polarization, colloid phase transition/dispersion, electrochemical detection, or semiconductor based-sensing.

In some embodiments, the labeled reporter nucleic acid can include a fluorescence-emitting dye pair, a fluorescence resonance energy transfer (FRET) pair, or a quencher/fluorophore pair, wherein cleavage of the labeled reporter nucleic acid by the effector protein results in an increase or a decrease of the amount of signal produced by the labeled reporter nucleic acid.

Turning to another aspect of this disclosure, methods of modifying a target RNA are provided that generally include contacting the target RNA with a complex comprising a CRISPR-Cas Type V-G (i.e., Cas12g) effector protein and an engineered Type V-G RNA guide (e.g., a crRNA, guide RNA, RNA guide, or like structure, optionally comprising one or more nucleotide, nucleobase or backbone modifications). The Type V-G RNA guide is designed to hybridize with (e.g., is at least 70%, 75%, 80%, 85%, 90%, 91%, 92%, 93%, 94%, 95%, 96%, 97%, 98%, 99%, or 100% complementary to) a target sequence of the target RNA, and the system is distinguished by the Cas12g effector protein, Type V-G RNA guide, and Type V-G tracrRNA (either fused to expressed separately from the RNA guide) form a complex that associates with the target RNA, thereby modifying the target RNA.

In certain embodiments, modifying the target RNA includes cleaving at least one strand of the target RNA (e.g., creating a single-stranded break or, if the target RNA is an RNA duplex, creating a "nick," or creating a double-stranded break). In certain embodiments, contacting the target RNA activates the Type V-G complex to cleave at least one strand of a non-target RNA (e.g., creating a single-strand break or, if the target RNA is an RNA duplex, creating a "nick," or creating a double strand break). In certain embodiments, contacting the target RNA activates the Type V-G complex to cleave at least one strand of a non-target DNA (e.g., creating a single-strand break or, creating a "nick," or creating a double strand break). Alternatively, or additionally, modification of the target RNA comprises either (i) binding to the target RNA, thereby preventing the target RNA from associating with another biomolecule or complex. The Cas12g effector protein is, in certain embodiments, a Cas12g1 effector protein.

Continuing with this aspect of the disclosure, in certain embodiments the contacting of the target RNA with the complex occurs in a diagnostic assay, for instance by contacting a target RNA with the complex, which complex is formed in vitro.

In another aspect, this disclosure relates to methods of altering a non-target RNA or non-target DNA, including contacting the target RNA with a complex including a Type V-G CRISPR-Cas (i.e., Cas12g) effector protein and a Type V-G RNA guide (e.g., a crRNA, guide RNA, or like structure, optionally comprising one or more nucleotide, nucleobase or backbone modifications) comprising a 27-39 nucleotide spacer sequence having at least 70%, 75%, 80%, 85%, 90%, or 95%, e.g., 96%, 97%, 98%, 99%, or 100%, complementarity to a sequence in the target RNA, and a Type V-G tracrRNA (either fused to expressed separately from the RNA guide) resulting in activation of the complex and alteration of the non-target RNA or non-target DNA.

In various embodiments, the non-target RNA or non-target DNA contain fluorophore quencher pairs at the sequence termini, and alteration by the activated Type V-G complex results in a fluorescent signal. In various embodiments, alteration the non-target RNA or non-target DNA by the activated Type V-G complex provides a diagnostic reporter indicating the presence of the target RNA. In various embodiments, the Cas12g protein comprises an amino acid sequence having at least 95%, e.g., at least 96%, 97%, 98%, 99%, or 100%, sequence identity to SEQ ID NO: 6, the Type V-G RNA guide comprises a direct repeat sequence with at least 95%, e.g., at least 96%, 97%, 98%, 99%, or 100%, sequence identity to one of SEQ ID NO: 13, and the Type V-G tracrRNA comprises a direct repeat sequence with at least 95%, e.g., at least 96%, 97%, 98%, 99%, or 100%, sequence identity to one of SEQ ID NO: 250. The target RNA is optionally a cellular RNA, a viral RNA, or a synthetic RNA.

Continuing with this aspect of the disclosure, in certain embodiments the contacting of the target RNA with the complex can occur in a cell, for instance by (a) contacting the cell with the complex, which complex is formed in vitro, or (b) contacting the cell with one or more nucleic acids encoding the Cas12g effector protein, the Type V-G RNA guide, and the Type V-G tracrRNA (either fused to expressed separately from the Type V-G RNA guide) which are then expressed by the cell and which form the complex within the cell. In some cases, the cell is a prokaryotic cell; in other cases, it is a eukaryotic cell.

In another aspect, this disclosure relates to method of altering a target RNA, comprising the step of contacting the target RNA within the cell with a genome editing system comprising a Cas12g protein and a Type V-G RNA guide (e.g., a crRNA, guide RNA or like structure, optionally including one or more nucleotide, nucleobase, or backbone modifications) comprising a 27-39 nucleotide spacer sequence having at least 70%, 75%, 80%, 85%, 90%, 91%, 92%, 93%, 94%, 95%, 96%, 97%, 98%, 99%, or 100% complementarity to a sequence in the target RNA, and a Type V-G tracrRNA (either fused to or expressed separately from the RNA guide). In various embodiments, the Cas12g protein comprises an amino acid sequence having at least 95%, e.g., 96%, 87%, 98%, 99%, or 100%, sequence identity to SEQ ID NO: 6, the Type V-G RNA guide comprises a direct repeat sequence with at least 95%, e.g., 96%, 87%, 98%, 99%, or 100%, sequence identity to one of SEQ ID NO: 13, and the Type V-G tracrRNA comprises a direct repeat sequence with at least 95%, e.g., 96%, 87%, 98%, 99%, or 100%, sequence identity to one of SEQ ID NO: 250. The target RNA is optionally a cellular RNA, and the contacting optionally occurs within a cell such as a prokaryotic cell or a eukaryotic cell (e.g., a mammalian cell, a plant cell, a human cell, etc.).

In yet another aspect, this disclosure relates to an engineered, non-naturally occurring Clustered Regularly Interspaced Short Palindromic Repeat (CRISPR)-associated (Cas) system comprising one or more Type V-G RNA guides or one or more nucleic acids encoding the one or more Type V-G RNA guides, wherein the Type V-G RNA guide includes a direct repeat sequence and a spacer sequence capable of hybridizing to a target nucleic acid; and a Type V-G CRISPR-Cas effector protein or a nucleic acid encoding the Type V-G CRISPR-Cas effector protein, wherein the Type V-G CRISPR-Cas effector protein is capable of binding to the RNA guide and of targeting the target nucleic acid sequence complementary to the spacer sequence, and wherein the target nucleic acid is a RNA.

In some embodiments, the Type V-G CRISPR-Cas effector protein comprises an amino acid sequence having at least 90%, or at least 95%, sequence identity to one of SEQ ID NOs: 1-24. According to certain embodiments, the Type V-G CRISPR-Cas effector protein comprises an amino acid sequence given by SEQ ID NO: 6. The total length of the CRISPR-Cas effector protein according to certain embodiments is less than 850 amino acids, excluding any amino acid signal sequence or peptide tag fused thereto. In some cases, the CRISPR-Cas effector protein comprises an amino acid substitution, for instance a substitution at an amino acid residue corresponding to D513, E655, or D745 of SEQ ID NO: 6. The substitution is optionally an alanine.

In yet another aspect, this disclosure relates to an engineered, non-naturally occurring CRISPR-Cas system, including a Cas12g effector protein, and an engineered Type V-G RNA guide (e.g., a crRNA, guide RNA, RNA guide or like structure, optionally comprising one or more nucleotide, nucleobase or backbone modifications) having a 27-39 nucleotide spacer sequence that is at least 80%, e.g., 85%, 90%, 91%, 92%, 93%, 94%, 95%, 96%, 97%, 98%, 99%, or 100%, complementary to a target sequence. The system also contains a Type V-G tracrRNA (either fused or expressed separately from the RNA guide). The Cas12g effector protein, the Type V-G RNA guide, and the Type V-G tracrRNA (either fused or expressed separately from the RNA guide) form a complex that associates with the target sequence.

In some instances, the complex of the Cas12g effector protein, Type V-G RNA guide, and Type V-G tracrRNA causes cleavage of at least one strand of a RNA comprising the target sequence. In certain embodiments, the Cas12g effector protein comprises an amino acid sequence having at least 95% sequence identity to SEQ ID NO: 6 and the direct repeat sequence has at least 95% sequence identity to SEQ ID NO: 13 and the tracr sequence has at least 95% sequence identity to SEQ ID NO: 250. Alternatively, or additionally, the Cas12g effector protein comprises an amino acid substitution (optionally, an alanine substitution) selected from the group consisting of (a) a substitution at an amino acid residue corresponding to D513, E655, or D745 of SEQ ID NO: 6.

In still another aspect, this disclosure relates to a composition including one or more nucleic acids encoding a CRISPR-Cas system (or a genome editing system) according to one of the aspects of the disclosure. In another aspect, the disclosure relates to a viral vector encoding a CRISPR- Cas system (or a genome editing system) according to one of the aspects of the disclosure.

In still another aspect, this disclosure relates to a composition including one or more nucleic acids encoding a CRISPR-Cas system (or a genome editing system) according to one of the aspects of the disclosure. In another aspect, the disclosure relates to a viral vector encoding a CRISPR-Cas system (or a genome editing system) according to one of the aspects of the disclosure.

The disclosure also includes methods of cleaving a single-stranded DNA substrate, a single-stranded RNA substrate, or a double-stranded RNA substrate with the CRISPR-Cas systems described herein. The methods include contacting the single-stranded DNA substrate, single-stranded RNA substrate, or double-stranded RNA substrate with the CRISPR-Cas system, optionally wherein the single-stranded DNA substrate, single-stranded RNA substrate, or double-stranded RNA substrate lacks a protospacer adjacent motif (PAM) sequence protospacer flanking sequence (PFS) with a target nucleic acid. In these methods, (a) when the method occurs at a temperature of about 37° C., the target nucleic acid substrate that is cleaved is a single-stranded RNA substrate is cleaved; or (b) when the method occurs at a temperature of about 50° C., a collateral nucleic acid is non-specifically cleaved, and the collateral nucleic acid is a single-stranded RNA or a single-stranded DNA, or both a single-stranded RNA and a single-stranded DNA.

In another aspect, this disclosure relates to methods of non-specifically cleaving a collateral nucleic acid, the method including contacting the collateral nucleic acid with a activated CRISPR complex disclosed herein, where the collateral nucleic is a single-stranded DNA, single-stranded RNA, or double-stranded RNA, and where the collateral nucleic acid comprises a nucleic acid sequence that does not have sequence similarity to the target nucleic acid.

In some embodiments, when the method occurs at a temperature of about 37° C., the collateral nucleic acid that is non-specifically cleaved can be a single-stranded RNA. In other embodiments, when the method occurs at a temperature of about 50° C., the collateral nucleic acid that is non-specifically cleaved can be a single-stranded RNA or a single-stranded DNA, or both a single-stranded RNA and a single-stranded DNA.

In another aspect, this disclosure relates to methods of detecting a target RNA in a sample, the method including contacting the sample with a CRISPR-Cas system disclosed herein and a labeled detector RNA, where hybridization of the RNA guide to the target RNA causes cleavage of the labeled detector RNA; and measuring a detectable signal produced by cleavage of the labeled detector RNA, thereby detecting the target RNA in the sample.

In some embodiments, the methods described herein can include comparing a level of the detectable signal with a reference signal level, and determining an amount of target RNA in the sample based on the level of the detectable signal.

In some embodiments, the measuring is performed using gold nanoparticle detection, fluorescence polarization, colloid phase transition/dispersion, electrochemical detection, or semiconductor based-sensing.

In some embodiments, the labeled detector RNA can include a fluorescence-emitting dye pair, a fluorescence resonance energy transfer (FRET) pair, or a quencher/fluor pair, wherein cleavage of the labeled detector RNA by the Type V-G CRISPR-Cas effector protein results in an increase or a decrease of an amount of signal produced by the labeled detector RNA.

In another aspect, this disclosure relates to methods of inducing genotype-specific or transcriptional-state-specific cell death or dormancy in a cell, the method including contacting a cell with a CRISPR-Cas system, e.g., the Type V-G CRISPR-Cas system, or a complex disclosed herein, where hybridization of the RNA guide to the target RNA causes a collateral RNAse activity-mediated cell death or dormancy.

In some embodiments, the cell is a prokaryotic cell or a eukaryotic cell. Further, in some embodiments the cell is a mammalian cell. In some embodiments, the cell is a cancer cell.

In some embodiments, the cell is an infectious cell or a cell infected with an infectious agent. In some embodiments, the cell is a cell infected with a virus, a cell infected with a prion, a fungal cell, a protozoan, or a parasite cell.

In some embodiments, the target nucleic acid does not have a protospacer adjacent motif (PAM) or protospacer flanking sequence (PFS).

In another aspect, this disclosure relates to methods of detecting a target nucleic acid in a sample, the method including contacting the sample with the CRISPR-Cas system, e.g., the TYPE V-G CRISPR-Cas system disclosed herein, and a labeled reporter nucleic acid, where hybridization of the crRNA to the target nucleic acid causes cleavage of the labeled reporter nucleic acid; and measuring a detectable signal produced by cleavage of the labeled reporter nucleic acid, thereby detecting a presence of the target nucleic acid in the sample.

In some embodiments, the methods described herein can include comparing a level of the detectable signal with a reference signal level, and determining an amount of target nucleic acid in the sample based on the level of the detectable signal.

In some embodiments, the measuring is performed using gold nanoparticle detection, fluorescence polarization, colloid phase transition/dispersion, electrochemical detection, or semiconductor based-sensing.

In some embodiments, the labeled reporter nucleic acid can include a fluorescence-emitting dye pair, a fluorescence resonance energy transfer (FRET) pair, or a quencher/fluor pair, wherein cleavage of the labeled reporter nucleic acid by the effector protein results in an increase or a decrease of the amount of signal produced by the labeled reporter nucleic acid.

In another aspect, this disclosure relates to methods of editing a double-stranded DNA, the method including contacting, under sufficient conditions and for a sufficient amount of time, a Cas12g enzyme and a RNA guide that directs the Cas12g enzyme to nascently transcribed RNA at a transcriptional fork; cleave one or both ssDNA strand of the double-stranded DNA at the transcriptional fork; where the method results in specific editing of a double-stranded nucleic acid with reduced off-target modification due to the cleavage prerequisite of active transcription and target recognition.

In another aspect, this disclosure relates to methods of editing a single-stranded nucleic acid, the method including contacting, under sufficient conditions and for a sufficient amount of time, a fusion protein including a Cas12g enzyme, a protein domain with RNA modifying activity, and an RNA guide targeting the double-stranded nucleic acid; and the single-stranded nucleic acid, where the contact yields a modification to the base identity of the single-stranded nucleic acid.

In another aspect, this disclosure relates to methods of treating a condition or disease in a subject in need thereof, the method comprising administering to the subject a CRISPR-Cas system, e.g., a Type V-G CRISPR-Cas system or a complex described herein, where the spacer sequence is complementary to at least 15 nucleotides of a target nucleic acid associated with the condition or disease; where the effector protein, e.g., Type V-G CRISPR-Cas effector protein, associates with the RNA guide to form a complex; where the complex binds to a target nucleic acid sequence that is complementary to the at least 15 nucleotides of the spacer sequence; and where upon binding of the complex to the target nucleic acid sequence, the effector protein, e.g., Type V-G CRISPR-Cas effector protein described herein, cleaves the target nucleic acid, thereby treating the condition or disease in the subject.

In some embodiments, the condition or disease is selected from the group consisting of Myotonic dystrophy, Huntington's disease, Familial hypobetalipoproteinemia, hereditary transthyretin-mediated amyloidosis, Familial hypercholesterolemia, Prader Willi syndrome, Spinal muscular atrophy, Dyskeratosis congenita, primary age-related tauopathy, neurofibrillary tangle predominant senile dementia, Dementia pugilistica, Duchenne Muscular Dystrophy, Becker Muscular Dystrophy, Frontotemporal dementia, Hereditary Parkinsonism Cystic fibrosis, Friedreich's ataxia, and chronic myelogenous leukemia.

In some embodiments, the condition or disease is a cancer or an infectious disease.

In some embodiments, the cancer can be Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, or urinary bladder cancer.

In some embodiments, the condition or disease is infectious in nature, and where the infectious agent is selected from the group consisting of human immunodeficiency virus (HIV), respiratory syncytial virus (RSV), hepatitis C virus (HCV), hepatitis B virus (HBV), herpes simplex virus-1 (HSV1), and herpes simplex virus-2 (HSV2).

In some embodiments, the system, activated CRISPR complex, or cells described herein is use as a medicament or for treatment or prevention of a cancer or an infectious disease, or as an antimicrobial or antiviral.

In some embodiments, the system, activated CRISPR complex, or cells described herein is used in an in vitro or ex vivo method of: targeting and editing a target nucleic acid; cleaving a single-stranded DNA substrate, a single-stranded RNA substrate, or a double-stranded RNA substrate; non-specifically cleaving and/or degrading a collateral nucleic acid; detecting a target RNA in a sample; specifically editing a double-stranded nucleic acid; base editing a double-stranded nucleic acid, specifically editing a single-stranded nucleic acid; base editing a single-stranded nucleic acid, inducing genotype-specific or transcriptional-state-specific cell death or dormancy in a cell.

In some embodiments, the system, activated CRISPR complex, or cells described herein is used in targeting and editing a target nucleic acid; cleaving a single-stranded DNA substrate, a single-stranded RNA substrate, or a double-stranded RNA substrate; non-specifically cleaving and/or degrading a collateral nucleic acid; detecting a target RNA in a sample; specifically editing a double-stranded nucleic acid; base editing a double-stranded nucleic acid, specifically editing a single-stranded nucleic acid; base editing a single-stranded nucleic acid, inducing genotype-specific or transcriptional-state-specific cell death or dormancy in a cell, where the use does not comprise a process for modifying the germ line genetic identity of a human being and does not comprise a method of treatment of the human or animal body.

Yet another aspect, method of cleaving a first and a second nucleic acid substrate, comprising contacting the first and second nucleic acid substrates with the system disclosed herein where the first nucleic acid substrate is a single-stranded (ss)DNA or an ssRNA comprising a target sequence that is at least partially complementary to the spacer sequence, the second nucleic acid substrate is an ssDNA or an ssRNA that does not comprise the target sequence.

In some embodiments, the first nucleic acid substrate is a first strand of a DNA and the second nucleic acid substrate is an RNA transcript of the first strand or a second strand of the DNA that is at least partially complementary to the first strand.

In some embodiments, the CRISPR-Cas effector protein lacks both an HNH domain and an HEPN domain.

The term "cleavage event," as used herein, refers to: (1) a DNA or RNA break in a target nucleic acid created by a nuclease of a CRISPR system described herein; or (2) a DNA or RNA break in a collateral (i.e., non-specific or non-target) nucleic acid substrate. In some embodiments, the cleavage event is a double-stranded DNA break. In some embodiments, the cleavage event is a single-stranded DNA break. In some embodiments, the cleavage event is a single-stranded RNA break. In some embodiments, the cleavage event is a double-stranded RNA break.

The terms "CRISPR-Cas system," "Type V-G CRISPR-Cas system," "Type V-G system," or "Cas12g effector protein," as used herein refer to a Type V-G CRISPR-Cas effector protein and a Type V-G RNA guide, and/or nucleic acids encoding the Type V-G CRISPR-Cas effector protein or Type V-G RNA guide, where the Type V-G RNA guide includes a tracrRNA and a crRNA, and optionally promoters operably linked to the expression of the CRISPR effector or the RNA guide or to both.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The terms "CRISPR repeat," or "CRISPR direct repeat," or "direct repeat," as used herein, refer to multiple short direct repeating sequences, which show very little or no sequence variation within a CRISPR array. Suitably, a Type V-G direct repeat may form a stem-loop structure and/or may form a stem-loop structure in combination with a trans-activating CRISPR RNA.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing.

Thus, the stem may include one or more base mismatches. Alternatively, the base-pairing may be exact, i.e. not include any mismatches. The predicted stem-loop structures of some Type V-G direct repeats are illustrated in FIG. 3, and the predicted stem-loop structure of one Type V-G repeat when hybridized to a tracrRNA is shown in FIG. 13.

The terms "CRISPR RNA" or "crRNA" as used herein refer to an RNA molecule comprising a guide sequence used by a CRISPR effector to specifically target a nucleic acid sequence. Typically, crRNAs contain a spacer sequence that mediates target recognition, and a direct repeat sequence (referred to herein as a direct repeat or "DR" sequence) that forms a duplex with a tracrRNA. The crRNA:tracrRNA duplex binds to a CRISPR-Cas effector protein.

The term "donor template nucleic acid," as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The terms "CRISPR-Cas effector," "CRISPR effector," "effector," "CRISPR-associated protein," or "CRISPR enzyme," "Type V-G CRISPR-Cas effector protein," "Type V-G CRISPR-Cas effector," "Type V-G effector," or Cas12g effector protein," as used herein refer to a protein that carries out an enzymatic activity or that binds to a target site on a nucleic acid specified by an RNA guide. In addition, a CRISPR-Cas effector protein associated with Type V-G CRISPR-Cas systems may be referred to herein as Cas12g or a Cas12g enzyme. In some embodiments, a Type V-G CRISPR-Cas effector protein has RNA nuclease activity and/or DNA nuclease activity.

The terms "CRISPR effector complex," "effector complex," or "surveillance complex" as used herein refer to a complex containing a CRISPR effector and an RNA guide.

The term "RNA guide" as used herein refers to any RNA molecule that facilitates the targeting of a protein described herein to a target nucleic acid. Exemplary "RNA guides" include, but are not limited to, a crRNA, as well as a crRNA hybridized to or fused to a tracrRNA. In some embodiments, an RNA guide includes a crRNA in the form of a pre-crRNA (e.g. DR-spacer-DZ). In some embodiments, an RNA guide includes a crRNA in the form of a mature crRNA (e.g. mature_DR-spacer or mature_DR-spacer-mature_DR). In some embodiments, an RNA guide includes both a crRNA and a tracrRNA, either fused into a single RNA molecule or as separate RNA molecules.

As used herein, the term "targeting" refers to the ability of a complex including a CRISPR-associated protein and a RNA guide, such as a crRNA, to preferentially or specifically bind to, e.g., hybridize to, a specific target nucleic acid and compared to other nucleic acids that do not have the same sequence as the target nucleic acid.

As used herein, the term "target nucleic acid" refers to a specific nucleic acid substrate that contains a nucleotide sequence complementary to the entirety or a part of the spacer in the RNA guide. In some embodiments, the target nucleic acid comprises a gene or a sequence within a gene. In some embodiments, the target nucleic acid comprises a non-coding region (e.g., a promoter). In some embodiments, the target nucleic acid is single-stranded. In some embodiments, the target nucleic acid is double-stranded.

The terms "trans-activating crRNA" or "tracrRNA" as used herein refer to an RNA including an anti-repeat region complimentary to all or part of the direct repeat sequence of a CRISPR RNA (crRN A). The CRISPR effector bound to the crRNA and tracrRNA (RNA guide) form a functional complex capable of binding to a target nucleic acid.

A "transcriptionally-active site" as used herein refers to a site in a nucleic acid sequence that includes one or more promoter regions at which transcription is initiated and actively occurs.

The terms "activated CRISPR complex" or "activated complex" as used herein refer to a CRISPR effector complex after it has bound to or has modified a target nucleic acid.

The terms "collateral RNA" or "collateral DNA" as used herein refer to a nucleic acid substrate that is cleaved non-specifically by an activated CRISPR complex. Suitably, a "collateral RNA" or "collateral DNA" may have no sequence similarity to a target nucleic acid or spacer sequence.

The term "collateral RNase activity," as used herein in reference to a CRISPR enzyme, refers to non-specific RNase activity of an activated CRISPR complex.

The term "collateral DNase activity," as used herein in reference to a CRISPR enzyme, refers to non-specific DNase activity of an activated CRISPR complex.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

The figures are a series of schematics and nucleic acid and amino acid sequences that represent the results of locus analysis of various protein clusters.

FIGS. 1A and 1B together depict a classification tree of Type V effectors (Cas12 proteins). The corresponding CRISPR-Cas loci organization is shown for each branch, with the need for a tracrRNA depicted by a white rectangle adjacent to a CRISPR array. CLUST.019143 (Type V-G) systems are depicted as Cas12g.

FIG. 2A is a schematic representation of the functional domains of the CLUST.019143 (Type V-G) effector, designated Cas12g. The solid grey shading indicates the location of the C-terminal RuvC domain, with the catalytic residues in the three conserved sequence motifs (RuvC-I, RuvC-II and RuvC-III) indicated and shown to scale. The bridge helix (h) and Zn-finger domain (z, CxxC.CxxC) are shown only approximately to scale.

Figure 4A:
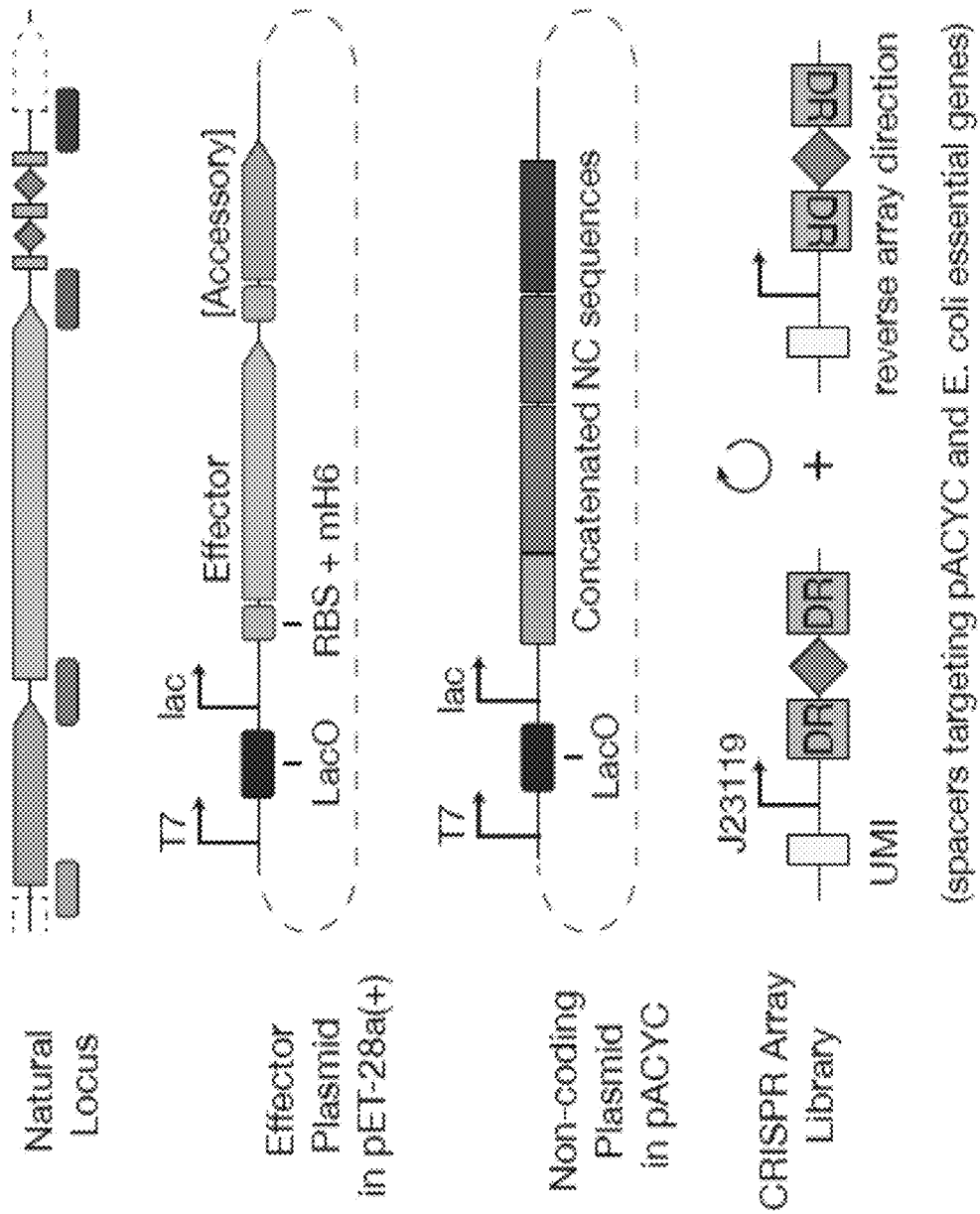
FIG. 4A is a schematic representation of the design of in vivo screen Effector and Non-coding Plasmids. CRISPR array libraries were designed including non-repetitive spacers uniformly sampled from both strands of pACYC184 or *E. coli* essential genes flanked by two DRs and expressed by J23119.
Figure 4B:
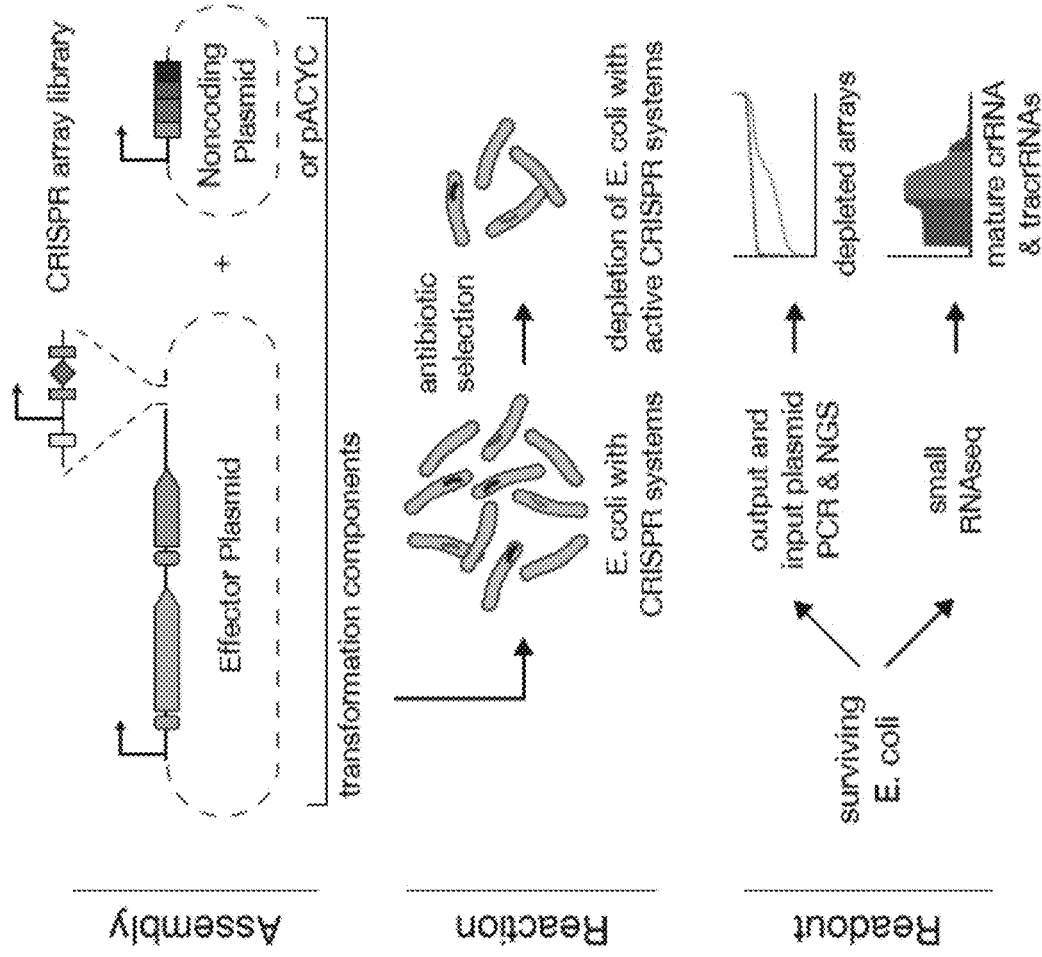

FIG. 4B is a schematic representation of the negative selection screening workflow; 1) CRISPR array libraries were cloned into the Effector Plasmid, 2) the Effector Plasmid and, when present, the Non-coding Plasmid were transformed into *E. coli* followed by outgrowth for negative selection of CRISPR arrays conferring interference against DNA or RNA transcripts from pACYC184 or *E. coli* essential genes, 3) Targeted sequencing of the Effector Plasmid was used to identify depleted CRISPR arrays and small RNA sequencing was used to identify mature crRNAs and tracrRNAs.

Figure 5A:
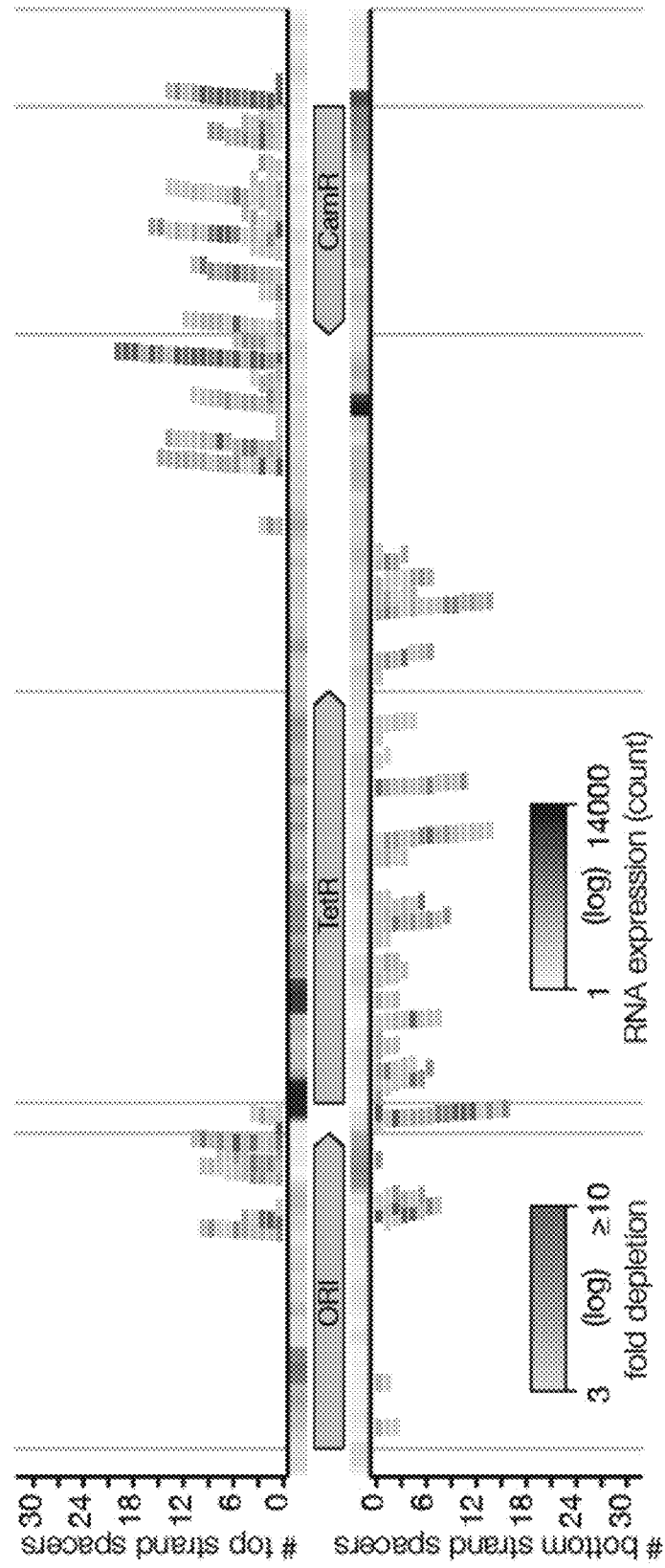

FIG. 5A is a graphic representation of the distribution of targets for Cas12g1 strongly depleted CRISPR arrays over the pACYC184 plasmid. Targets on the top strand and bottom strand are shown separately, and in relation to the orientation of the annotated genes.

Figure 5B:
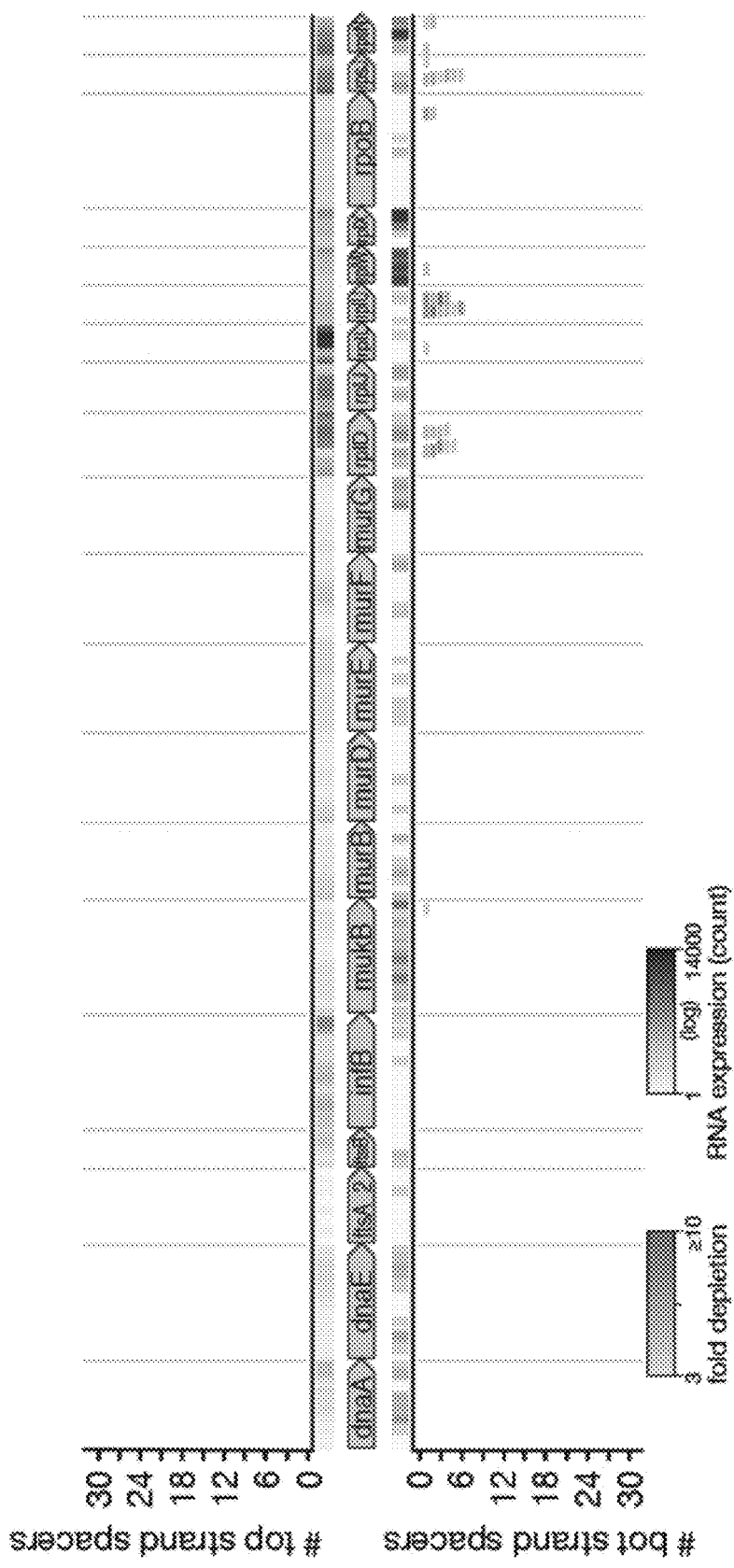

FIG. 5B is a graphic representation of the distribution of targets for Cas12g1 strongly depleted CRISPR arrays over *E. coli* essential genes. Targets on the top strand and bottom strand are shown separately, and in relation to the orientation of the annotated genes.

Figure 6A:
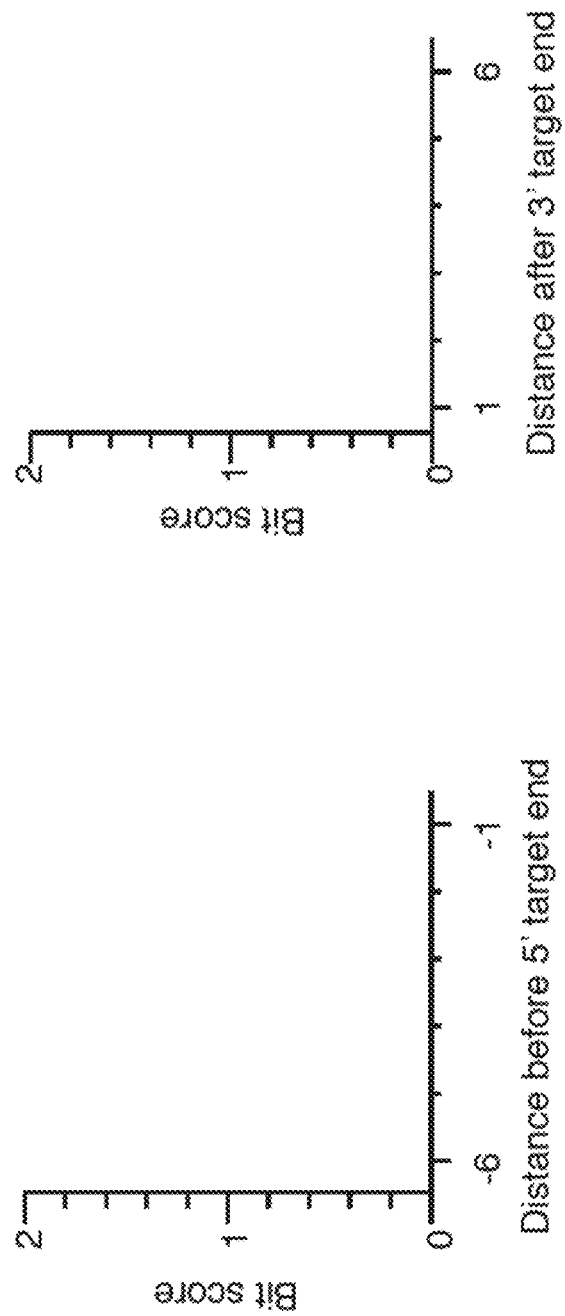

FIG. 6A shows sequence logos the left flank and right flank of targets corresponding to strongly depleted Cas12g1 CRISPR arrays from in vivo screening.

Figure 6B:
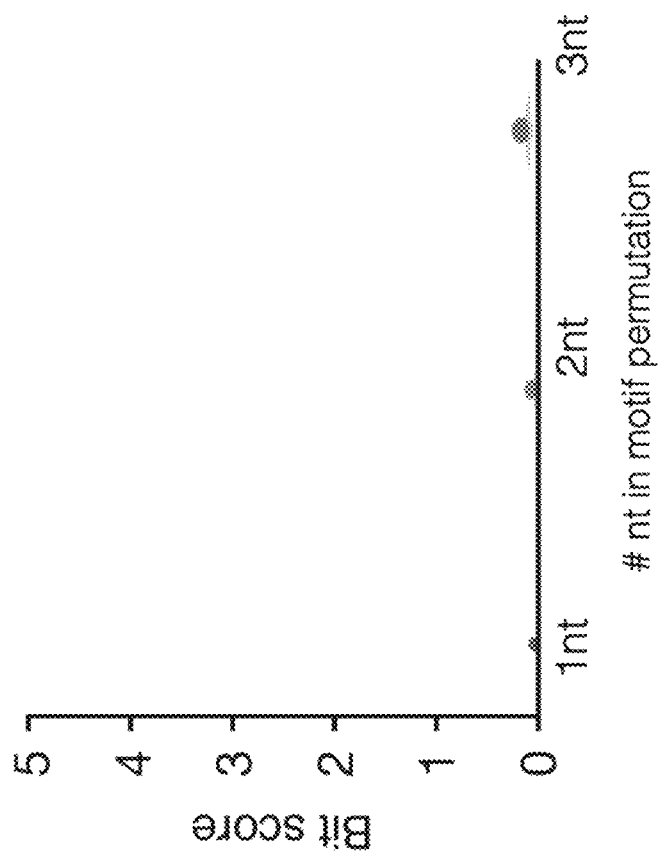

FIG. 6B shows the bit scores for all nucleotide permutations target and flanking nucleotides up to length 3 for strongly depleted Cas12g1 CRISPR arrays from in vivo screening.

Figure 7:
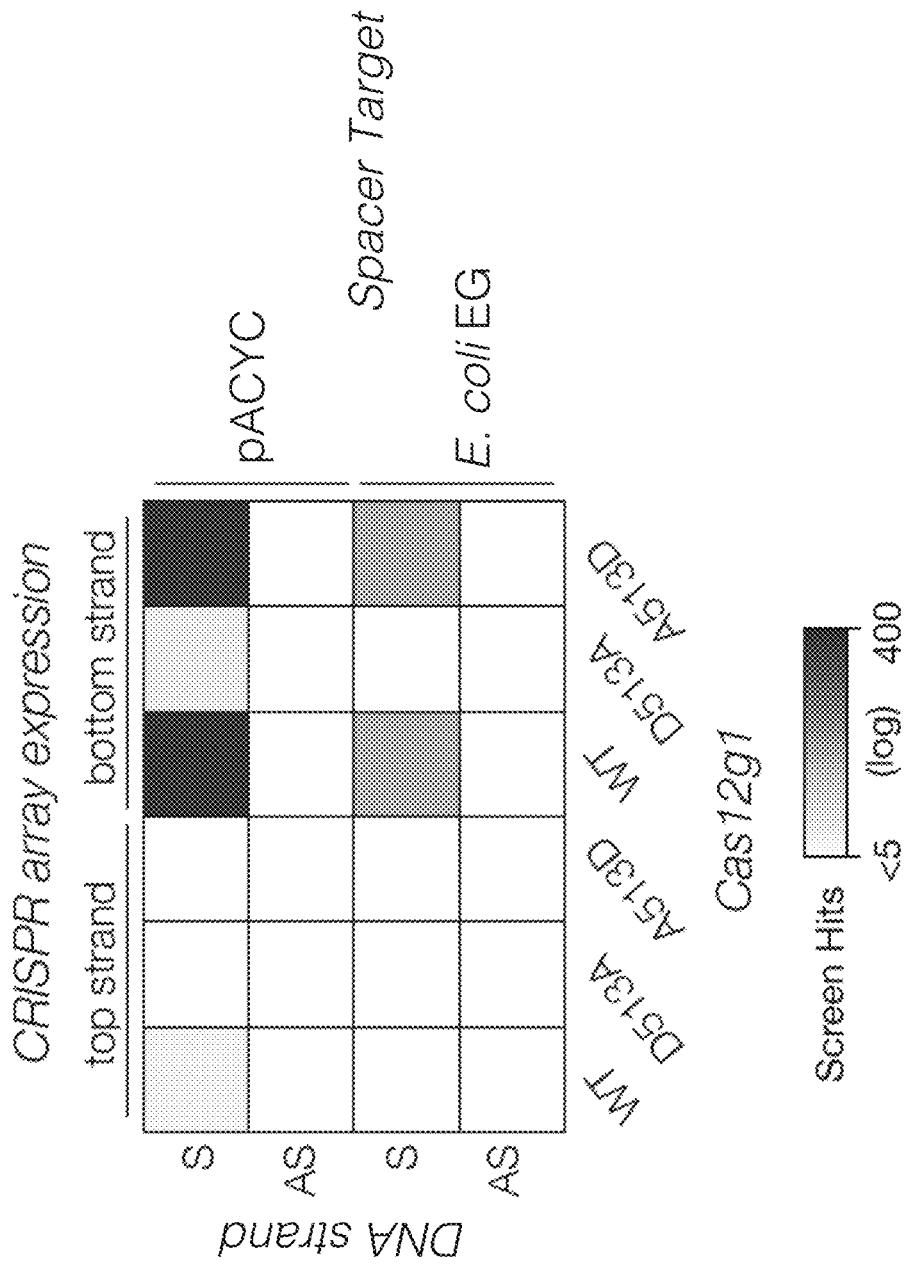

FIG. 7 is a heatmap that summarizes the number of strongly depleted CRISPR arrays detected for different Cas12g1 system compositions enumerated along the x-axis as follows; 1) Cas12g1 Effector Plasmid library with Non-coding Plasmid (minimal active system), 2) dCas12g1-D513A Effector Plasmid library with Non-coding Plasmid, and 3) Cas12g1-A513D Effector Plasmid library with Non-coding Plasmid (mutant clone restored to WT). Screen systems are additionally separated by CRISPR array expression direction. Along the y-axis, strongly depleted spacers for each system are separated by target substrate (pACYC184 or *B. coli* essential genes, EG) and DNA strand (S, sense; AS, antisense). CRISPR arrays strongly depleted in negative controls without Cas12g1 are subtracted from the analysis.

Figure 8:
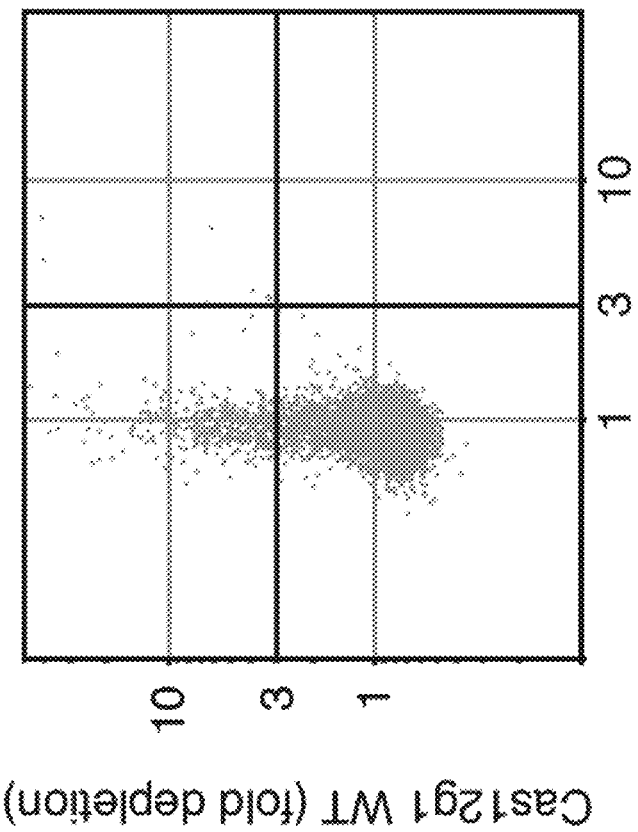

FIG. 8 is a scatter plot that shows the in vivo screening comparison of Cas12g1 WT versus the dCas12g1 D513A mutant (where the RuvC-I catalytic residue aspartate is mutated to alanine). Each point represents a spacer, and the value indicates the x-fold depletion under the condition specified for the axis (wild type vs mutant). Higher values indicate stronger depletion (i.e. fewer surviving colonies). Red lines indicate threshold for "strongly depleted" (>3 fold depiction).

Figure 9:
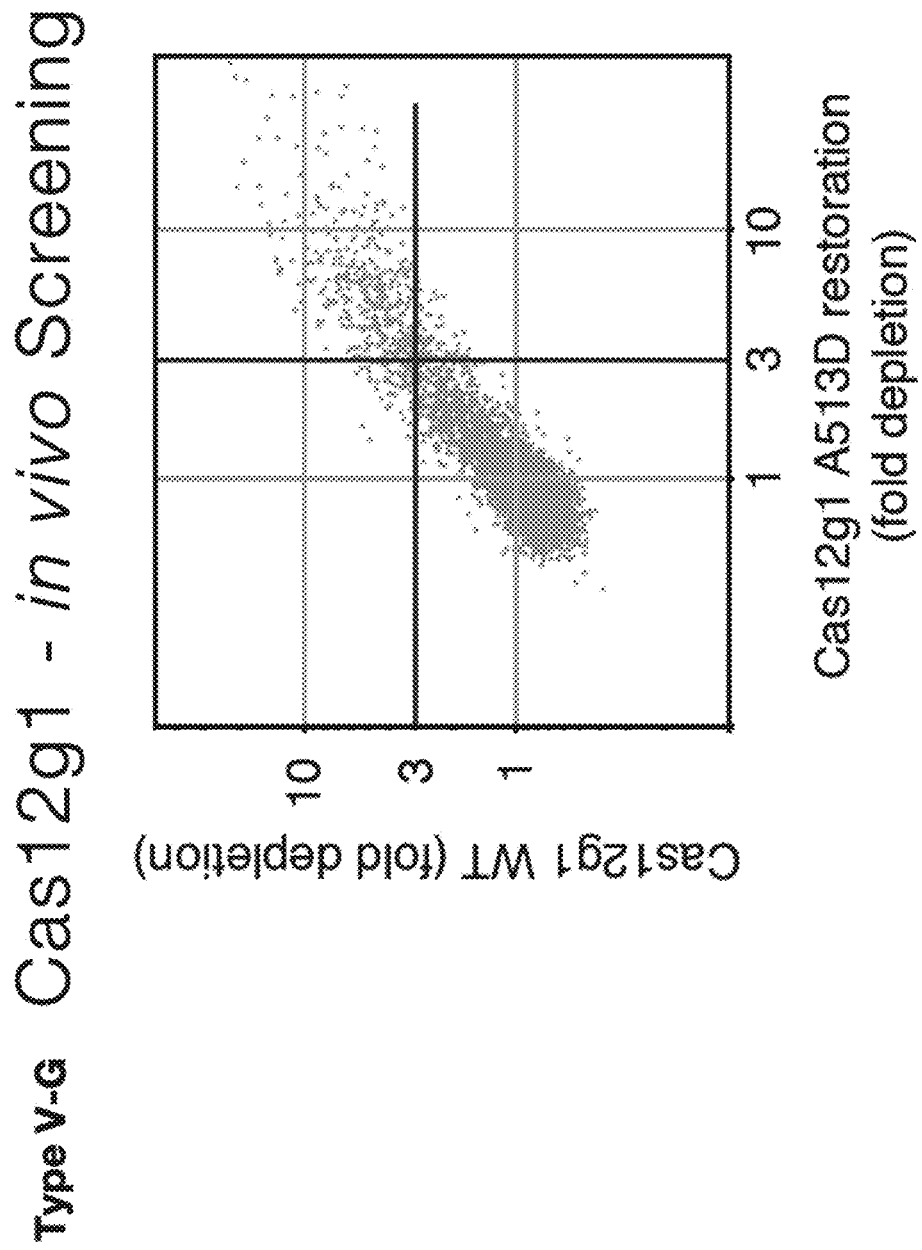

FIG. 9 is a scatter plot that shows the in vivo screening comparison of Cas12g1 WT versus the A513D rescue mutant cloned from dCas12g1 D513A. Each point represents a spacer, and the value indicates the x-fold depletion under the condition specified for the axis. Higher values indicate stronger depletion (i.e. fewer surviving colonies). Red lines indicate threshold for "strongly depleted" (>3 fold depletion).

Figure 10:
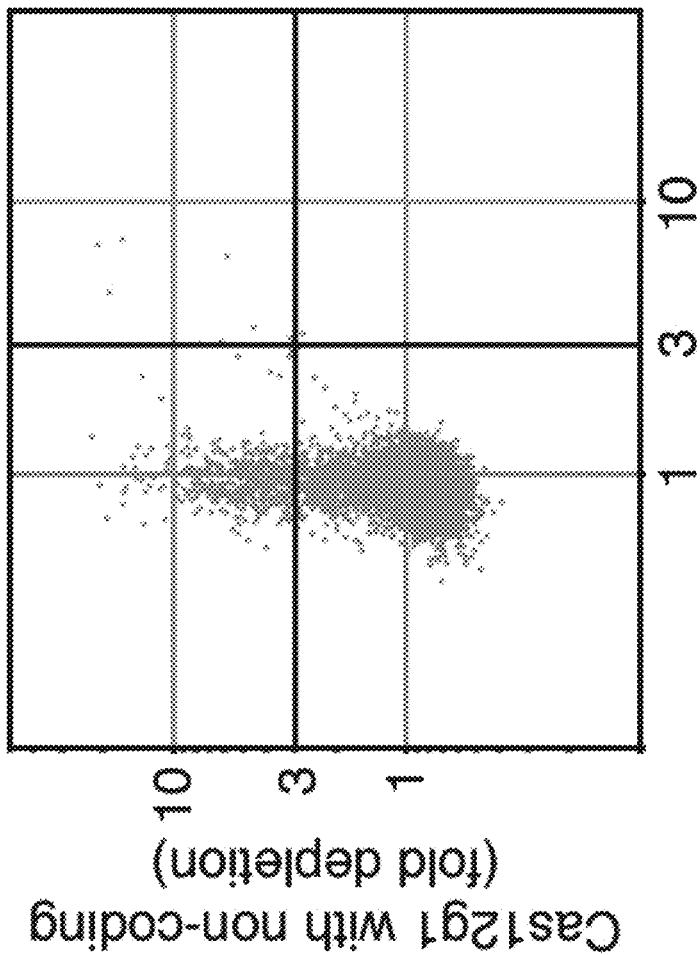

FIG. 10 is a scatter plot that shows the in vivo screening comparison of Cas12g1 WT with and without the Non-coding Plasmid. Each point represents a spacer, and the value indicates the x-fold depletion under the condition specified for the axis. Higher values indicate stronger depletion (i.e. fewer surviving colonies). Red lines indicate threshold for "strongly depleted" (>3 fold depletion).

Figure 11:
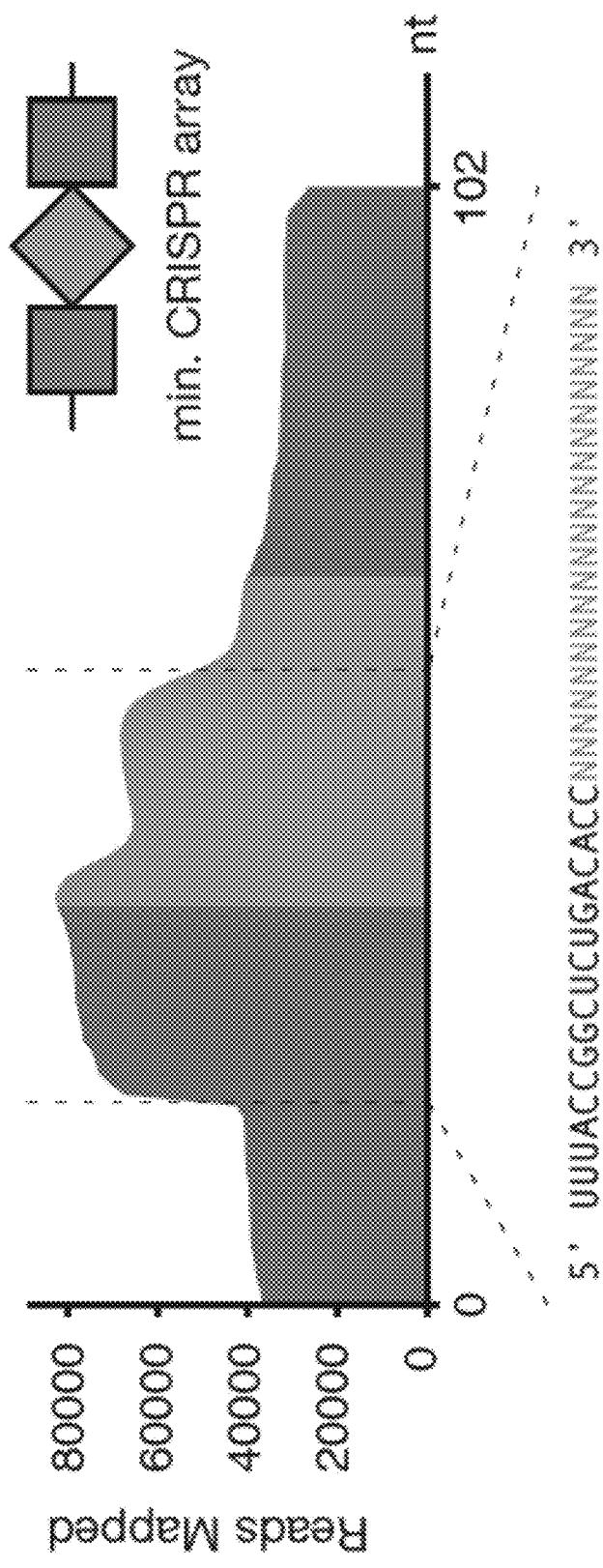

FIG. 11 depicts the read mapping of small RNA sequencing of in vivo screening samples of the minimal Cas12g1 system, revealing the mature crRNA for Cas12g1 (SEQ ID NO: 202).

Figure 12:
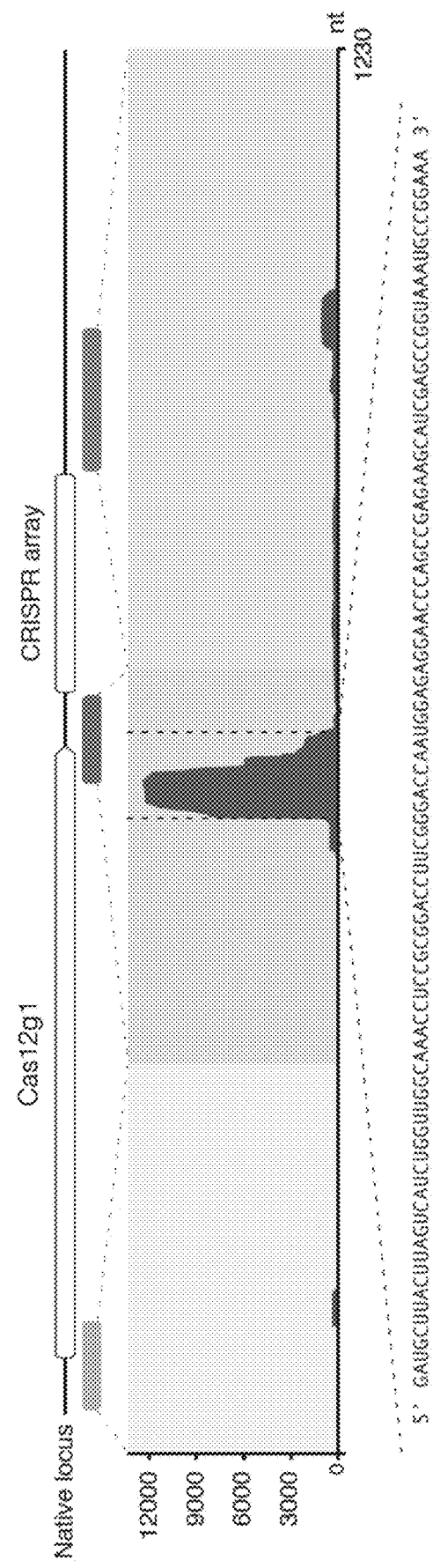

FIG. 12 depicts the read mapping of small RNA sequencing of in vivo screening samples of the minimal Cas12g1 system mapped to the Non-Coding Plasmid, revealing the tracrRNA for Cas12g1 (SEQ ID NO. 250).

Figure 13:
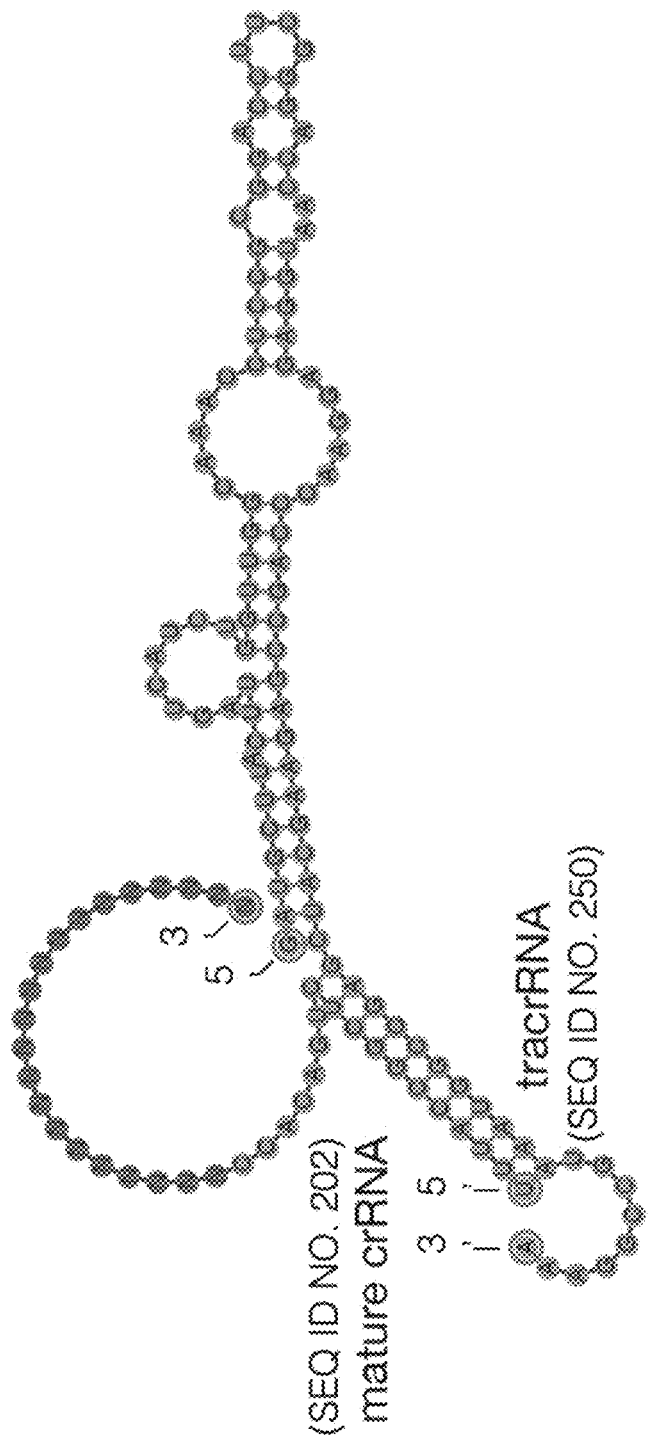

FIG. 13 depicts a co-fold of the mature crRNA (SEQ ID NO. 202) and tracrRNA (SEQ ID NO. 250) with sequences determined by small RNAseq of *E. coli* expressing the Cas12g1 system from the in vivo screen.

Figure 14:
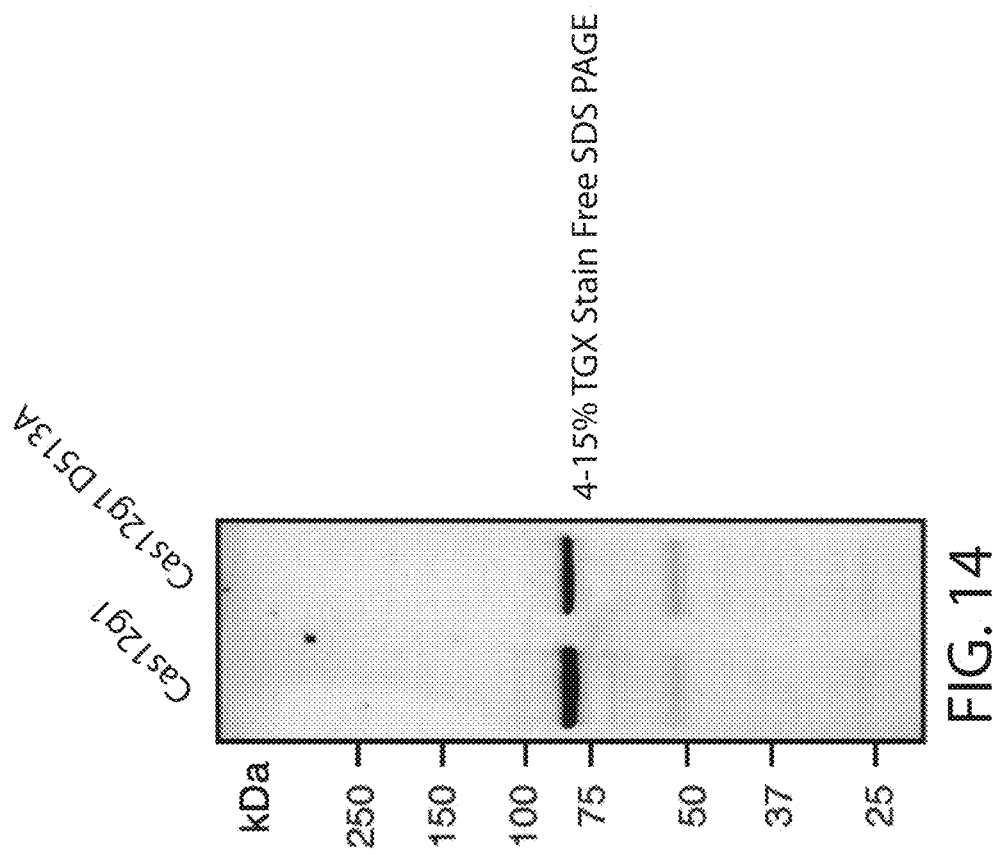

FIG. 14 depicts a stain free 4-15% SDS-Page (BioRad) gel of effector proteins post His-tag purification, fraction pooling, and concentration.

Figure 15B:
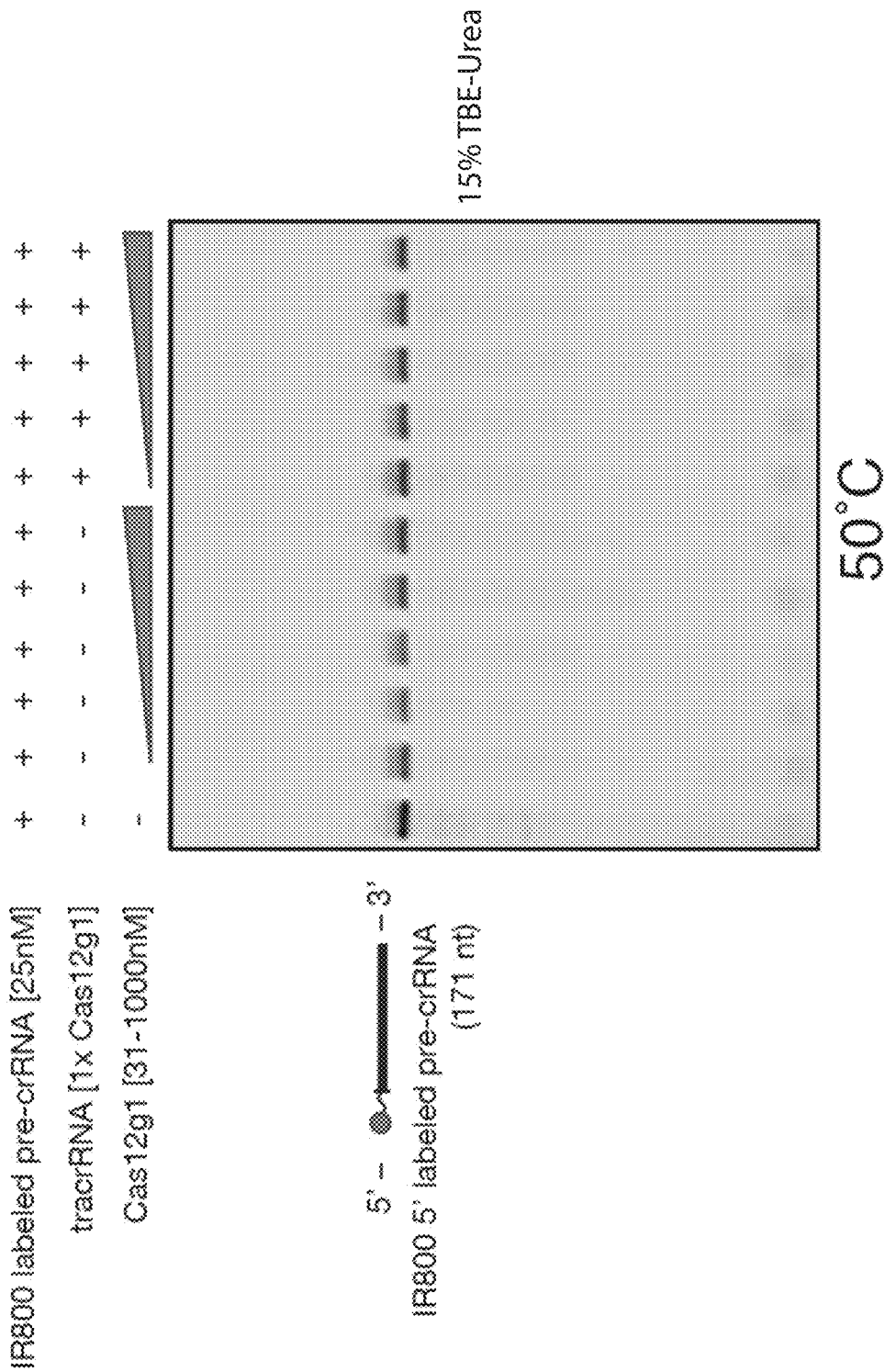

FIGS. 15A-B depict denaturing gels showing lack of in vitro pre-crRNA processing by Cas12g1 effector protein at (FIG. 15A) 37° C. and (FIG. 15B) 50° C. Pre-crRNA with and without tracrRNA was incubated with Cas12g1 for 1 hour at 37° C. and analyzed on a 15% TBE-Urea gel.

Figure 16A:
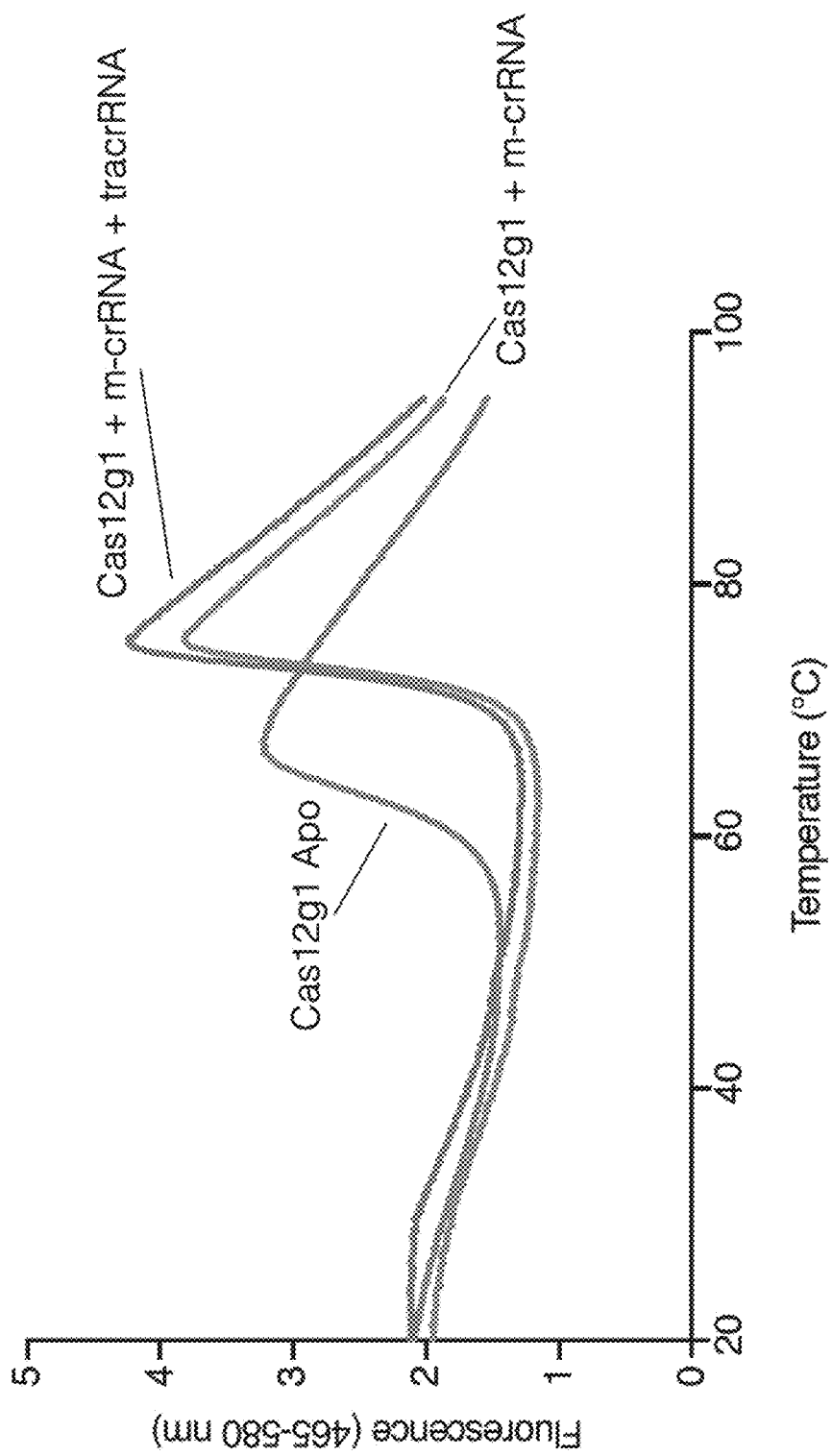

FIG. 16A is a melting curve graph of Cas12g1 displaying the thermostability of apo Cas12g1 and increased thermostability of binary (Cas12g1+crRNA) and ternary (Cas12g1+crRNA+tracrRNA) complex of Cas12g1. Melting curve was obtained using differential scanning fluorimetry (DSF).

Figure 16B:
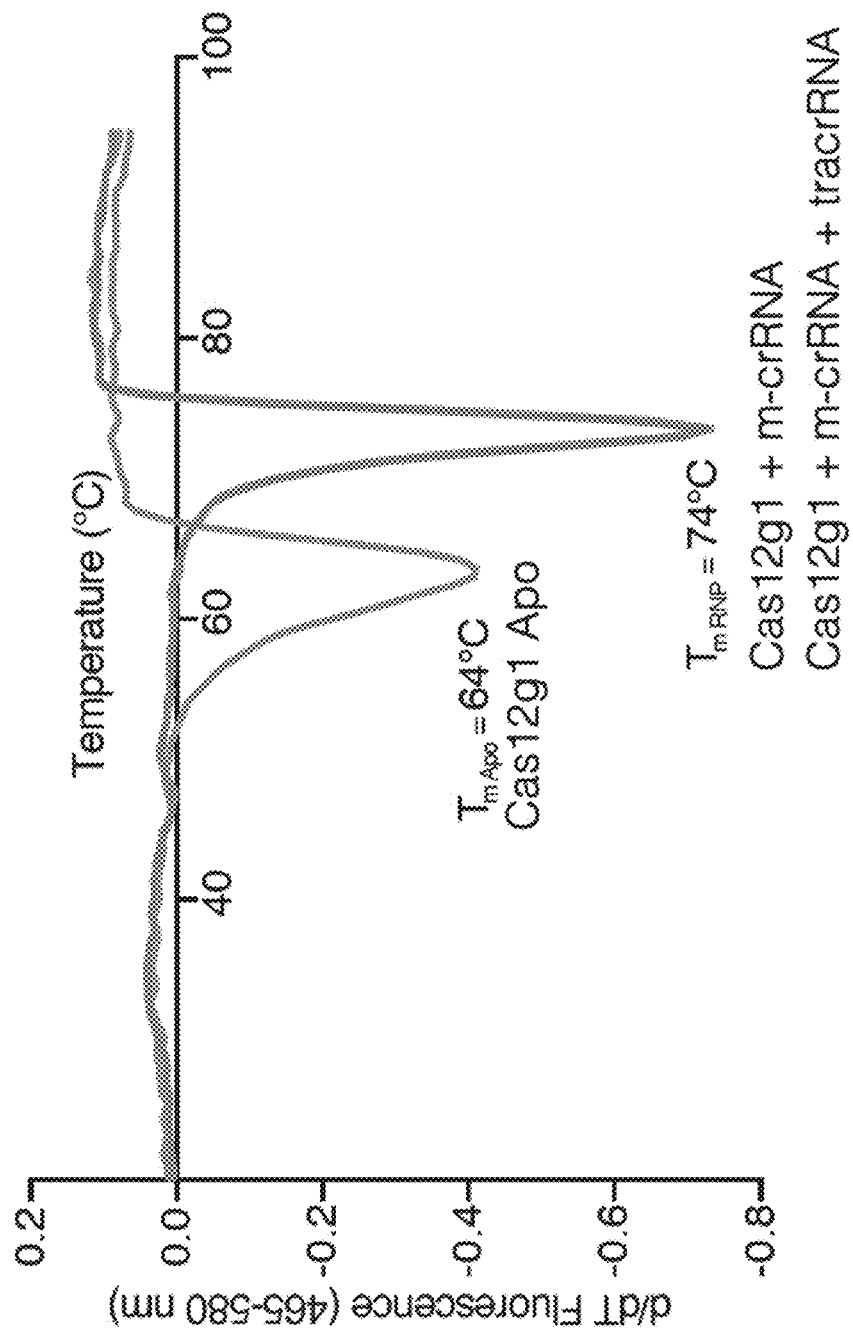

FIG. 16B depicts the first derivative of the thermal melts from showing the melting temperatures of apo, binary (Cas12g1+crRNA), and ternary (Cas12g1+crRNA+tracrRNA) complexes of Cas12g1. The first derivative traces of the Cas12g1 binary and ternary complexes are nearly overlapping.

Figure 17A:
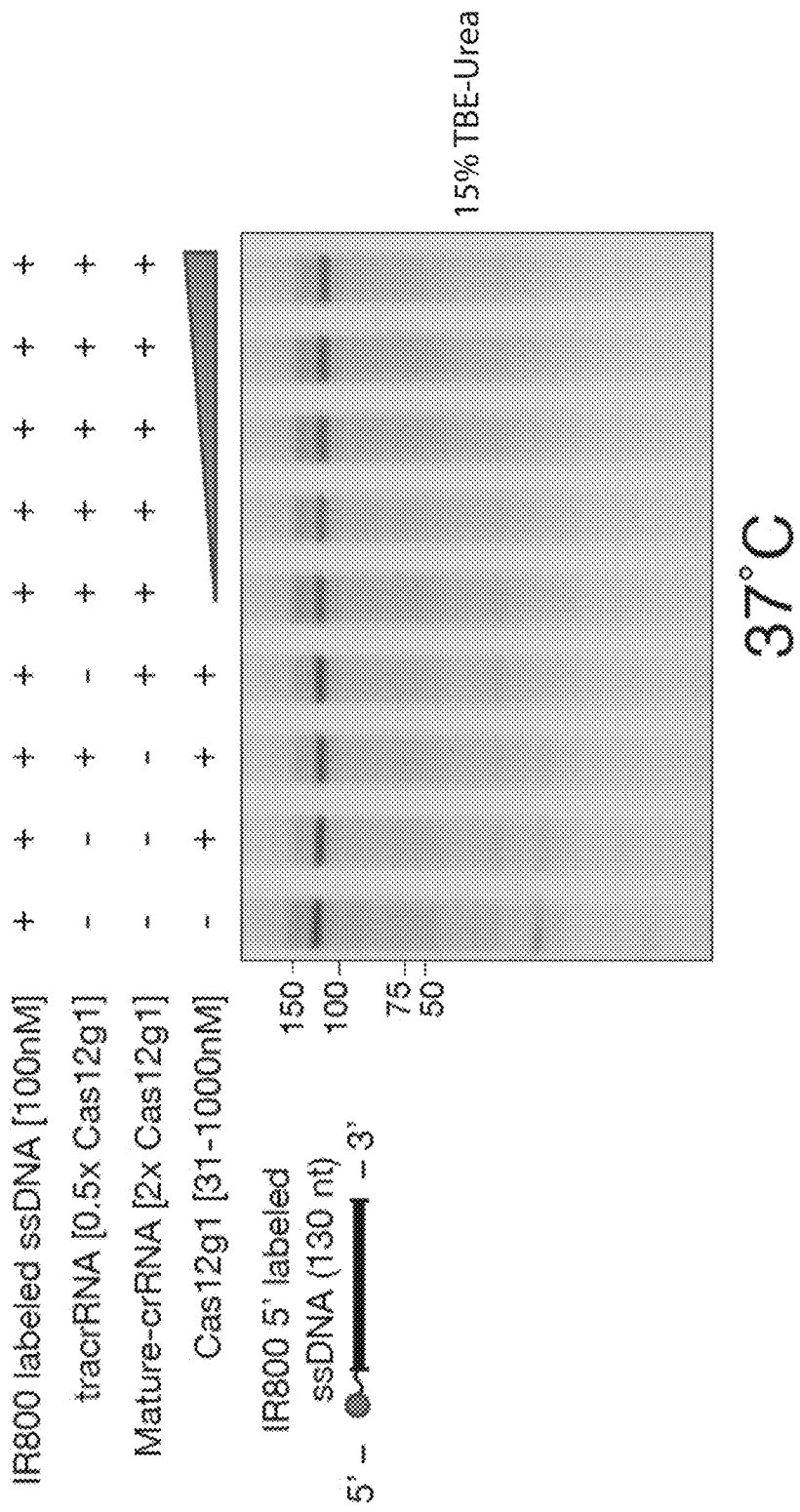
Figure 17B:
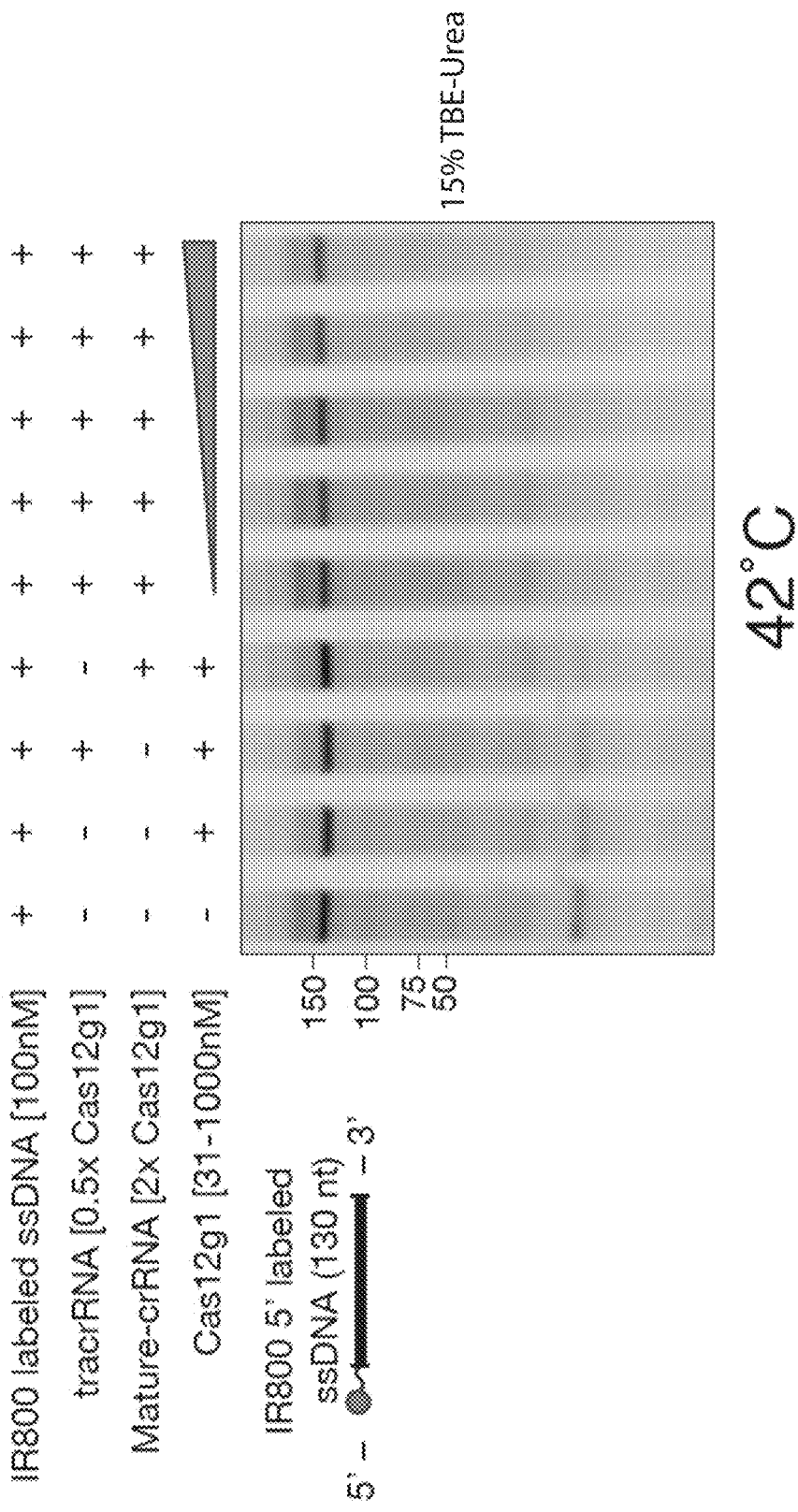
Figure 17C:
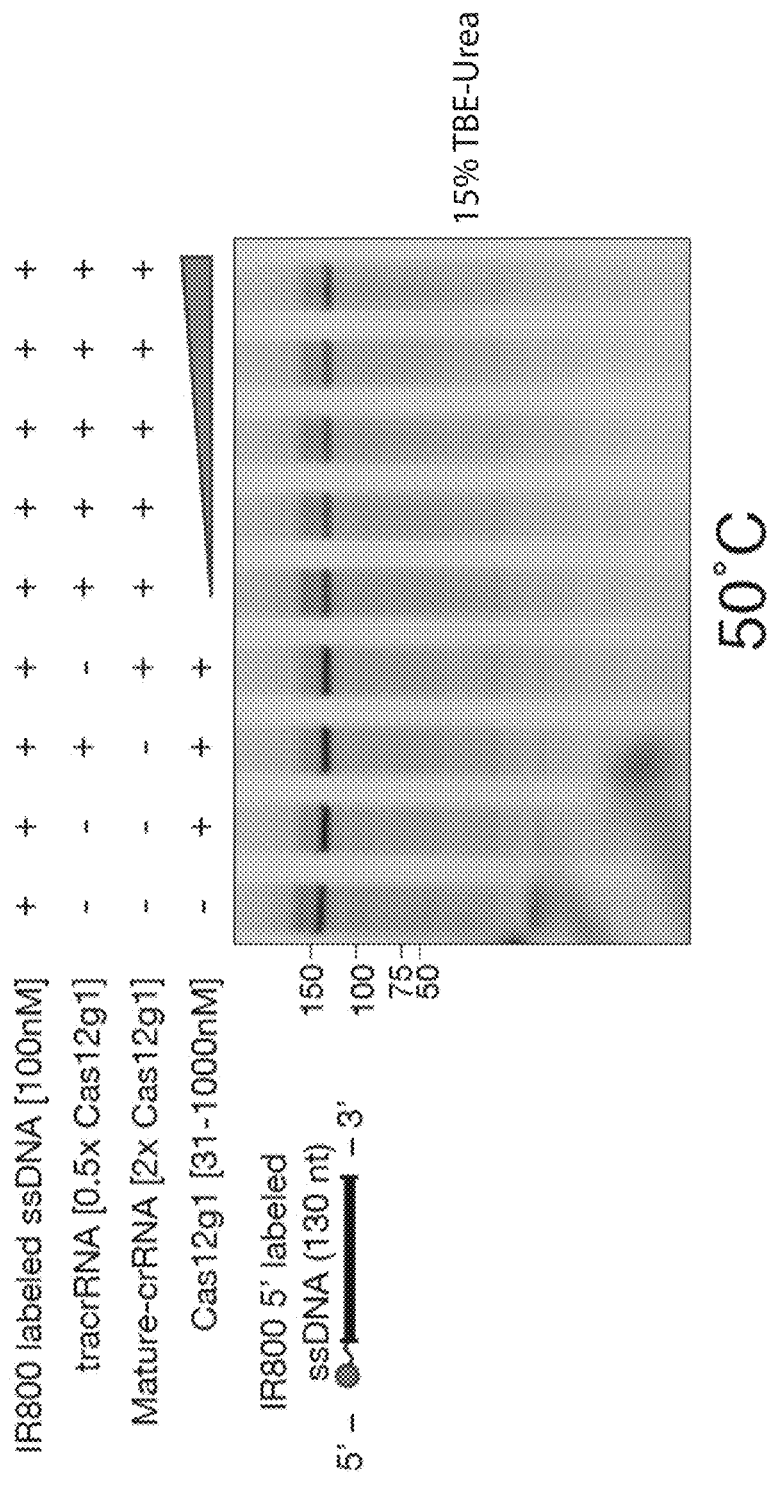
Figure 17D:
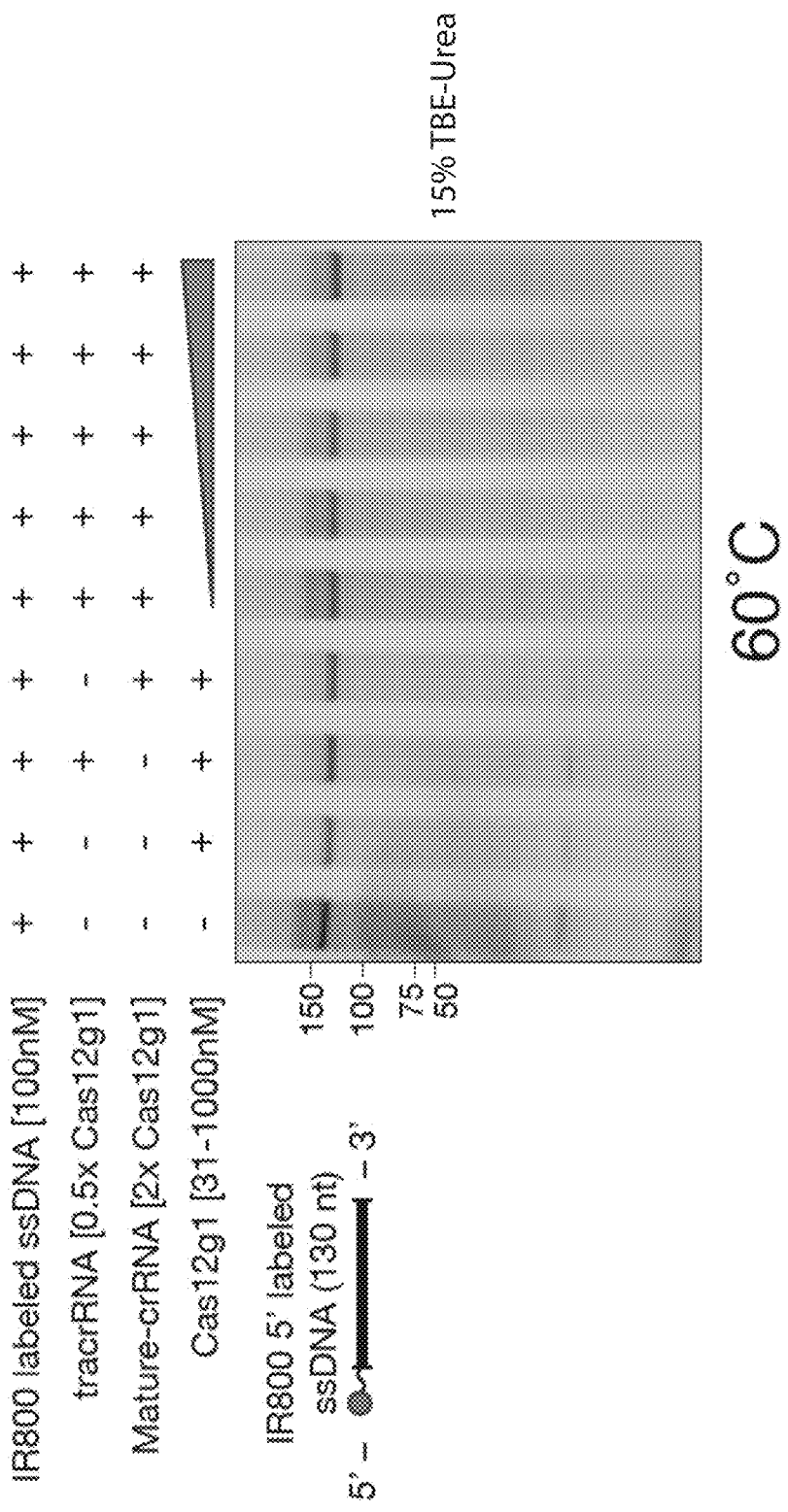

FIGS. 17A-D depict denaturing gels demonstrating the absence of activity for Cas12g1 surveillance complex (Cas12g1+crRNA+tracrRNA) against ssDNA targets. Cas12g1 surveillance complex was tested for nuclease activity against DNA substrates at 37° C. (FIG. 17A), 42° C. (FIG. 17B), 50° C. (FIG. 17C) and 60° C. (FIG. 17D). The ssDNA target is 5' end labeled with IR800 dye. For all reactions, the Cas12g1 surveillance complex was formed by pre-incubating Cas12g1, mature crRNA and tracrRNA for 10 minutes at 37° C. prior to adding the substrates and incubating for 1 hour at the specified temperature.

Figure 18A:
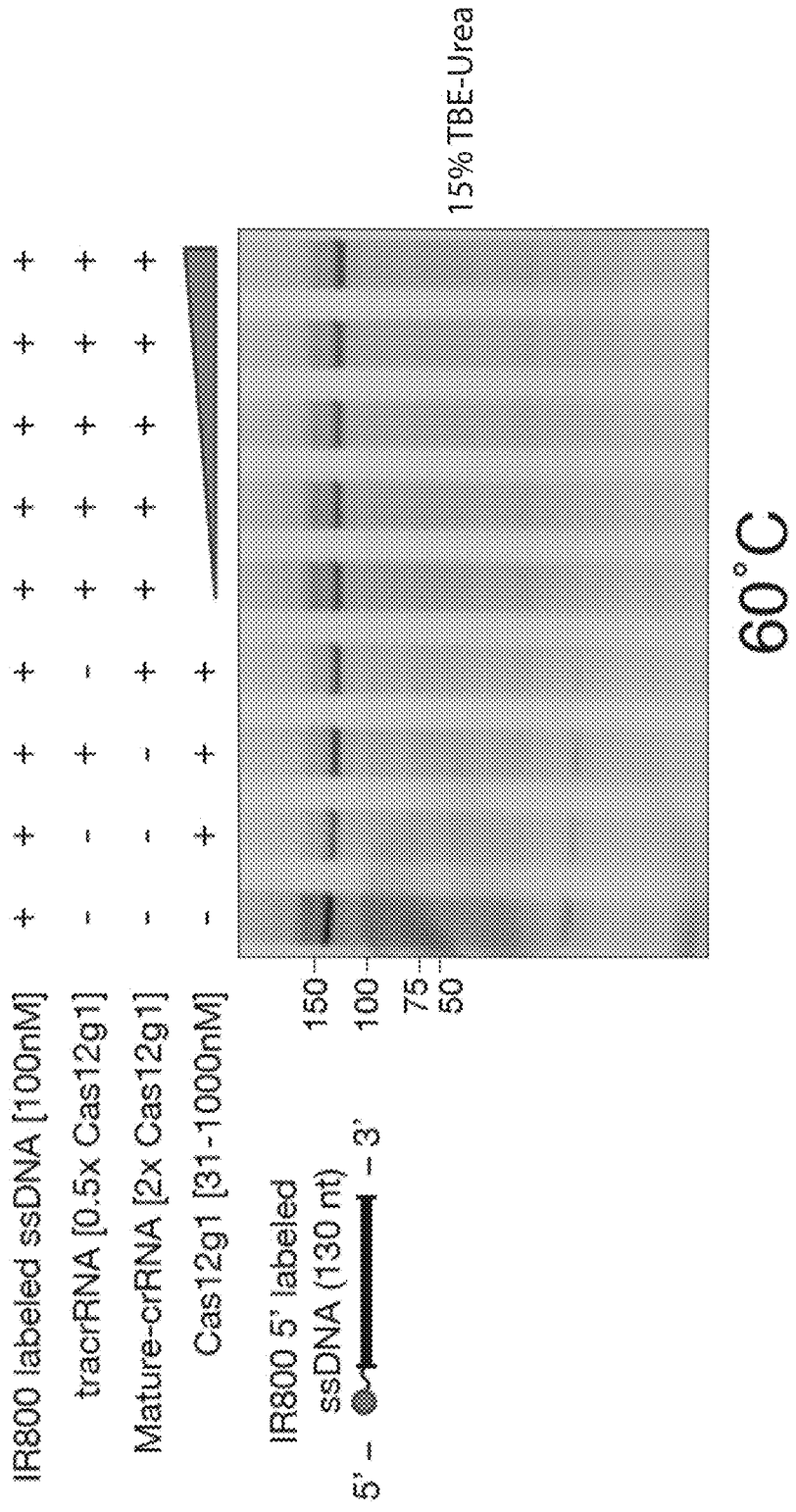
Figure 18B:
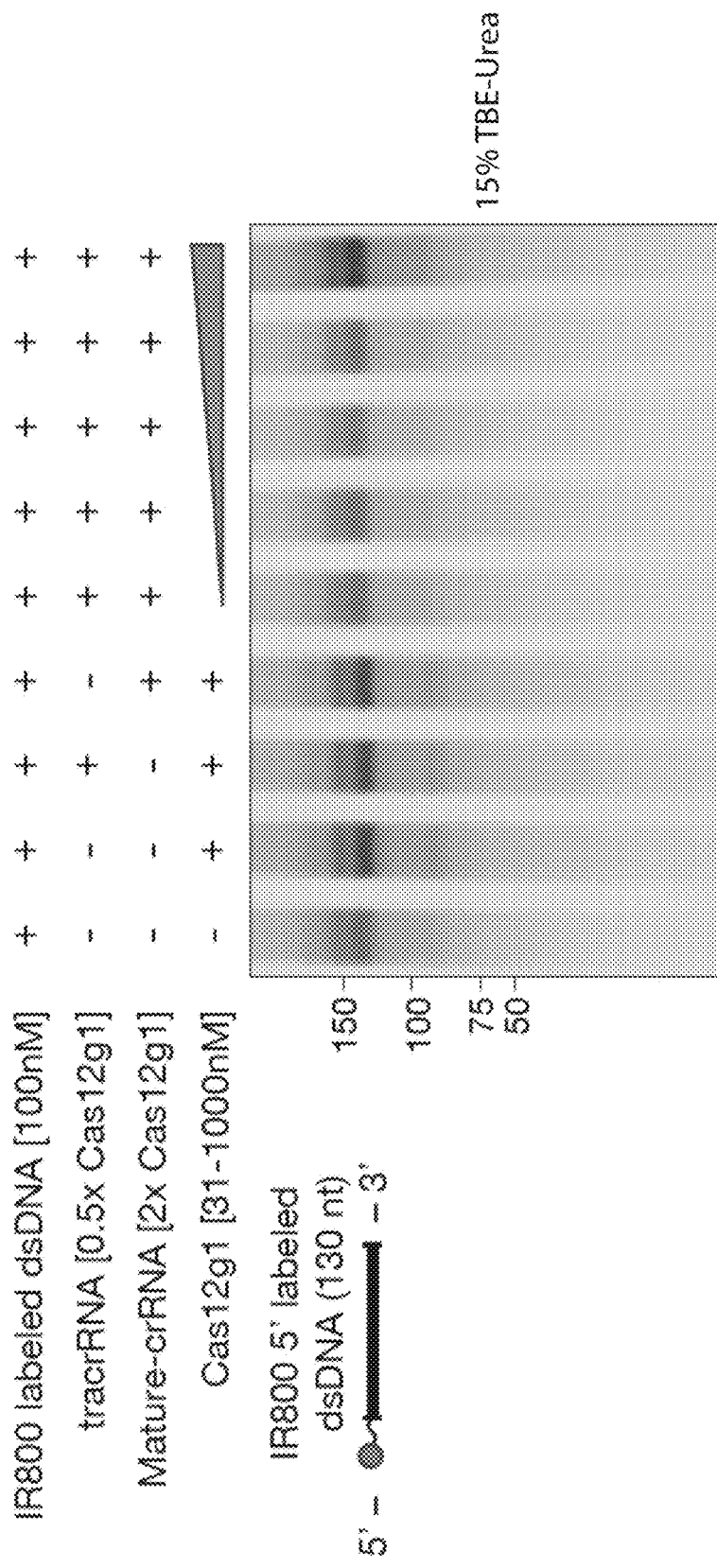
Figure 18C:
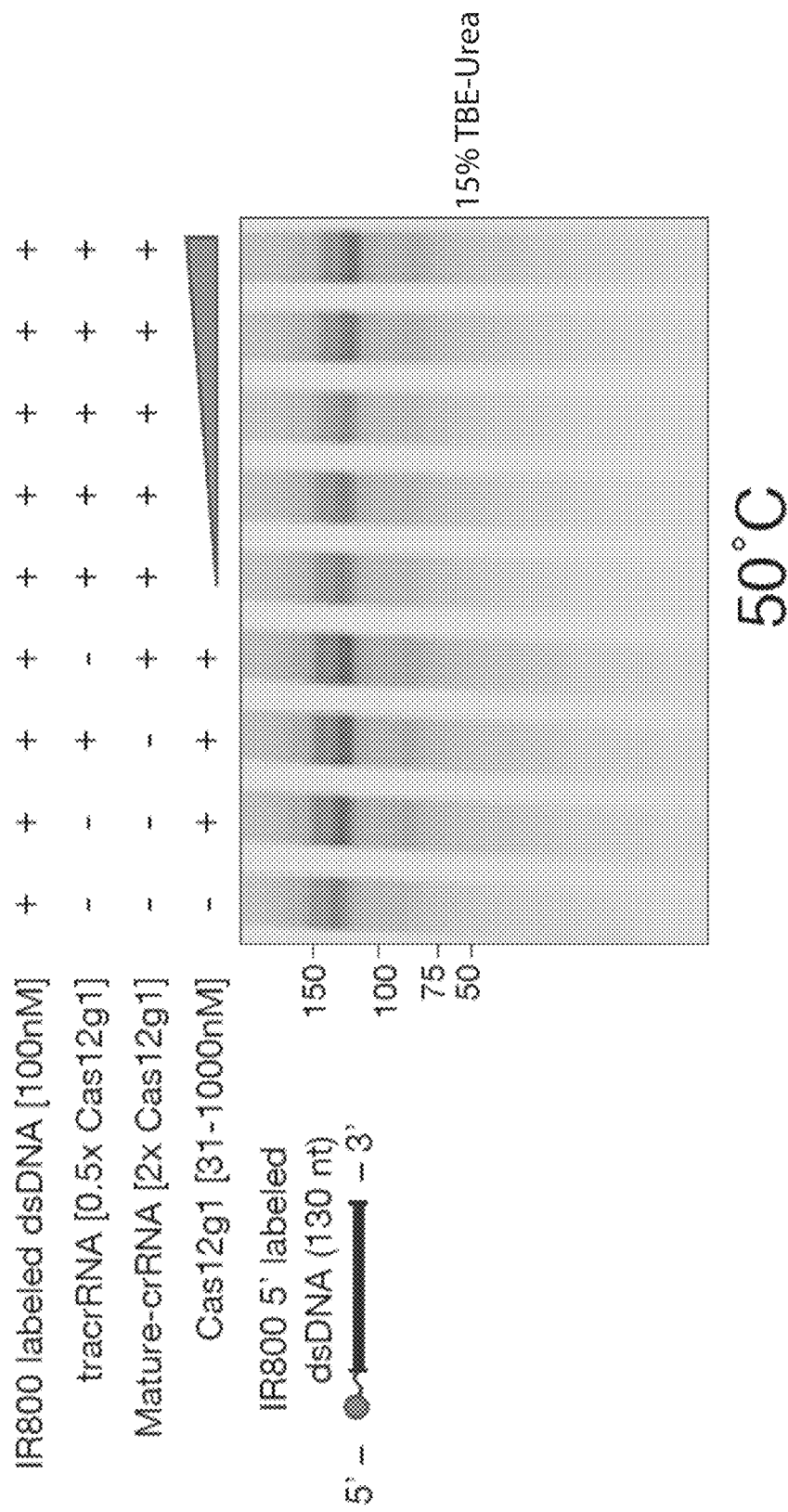
Figure 18D:
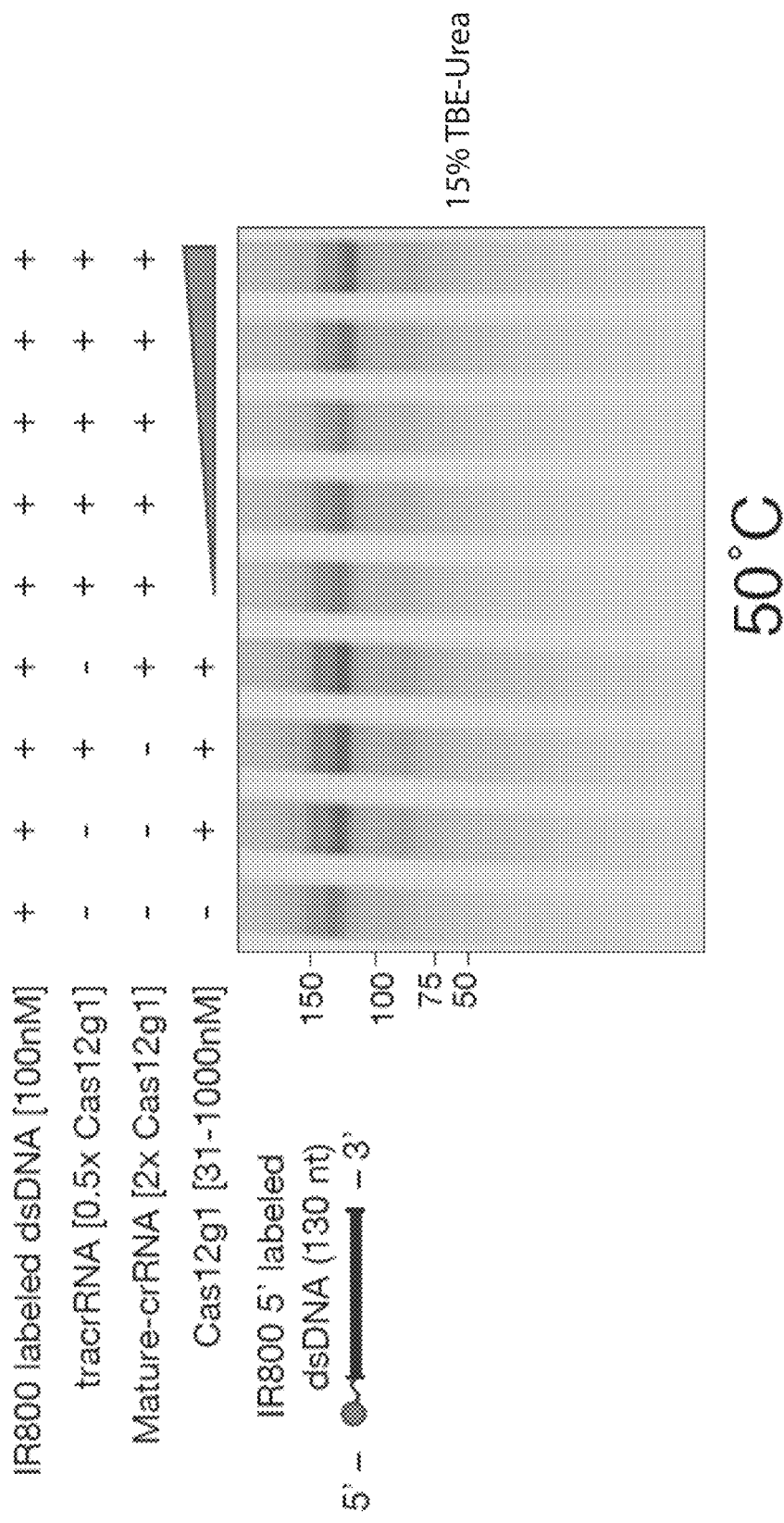

FIGS. 18A-D depict denaturing gels demonstrating the absence of activity for Cas12g1 surveillance complex (Cas12g1+crRNA+tracrRNA) against dsDNA targets. Cas12g1 surveillance complex was tested for nuclease activity against DNA substrates at 37° C. (FIG. 18A), 42° C. (FIG. 18B), 50° C. (FIG. 18C) and 60° C. (FIG. 18D). The dsDNA target is labeled with IR800 dye on the 5' end of the non-spacer complementary strand. For all reactions, the Cas12g1 surveillance complex was formed by pre-incubating Cas12g1, mature crRNA and tracrRNA for 10 minutes at 37° C. prior to adding the substrates and incubating for 1 hour at the specified temperature.

Figure 19:
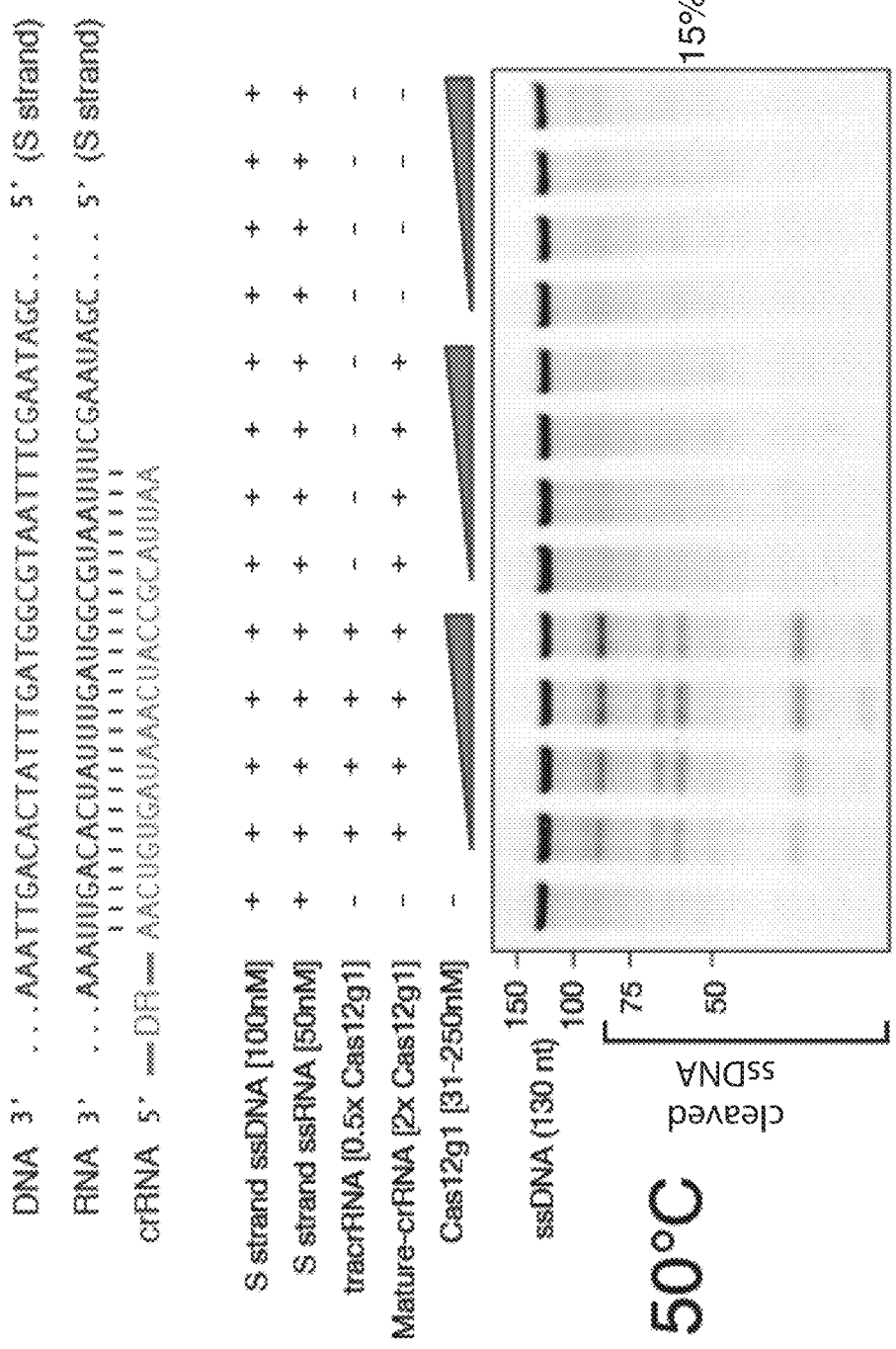

FIG. 19 depicts a denaturing gel showing cleavage of sense (S) ssDNA (SEQ ID NO: 422) in the presence of sense (S) ssRNA transcripts (SEQ ID NO: 421) (with both ssDNA and ssRNA substrates having complementarity to the crRNA spacer (SEQ ID NO: 412)) by Cas12g1 apo (Cas12g only), binary (Cas12g+m-crRNA), and ternary (Cas12g+m-crRNA+tracrRNA) complexes at 50° C. Cas12g1 ternary complex was formed by pre-incubating Cas12g1 and mature crRNA and tracrRNA for 10 minutes at 37° C. prior to adding the substrates and incubating for 1 hour at the specified temperature. In the reactions, ssDNA and ssRNA substrates were hybridized prior to adding the Cas12g1 ternary complex, yielding a DNA-RNA hybrid for the sense-antisense pairings of ssDNA and ssRNA. Samples were RNase treated and analyzed on a 15% TBE-urea denaturing gel using SYBR Gold nucleic acid staining.

Figure 20:
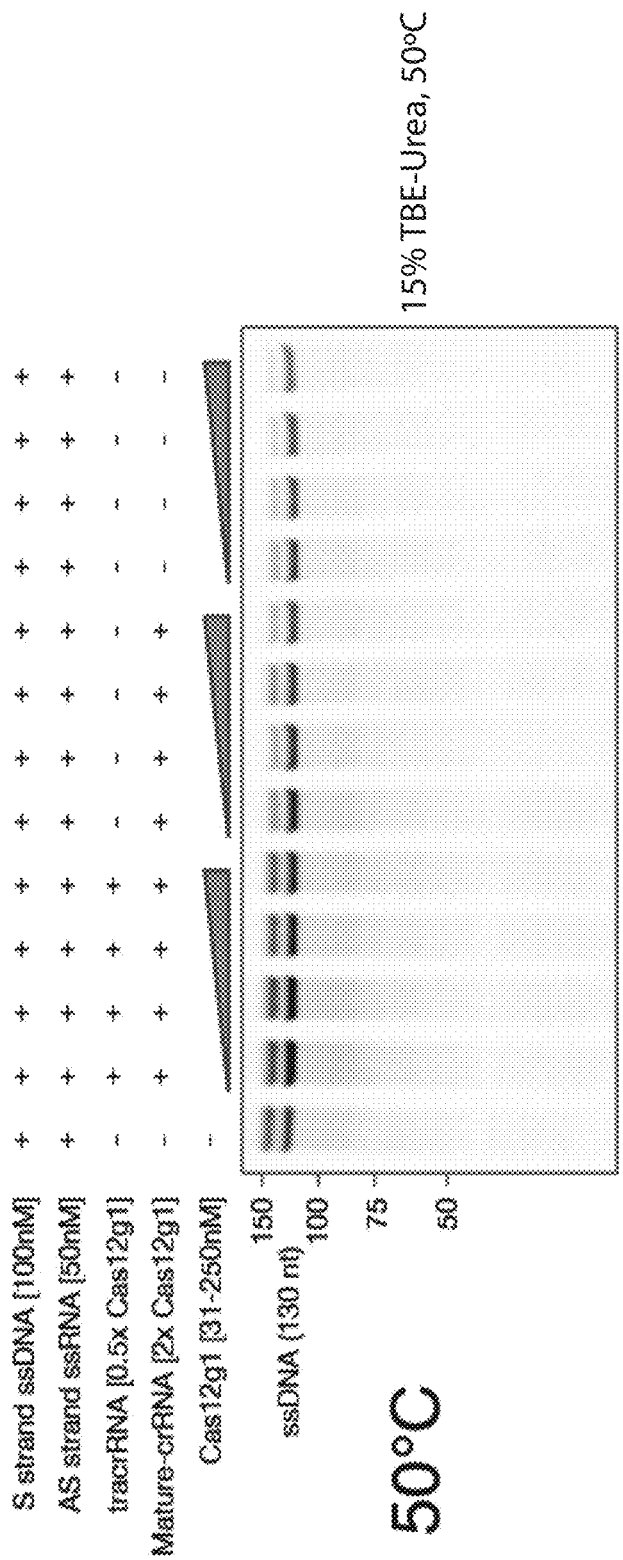

FIG. 20 depicts a denaturing gel showing the absence of cleavage of sense (S) ssDNA (SEQ ID NO: 422) in the presence of antisense (AS) ssRNA transcripts (SEQ ID NO: 423) by Cas12g1 apo (Cas12g only), binary (Cas12g+m-crRNA (SEQ ID NO: 412)), and ternary (Cas12g+m-crRNA+tracrRNA) complexes at 50° C. Note that only the sense ssDNA sequence has complementarity to the crRNA spacer. In the reactions, ssDNA and ssRNA substrates were hybridized prior to adding the Cas12g1 ternary complex, yielding a DNA-RNA hybrid for the sense-antisense pairings of ssDNA and ssRNA. Cas12g1 ternary complex was formed by pre-incubating Cas12g1 and mature crRNA and tracrRNA for 10 minutes at 37° C. prior to adding the substrates and incubating for 1 hour at the specified temperature. Samples were RNase treated and analyzed on a 15% TBE-urea denaturing gel using SYBR Gold nucleic acid staining.

Figure 21:
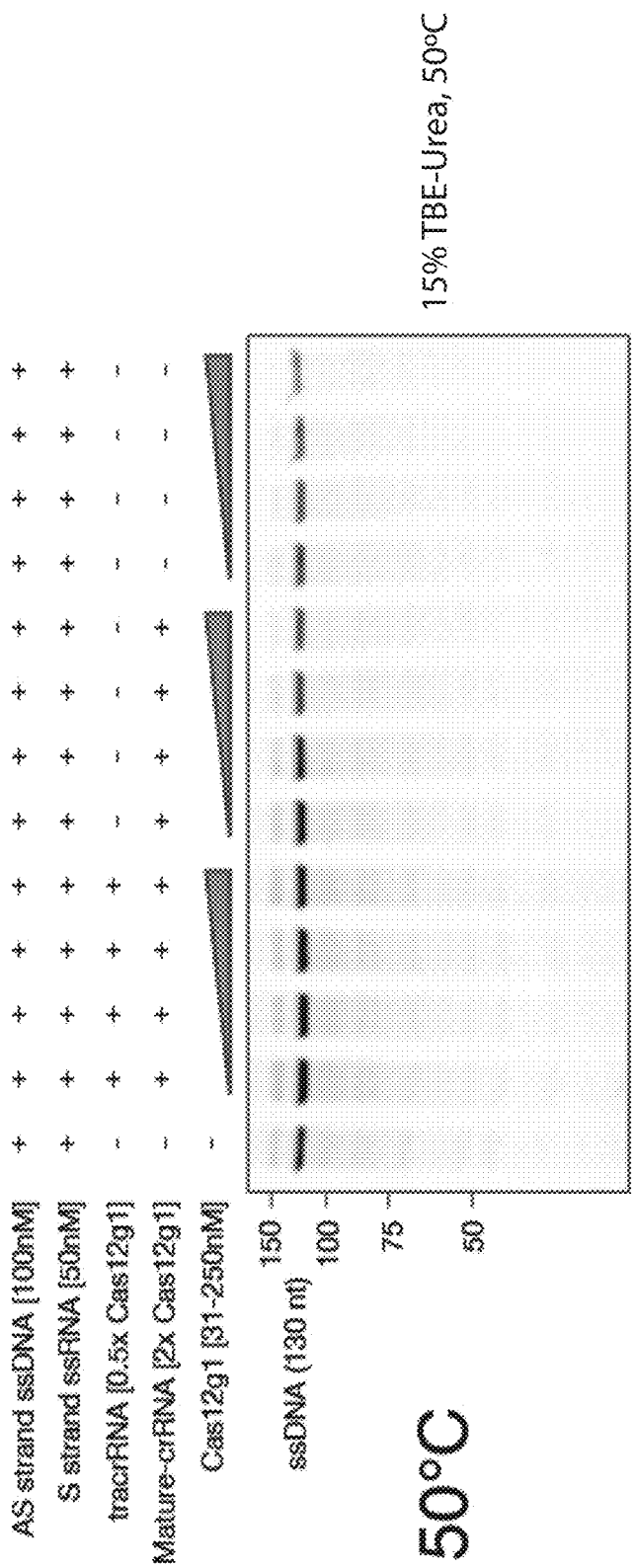

FIG. 21 depicts a denaturing gel showing the absence of cleavage of antisense (AS) ssDNA (SEQ ID NO: 424) in the presence of sense (S) ssRNA transcripts (SEQ ID NO: 421) by Cas12g1 apo (Cas12g only), binary (Cas12g+m-crRNA (SEQ ID NO: 412)), and ternary (Cas12g+m-crRNA+tracrRNA) complexes at 50° C. The sense ssRNA substrate sequence has complementarity to the crRNA spacer. In the reactions, ssDNA and ssRNA substrates were hybridized prior to adding the Cas12g1 ternary complex, yielding a DNA-RNA hybrid for the sense-antisense pairings of ssDNA and ssRNA. Cas12g1 ternary complex was formed by pre-incubating Cas12g1 and mature crRNA and tracrRNA for 10 minutes at 37° C. prior to adding the substrates and incubating for 1 hour at the specified temperature. Samples were RNase treated and analyzed on a 15% TBE-urea denaturing gel using SYBR Gold nucleic acid staining.

Figure 22:
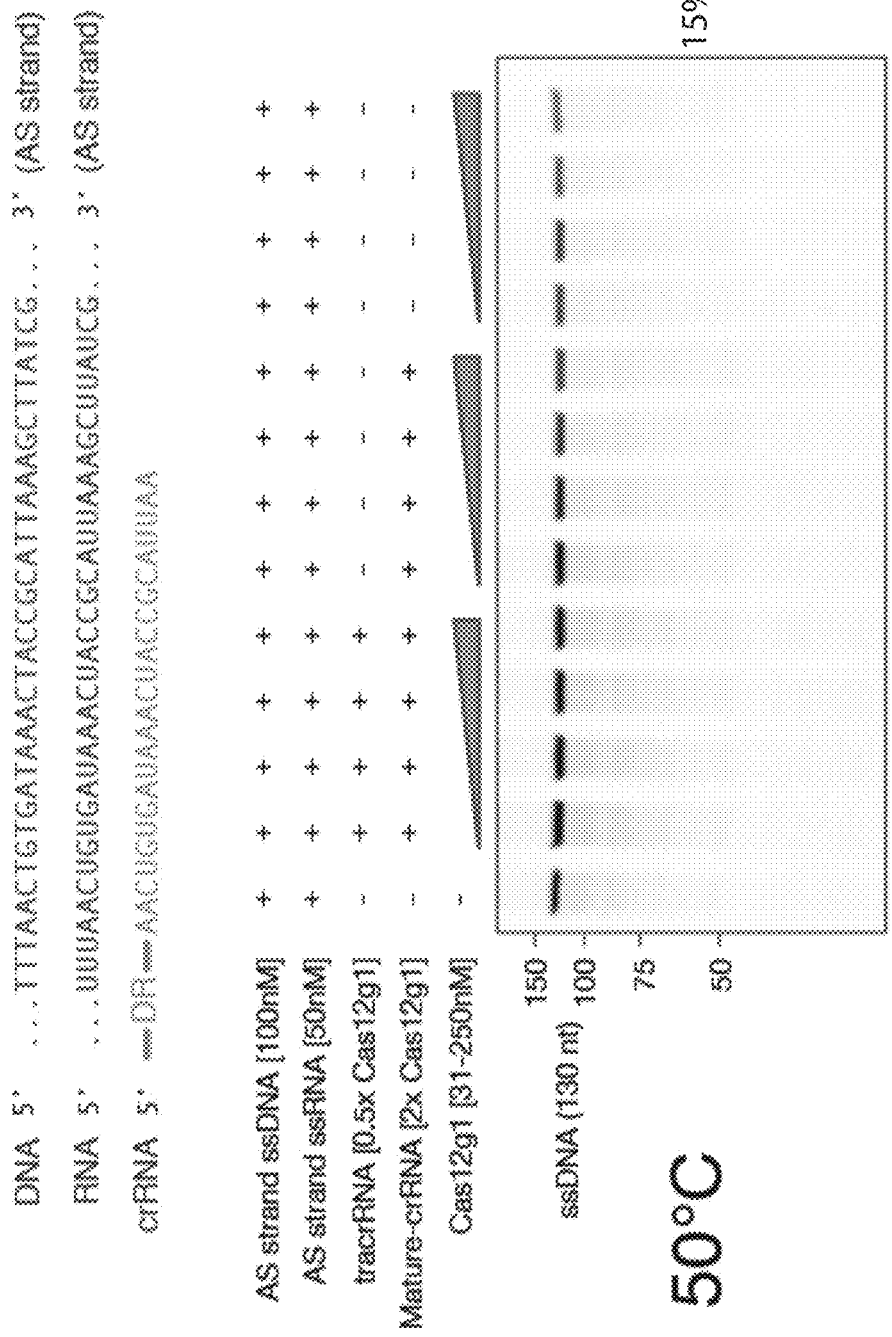

FIG. 22 depicts a denaturing gel showing the absence of cleavage of antisense (AS) ssDNA (SEQ ID NO: 424) in the presence of antisense (AS) ssRNA transcripts (SEQ ID NO: 423) by Cas12g1 apo (Cas12g only), binary (Cas12g+m-crRNA (SEQ ID NO: 412)), and ternary (Cas12g+m-crRNA+tracrRNA) complexes at 50° C. Neither ssDNA nor ssRNA substrates have sequence complementarity to the crRNA spacer. In the reactions, ssDNA and ssRNA substrates were hybridized prior to adding the Cas12g1 ternary complex. Cas12g1 ternary complex was formed by pre-incubating Cas12g1 and mature crRNA and tracrRNA for 10 minutes at 37° C. prior to adding the substrates and incubating for 1 hour at the specified temperature. Samples were RNase treated and analyzed on a 15% TBE-urea denaturing gel using SYBR Gold nucleic acid staining.

Figure 23A:
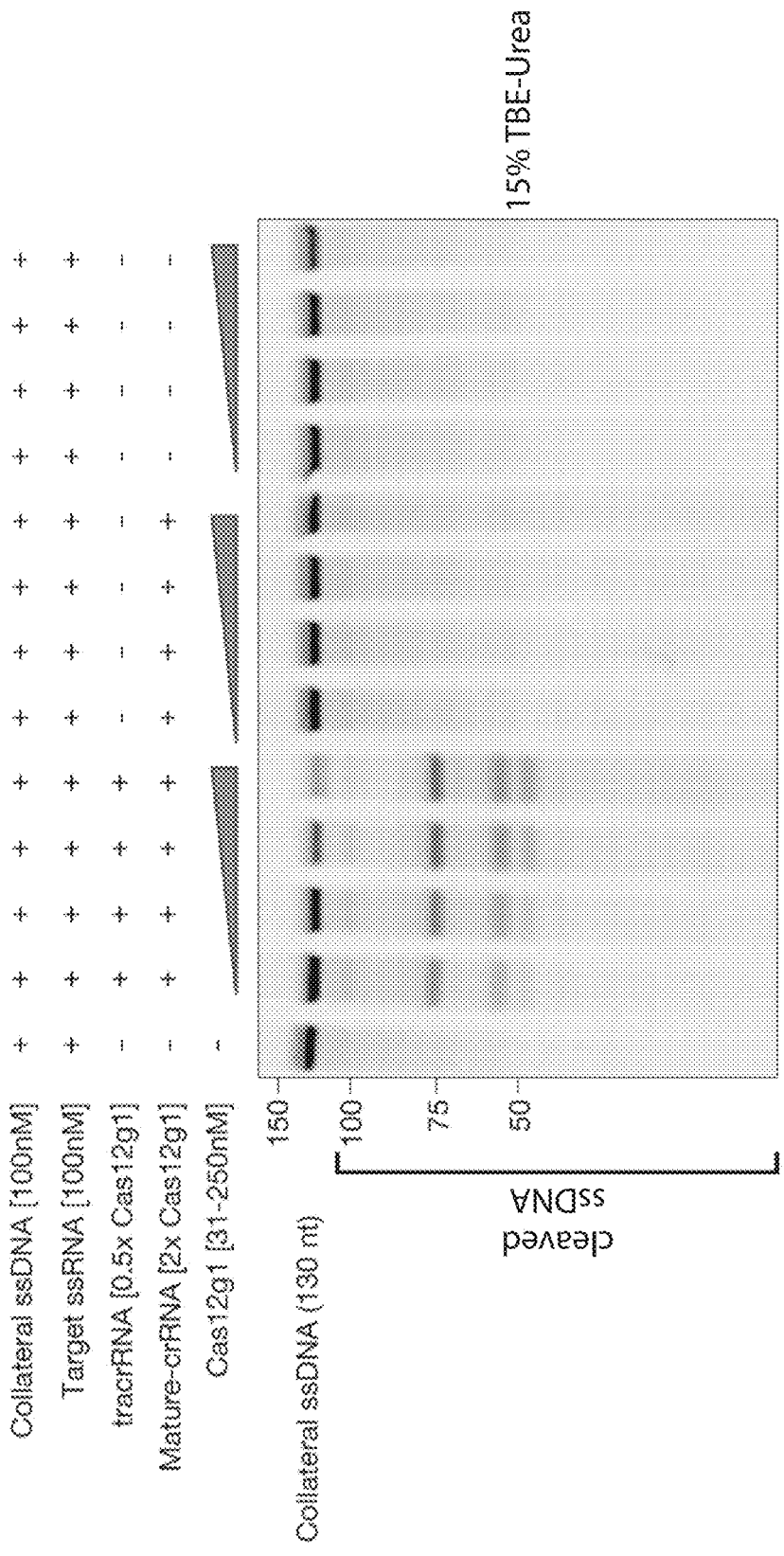
Figure 23B:
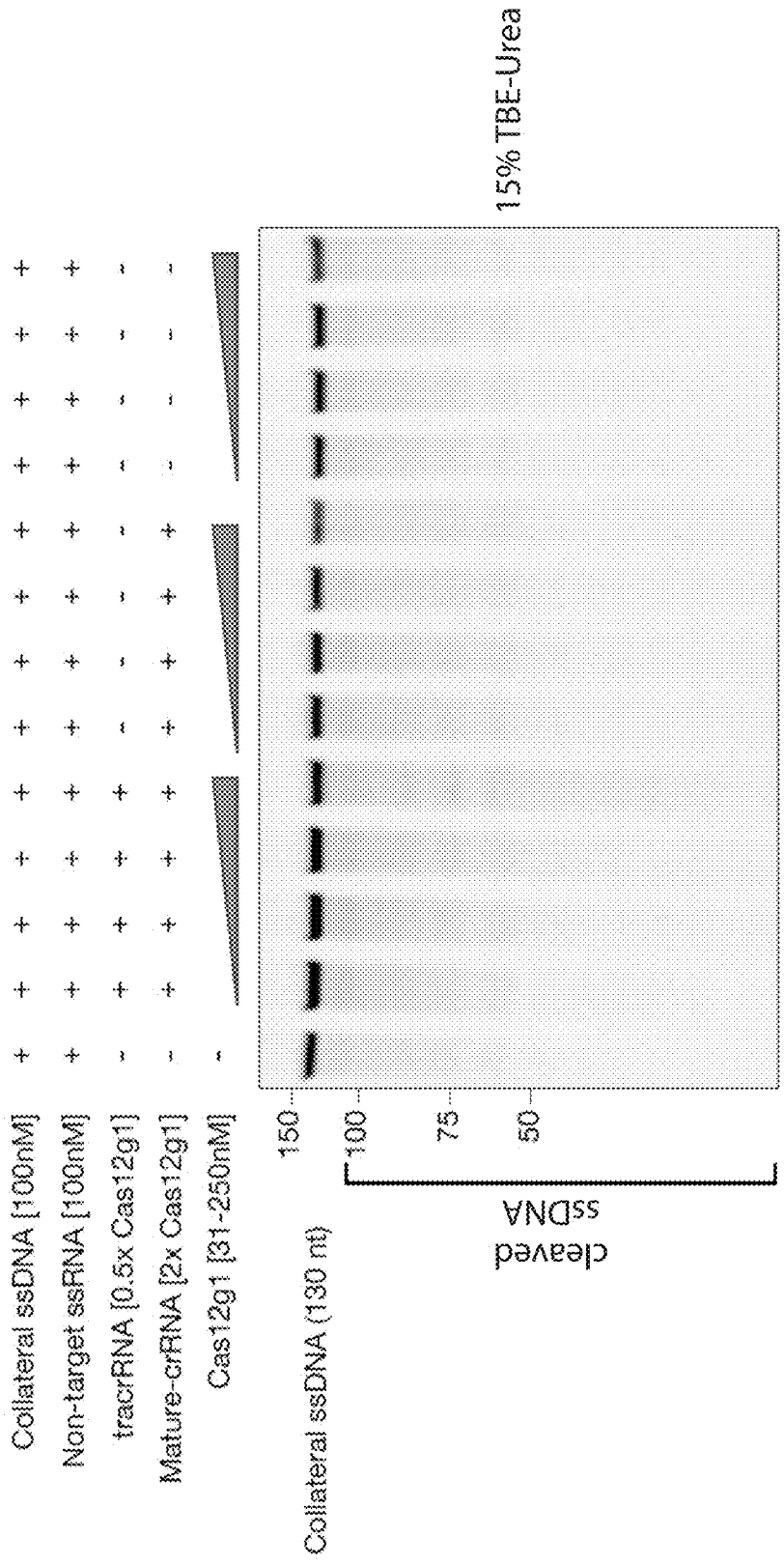

FIGS. 23A-B depict denaturing gels displaying non-specific (i.e., collateral) nuclease activity of Cas12g1 surveillance complex (Cas12g1+crRNA+tracrRNA) against collateral ssDNA substrate upon recognition of the target ssRNA. IR800 dye-labeled collateral ssDNA substrate is cleaved at 50° C. by Cas12g1 surveillance complex only in the presence of unlabeled target ssRNA (FIG. 23A) and not in the presence of unlabeled non-target ssRNA (FIG. 23B). Cas12g1 surveillance complex was formed by pre-incubating Cas12g1 and mature crRNA and tracrRNA for 10 minutes at 37° C. prior to adding the substrates and incubating for 1 hour at 37° C.

Figure 24:
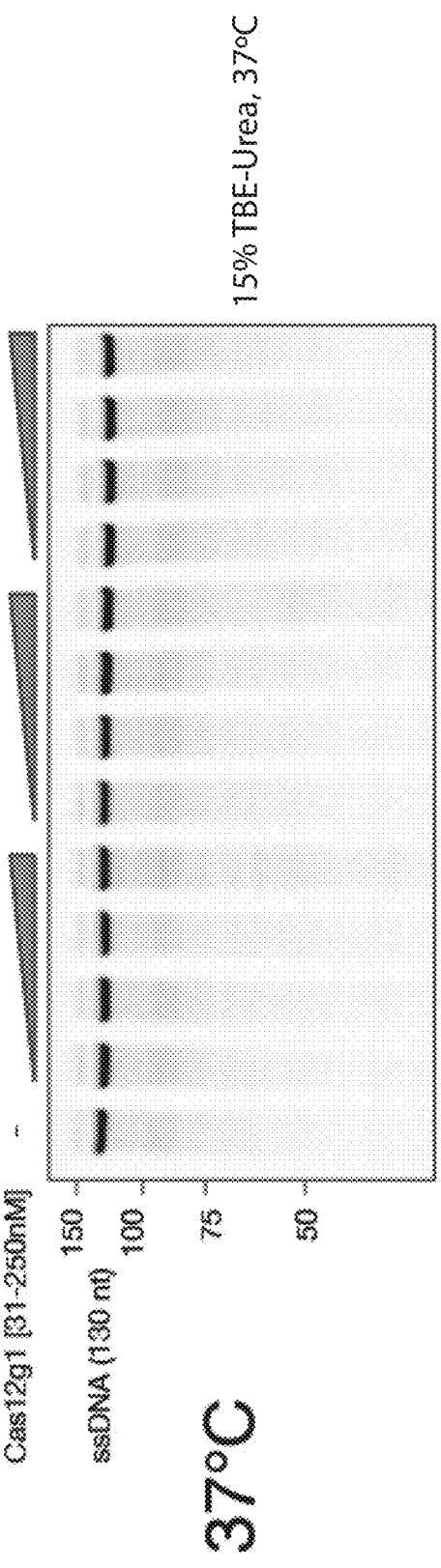

FIG. 24 depicts a denaturing gel showing cleavage of sense (S) ssDNA (SEQ ID NO: 422) in the presence of sense (S) ssRNA transcripts (SEQ ID NO: 421) (with both ssDNA and ssRNA substrates having complementarity to the crRNA spacer (SEQ ID NO: 412)) by Cas12g1 apo (Cas12g only), binary (Cas12g+m-crRNA), and ternary (Cas12g+m-crRNA+tracrRNA) complexes at 37° C. Cas12g1 ternary complex was formed by pre-incubating Cas12g1 and mature crRNA and tracrRNA for 10 minutes at 37° C. prior to adding the substrates and incubating for 1 hour at the specified temperature. In the reactions, ssDNA and ssRNA substrates were hybridized prior to adding the Cas12g1 ternary complex, yielding a DNA-RNA hybrid for the sense-antisense pairings of ssDNA and ssRNA. Samples were RNase treated and analyzed on a 15% TBE-urea denaturing gel using SYBR Gold nucleic acid staining.

Figure 25:
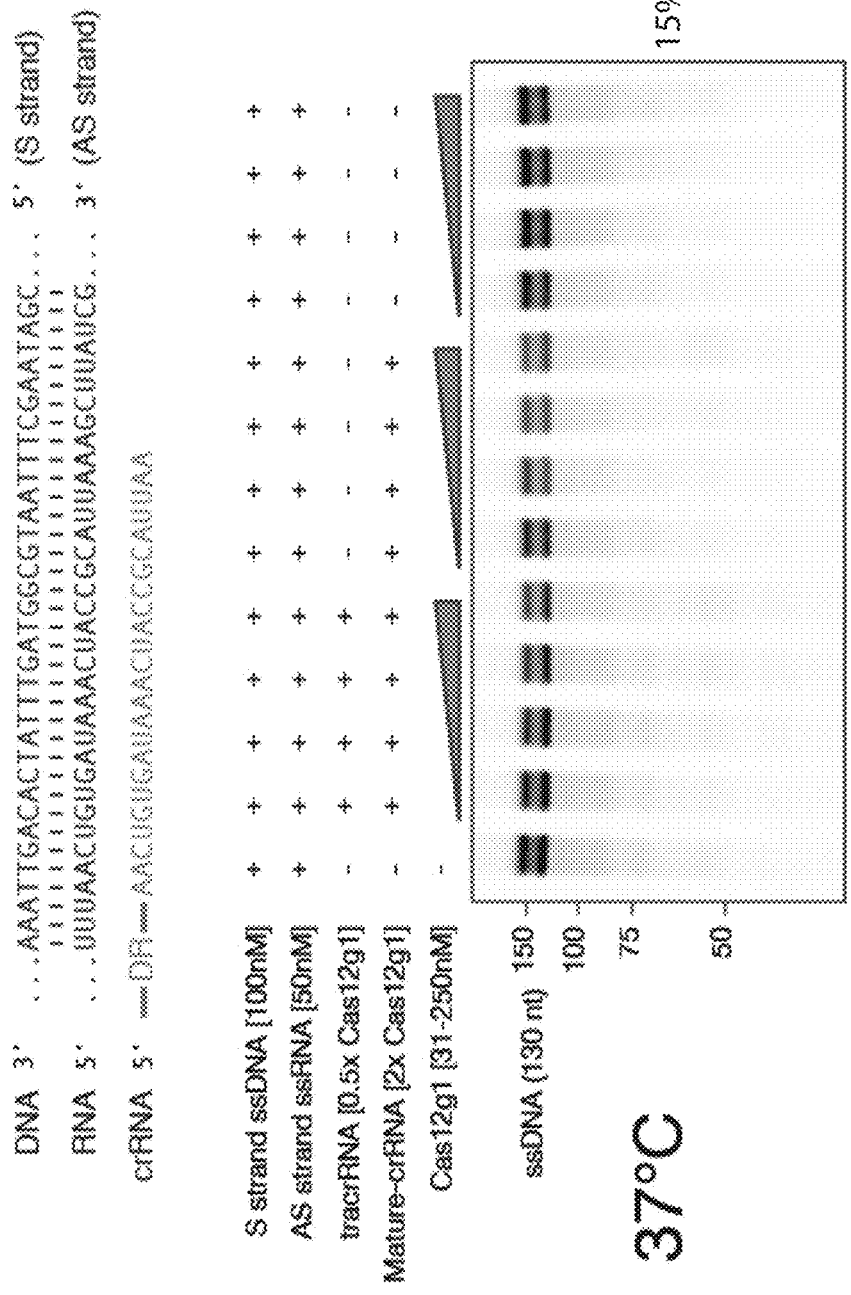

FIG. 25 depicts a denaturing gel showing the absence of cleavage of sense (S) ssDNA (SEQ ID NO: 422) in the presence of antisense (AS) ssRNA transcripts (SEQ ID NO: 423) by Cas12g1 apo (Cas12g only), binary (Cas12g+m-crRNA (SEQ ID NO: 412)), and ternary (Cas12g+m-crRNA+tracrRNA) complexes at 37° C. Note that only the sense ssDNA sequence has complementarity to the crRNA spacer. In the reactions, ssDNA and ssRNA substrates were hybridized prior to adding the Cas12g1 ternary complex, yielding a DNA-RNA hybrid for the sense-antisense pairings of ssDNA and ssRNA. Cas12g1 ternary complex was formed by pre-incubating Cas12g1 and mature crRNA and tracrRNA for 10 minutes at 37° C. prior to adding the substrates and incubating for 1 hour at the specified temperature. Samples were RNase treated and analyzed on a 15% TBE-urea denaturing gel using SYBR Gold nucleic acid staining.

Figure 26:
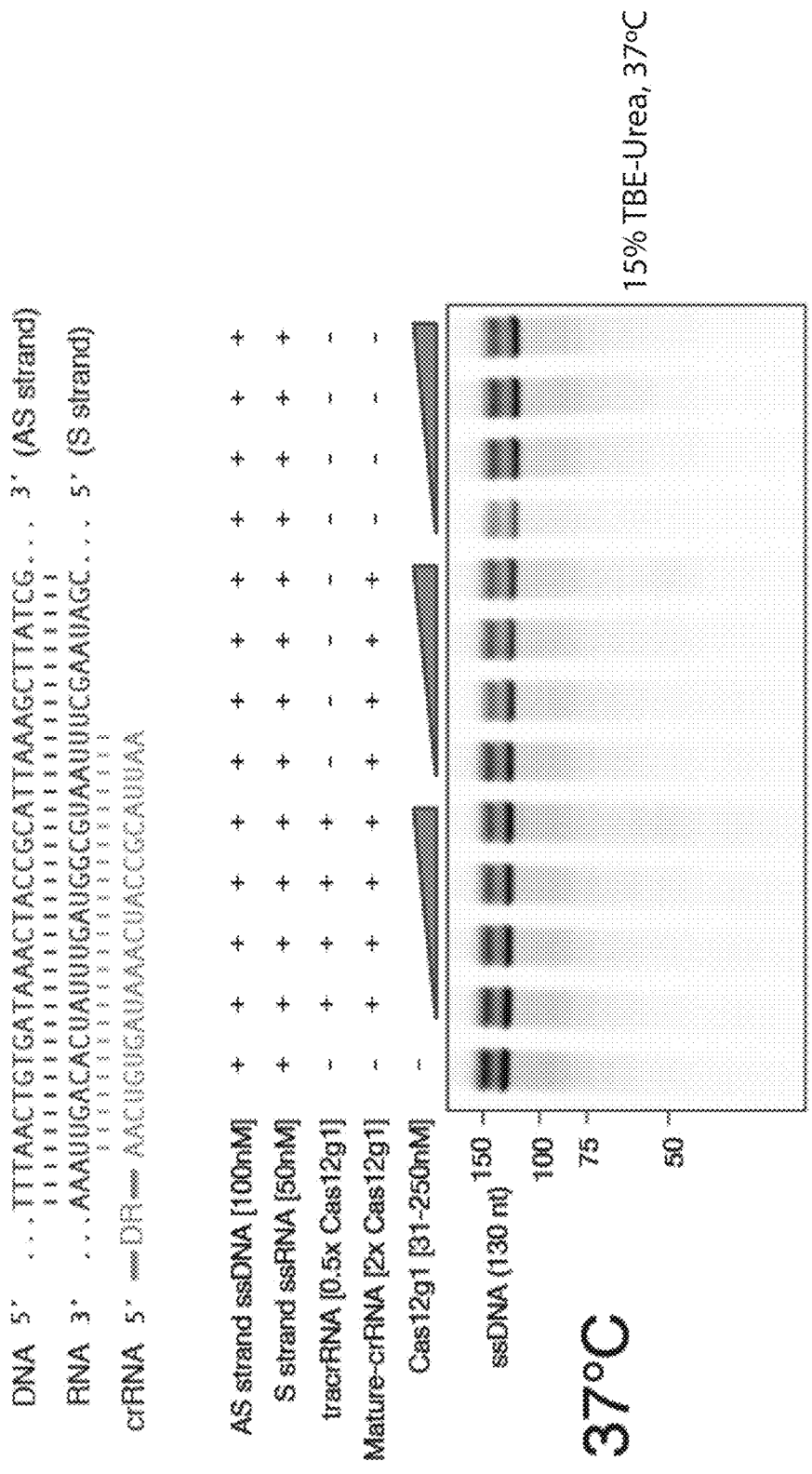

FIG. 26 depicts a denaturing gel showing the absence of cleavage of antisense (AS) ssDNA (SEQ ID NO: 424) in the presence of sense (S) ssRNA transcripts (SEQ ID NO: 421) by Cas12g1 apo (Cas12g only), binary (Cas12g+m-crRNA (SEQ ID NO: 412)), and ternary (Cas12g+m-crRNA+tracrRNA) complexes at 37° C. The sense ssRNA substrate sequence has complementarity to the crRNA spacer. In the reactions, ssDNA and ssRNA substrates were hybridized prior to adding the Cas12g1 ternary complex, yielding a DNA-RNA hybrid for the sense-antisense pairings of ssDNA and ssRNA. Cas12g1 ternary complex was formed by pre-incubating Cas12g1 and mature crRNA and tracrRNA for 10 minutes at 37° C. prior to adding the substrates and incubating for 1 hour at the specified temperature. Samples were RNase treated and analyzed on a 15% TBE-urea denaturing gel using SYBR Gold nucleic acid staining.

Figure 27:
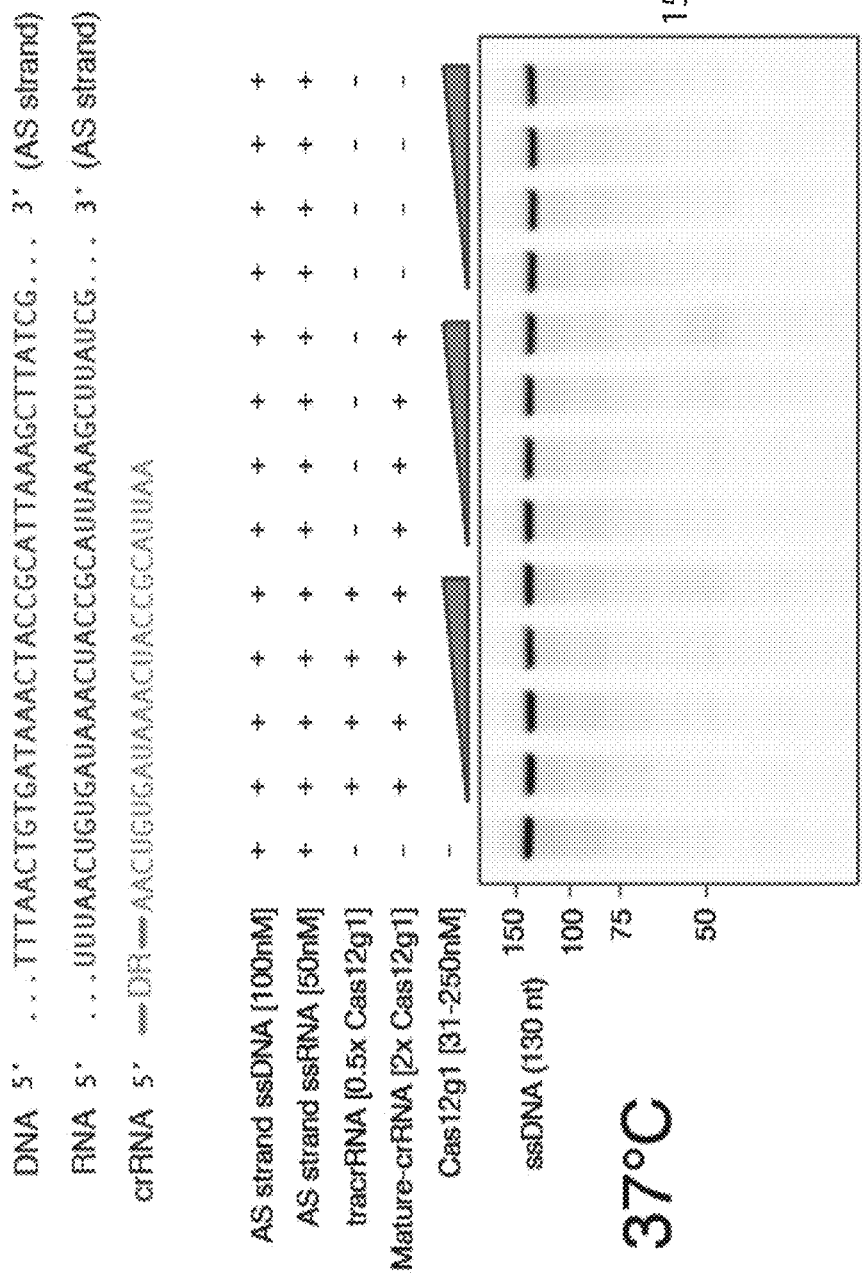

FIG. 27 depicts a denaturing gel showing the absence of cleavage of antisense (AS) ssDNA (SEQ ID NO: 424) in the presence of antisense (AS) ssRNA transcripts (SEQ ID NO: 423) by Cas12g1 apo (Cas12g only), binary (Cas12g+m-crRNA (SEQ ID NO: 412)), and ternary (Cas12g+m-crRNA+tracrRNA) complexes at 37° C. Neither ssDNA nor ssRNA substrates have sequence complementarity to the crRNA spacer. In the reactions, ssDNA and ssRNA substrates were hybridized prior to adding the Cas12g1 ternary complex. Cas12g1 ternary complex was formed by pre-incubating Cas12g1 and mature crRNA and tracrRNA for 10 minutes at 37° C. prior to adding the substrates and incubating for 1 hour at the specified temperature. Samples were RNase treated and analyzed on a 15% TBE-urea denaturing gel using SYBR Gold nucleic acid staining.

Figure 28A:
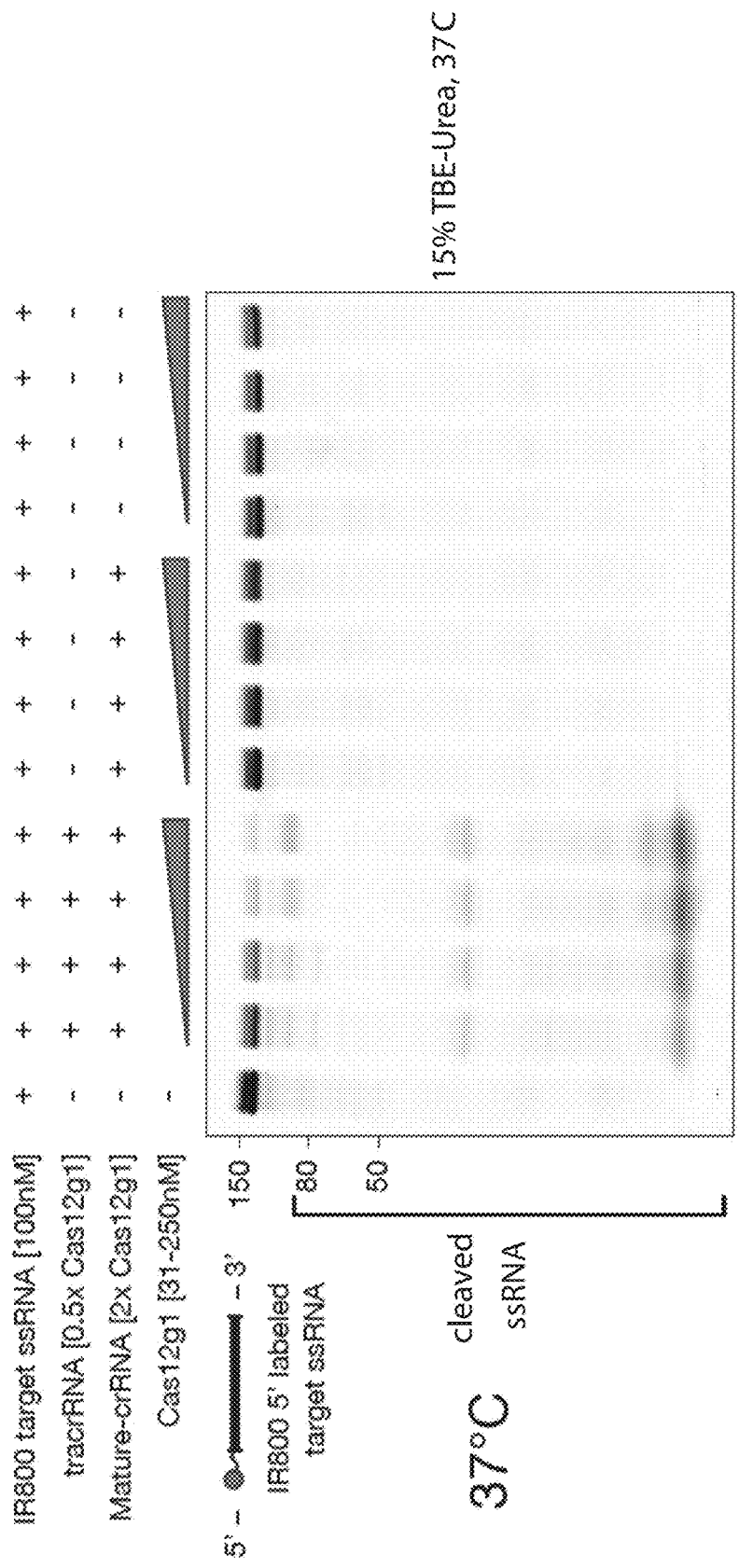
Figure 28B:
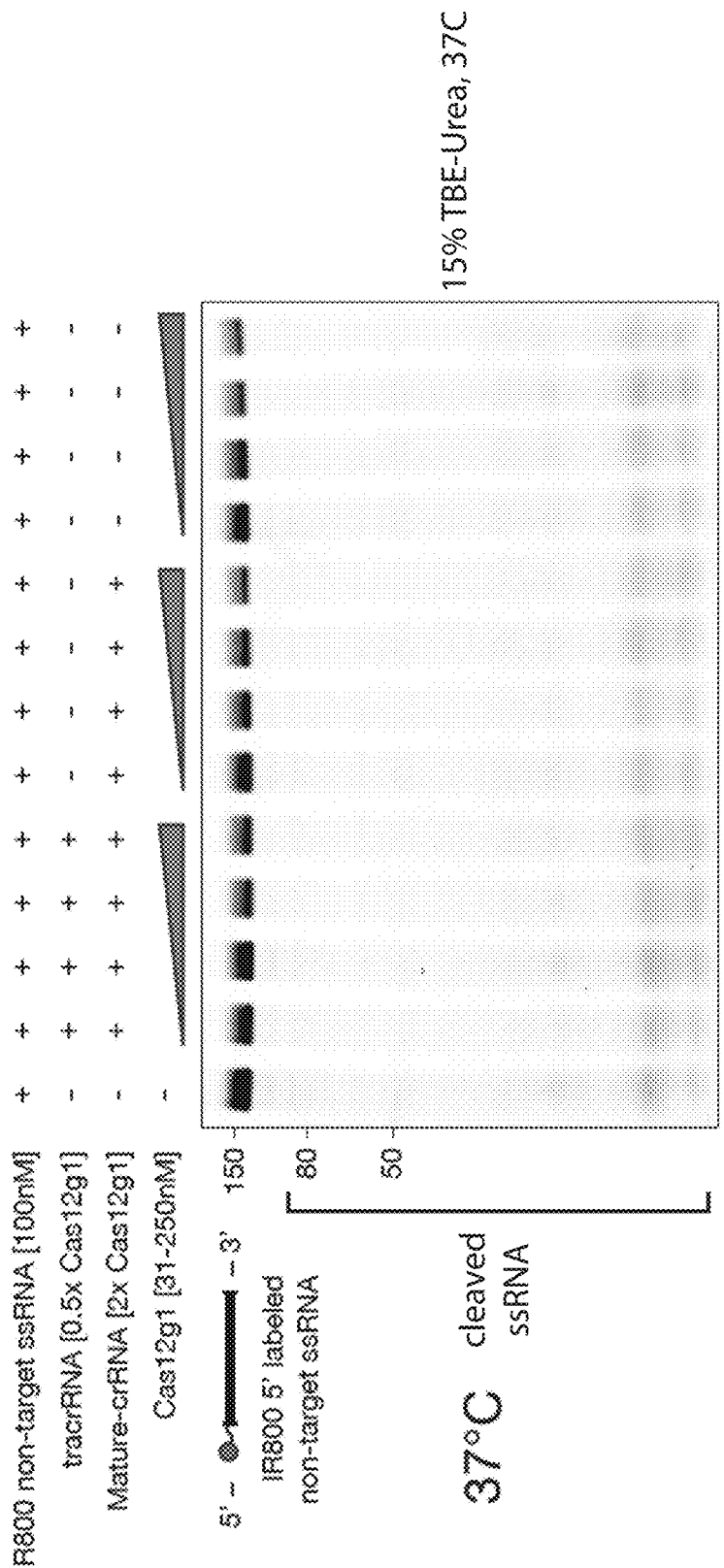

FIGS. 28A-B depict denaturing gels displaying target and non-target ssRNA cleavage activity of the Cas12g1 apo (Cas12g only), binary (Cas12g+m-crRNA), and ternary (Cas12g+m-crRNA+tracrRNA) complexes at 37° C. FIG. 28A depicts manipulation of IR 800-labeled target ssRNA substrates, while FIG. 28B depicts the lack of cleavage of IR 800-labeled non-target ssRNA substrates.

Figure 29A:
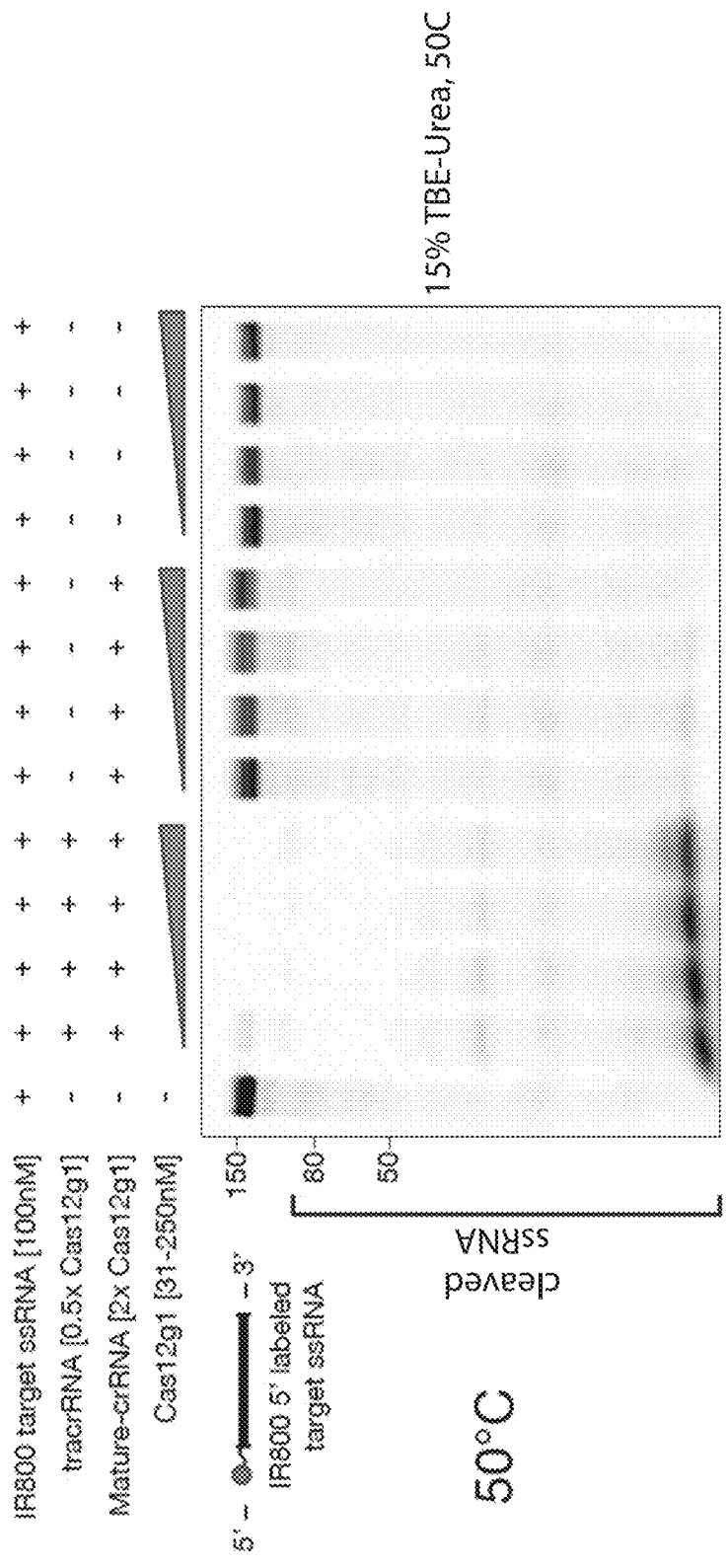
Figure 29B:
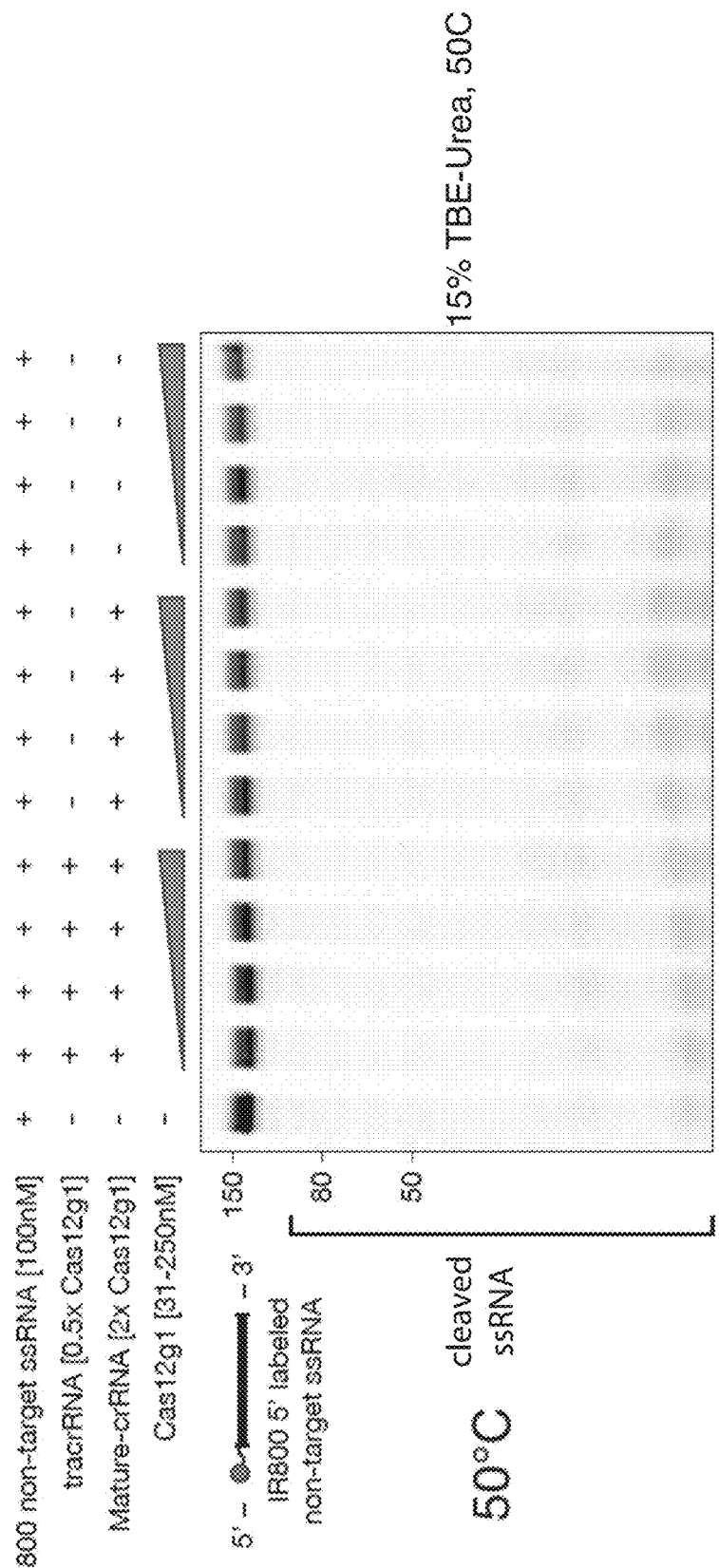

FIGS. 29A-B depict denaturing gels displaying target and non-target ssRNA cleavage activity of the Cas12g1 apo (Cas12g only), binary (Cas12g+m-crRNA), and ternary (Cas12g+m-crRNA+tracrRNA) complexes at 50° C. FIG. 29A depicts cleavage of IR 800-labeled target ssRNA substrates, while FIG. 29B depicts the lack of cleavage of non-target ssRNA substrates.

Figure 30A:
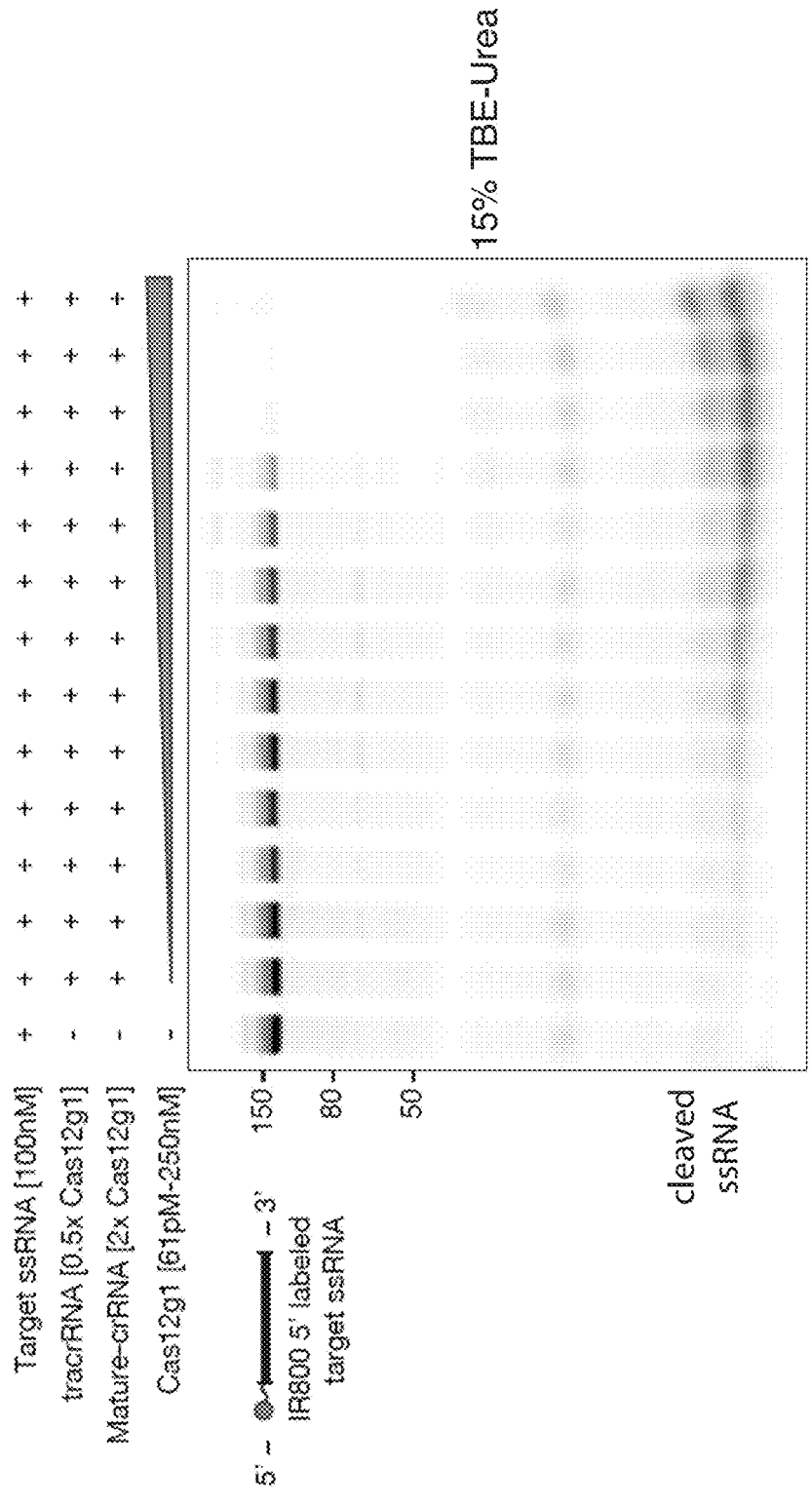

FIG. 30A depicts a denaturing gel showing that Cas12g1 surveillance complex completely cleaves target ssRNA down to nucleotides at complex concentrations above 32 nM, and shows detectable RNase activity on target ssRNA at complex concentrations as low as 125 pM when assayed at 50° C.

Figure 30B:
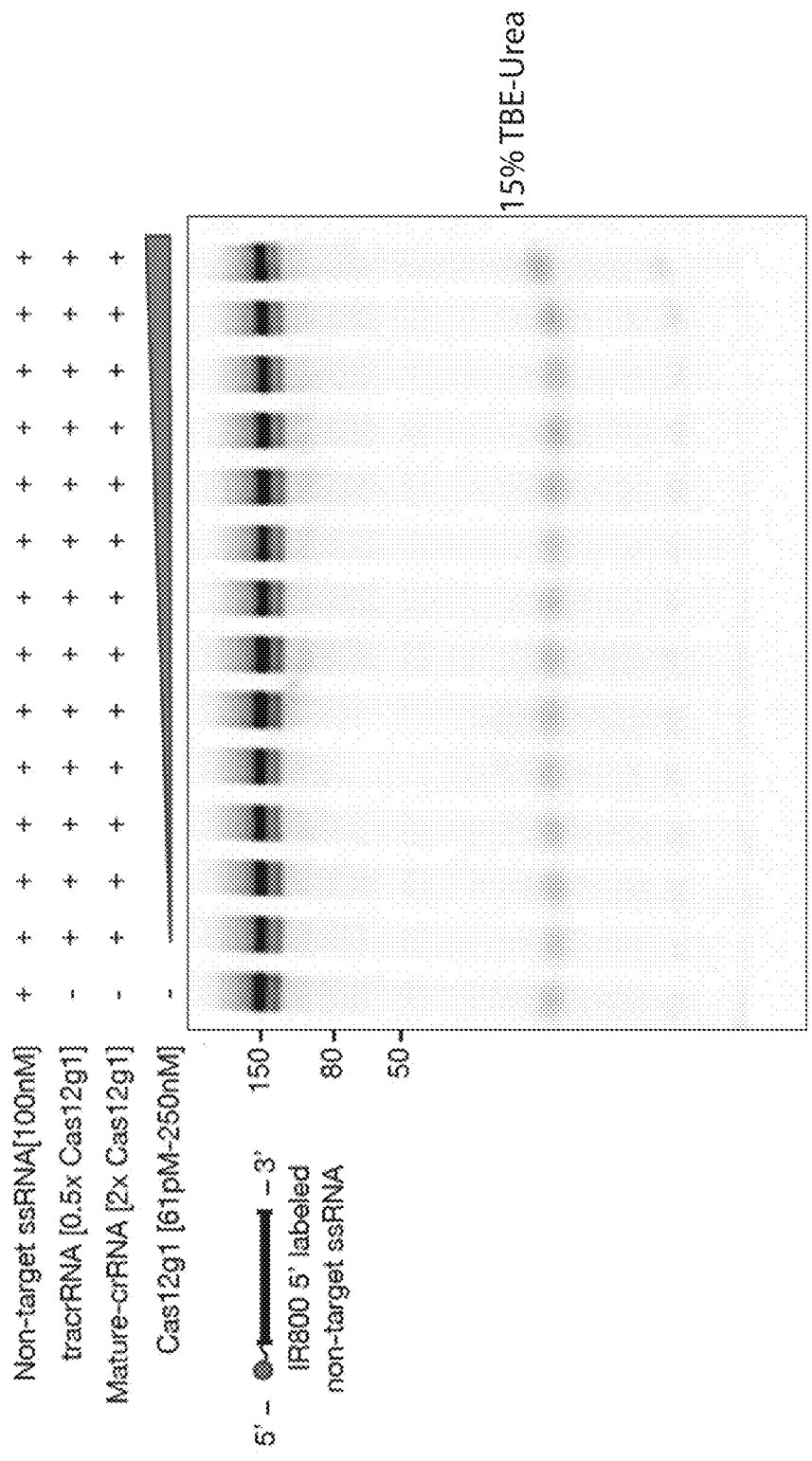

FIG. 30B depicts a denaturing gel showing that Cas12g1 surveillance complex displays no RNase activity with a non-target ssRNA at complex concentrations as high as 250 nM. All ssRNA substrates were labeled at the 5' end with IR800 dye. Cas12g1 surveillance complex was formed by pre-incubating Cas12g1 and mature crRNA and tracrRNA for 10 minutes at 37° C. prior to adding the substrates and incubating for 1 hour at 50° C.

Figure 31A:
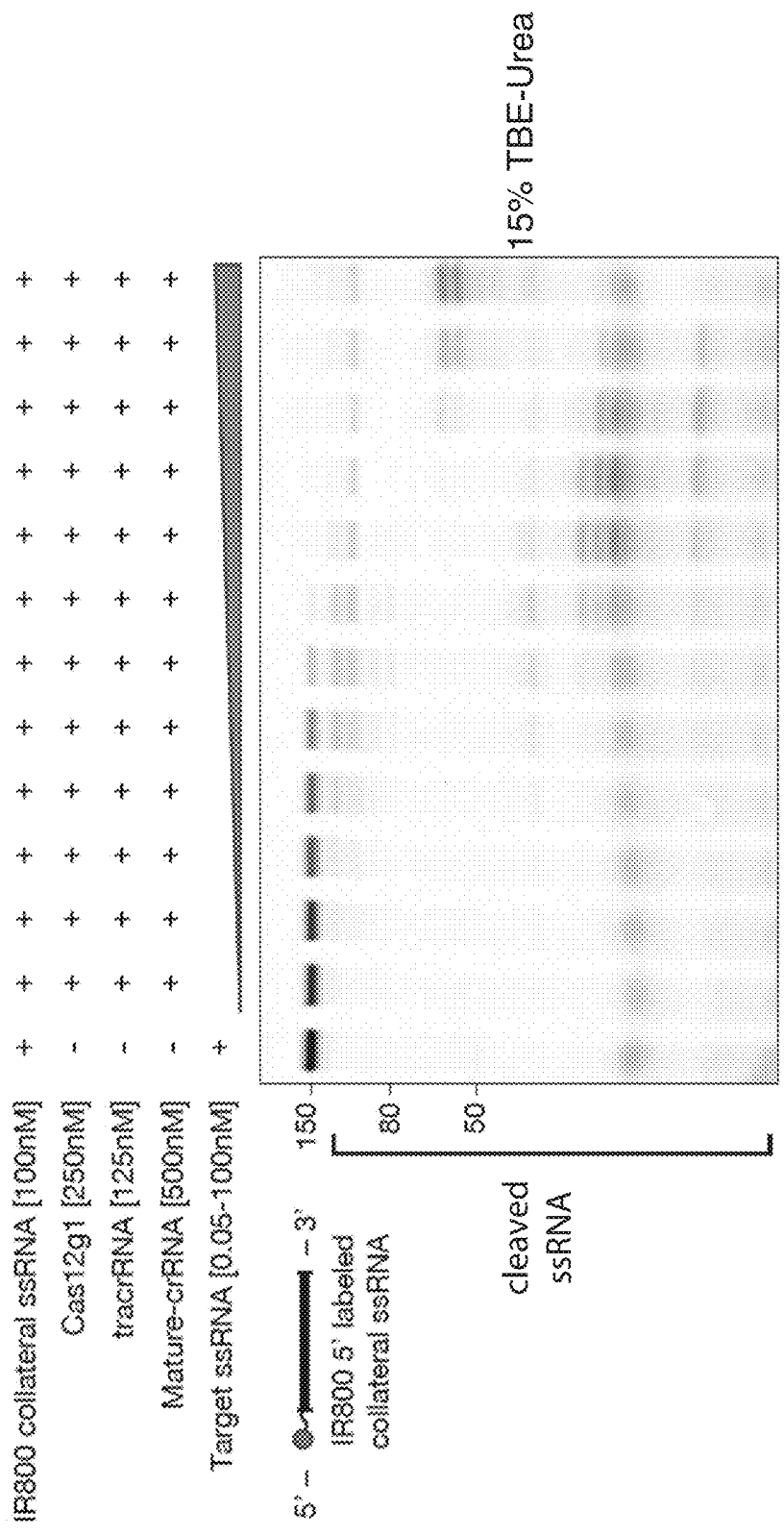

FIG. 31A depicts a denaturing gel showing robust cleavage of collateral ssRNA by Cas12g1 surveillance complex in the presence of increasing concentrations of unlabeled target ssRNA.

Figure 31B:
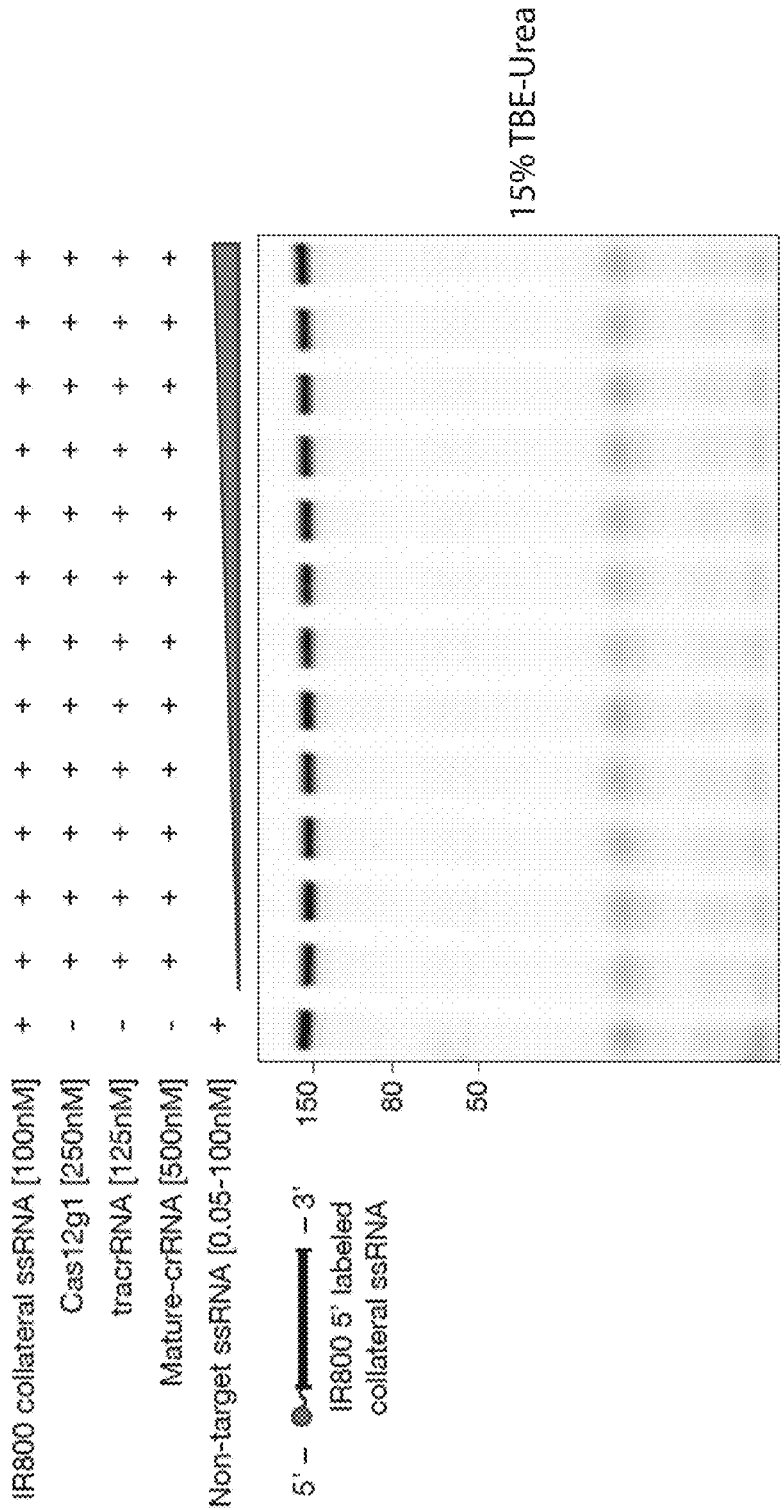

FIG. 31B depicts a denaturing gel showing that Cas12g1 surveillance complex does not cleave collateral ssRNA in the presence of non-target ssRNA. All collateral ssRNA substrates were labeled at the 5' end with IR800 dye. Cas12g1 surveillance complex was formed by pre-incubating Cas12g1 with mature crRNA and tracrRNA for 10 minutes at 37° C. prior to adding the substrates and incubating for 1 hour at 50° C.

Figure 32:
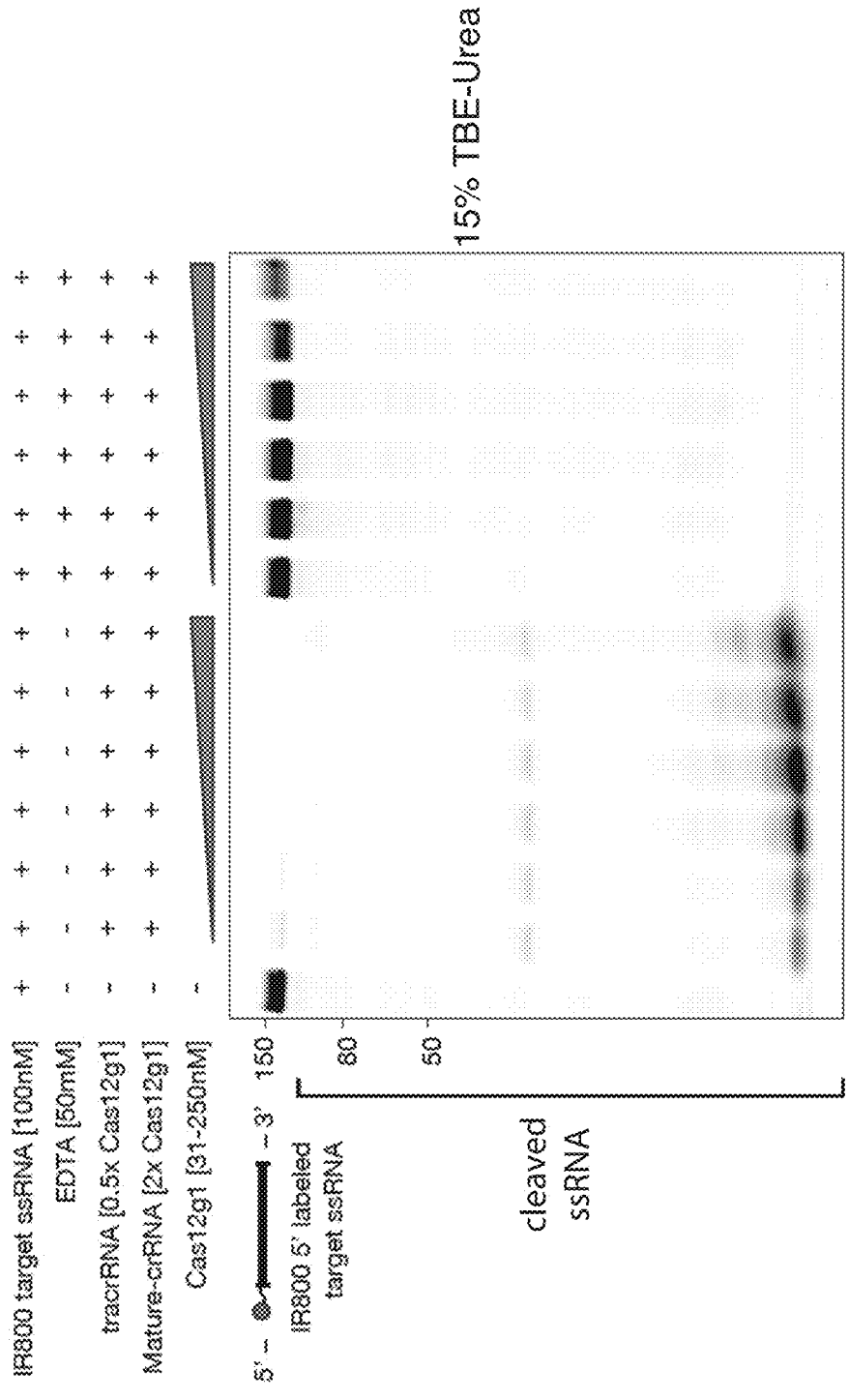

FIG. 32 depicts a denaturing gel showing nuclease activity of Cas12g1 surveillance complex on target ssRNA substrates inhibited by EDTA at 50° C.

Figure 33:
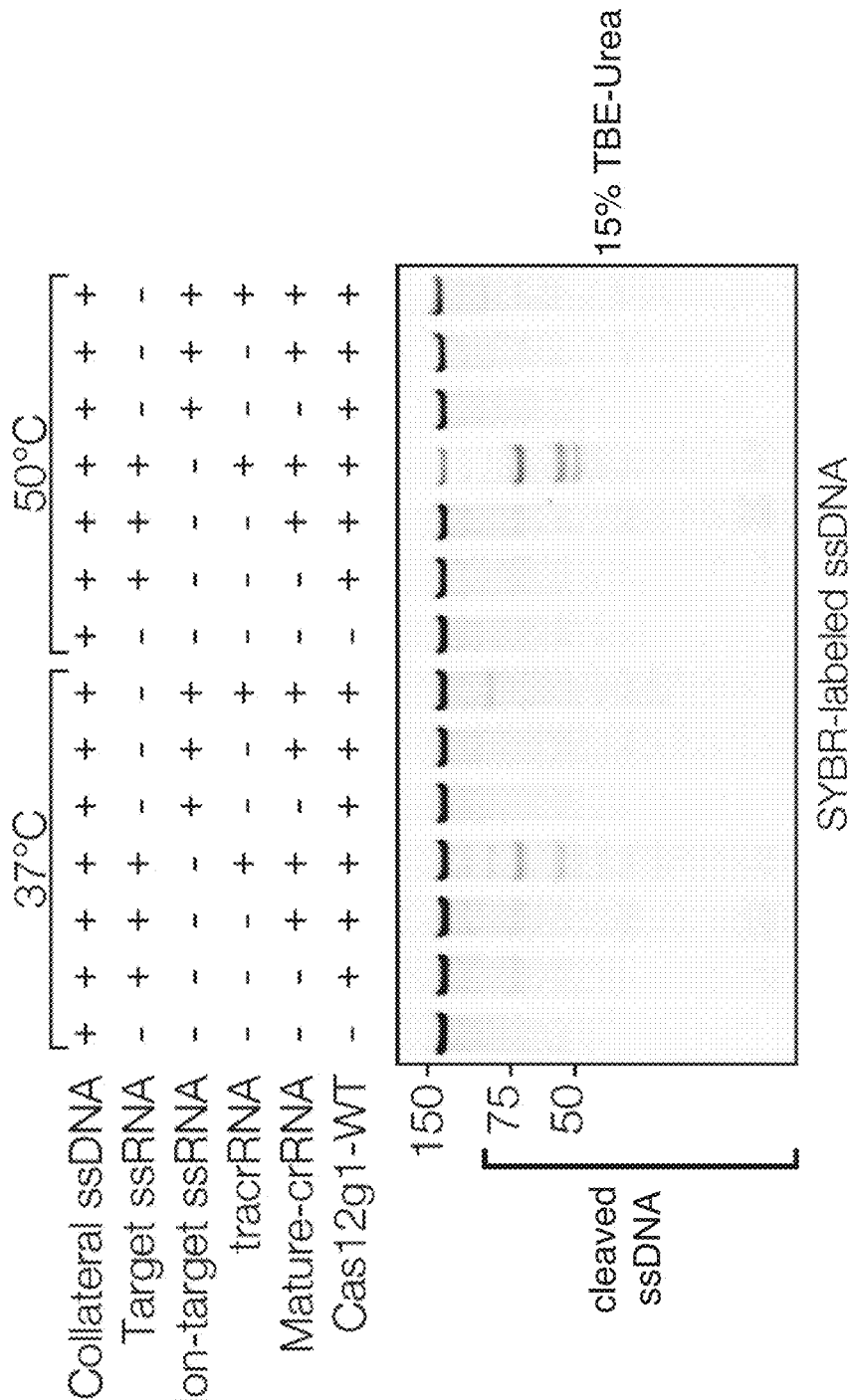

FIG. 33 depicts a denaturing gel showing target ssRNA activated collateral ssDNA cleavage by Cas12g1 surveillance complex at 37° C. and 50° C. Samples were analyzed by 15% TBE-urea denaturing gel electrophoresis.

Figure 34:
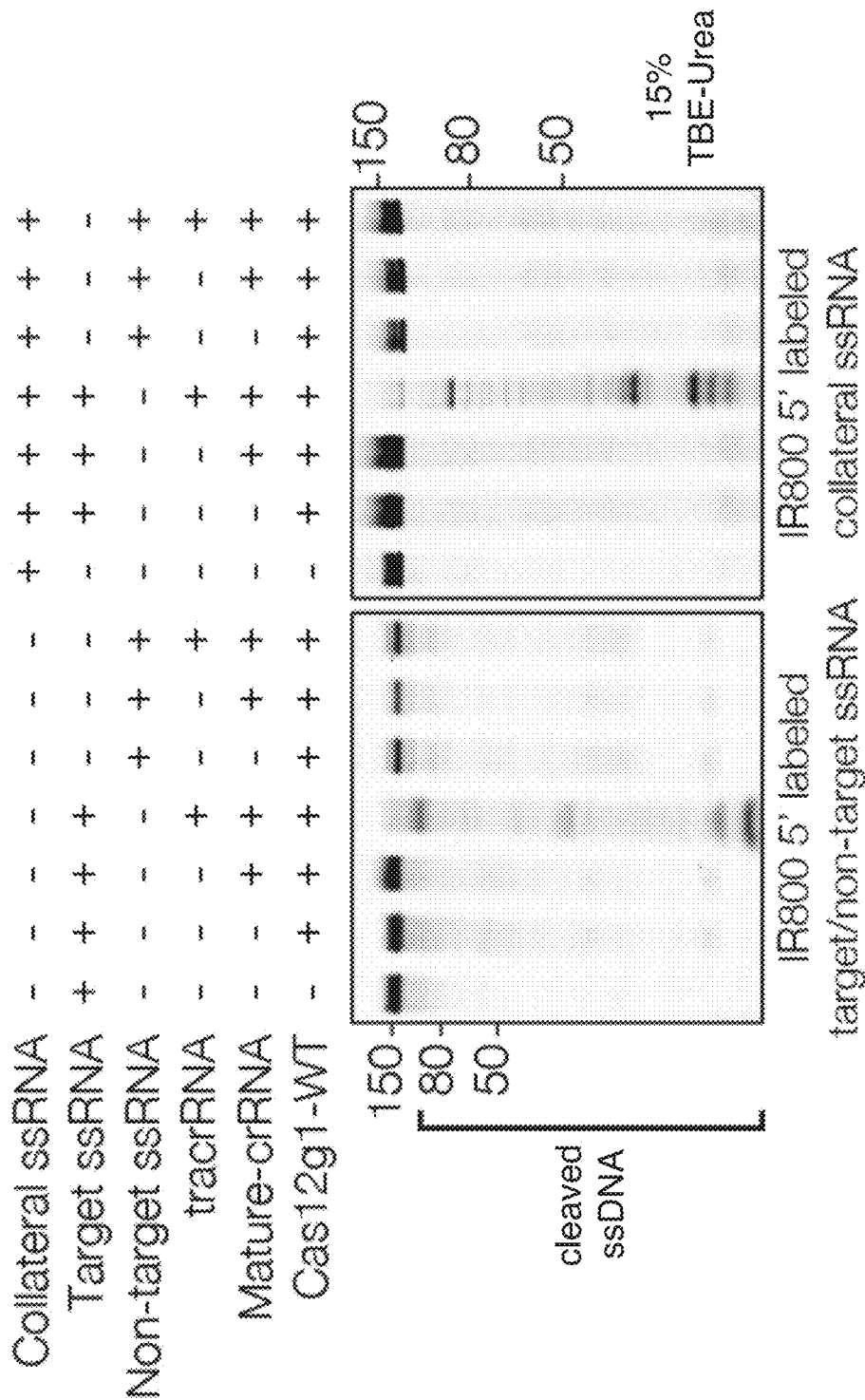

FIG. 34 depicts a denaturing gel showing target ssRNA activated target and collateral ssRNA cleavage by Cas12g1 surveillance complex at 37° C. Samples were analyzed by 15% TBE-urea denaturing gel electrophoresis.

Figure 35:
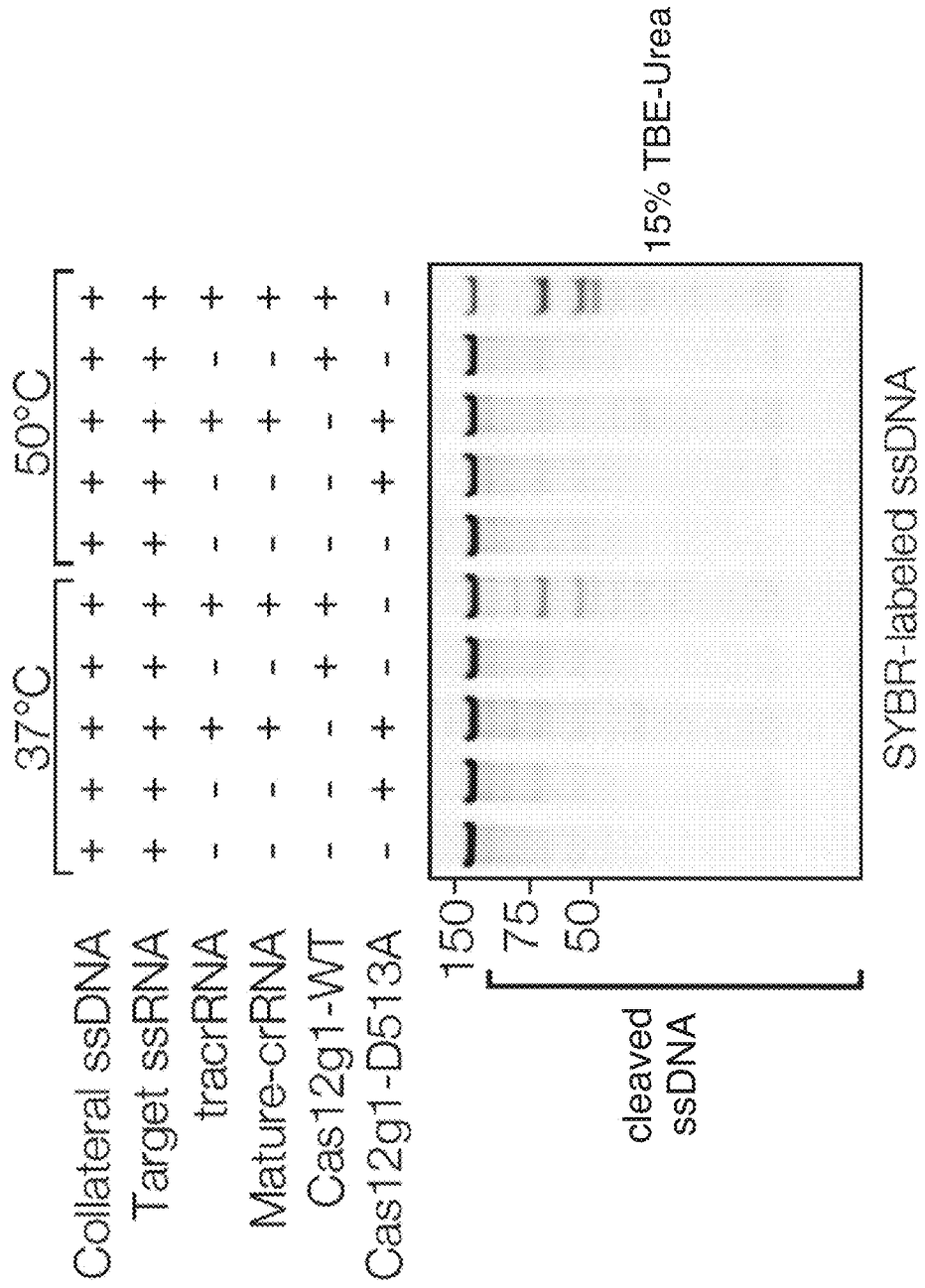

FIG. 35 depicts a denaturing gel showing the absence of target ssRNA activated collateral ssDNA cleavage by dCas12g1 D513A surveillance complex at 37° C. and 50° C. Samples were analyzed by 15% TBE-urea denaturing gel electrophoresis.

Figure 36:
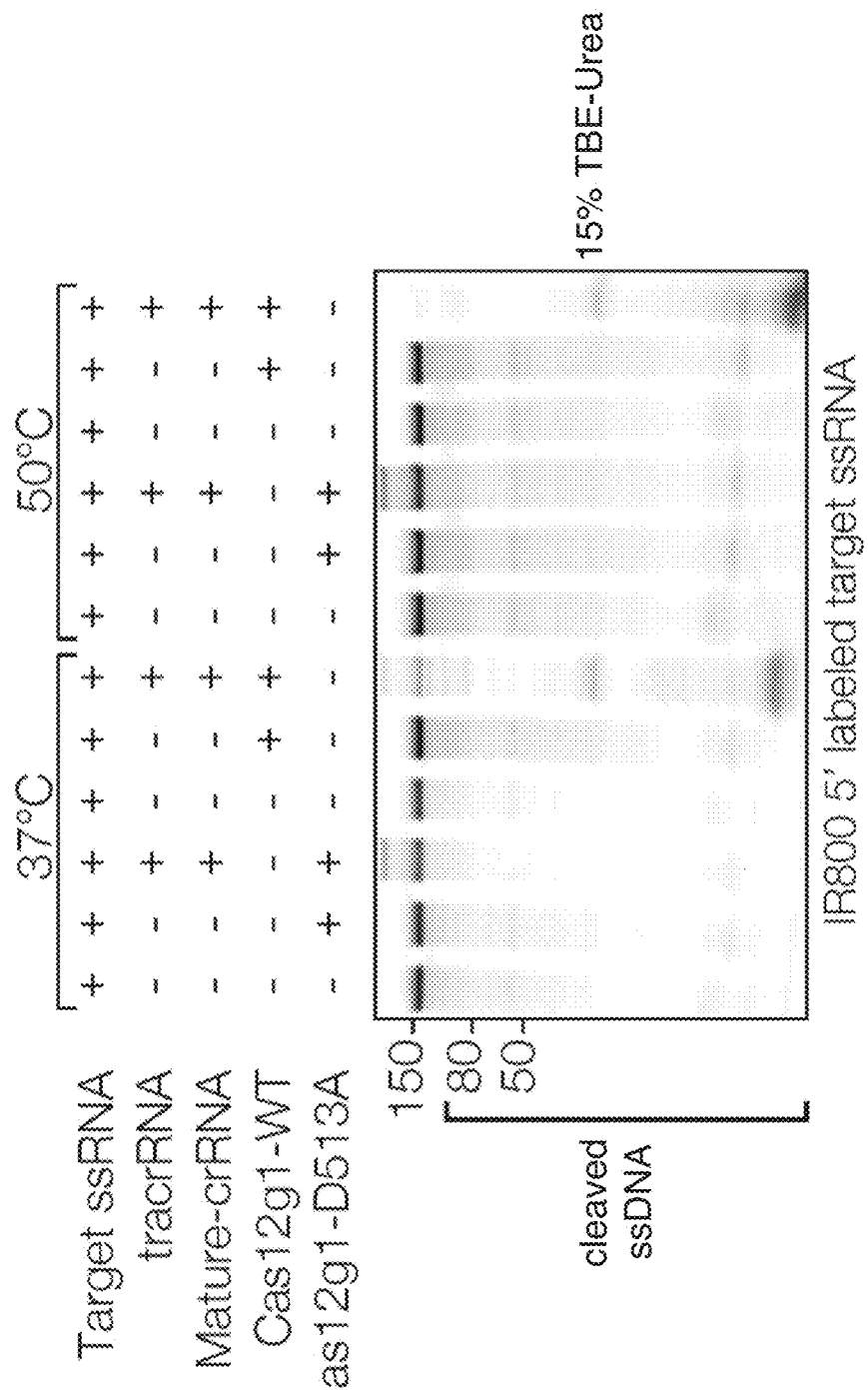

FIG. 36 depicts a denaturing gel showing the absence of target ssRNA activated target and collateral ssRNA cleavage by dCas12g1 D513A surveillance complex at 37° C. Samples were analyzed by 15% TBE-urea denaturing gel electrophoresis.

Figure 37A:
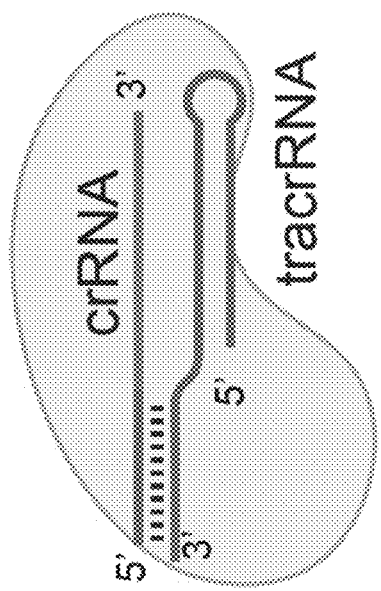
Figure 37B:
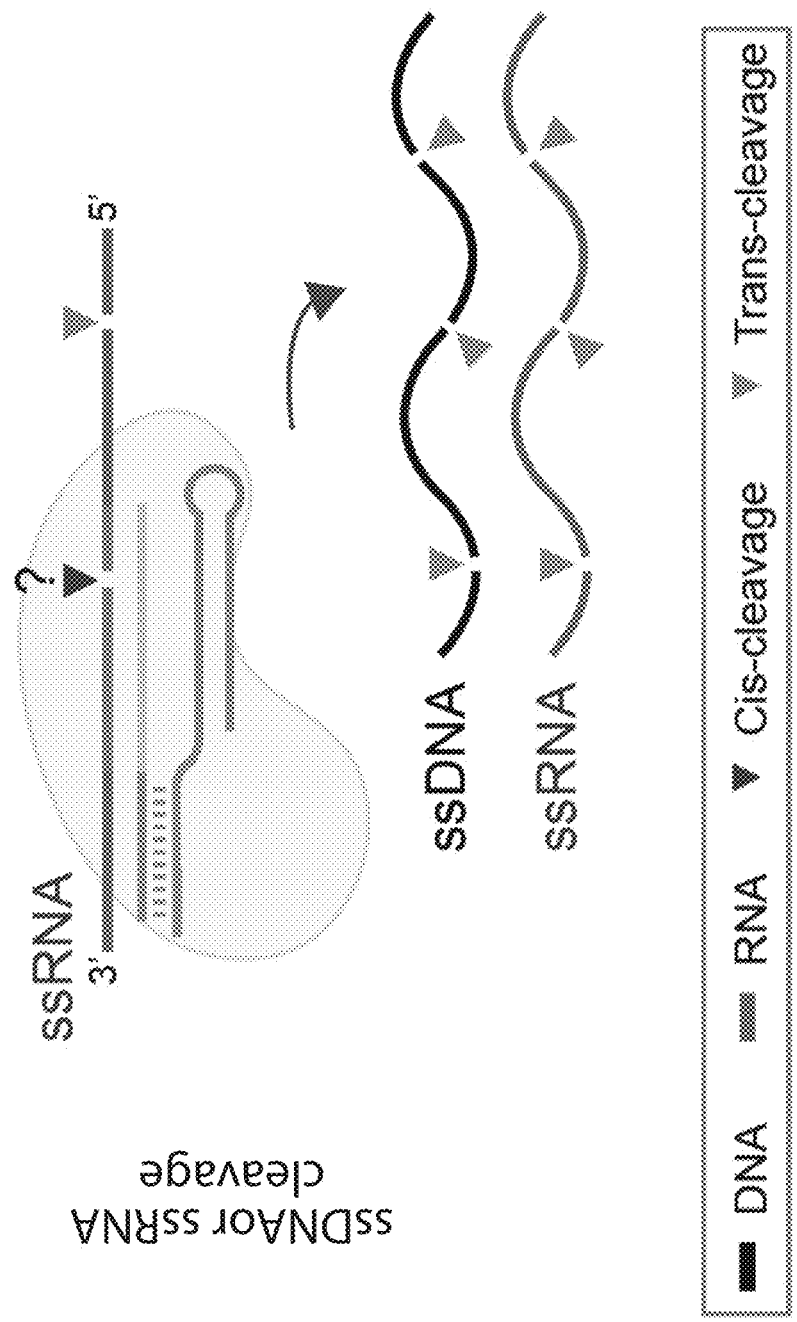
Figure 37C:
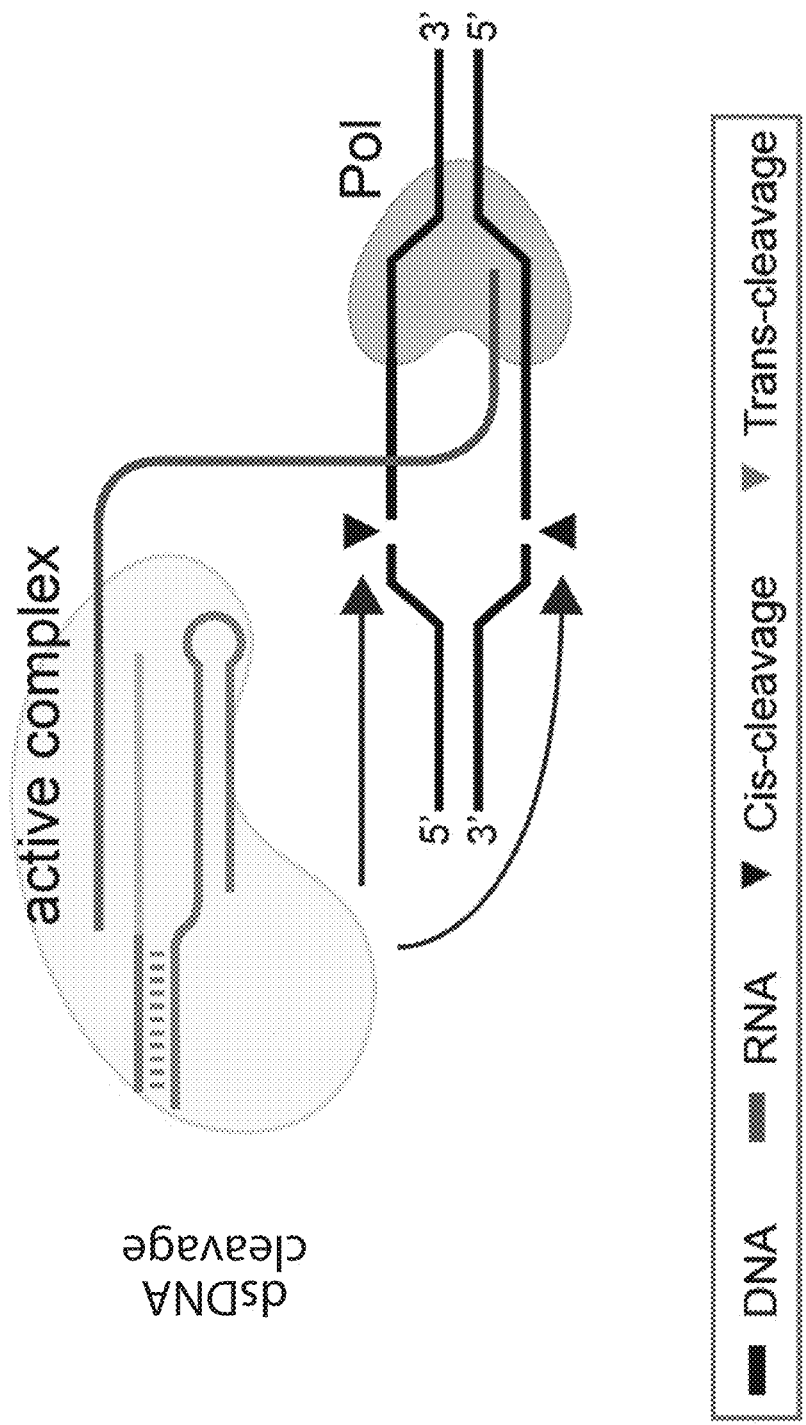

FIGS. 37A-C are a series of schematics showing system components and interference mechanisms of Cas12g.

DETAILED DESCRIPTION

The broad natural diversity of CRISPR-Cas defense systems contains a wide range of activity mechanisms and functional elements that can be harnessed for programmable biotechnologies. In a natural system, these mechanisms and parameters enable efficient defense against foreign DNA and viruses while providing self vs. non-self-discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein have been used to discover additional mechanisms and parameters within single subunit Class 2 effector systems that can be more effectively harnessed for programmable biotechnologies.

In one aspect, the disclosure relates to the use of computational methods and algorithms to search for and identify novel protein families that exhibit a strong co-occurrence pattern with certain other features within naturally occurring genome sequences. In certain embodiments, these computational methods are directed to identifying protein families that co-occur in close proximity to CRISPR arrays. However, the methods disclosed herein are useful in identifying proteins that naturally occur within close proximity to other features, both non-coding and protein-coding (e.g., fragments of phage sequences in non-coding areas of bacterial loci; or CRISPR Cas1 proteins). It should be understood that the methods and calculations described herein may be performed on one or more computing devices.

In some embodiments, a set of genomic sequences may be obtained from genomic or metagenomic databases. The databases comprise short reads, or contig level data, or assembled scaffolds, or complete genomic sequences of organisms. Likewise, the database may comprise genomic sequence data from prokaryotic organisms, or eukaryotic organisms, or may include data from metagenomic environmental samples. Examples of database repositories include National Center for Biotechnology Information (NCBI) RefSeq. NCBI GenBank, NCBI Whole Genome Shotgun (WGS), and the Joint Genome JGI Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g. 2, 3, or 4 times), where the spacing between consecutive occurrences of a repeated motif does not exceed a specified length (e.g. 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CRISPR arrays, a BLAST search of each member of the protein family may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One example of a metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR associated cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening

To efficiently validate the activity of the engineered novel CRISPR-Cas systems and simultaneously evaluate in an unbiased manner different activity mechanisms and functional parameters, a new pooled-screening approach is used in *E. coli*. First, from the computational identification of the conserved protein and noncoding elements of the novel CRISPR-Cas system, DNA synthesis and molecular cloning is used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers are replaced with a library of unprocessed crRNAs containing non-natural spacers targeting a second plasmid, pACYC184. This crRNA library is cloned into the vector backbone containing the protein effectors and noncoding elements (e.g. pET-28a+), and then subsequently transformed the library into *E. coli* along with the pACYC184 plasmid target. Consequently, each resulting *E. coli* cell contains no more than one targeting spacer. In an alternate embodiment, the library of unprocessed crRNAs containing non-natural spacers additionally target *E. coli* essential genes drawn from resources such as those described in Baba et al. (2006) *Mol. Syst. Biol.* 2: 2006.0008; and Gerdes et al. (2003), *J. Bacteriol.* 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets to add another dimension to the assay.

Third, the *E. coli* are grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Examining the population of surviving cells at a later time point compared to an earlier time point typically provides a depleted signal compared to the inactive crRNAs. In some embodiments, double antibiotic selection is used. For example, withdrawal of either chloramphenicol or tetracycline to remove selective pressure can provide novel information about the targeting substrate, sequence specificity, and potency.

In some embodiments, only kanamycin is used to ensure successful transformation of the pET-28a+ vector containing the engineered CRISPR-Cas effector system. This embodiment is suitable for libraries containing spacers targeting *E. coli* essential genes, as no additional selection beyond kanamycin is needed to observe growth alterations. In this embodiment, chloramphenicol and tetracycline dependence is removed, and their targets (if any) in the library provides an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

Certain important advantages of the in vivo pooled-screen described herein include:
(1) Versatility—plasmid design allows multiple effectors and/or noncoding elements to be expressed; library cloning strategy enables both transcriptional directions of the computationally predicted crRNA to be expressed;
(2) Comprehensive tests of activity mechanisms and functional parameters can be used to evaluate diverse interference mechanisms, including DNA or RNA cleavage; to examine co-occurrence of features such as transcription, plasmid DNA replication; and to examine flanking sequences for a crRNA library to reliably determine PAMs, wherein any combination of up to 4 bases (representing a PAM of 4N complexity) are present at least 3-10 times in the targeting library;
(3) Sensitivity—pACYC184 is a low copy plasmid, enabling high sensitivity for CRISPR-Cas activity, because even modest interference rates can eliminate the antibiotic resistance encoded by the plasmid; and
(4) Efficiency—the pooled-screen includes optimized molecular biology steps that enable greater speed and throughput for RNA-sequencing, and the protein expression samples can be directly harvested from the surviving cells in the screen.

As discussed in more detail in the Examples below, the novel CRISPR-Cas families described herein were evaluated using this in vivo pooled-screen to evaluate their operational elements, mechanisms, and parameters, as well as their ability to be active and reprogrammed in an engineered system outside of their natural cellular environment.

Class 2 CRISPR-Cas Effectors Having a RuvC Domain

In one aspect, the disclosure provides Class 2 CRISPR-Cas systems referred to herein as CLUST.019143 (Type V-G). These Class 2 CRISPR-Cas systems contain an isolated CRISPR-Cas effector protein having a RuvC domain and an isolated RNA guide, comprising a tracrRNA and a crRNA, wherein the crRNA includes a spacer sequence that is complementary to a target nucleic acid sequence such as an RNA sequence.

In some embodiments, an CRISPR-Cas effector protein having a RuvC domain may include one or more of the motifs from the set of the RuvC I motif (SEQ ID NO: 210), the RuvC II motif (SEQ ID NO: 211), and the RuvC III motif (SEQ ID NO: 212).

In some implementations, a Type V-G CRISPR-Cas system includes a CRISPR-Cas effector having a RuvC domain, a Type V-G crRNA, and a Type V-G tracrRNA. Suitably, a Type V-G crRNA may include SEQ ID NO: 200 proximal to its 3' end and adjacent to the spacer sequence. Suitably, a Type V-G crRNA may include SEQ ID NO: 201 proximal to its 3' end and adjacent to the spacer sequence. Suitably, a Type V-G crRNA may form a stem-loop structure with a Type V-G tracrRNA.

In some embodiments, Type V-G systems can be used to bind to sequence-specific target RNA. Suitably, Type V-G systems can be used to degrade sequence-specific target RNA upon recognition and binding. Suitably, Type V-G systems can be used to degrade "collateral" RNA upon binding to sequence-specific target RNA. Suitably, Type V-G systems can be used at higher temperatures (e.g. 50° C.) to degrade "collateral" RNA upon binding to sequence-specific target RNA with greater efficiency compared to lower temperatures (e.g. 37° C.). Suitably, Type V-G systems can be used to degrade "collateral" single-stranded DNA upon binding to sequence-specific target RNA. Suitably, Type V-G systems can be used at higher temperatures (e.g. 50° C.) to degrade "collateral" ssDNA upon binding to sequence-specific target RNA with greater efficiency compared to lower temperatures (e.g. 37° C.).

Suitably, a Type V-G CRISPR-Cas effector has an amino acid sequence of less than approximately 860 amino acids. Suitably, a Type V-G CRISPR-Cas effector has an amino acid sequence between 650 and 860 amino acids or between 700 and 850 amino acids.

In some embodiments, the Type V-G CRISPR-associated effector protein and the RNA guide form a surveillance complex that can include other components. The surveillance complex is activated upon binding to a nucleic acid substrate that is complementary to a spacer sequence in the RNA guide (i.e., a sequence-specific substrate, also referred to herein as a target nucleic acid). In some embodiments, the target nucleic acid is a double-stranded DNA. In some embodiments, the target nucleic acid is a single-stranded DNA. In some embodiments, the target nucleic acid is a single-stranded RNA. In some embodiments, the target nucleic acid is a double-stranded RNA. In some embodiments, the sequence-specificity requires a complete match of the spacer sequence in the RNA guide to the target substrate. In other embodiments, the sequence specificity requires a partial (contiguous or non-contiguous) match of the spacer sequence in the RNA guide to the target substrate.

In some embodiments, the surveillance complex becomes activated upon binding to the target substrate. In some embodiments, the target substrate is a DNA (e.g., a single-stranded or a double-stranded DNA). In some embodiments, the target substrate is a RNA (e.g., a single-stranded or a double-stranded RNA). In some embodiments, the activated complex exhibits "multiple turnover" activity, whereby upon acting on (e.g., cleaving) the target substrate, the activated complex remains in an activated state. In some embodiments, the activated complex exhibits "single turnover" activity, whereby upon acting on the target substrate, the surveillance complex reverts to an inactive state. In some embodiments, the activated complex exhibits non-specific (i.e., "collateral") cleavage activity, whereby the activated complex cleaves nucleic acids with no sequence similarity to the target ("collateral nucleic acids"). In some embodiments, the collateral nucleic acid substrate is a DNA (e.g., a single-stranded or a double-stranded DNA). In some embodiments, the collateral nucleic acid substrate is an RNA (e.g., a single-stranded or a double-stranded RNA).

CRISPR Class 2 RNA-Guided RNases

In another aspect, this disclosure describes a novel family of CRISPR Class 2 effectors having RNA-targeting capabilities. The underlying one or more RNase domains confer the ability to bind to and cleave any target RNA molecule.

The target RNA may be any form of RNA, including, but not limited to, mRNA, tRNA, ribosomal RNA, non-coding RNA, lincRNA, and nuclear RNA. For example, in some embodiments, the CRISPR-associated protein recognizes and cleaves targets located on the coding strand of open reading frames (ORFs).

In one embodiment, the disclosure provides a family of CRISPR Class 2 effectors, referred to herein generally as CLUST.019143 (Type V-G) CRISPR-Cas effector proteins. This newly-identified family of CRISPR Class 2 effectors can be used in a variety of applications, and the new effector proteins are particularly suitable for therapeutic applications, because they are significantly smaller than other RNA-targeting CRISPR effectors (e.g., CRISPR Cas13a, Cas13b, or Cas13c effectors), which allows for the packaging of the effectors and/or nucleic acids encoding the effectors into delivery systems having size limitations.

Collateral RNase Activity

In some embodiments, a surveillance complex comprised of (but not necessarily limited to) a Cas12g CRISPR-associated protein and an RNA guide is activated upon binding to a target nucleic acid (e.g., a target RNA). Activation induces a conformational change, which results in the activated complex acting as a non-specific RNase, cleaving and/or degrading nearby RNA molecules (e.g., ssRNA or dsRNA molecules)(i.e., "collateral" effects).

Collateral DNase Activity

In some embodiments, a surveillance complex comprised of (but not necessarily limited to) a Cas12g effector and an RNA guide is activated upon binding to a target nucleic acid (e.g., a target RNA). Activation induces a conformational change, which results in the complex acting as a non-specific DNase, cleaving and/or degrading nearby DNA molecules (e.g., ssDNA or dsDNA molecules)(i.e., "collateral" effects).

Collateral-Free Target Recognition

In other embodiments, a surveillance complex comprised of (but not necessarily limited to) a Cas12g effector and an RNA guide does not exhibit collateral nuclease activity subsequent to target recognition. This "collateral-free" embodiment may comprise wild-type or engineered effector proteins.

PAM/PFS-Independent Targeting

In some embodiments, a surveillance complex comprised of (but not necessarily limited to) a Cas12g effector and an RNA guide recognizes and cleaves the target nucleic acid without any additional requirements adjacent to or flanking the protospacer (i.e., protospacer adjacent motif "PAM" or protospacer flanking sequence "PFS" requirements).

CRISPR Enzyme Modifications

Nuclease-Deficient CRISPR Enzymes

Where the CRISPR enzymes described herein have nuclease activity, the CRISPR enzymes can be modified to have diminished nuclease activity, e.g., nuclease inactivation of at least 50%, at least 60%, at least 70%, at least 80%, at least 90%, at least 95%, at least 97%, or 100% as compared with the wild type CRISPR enzymes. The nuclease activity can be diminished by, for example, introducing mutations (such as amino acid insertions, deletions, or substitutions) into the nuclease domains of the CRISPR enzymes. In some embodiments, catalytic residues for the nuclease activities are identified, and these amino acid residues can be substituted by different amino acid residues (e.g., glycine or alanine) to diminish the nuclease activity. An example of such a mutation for Cas12g1 includes D513A.

The inactivated CRISPR enzymes can comprise (e.g., via fusion protein, linker peptides, Gly4Ser (GS) peptide linkers, etc.) or be associated (e.g., via co-expression of multiple proteins) with one or more functional domains. These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR enzymes allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor (e.g., KRAB) is positioned to affect the transcription of the target, and a nuclease (e.g., Fok1) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the inactivated CRISPR enzyme is modified to comprise a first functional domain at the N-terminus and a second functional domain at the C-terminus.

Split Enzymes

The present disclosure also provides a split version of the CRISPR enzymes described herein. The split version of the CRISPR enzymes may be advantageous for delivery. In some embodiments, the CRISPR enzymes are split into two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the RNA guide recruits them into a surveillance complex that recapitulates the activity of full-length CRISPR enzymes and catalyzes site-specific DNA cleavage. The use of a modified RNA guide abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can cleave the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional RNA guide, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme and RNA guide(s) that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR-Cas9 switch," Nucl. Acids Res., 2017 Jul. 27; 45(13): e118).

Inducible CRISPR Enzymes

The CRISPR enzymes can be inducible, e.g., light inducible or chemically inducible. This mechanism allows for activation of the functional domain in the CRISPR enzymes with a known trigger. Light inducibility can be achieved by various methods known in the art, e.g., by designing a fusion complex wherein CRY2 PHR/CIBN pairing is used in split CRISPR Enzymes (see, e.g., Konermann et al. "Optical control of mammalian endogenous transcription and epigenetic states," Nature, 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," Nature Biotech., 33.2 (2015): 139-142).

Furthermore, expression of the CRISPR enzymes can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," Nucl. Acids Res., 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 300); the NLS from nucleoplasmin (e.g., the nucleoplasmin bipartite NLS with the sequence KRPAATKKAGQAKKKK (SEQ ID NO: 301)); the c-myc NLS having the amino acid sequence PAAKRVKLD (SEQ ID NO: 302) or RQRRNELKRSP (SEQ ID NO: 303); the hRNPA1 M9 NLS having the sequence NQSSNFGPMKGGNFG-GRSSGPYGGGGQYFAKPRNQGGY (SEQ ID NO: 304); the sequence RMRIZFKNKGKDTAELRRRRVEVS-VELRKAKKDEQILKRRNV (SEQ ID NO: 305) of the IBB domain from importin-alpha; the sequences VSRKRPRP (SEQ ID NO: 306) and PPKKARED (SEQ ID NO: 307) of the myoma T protein; the sequence PQPKKKPL (SEQ ID NO: 308) of human p53; the sequence SALIKKKKKMAP (SEQ ID NO: 309) of mouse c-abl IV; the sequences DRLRR (SEQ ID NO: 310) and PKQKKRK (SEQ ID NO: 311) of the influenza virus NS1; the sequence RKLKK-KIKKL (SEQ ID NO: 312) of the Hepatitis virus delta antigen; the sequence REKKKFLKRR (SEQ ID NO: 313) of the mouse Mx1 protein; the sequence KRKGDEVDGVDEVAKKKSKK (SEQ ID NO: 314) of the human poly(ADP-ribose) polymerase; and the sequence RKCLQAGMNLEARKTKK (SEQ ID NO: 315) of the human glucocorticoid receptor. In some embodiments, the CRISPR-associated protein includes at least one (e.g., 1, 2, 3, 4, 5, 6, 7, 8, 9, or 10) Nuclear Export Signal (NES) attached the N-terminal or C-terminal of the protein. In a preferred embodiment a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its helicase activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a RNA guide. In some embodiments, the CRISPR enzyme is mutated at one or more amino acid residues to alter its ability to functionally associate with a target nucleic acid.

In some embodiments, the CRISPR enzymes described herein are capable of cleaving a target nucleic acid molecule. In some embodiments, the CRISPR enzyme cleaves both strands of the target nucleic acid molecule. However, in some embodiments, the CRISPR enzyme is mutated at one or more amino acid residues to alter its cleaving activity. For example, in some embodiments, the CRISPR enzyme may comprise one or more mutations that render the enzyme incapable of cleaving a target nucleic acid. In other embodiments, the CRISPR enzyme may comprise one or more mutations such that the enzyme is capable of cleaving a single strand of the target nucleic acid (i.e., nickase activity). In some embodiments, the CRISPR enzyme is capable of cleaving the strand of the target nucleic acid that is complementary to the strand to which the RNA guide hybridizes. In some embodiments, the CRISPR enzyme is capable of cleaving the strand of the target nucleic acid to which the RNA guide hybridizes.

In some embodiments, a CRISPR enzyme described herein can be engineered to include a deletion in one or more amino acid residues to reduce the size of the enzyme while retaining one or more desired functional activities (e.g., nuclease activity and the ability to interact functionally with a RNA guide). The truncated CRISPR enzyme may be advantageously used in combination with delivery systems having load limitations.

Nucleic acids encoding the proteins (e.g., a CRISPR-associated protein) and RNA guides (e.g., a crRNA) described herein are also provided. In some embodiments, the nucleic acid is a synthetic nucleic acid. In some embodiments, the nucleic acid is a DNA molecule. In some embodiments, the nucleic acid is an RNA molecule (e.g., an mRNA molecule). In some embodiments, the mRNA is capped, polyadenylated, substituted with 5-methylcytidine, substituted with pseudouridine, or a combination thereof. In some embodiments, the nucleic acid (e.g., DNA) is operably-linked to a regulatory element (e.g., a promoter) to control the expression of the nucleic acid. In some embodiments, the promoter is a constitutive promoter. In some embodiments, the promoter is an inducible promoter. In some embodiments, the promoter is a cell-specific promoter, such as Syn and CamKIIa for neuronal cell types, or thyroxine binding globulin (TBG) for hepatocyte expression. In some embodiments, the promoter is an organism-specific promoter. Suitable promoters are known in the art and include, for example, a pol I promoter, a pol II promoter, a pol III promoter. In some embodiments, short RNAs such as the RNA guide are effectively expressed using a pol III promoter, which includes a U6 promoter, a H1 promoter, a 7SK promoter. In some embodiments, the promoter is prokaryotic, such as a T7 promoter. In some embodiments, the promoters are eukaryotic and include retroviral Rous sarcoma virus LTR promoter, a cytomegalovirus (CMV) promoter, a SV40 promoter, a dihydrofolate reductase promoter, a β-actin promoter, elongation factor 1 alpha promoter, elongation factor 1 alpha short promoter, SV40 promoter, and the synthetic CAG promoter. In some embodiments, the termination signals for induction of mRNA polyadenylation include, but are not limited to, SV40, hGH, and bGH.

In some embodiments, the nucleic acid(s) are present in a vector (e.g., a viral vector or a phage). The vectors can include one or more regulatory elements that allow for the propagation of the vector in a cell of interest (e.g., a bacterial cell or a mammalian cell). In some embodiments, the vector includes a nucleic acid encoding a single component of a CRISPR-associated (Cas) system described herein. In some embodiments, the vector includes multiple nucleic acids, each encoding a component of a CRISPR-associated (Cas) system described herein.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

In some embodiments, the CRISPR-associated proteins and accessory proteins described herein can be fused to one or more peptide tags, including a His-tag, GST-tag, FLAG-tag, or myc-tag. In some embodiments, the CRISPR-associated proteins or accessory proteins described herein can be fused to a detectable moiety such as a fluorescent protein (e.g., green fluorescent protein or yellow fluorescent protein). In those embodiments where a tag is fused to a CRISPR-associated protein, such tag may facilitate affinity-based and/or charge-based purification of the CRISPR-associated protein, e.g., by liquid chromatography or bead separation utilizing an immobilized affinity or ion-exchange reagent. As a non-limiting example, a recombinant CRISPR-associated protein of this disclosure (such as a Cas12g) comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin), or ready to use column such as the HisTrap FF column commercialized by GE Healthcare Life Sciences, Marlborough, Massachusetts). Following the loading step, the column is optionally rinsed, e.g., using one or more suitable buffer solutions, and the His-tagged protein is then eluted using a suitable elution buffer. Alternatively, or additionally, if the recombinant CRISPR-associated protein of this disclosure utilizes a FLAG-tag, such protein may be purified using immunoprecipitation methods known in the industry. Other suitable purification methods for tagged CRISPR-associated proteins or accessory proteins of this disclosure will be evident to those of skill in the art.

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized, as described in further detail below. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available online with a search for kazusa.or.jp/codon/ and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

In some instances, nucleic acids of this disclosure which encode CRISPR-associated proteins or accessory proteins for expression in eukaryotic (e.g., human, mammalian, etc.) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively, or additionally, nucleic acids of this disclosure encoding CRISPR-associated proteins or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

RNA Guides

In some embodiments, the CRISPR systems described herein include at least one RNA guide. The architecture of multiple RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., two, three, four, five, six, seven, eight, or more RNA guides). In some embodiments, the RNA guide includes a crRNA and a tracrRNA. In some embodiments, the RNA guide is an engineered construct that comprises a tracrRNA and a crRNA (in a single RNA guide). Sequences for RNA guides from multiple CRISPR systems are known in the art and can be searched using public databases (see, e.g., Grissa et al. (2007) Nucleic Acids Res. 35 (web server issue): W52-7; Grissa et al. (2007) BMC Bioinformatics 8: 172; Grissa et al. (2008) Nucleic Acids Res. 36 (web server issue): W145-8; and Moller and Liang (2017) PeerJ 5: e3788; see also the CRISPR database available at: crispr.i2bc.paris-saclay.fr/crispr/BLAST/CRISPRs-Blast.php; and MetaCRAST available at: github.com/molleraj/MetaCRAST).

In some embodiments, the CRISPR systems described herein include at least one RNA guide or a nucleic acid encoding at least one RNA guide. In some embodiments, the RNA guide includes a crRNA. Generally, the crRNAs described herein include a direct repeat sequence and a spacer sequence. In certain embodiments, the crRNA includes, consists essentially of, or consists of a direct repeat sequence linked to a guide sequence or spacer sequence. In some embodiments, the crRNA includes a direct repeat sequence, a spacer sequence, and a direct repeat sequence (DR-spacer-DR), which is typical of precursor crRNA (pre-crRNA) configurations in other CRISPR systems. In some embodiments, the crRNA includes a truncated direct repeat sequence and a spacer sequence, which is typical of processed or mature crRNA. In some embodiments, the crRNA hybridizes with an anti-repeat region of a tracrRNA complementary to the crRNA direct repeat region. In some embodiments, the CRISPR-associated protein forms a complex with the crRNA, and the spacer sequence directs the complex to a sequence-specific binding with the target nucleic acid that is complementary to the spacer sequence. In some embodiments, the CRISPR-associated protein forms a complex with the crRNA and tracrRNA, and the spacer sequence directs the complex to a sequence-specific binding with the target nucleic acid that is complementary to the spacer sequence.

In some embodiments, the CRISPR systems described herein include at least one RNA guide or a nucleic acid encoding at least one RNA guide. In some embodiments, the RNA guide includes a mature crRNA. In some embodiments, the CRISPR systems described herein include a mature crRNA and a tracrRNA. In some embodiments, the CRISPR systems described herein include a pre-crRNA. In some embodiments, the CRISPR systems described herein include a pre-crRNA and a tracrRNA.

Suitably, the Type V-G RNA guide may form a secondary structure such as a stem-loop structure. Suitably, the Type V-G RNA guide may include both a Type V-G crRNA and a Type V-G tracrRNA, either fused into a single RNA molecule or as separate RNA molecules. In some embodiments, a Type V-G crRNA can hybridize with a Type V-G tracrRNA to form a stem-loop structure. An example stem-loop structure of one Type V-G mature crRNA:tracrRNA is shown in FIG. 13. The complementary sections of the crRNA and tracrRNA form the stem. For example, the stem may include at least 8 or at least 9 or at least 10 or at about 11 base pairs.

In some examples, the direct repeat may comprise at least 12 or at least 14 or at least 16 or about 18 nucleotides. The direct repeat can include the nucleic acid sequence $X_1$ACACC (SEQ ID NO:203) proximal to the spacer, wherein $X_1$ denotes G or T.

In some embodiments, the CRISPR systems described herein include a plurality of RNA guides (e.g., 2, 3, 4, 5, 10, 15, or more) or a plurality of nucleic acids encoding a plurality of RNA guides.

In some embodiments, the CRISPR system described herein includes an RNA guide or a nucleic acid encoding the RNA guide. In some embodiments, the RNA guide comprises or consists of a direct repeat sequence and a spacer sequence capable of hybridizing (e.g., hybridizes under appropriate conditions) to a target nucleic acid, wherein the direct repeat sequence includes SEQ ID NO: 200 proximal to its 3' end and adjacent to the spacer sequence. In some embodiments, the RNA guide comprises or consists of a direct repeat sequence and a spacer sequence capable of hybridizing (e.g., hybridizes under appropriate conditions) to a target nucleic acid, wherein the direct repeat sequence includes SEQ ID NO: 201 proximal to its 3' end and adjacent to the spacer sequence.

Examples of RNA guide direct repeat sequences and effector protein pairs are provided in Table 5A. In some embodiments, the direct repeat sequence comprises or consists of a nucleic acid sequence listed in Table 5A (e.g., SEQ ID NOs: 9-13, 25-34). In some embodiments, the direct repeat sequence comprises or consists of a nucleic acid having a nucleic acid sequence listed in Table 5A with a truncation of the initial three 5' nucleotides. In some embodiments, the direct repeat sequence comprises or consists of a nucleic acid having a nucleic acid sequence listed in Table 5A with a truncation of the initial four 5' nucleotides. In some embodiments, the direct repeat sequence comprises or consists of a nucleic acid having a nucleic acid sequence listed in Table 5A with a truncation of the initial five 5' nucleotides. In some embodiments, the direct repeat sequence comprises or consists of a nucleic acid having a nucleic acid sequence listed in Table 5A with a truncation of the initial six 5' nucleotides. In some embodiments, the direct repeat sequence comprises or consists of a nucleic acid having a nucleic acid sequence listed in Table 5A with a truncation of the initial seven 5' nucleotides. In some embodiments, the direct repeat sequence comprises or consists of a nucleic acid having a nucleic acid sequence listed in Table 5A with a truncation of the initial eight 5' nucleotides.

Examples of pairs of effector protein and tracrRNA-encoding sequences are provided in Table 7 (e.g., SEQ ID Nos: 117-134). Table 7 contains sequences with complementarity to the DRs of different Cas12g systems. This set of putative tracrRNA-containing loci includes a locus that contains the Cas12g1 tracrRNA.

In some embodiments, the Type V-G CRISPR-Cas system includes the effector protein that comprises the amino acid sequence of SEQ ID NO: 6, and a RNA guide that includes a tracrRNA sequence that contains the sequence GAUGCUUACUUAGUCAUCUGGUUGGCAAAC-CUCCGCGGACCUUCGGGACCAAUGG AGAG-GAACCCAGCCGAGAAGCAUCGAGCCGGUAAAUGCCG-GAAA (SEQ ID NO: 250) and a crRNA sequence that contains the sequence UUUACCGGCUCUGACACC (SEQ ID NO: 202).

Multiplexing RNA Guides

Type V-G (CLUST.019143) CRISPR-Cas effector proteins have been demonstrated to employ more than one RNA guide, thus enabling the ability of these effectors, and systems and complexes that include them, to target multiple different nucleic acid targets. In some embodiments, the CRISPR systems described herein include multiple RNA guides (e.g., two, three, four, five, six, seven, eight, nine, ten, fifteen, twenty, thirty, forty, or more RNA guides). In some embodiments, the CRISPR systems described herein include a single RNA strand or a nucleic acid encoding a single RNA strand, wherein the RNA guides are arranged in tandem. The single RNA strand can include multiple copies of the same RNA guide, multiple copies of distinct RNA guides, or combinations thereof.

In some embodiments, the Type V-G CRISPR-Cas effector proteins are delivered complexed with multiple RNA guides directed to different target nucleic acids. In some embodiments, the Type V-G CRISPR-Cas effector proteins can be co-delivered with multiple RNA guides, each specific for a different target nucleic acid. Methods of multiplexing using CRISPR-associated proteins are described, for example, in U.S. Pat. No. 9,790,490, and EP 3009511, the entire contents of each of which are expressly incorporated herein by reference.

RNA Guide Modifications

Spacer Lengths

The spacer length of RNA guides can range from about 15 to 50 nucleotides. In some embodiments, the spacer length of a RNA guide is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 15 to 23 nucleotides, from 15 to 30 nucleotides, from 16 to 22 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the spacer length of the RNA guide is at least 16 nucleotides, or is from 16 to 20 nucleotides (e.g., 16, 17, 18, 19, or 20 nucleotides). In some embodiments, the spacer length of the RNA guide is 19 nucleotides.

Exemplary RNA guide direct repeat sequences and effector protein pairs are provided in Table 5A. In some embodiments, the direct repeat sequence comprises or consists of a nucleic acid sequence listed in Table 5A (e.g., SEQ ID NOs: 9-14).

The RNA guide sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective RNA guides that have nuclease activity. Dead guide sequences of RNA guides can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a RNA guide wherein the RNA guide includes a dead guide sequence whereby the RNA guide is capable of hybridizing to a target sequence such that the CRISPR system is directed to a genomic locus of interest in a cell without detectable cleavage activity.

A detailed description of dead guides is described, e.g., in WO 2016094872, which is incorporated herein by reference in its entirety.

Inducible Guides

RNA guides can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of RNA guides can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in their entirety.

Chemical Modifications

Chemical modifications can be applied to the RNA guide's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.* 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized RNA guide molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the RNA guide includes one or more phosphorothioate modifications. In some embodiments, the RNA guide includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965 B2; each which is incorporated by reference in its entirety.

Sequence Modifications

The sequences and the lengths of the RNA guides (e.g., tracrRNAs and crRNAs) described herein can be optimized. In some embodiments, the optimized length of RNA guides can be determined by identifying the processed form of tracrRNA and/or crRNA, or by empirical length studies for RNA guides, tracrRNAs, crRNAs, and the tracrRNA tetraloops.

The RNA guides can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the RNA guide has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 binding loop, QBeta binding loop, or PP7 binding loop. A detailed description of aptamers can be found, e.g., in Nowak et al., "Guide RNA engineering for versatile Cas9 functionality," *Nucl. Acid. Res.*, 2016 Nov. 16; 44(20):9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The RNA guides can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

For all embodiments of the systems and methods described herein, it is known in the field that complete complementarity is not required for hybridization or binding as described herein, provided that there is sufficient complementarity to be functional. Modulations of cleavage efficiency can be exploited by introducing mismatches, e.g., one or more mismatches, such as 1 or 2 mismatches between a spacer sequence and a target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Optimization of CRISPR Systems for Use in Select Organisms

Codon-Optimization

The invention contemplates all possible variations of nucleic acids, such as cDNA, that could be made by selecting combinations based on possible codon choices. These combinations are made in accordance with the standard triplet genetic code as applied to the polynucleotide encoding naturally occurring variant, and all such variations are to be considered as being specifically disclosed. Nucleotide sequences encoding type V-G CRISPR-Cas-associated effector protein variants that have been codon-optimized for expression in bacteria (e.g., *E. coli*) and in human cells are disclosed herein. For example, the codon-optimized sequences for human cells can be generated by substituting codons in the nucleotide sequence that occur at lower frequency in human cells for codons that occur at higher frequency in human cells. The frequency of occurrence for codons can be computationally determined by methods known in the art. An exemplary calculation of these codon frequencies for various host cells (e.g., *E. coli*, yeast, insect, *C. elegans*, *D. melanogaster*, human, mouse, rat, pig, *P. pastoris*, *A. thalian*, maize, and tobacco) have been published or made available by sources such as the GenScript® Codon Usage Frequence Table Tool (example codon usage tables for *E. coli* and Humans are included below.

TABLE 1

*E. coli* Codon Usage Table

| Triplet | Amino acid | Fraction | Number | Triplet | Amino acid | Fraction | Number |
|---|---|---|---|---|---|---|---|
| TTT | F | 0.58 | 80995 | TCT | S | 0.17 | 38027 |
| TTC | F | 0.42 | 58774 | TCC | S | 0.15 | 33430 |
| TTA | L | 0.14 | 52382 | TCA | S | 0.14 | 32715 |
| TTG | L | 0.13 | 47500 | TCG | S | 0.14 | 31146 |
| TAT | Y | 0.59 | 63937 | TGT | C | 0.46 | 19138 |
| TAC | Y | 0.41 | 44631 | TGC | C | 0.54 | 22188 |
| TAA | * | 0.61 | 7356 | TGA | * | 0.3 | 3623 |
| TAG | * | 0.09 | 989 | TGG | W | 1 | 50991 |
| CTT | L | 0.12 | 43449 | CCT | P | 0.18 | 27340 |
| CTC | L | 0.1 | 37347 | CCC | P | 0.13 | 19666 |
| CTA | L | 0.04 | 15409 | CCA | P | 0.2 | 31534 |
| CTG | L | 0.47 | 177210 | CCG | P | 0.49 | 76644 |
| CAT | H | 0.57 | 45879 | CGT | R | 0.36 | 73197 |
| CAC | H | 0.43 | 34078 | CGC | R | 0.36 | 72212 |
| CAA | Q | 0.34 | 53394 | CGA | R | 0.07 | 13844 |
| CAG | Q | 0.66 | 104171 | CGG | R | 0.11 | 21552 |
| ATT | I | 0.49 | 109072 | ACT | T | 0.19 | 37842 |
| ATC | I | 0.39 | 86796 | ACC | T | 0.4 | 80547 |
| ATA | I | 0.11 | 24984 | ACA | T | 0.17 | 33910 |
| ATG | M | 1 | 96695 | ACG | T | 0.25 | 50269 |
| AAT | N | 0.49 | 75436 | AGT | S | 0.16 | 36097 |
| AAC | N | 0.51 | 78443 | AGC | S | 0.25 | 55551 |
| AAA | K | 0.74 | 129137 | AGA | R | 0.07 | 13152 |
| AAG | K | 0.26 | 45459 | AGG | R | 0.04 | 7607 |
| GTT | V | 0.28 | 72584 | GCT | A | 0.18 | 62479 |
| GTC | V | 0.2 | 52439 | GCC | A | 0.26 | 88721 |
| GTA | V | 0.17 | 42420 | GCA | A | 0.23 | 77547 |
| GTG | V | 0.35 | 89265 | GCG | A | 0.33 | 110308 |
| GAT | D | 0.63 | 119939 | GGT | G | 0.35 | 93325 |
| GAC | D | 0.37 | 70394 | GGC | G | 0.37 | 99390 |
| GAA | E | 0.68 | 143353 | GGA | G | 0.13 | 34799 |
| GAG | E | 0.32 | 68609 | GGG | G | 0.15 | 41277 |

TABLE 2

Human Codon Usage Table

| Triplet | Amino acid | Fraction | Number | Triplet | Amino acid | Fraction | Number |
|---|---|---|---|---|---|---|---|
| TTT | F | 0.45 | 336562 | TCT | S | 0.18 | 291040 |
| TTC | F | 0.55 | 406571 | TCC | S | 0.22 | 346943 |
| TTA | L | 0.07 | 143715 | TCA | S | 0.15 | 233110 |
| TTG | L | 0.13 | 249879 | TCG | S | 0.06 | 89429 |
| TAT | Y | 0.43 | 239268 | TGT | C | 0.45 | 197293 |
| TAC | Y | 0.57 | 310695 | TGC | C | 0.55 | 243685 |
| TAA | * | 0.28 | 14322 | TGA | * | 0.52 | 25383 |
| TAG | * | 0.2 | 10915 | TGG | W | 1 | 255512 |
| CTT | L | 0.13 | 253795 | CCT | P | 0.28 | 343793 |
| CTC | L | 0.2 | 386182 | CCC | P | 0.33 | 397790 |
| CTA | L | 0.07 | 138154 | CCA | P | 0.27 | 331944 |
| CTG | L | 0.41 | 800774 | CCG | P | 0.11 | 139414 |
| CAT | H | 0.41 | 207826 | CGT | R | 0.08 | 93458 |
| CAC | H | 0.59 | 297048 | CGC | R | 0.19 | 217130 |
| CAA | Q | 0.25 | 234785 | CGA | R | 0.11 | 126113 |
| CAG | Q | 0.75 | 688316 | CGG | R | 0.21 | 235938 |
| ATT | I | 0.36 | 313225 | ACT | T | 0.24 | 255582 |
| ATC | I | 0.48 | 426570 | ACC | T | 0.36 | 382050 |
| ATA | I | 0.16 | 140652 | ACA | T | 0.28 | 294223 |
| ATG | M | 1 | 443795 | ACG | T | 0.12 | 123533 |
| AAT | N | 0.46 | 331714 | AGT | S | 0.15 | 237404 |
| AAC | N | 0.54 | 387148 | AGC | S | 0.24 | 385113 |
| AAA | K | 0.42 | 476554 | AGA | R | 0.2 | 228151 |
| AAG | K | 0.58 | 654280 | AGG | R | 0.2 | 227281 |

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders. Without wishing to be bound by any particular theory, CRISPR systems including a Cas12g protein may exhibit increased activity or may be preferentially active when targeting in certain classes of loci, such as transcriptionally-active genomic regions. Therefore, CRISPR systems including a Cas12g protein may be advantageously used in applications targeting transcriptionally-active loci.

DNA/RNA Detection

In one aspect, the CRISPR-Cas systems described herein can be used in DNA/RNA detection by RNA sensing. Single effector RNA-guided nucleases can be reprogrammed with RNA guides to provide a platform for specific RNA sensing. Upon recognition of its RNA target, activated Type V-G single effector RNA-guided nucleases engage in "collateral" cleavage of nearby ssDNA and RNA with no sequence similarity to the target. This RNA guide-programmed collateral cleavage activity allows the CRISPR systems to detect the presence of a specific RNA by nonspecific degradation of labeled ssDNA and RNA.

The collateral nuclease activity of the CRISPR-Cas system described herein can be combined with a reporter in RNA detection applications such as described by methods called SHERLOCK (Specific High Sensitivity Enzymatic Reporter UnLOCKing) or the DNA Endonuclease-Targeted CRISPR trans reporter (DETECTR), which achieve attomolar sensitivity for nucleic acid detection. Methods of using CRISPR-Cas systems in SHERLOCK are described in detail, e.g., in Gootenberg, et al. "Nucleic acid detection with CRISPR-Cas13a/C2c2," Science, 356(6336):438-442 (2017), which is incorporated herein by reference in its entirety. Methods of using CRISPR-Cas systems in DETECTR are described in detail, e.g., Chen et al., Science, 360(6387):436-439, 2018, which is incorporated herein by reference in its entirety.

The CRISPR-associated proteins can further be used in Northern blot assays, which use electrophoresis to separate RNA samples by size. The CRISPR-associated proteins can be used to specifically bind and detect the target RNA sequence. The CRISPR-associated proteins can also be fused to a fluorescent protein (e.g., GFP) and used to track RNA localization in living cells. More particularly, the CRISPR-associated proteins can be inactivated in that they no longer cleave RNAs as described above. Thus, CRISPR-associated proteins can be used to determine the localization of the RNA or specific splice variants, the level of mRNA transcripts, up- or down-regulation of transcripts and disease-specific diagnosis. The CRISPR-associated proteins can be used for visualization of RNA in (living) cells using, for example, fluorescent microscopy or flow cytometry, such as fluorescence-activated cell sorting (FACS), which allows for high-throughput screening of cells and recovery of living cells following cell sorting. A detailed description regarding how to detect DNA and RNA can be found, e.g., in International Publication No. WO 2017/070605, which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," Science, 2015 Apr. 24; 348(6233):aaa6090, which is incorporated herein by reference in its entirety.

In some embodiments, CRISPR systems including a Cas12g protein described herein exhibit increased activity (e.g., increased nuclease activity) when the effector protein targets a transcriptionally-active genomic region, and can be used to detect active expression (e.g., transcription) of a target sequence of interest. In some embodiments, the level of expression (e.g., transcription) of a sequence of interest (e.g., a gene of interest) may be quantitated by determining a level of activity (e.g., nuclease activity) of a CRISPR system described herein that targets the sequence of interest, and the level of activity of the CRISPR system may be used to determine the expression level of the sequence of interest.

In some embodiments, the CRISPR systems described herein can be used to detect a target RNA in a sample (e.g., a clinical sample, a cell, or a cell lysate). The collateral RNAse activity of the Type V-G CRISPR-Cas effector proteins (CLUST.019143) described herein is activated when the effector proteins bind to a target nucleic acid. Upon binding to the target RNA of interest, the effector protein cleaves a labeled detector RNA to generate or change a signal (e.g., an increased signal or a decreased signal) thereby allowing for the qualitative and quantitative detection of the target RNA in the sample. The specific detection and quantification of RNA in the sample allows for a multitude of applications including diagnostics.

In some embodiments, the methods include a) contacting a sample with: (i) an RNA guide (e.g., crRNA) and/or a nucleic acid encoding the RNA guide, wherein the RNA guide consists of a direct repeat sequence and a spacer sequence capable of hybridizing to the target RNA; (ii) a Type V-G CRISPR-Cas effector protein and/or a nucleic acid encoding the effector protein; and (iii) a labeled detector RNA; wherein the effector protein associates with the RNA guide to form a complex; wherein the RNA guide hybridizes to the target RNA; and wherein upon binding of the complex to the target RNA, the effector protein exhibits collateral RNAse activity and cleaves the labeled detector RNA; and b) measuring a detectable signal produced by cleavage of the labeled detector RNA, wherein said measuring provides for detection of the single-stranded target RNA in the sample.

In some embodiments, the methods further include comparing the detectable signal with a reference signal and determining the amount of target RNA in the sample. In some embodiments, the measuring is performed using gold nanoparticle detection, fluorescence polarization, colloid phase transition/dispersion, electrochemical detection, and semiconductor based-sensing. In some embodiments, the labeled detector RNA includes a fluorescence-emitting dye pair, a fluorescence resonance energy transfer (FRET) pair, or a quencher/fluor pair. In some embodiments, upon cleavage of the labeled detector RNA by the effector protein, an amount of detectable signal produced by the labeled detector RNA is decreased or increased. In some embodiments, the labeled detector RNA produces a first detectable signal prior to cleavage by the effector protein and a second detectable signal after cleavage by the effector protein.

In some embodiments, a detectable signal is produced when the labeled detector RNA is cleaved by the effector protein. In some embodiments, the labeled detector RNA includes a modified nucleobase, a modified sugar moiety, a modified nucleic acid linkage, or a combination thereof.

In some embodiments, the methods include the multi-channel detection of multiple independent target RNAs in a sample (e.g., two, three, four, five, six, seven, eight, nine, ten, fifteen, twenty, thirty, forty, or more target RNAs) by using multiple Type V-G CRISPR-Cas effector protein systems, each including a distinct orthologous effector protein and corresponding RNA guides, allowing for the differentiation of multiple target RNAs in the sample. In some embodiments, the methods include the multi-channel detection of multiple independent target RNAs in a sample, with the use of multiple instances of Type V-G CRISPR-Cas effector protein systems, each containing an orthologous effector protein with differentiable collateral RNAse substrates. Methods of detecting an RNA in a sample using CRISPR-associated proteins are described, for example, in U.S. Patent Publication No. 2017/0362644, the entire contents of which are incorporated herein by reference.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605; each of which is incorporated herein by reference in its entirety.

RNA Isolation, Purification, Enrichment, and/or Depletion

The CRISPR systems (e.g., CRISPR-associated proteins) described herein can be used to isolate and/or purify RNA. For example, the CRISPR-associated proteins can be fused to an affinity tag that can be used to isolate and/or purify the RNA-CRISPR-associated protein complex. These applications are useful, e.g., for the analysis of gene expression profiles in cells.

In some embodiments, the CRISPR-associated proteins can be used to target a specific noncoding RNA (ncRNA) thereby blocking its activity. In some embodiments, the CRISPR-associated proteins can be used to specifically enrich a particular RNA (including but not limited to increasing stability, etc.), or alternatively, to specifically deplete a particular RNA (e.g., particular splice variants, isoforms, etc.).

These methods are generally described, e.g., in U.S. Pat. No. 8,795,965, WO 2016205764, and WO 2017070605, each of which is incorporated by reference herein in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," BMC Genomics, 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems described herein can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, RNA guide sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae*," *Yeast*, 2017 Sep. 8. doi: 10.1002/yea.3278; and Hlavova et al., "Improving microalgae for biotechnology—from genetics to synthetic biology," *Biotechnol. Adv.*, 2015 Nov. 1; 33:1194-203, both of which are incorporated herein by reference in their entirety.

In some embodiments, the CRISPR systems provided herein can be used to induce death or dormancy of a cell (e.g., a microorganism such as an engineered microorganism). These methods can be used to induce dormancy or death of a multitude of cell types including prokaryotic and eukaryotic cells, including, but not limited to, mammalian cells (e.g., cancer cells, or tissue culture cells), protozoans, fungal cells, cells infected with a virus, cells infected with an intracellular bacteria, cells infected with an intracellular protozoan, cells infected with a prion, bacteria (e.g., pathogenic and non-pathogenic bacteria), protozoans, and unicellular and multicellular parasites. For instance, in the field of synthetic biology it is highly desirable to have mechanisms of controlling engineered microorganisms (e.g., bacteria) in order to prevent their propagation or dissemination. The systems described herein can be used as "kill-switches" to regulate and/or prevent the propagation or dissemination of an engineered microorganism. Further, there is a need in the art for alternatives to current antibiotic treatments.

The systems described herein can also be used in applications where it is desirable to kill or control a specific microbial population (e.g., a bacterial population). For example, the systems described herein may include an RNA guide (e.g., a crRNA) that targets a nucleic acid (e.g., an RNA) that is genus-, species-, or strain-specific, and can be delivered to the cell. Upon complexing and binding to the target nucleic acid, the collateral RNAse activity of the CLUST.019143 (Type V-G) CRISPR-Cas effector proteins is activated leading to the cleavage of collateral RNA within the microorganisms, ultimately resulting in dormancy or death. In some embodiments, the methods comprise contacting the cell with a system described herein including a CLUST.019143 (Type V-G) CRISPR-Cas effector proteins or a nucleic acid encoding the effector protein, and a RNA guide (e.g., a crRNA) or a nucleic acid encoding the RNA guide, wherein the spacer sequence is complementary to at least 15 nucleotides (e.g., 16, 17, 18, 19, 20, 21, 22, 23, 24, 25, 26, 27, 28, 29, 30, 35, 40, 45, 50 or more nucleotides) of a target nucleic acid (e.g., a genus-, strain-, or species-specific RNA guide).

Without wishing to be bound by any particular theory, the cleavage of collateral RNA by the CLUST.019143 (Type V-G) CRISPR-Cas effector proteins can induce programmed cell death, cell toxicity, apoptosis, necrosis, necroptosis, cell death, cell cycle arrest, cell anergy, a reduction of cell growth, or a reduction in cell proliferation. For example, in bacteria, the cleavage of collateral RNA by the CLUST.019143 (Type V-G) CRISPR-Cas effector proteins can be bacteriostatic or bacteriocidal.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.* 11(3): 222-8 (2011), and WO 2016205764 A1; both of which are incorporated herein by reference in their entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of RNA guide-encoding vectors described herein, and the distribution of RNA guides is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled RNA guide library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527(7577):192-7, which is incorporated herein by reference in its entirety.

RNA-Related Applications

The CRISPR systems described herein have various RNA-related applications, e.g., modulating gene expression, degrading a RNA molecule, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A general description of these types of applications can be found, e.g., in WO 2016/205764 A1, which is incorporated herein by reference in its entirety. In different embodiments, the methods described herein can be performed in vitro, in vivo, or ex vivo.

For example, the CRISPR systems described herein can be administered to a subject having a disease or disorder to target and induce cell death in a particular cell or a group of particular cells in a diseased state (e.g., cancer cells or cells infected with an infectious agent). For instance, in some embodiments, the CRISPR systems described herein can be used to target and induce cell death in a cancer cell, wherein the cancer cell is from a subject having a Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, or urinary bladder cancer.

Modulating Gene Expression

The CRISPR systems described herein can be used to modulate gene expression. The CRISPR systems can be used, together with suitable RNA guides, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable RNA guides can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RNAs (dsRNA).

In some embodiments, if the RNA targeting protein and suitable RNA guides are selectively expressed (for example spatially or temporally under the control of a regulated promoter, for example a tissue- or cell cycle-specific promoter and/or enhancer), the new systems described herein can be used to protect the cells or systems (in vivo or in vitro) from RNA interference (RNAi) in those cells. These new methods are useful in neighboring tissues or cells where RNAi is not required or for the purposes of comparison of the cells or tissues where the CRISPR-associated proteins and suitable crRNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the RNA guides can recruit the RNA targeting proteins to these molecules so that the RNA targeting proteins are able to bind to them. These methods are described, e.g., in WO 2016205764 and WO 2017070605, both of which are incorporated herein by reference in the entirety.

Modifying Riboswitches and Controlling Metabolic Regulations

Riboswitches are regulatory segments of messenger RNAs that bind to small molecules and in turn regulate gene expression. This mechanism allows the cell to sense the intracellular concentration of these small molecules. A specific riboswitch typically regulates its adjacent gene by altering the transcription, the translation or the splicing of this gene. Thus, in some embodiments, the riboswitch activity can be controlled by the use of the RNA targeting proteins described herein in combination with suitable RNA guides to target the riboswitches. This can be achieved through cleavage of, or binding to, the riboswitch. Methods of using CRISPR systems to control riboswitches are described, e.g., in WO 2016205764 and WO 2017070605, both of which are incorporated herein by reference in their entireties.

RNA Modification

In some embodiments, the CRISPR-associated proteins described herein can be fused to a base-editing domain, such as ADAR1, ADAR2, APOBEC, or activation-induced cytidine deaminase (AID), and can be used to modify an RNA sequence (e.g., an mRNA). In some embodiments, the CRISPR-associated protein includes one or more mutations (e.g., in a catalytic domain), which renders the CRISPR-associated protein incapable of cleaving RNA.

In some embodiments, the CRISPR-associated proteins can be used with an RNA-binding fusion polypeptide comprising a base-editing domain (e.g., ADAR1, ADAR2, APOBEC, or AID) fused to an RNA-binding domain, such as MS2 (also known as MS2 coat protein), Qbeta (also known as Qbeta coat protein), or PP7 (also known as PP7 coat protein). The amino acid sequences of the RNA-binding domains MS2, Qbeta, and PP7 are provided below:

```
MS2 (MS2 coat protein)
                                   (SEQ ID NO: 316)
MASNFTQFVLVDNGGTGDVTVAPSNFANGVAEWISSNSRSQAYKVTCSVR
QSSAQKRKYTIKVEVPKVATQTVGGVELPVAAWRSYLNMELTIPIFATNS
DCELIVKAMQGLLKDGNPIPSAIAANSGIY Qbeta (Qbeta coat protein)
                                   (SEQ ID NO: 317)
MAKLETVTLGNIGKDGKQTLVLNPRGVNPTNGVASLSQAGAVPALEKRVT
VSVSQPSRNRKNYKVQVKIQNPTACTANGSCDPSVTRQAYADVTFSFTQY
STDEERAFVRTELAALLASPLLIDAIDQLNPAY PP7 (PP7 coat protein)
                                   (SEQ ID NO: 318)
MSKTIVLSVGEATRTLTEIQSTADRQIFEEKVGPLVGRLRLTASLRQNGA
KTAYRVNLKLDQADVVDCSTSVCGELPKVRYTQVWSHDVTIVANSTEASR
KSLYDLTKSLVVQATSEDLVVNLVPLGR
```

In some embodiments, the RNA binding domain can bind to a specific sequence (e.g., an aptamer sequence) or secondary structure motifs on a crRNA of the system described herein (e.g., when the crRNA is in an effector-crRNA complex), thereby recruiting the RNA binding fusion polypeptide (which has a base-editing domain) to the effector complex. For example, in some embodiments, the CRISPR system includes a CRISPR associated protein, a crRNA having an aptamer sequence (e.g., an MS2 binding loop, a QBeta binding loop, or a PP7 binding loop), and a RNA-binding fusion polypeptide having a base-editing domain fused to an RNA-binding domain that specifically binds to the aptamer sequence. In this system, the CRISPR-associated protein forms a complex with the crRNA having the aptamer sequence. Further the RNA-binding fusion polypeptide binds to the crRNA (via the aptamer sequence) thereby forming a tripartite complex that can modify a target RNA.

Methods of using CRISPR systems for base editing are described, e.g., in International Publication No. WO 2017/219027, which is incorporated herein by reference in its entirety, and in particular with respect to its discussion of RNA modification.

RNA Splicing

In some embodiments, an inactivated CRISPR-associated protein described herein (e.g., a CRISPR associated protein having one or more mutations in a catalytic domain) can be used to target and bind to specific splicing sites on RNA transcripts. Binding of the inactivated CRISPR-associated protein to the RNA may sterically inhibit interaction of the spliceosome with the transcript, enabling alteration in the frequency of generation of specific transcript isoforms. Methods of using CRISPR systems to alter splicing are described, e.g., in International Publication No. WO 2017/219027, which is incorporated herein by reference in its entirety, and in particular with respect to its discussion of RNA splicing.

Quantitative Trait Mapping (crisprQTL)

The CRISPR systems described herein can be used for mapping coding and non-coding regions of a genome that influence gene expression. For example, in some embodiments a population of cells may be transduced with multiple random, barcoded, CRISPR RNA guide-programmed perturbations. Single-cell RNA-sequencing may then be used to profile gene expression and the collection of RNA guides in each cell. The generated data can be used to identify associations between RNA guides and quantitative changes in gene expression, which facilitates the analysis of the cis-regulatory architecture of the cells. These methods are described, for example, in Gasperini et al., "crisprQTL mapping as a genome-wide association framework for cellular genetic screens," bioRxiv, posted May 4, 2018, doi: doi.org/10.1101/314344, which is incorporated herein by reference.

Lineage Tracing

The CRISPR systems described herein can be used for cell lineage tracing. CRISPR systems can be used to combinatorially edit a 'barcode' sequence in the genomes of the cells of an embryo as it develops. Based on knowledge of the on-target and off-target editing characteristics of the CRISPR system, this combinatorial editing activity can be tuned such that genomic editing events accumulate in informative ways as the cells grow and divide. The patterns of barcodes observed in the edited cells are used to reconstruct the developmental lineage relationships for cells in an organism. These methods, and variants thereof, are described, for example, in McKenna et al., "Whole organism lineage tracing by combinatorial and cumulative genome editing", Science, 29 Jul. 2016; 353(6298): aaf7907, which is incorporated herein by reference. These methods can also be used in cancer cells for example, to track the evolution of a tumor over time, and space, in the case of metastasis. In some embodiments, the Cas12g proteins that exhibit increased activity when the effector protein targets a transcriptionally-active genomic region (e.g., Cas12g1) can be used to perform lineage tracing of cells in which marker genes of interest are expressed. For example, in some embodiments, these systems can be used to trace the evolution of cancer cells expressing genes relevant to the diagnosis or treatment of disease.

Therapeutic Applications

The CRISPR systems described herein that have activity in a mammalian cellular context can have a diverse range of therapeutic applications. In some embodiments, the new CRISPR systems targeting RNA can be used to directly treat diseases and disorders. From the development of therapeutics based on RNA interference, it has been demonstrated that a number of diseases can be treatable by targeting endogenous RNA. The RNA targeting CRISPR systems described herein can thus be applied in a similar way.

In one aspect, the CRISPR systems described herein can be used for treating a disease caused by overexpression of RNAs, toxic RNAs, and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," Hum. Mol. Genet., 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain. Another example is Huntington's disease (HD), in which the trinucleotide expansion of CAG in the gene coding for the Huntingtin protein yields an aberrant protein. The specific knockdown of the mutated or allele-specific RNA encoding the abnormal Huntingtin protein may be beneficial. Mutations in APOB gene that cause familial hypobetalipoproteinemia (FHBL) cause mutated transcripts that interfere with the generation of the two natural forms of the transcript in unaffected individuals, and specific knockdown of the mutated APOB transcript may be beneficial to treat FHBL. Likewise, the recent FDA approval of Patisiran highlights the therapeutic potential of RNAi to knock down the toxic misfolded transthyretin protein (Kristen, et al. Neurodegener Dis Manag. 2019 February; 9(1): 5-23.) that causes hereditary transthyretin-mediated amyloidosis, and utilizing the CRISPR systems described herein for targeting the toxic mutation can be expected to have similar benefits.

In another aspect, the CRISPR systems described herein can target genes identified from genetic studies that provide a protective effect when knocked down. These may confer protective mutations, such as PCSK9 knockdown for reduction of plasma LDL and lowering the risk of cardiovascular disease (Frank-Kamenetsky, et al. Proc Natl Acad Sci USA. 2008 Aug. 19; 105(33): 11915-11920), to CCR5 knockdown for conferring protection against HIV infection (Shimizu et al, Mol Ther Nucleic Acids. 2015 February; 4(2): e227.).

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," Cell, 136.4 (2009): 777-793, and WO 2016205764 A1, both of which are incorporated herein by reference in their entirety.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne or Becker Muscular Dystrophy (DMD/BMD), frontotemporal dementia, and Parkinsonism linked to chromosome 17 (FTDP-17), and cystic fibrosis. In the example of Friedreich's ataxia, the disease is caused by a trinucleotide repeat expansion of GAA in the Frataxin (FXN) gene that interferes with normal splicing. The RNA-targeting effectors described herein can be targeted to affect the splice site and restore normal protein activity for therapeutic benefit.

The CRISPR systems described herein can also be used to treat a cancer in a subject (e.g., a human subject). For example, the CRISPR-associated proteins described herein can be programmed with a crRNA targeting an RNA molecule that is aberrant (e.g., comprises a point mutation or is alternatively spliced) and found in cancer cells, to induce cell death in the cancer cells (e.g., via apoptosis). One instance is the BCR-ABL fusion oncogene found in many patients with chronic myelogenous leukemia (CML), a mutation specific to the cancer and thus able to be targeted without affecting healthy somatic cells.

Furthermore, the CRISPR systems described herein can be used to treat an infectious disease in a subject. For example, the CRISPR-associated proteins described herein can be programmed with crRNA targeting RNA expressed by an infectious agent (e.g., a bacteria, a virus, a parasite or a protozoan) in order to target and induce cell death in the infectious agent cell. The CRISPR systems may also be used to treat diseases where an intracellular infectious agent infects the cells of a host subject. By programming the CRISPR-associated protein to target an RNA molecule encoded by an infectious agent gene, cells infected with the infectious agent can be targeted and cell death induced. The CRISPR systems can further be used for antiviral activity, in particular against RNA viruses such as HIV, respiratory syncytial virus (RSV) and Hepatitis C virus (HCV) although DNA viruses with RNA intermediates in their life cycle can also be targeted (such as herpes simplex virus types 1 and 2, and Hepatitis B virus). The effector proteins can target the viral RNAs using suitable RNA guides selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S.

Pat. No. 8,795,965, EP 3009511, WO 2016205764, and WO 2017070605; each of which is incorporated herein by reference in its entirety.

In another aspect, the CRISPR systems described herein can be engineered to enable additional functions that utilize enzymatically inactive Cas12g as a chassis on top of which protein domains can be attached to confer activities such as base editing (Cox et al., Science. 2017 Nov. 24; 358(6366): 1019-1027), and RNA splice modification (Konermann, et al. Cell. 2018 Apr. 19; 173(3):665-676.e14).

Suitably, there is provided CRISPR-Cas systems and cells of the present invention for use in the treatment or prevention of any of the disease disclosed herein.

Delivery of CRISPR Systems

The CRISPR systems described herein, or components thereof, nucleic acid molecules thereof, or nucleic acid molecules encoding or providing components thereof, can be delivered by various delivery systems such as vectors, e.g., plasmids, viral delivery vectors. The new CRISPR enzymes and/or any of the RNAs (e.g., RNA guides) can be delivered using suitable vectors, e.g., plasmids or viral vectors, such as adeno-associated viruses (AAV), lentiviruses, adenoviruses, and other viral vectors, or combinations thereof. The proteins and one or more RNA guides can be packaged into one or more vectors, e.g., plasmids or viral vectors. For bacterial applications, the nucleic acids encoding any of the components of the CRISPR systems described herein can be delivered to the bacteria using a phage. Exemplary phages, include, but are not limited to, T4 phage, Mu, λ phage, T5 phage, T7 phage, T3 phage, Φ29, M13, MS2, Qβ, and ΦX174.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be administered in a single dose containing at least $1\times10^5$ particles (also referred to as particle units, pu) of adenoviruses. In some embodiments, the dose is at least about $1\times10^6$ particles, at least about $1\times10^7$ particles, at least about $1\times10^8$ particles, or at least about $1\times10^9$ particles of the adenoviruses. The delivery methods and the doses are described, e.g., in WO 2016205764 and U.S. Pat. No. 8,454,972, both of which are incorporated herein by reference in their entirety.

In some embodiments, the delivery is via a recombinant adeno-associated virus (rAAV) vector. For example, in some embodiments, a modified AAV vector may be used for delivery. Modified AAV vectors can be based on one or more of several capsid types, including AAV1, AV2, AAV5, AAV6, AAV8, AAV8.2. AAV9, AAV rhlO, modified AAV vectors (e.g., modified AAV2, modified AAV3, modified AAV6) and pseudotyped AAV (e.g., AAV2/8, AAV2/5 and AAV2/6). Exemplary AAV vectors and techniques that may be used to produce rAAV particles are known in the art (see, e.g., Aponte-Ubillus et al. (2018) Appl. Microbiol. Biotechnol. 102(3): 1045-54; Zhong et al. (2012) J. Genet. Syndr. Gene Ther. S1: 008; West et al. (1987) Virology 160: 38-47 (1987); Tratschin et al. (1985) Mol. Cell. Biol. 5: 3251-60); U.S. Pat. Nos. 4,797,368 and 5,173,414; and International Publication Nos. WO 2015/054653 and WO 93/24641, each of which is incorporated by reference).

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in the delivery RNA.

Further means of introducing one or more components of the new CRISPR systems into cells is by using cell-penetrating peptides (CPP). In some embodiments, a cell-penetrating peptide is linked to the CRISPR enzymes. In some embodiments, the CRISPR enzymes and/or RNA guides are coupled to one or more CPPs to transport them inside cells effectively (e.g., plant protoplasts). In some embodiments, the CRISPR enzymes and/or RNA guide(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hällbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.*, 2014 June; 24(6):1020-7; and WO 2016205764 A1; each of which is incorporated herein by reference in its entirety.

Delivery of the Type V-G CRISPR system as a ribonucleoprotein complex by electroporation or nucleofection, in which purified Cas12g protein is pre-incubated with a RNA guide and electroporated (or nucleofected) into cells of interest, is another method of efficiently introducing the CRISPR system to cells for gene editing. This is particularly useful for ex vivo genome editing and the development of cellular therapies, and such methods are described in Roth et al. "Reprogramming human T cell function and specificity with non-viral genome targeting," Nature. 2018 July; 559 (7714): 405-409.

Various delivery methods for the CRISPR systems described herein are also described, e.g., in U.S. Pat. No. 8,795,965, EP 3009511, WO 2016205764, and WO 2017070605; each of which is incorporated herein by reference in its entirety.

Kits

This disclosure also encompasses kits for carrying out the various methods of the disclosure utilizing the CRISPR systems described herein. One exemplary kit of the present disclosure comprises (a) one or more nucleic acids encoding a CRISPR-associated protein and a cognate crRNA, and/or (b) a ribonucleoprotein complex of a CRISPR-associated protein and a cognate crRNA. In some embodiments, the kit comprises a Cas12g protein and a Cas12g RNA guide. As described above, a complex of the protein and RNA guide has an editing activity such as SSB formation, RNA cleavage, CRISPR interference, nucleobase modification, DNA methylation or demethylation, chromatin modification, etc. In certain embodiments, the CRISPR-associated protein is a variant, such as a variant having reduced endonuclease activity.

Kits of this disclosure also optionally include additional reagents, including one or more of a reaction buffer, a wash buffer, one or more control materials (e.g., a substrate or a nucleic acid encoding a CRISPR system component), etc. A kit of the present disclosure also optionally includes instructions for performing a method of this disclosure using materials provided in the kit. The instructions are provided in physical form, e.g., as a printed document physically packaged with another item of the kit, and/or in digital form, e.g., a digitally published document downloadable from a website or provided on computer readable media.

EXAMPLES

The invention is further described in the following examples, which do not limit the scope of the invention described in the claims.

Example 1: Identification of Minimal Components for CLUST.019143 (Type V-G CRISPR-Cas Effector Protein) System (FIGS. 1-3)

To achieve the broadest possible starting set of type V families, we explored additional members of the type V diversity within an expanded database of microbial genomic and metagenome sequences. Genome and metagenome sequences were downloaded from NCBI (Benson et al., 2013; Pruitt et al., 2012), NCBI whole genome sequencing (WGS), and DOE JGI Integrated Microbial Genomes (Markowitz et al., 2012) and compiled to construct a database of 293,985 putative CRISPR-Cas systems, each including a predicted effector and a CRISPR array, and where present, adaptation modules, accessory proteins, and tracrRNA (Yan et al., 2018).

A search of this database for CRISPR-Cas systems in which the effector protein contained a domain homologous to RuvC (TnpB) revealed a diversity of novel type V CRISPR-Cas families beyond the previously described subtypes V-A-E and V-U. The loci encoding these effectors are highly enriched for CRISPR arrays of different lengths, but the adaptation module consisting of Cas1, Cas2 and Cas4 is associated only with Cas12a, Cas12b and Cas12e, whereas subtype V-C and V-D loci, in accord with the previous observations, contain only the Cas1 gene (FIG. 1) (Burstein et al., 2017; Shmakov et al., 2015). The predicted effectors in the newly identified families ranged in size from 720aa to 1093aa, each including a C-terminal TnpB-derived RuvC domain with conserved catalytic amino acids typical of the RuvC-like nucleases, and N-terminal extensions that were variable in length and sequence (FIGS. 2A-B).

Figure 1A:
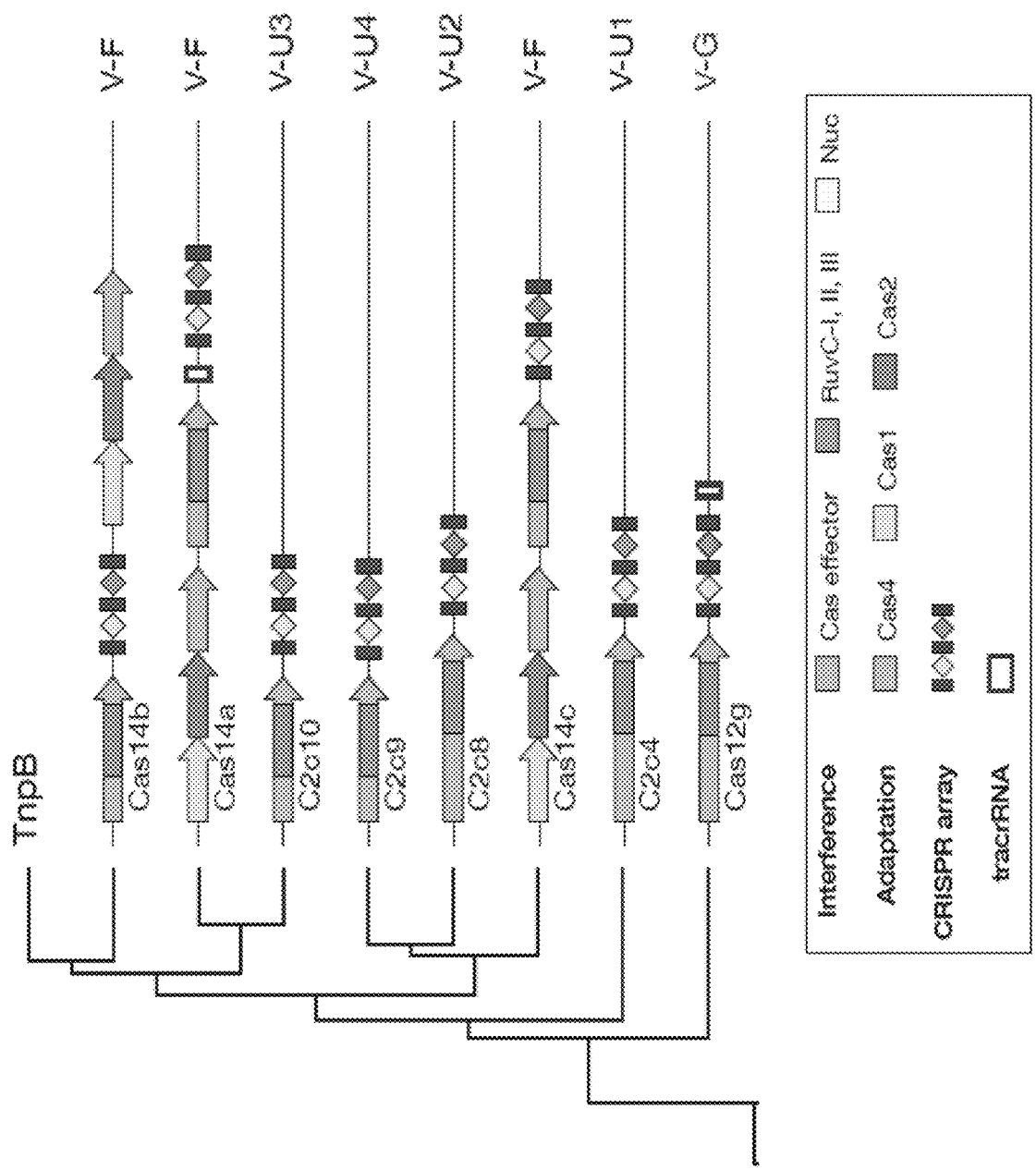
Figure 1B:
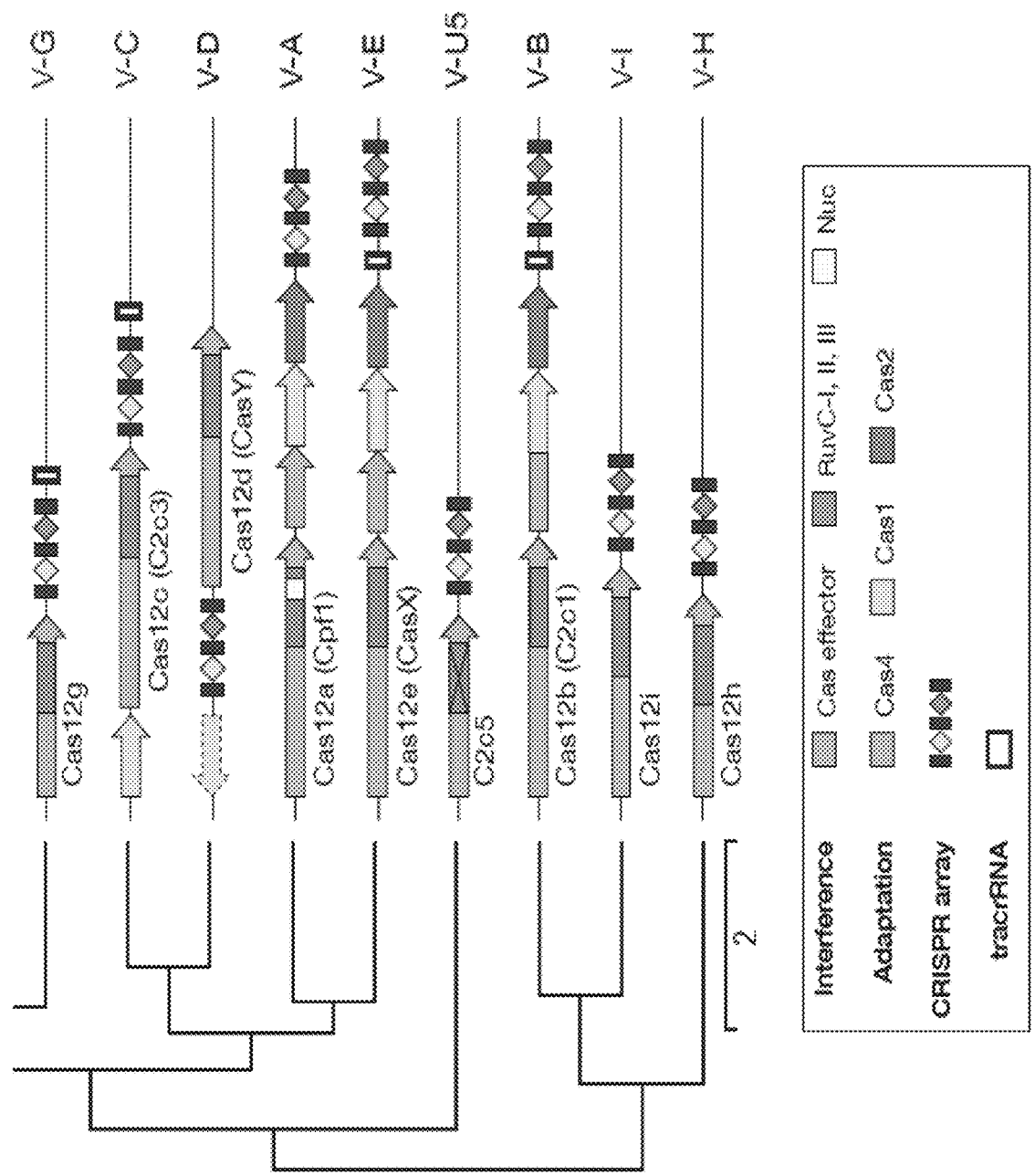

The classification tree depicted in FIG. 1 was constructed by comparing sequence profiles extracted from multiple alignments of groups of readily alignable Cas12 proteins. Profile-profile comparisons were performed using HHsearch (Söding et al., 2005); scores between two profiles were normalized by the minimum of the self-scores and converted to a distance matrix on the natural log scale. The UPGMA dendrogram was reconstructed from the distance matrix. The tree at the depth of 2 distance unites (corresponding to the pairwise HHsearch score of e 2D=0.02 relative to the self-score) typically reliably recovers profile similarity and can serve as a guide for subtype classification (Shmakov et al., 2017).

Figure 2A:
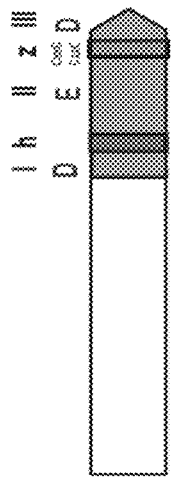
FIG. 2B is a schematic representation of a multiple sequence alignment of Cas12g effector proteins, with the relative locations of the conserved catalytic residues of the RuvC domain denoted by RuvC I/II/III.
Figure 2B:
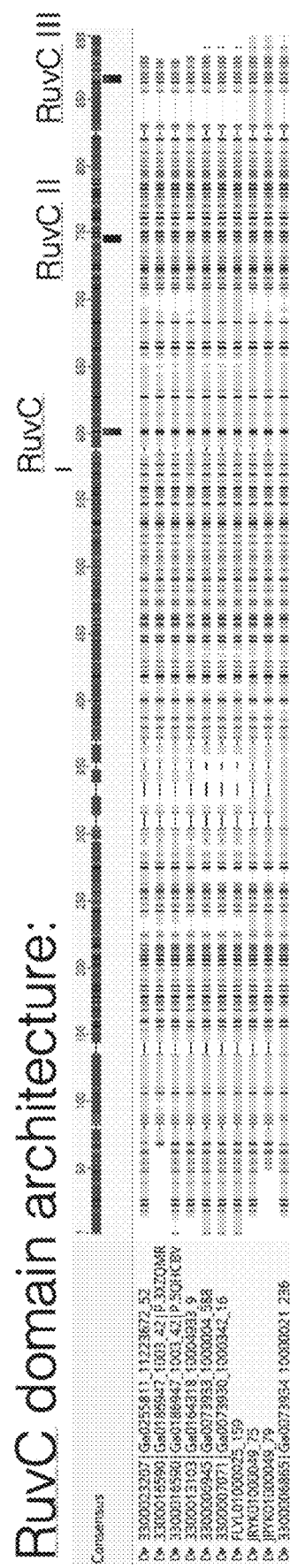
Figure 3:
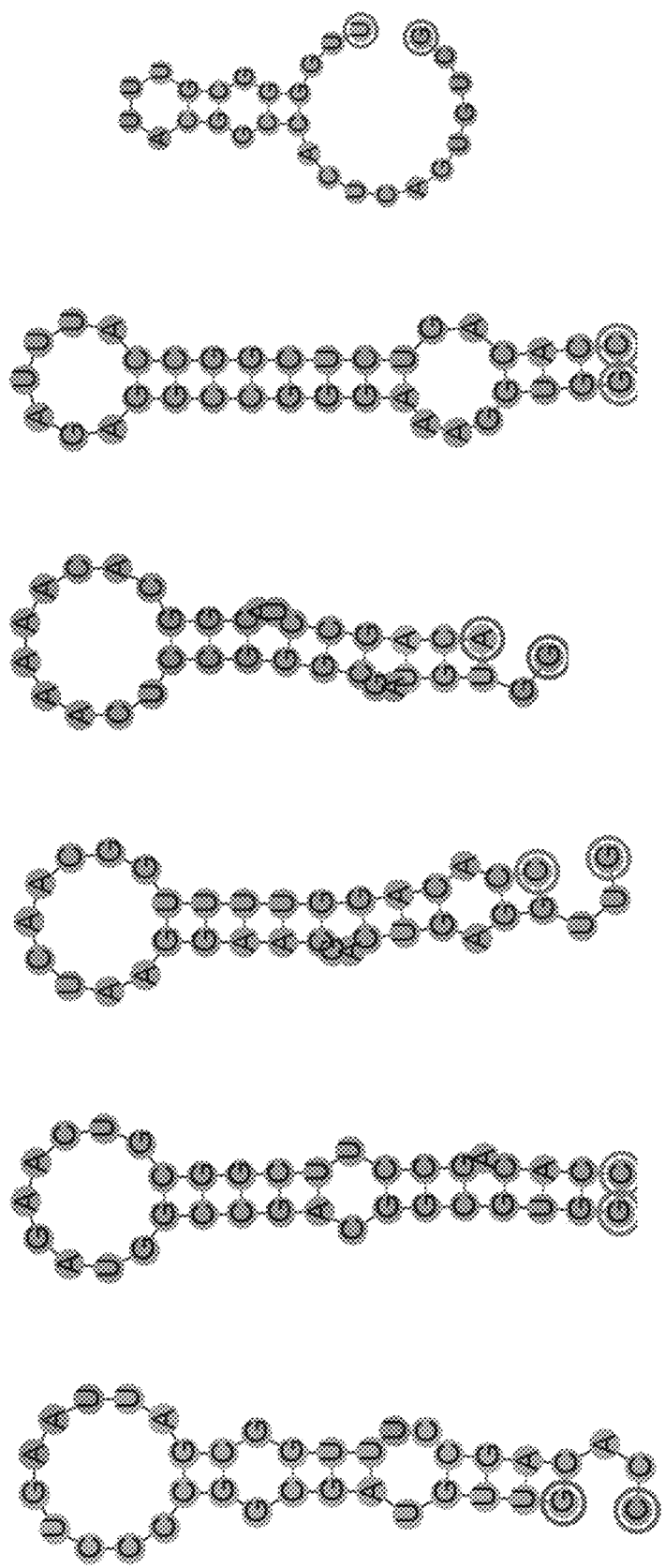
FIG. 3 is a group of schematic diagrams that show predicted secondary structure of the RNA transcript of examples of CLUST.019143 (Type V-G) direct repeat sequences. From L to R, the sequences are (SEQ ID NO: 9), (SEQ ID NO: 10), (SEQ ID NO: 4), (SEQ ID NO: 30), (SEQ ID NO: 13), (SEQ ID NO: 28).

The domain architecture of Cas12g, depicted in FIGS. 2A-2B indicate that the effector contains the active catalytic residues of the RuvC nuclease domain. The direct repeat sequence for CLUST.019143 (Type V-G) shows a consensus 5'-GACACC-3' nucleotide sequence proximal to the 3' end of the direct repeat sequence. The predicted secondary structure of direct repeat sequences of example CLUST.019143 (Type V-G) CRISPR-Cas system is depicted in FIG. 3.

Pipeline for Class 2 CRISPR-Cas Loci Identification

Genome and metagenome sequences were downloaded from NCBI (Benson et al., 2013; Pruitt et al., 2012), NCBI whole genome sequencing (WGS), and DOE JGI Integrated Microbial Genomes (Markowitz et al., 2012) and compiled to construct a database of 293,985 putative CRISPR-Cas loci within which we searched for novel RuvC containing type V effectors. As previously described in detail (Yan et al., 2018), this approach to pipeline engineering performs minimal filtering in the intermediate stages in order to expand the search space for novel CRISPR effector discovery and reduce biases.

Construction of the Classification Tree of Class 2 Effectors

The classification tree was constructed by comparing sequence profiles extracted from multiple alignments of groups of readily alignable Cas12 proteins Profile-profile comparisons were performed using HHsearch (Söding, 2005); scores between two profiles were normalized by the minimum of the self-scores and converted to a distance matrix on the natural log scale. The UPGMA dendrogram was reconstructed from the distance matrix. The tree at the depth of 2 distance unites (corresponding to the pairwise HHsearch score of $e^{-2D}$=0.02 relative to the self-score) typically reliably recovers profile similarity and can serve as a guide for subtype classification (Shmakov et al., 2017).

TABLE 3

Representative CLUST.019143 (Type V-G) Effector Proteins

| Source | Effector accession | # spacers | cas 1 | cas 2 | effector size |
|---|---|---|---|---|---|
| Planctomycetes bacterium (QEVG01000016) | RIK66295.1 | 5 | N | N | 761 |
| activated sludge metagenome (JRYK01000049) | JRYK01000049_75\|P | 13 | N | N | 821 |
| activated sludge metagenome (JRYK01000049) | JRYK01000049_79\|M | 13 | N | N | 786 |
| anaerobic digester metagenome (UOQF01000587) | UOQF01000587_2\|M | 10 | N | N | 772 |
| anaerobic digester metagenome (UOQK01013695) | UOQK01013695_2\|M | 3 | N | N | 772 |
| aquatic-marine-marine sediment (3300028920\|Ga0272441_10052198) | 3300028920\|Ga0272441_10052198_2\|M | 4 | N | N | 696 |
| aquatic-marine-marine sediment (3300028920\|Ga0272441_10052198) | 3300028920\|Ga0272441_10052198_4\|P | 4 | N | N | 768 |
| aquatic-sediment-hot spring sediment (3300016590\|Ga0186947_1003) | 3300016590\|Ga0186947_1003_42\|P | 2 | N | N | 774 |
| aquatic-sediment-hot spring sediment (3300016590\|Ga0186947_1003) | 3300016590\|Ga0186947_1003_42\|M | 2 | N | N | 720 |
| aquatic-thermal springs-hot spring fesi sediment (3300010938\|Ga0137716_10003017) | 3300010938\|Ga0137716_10003017_35\|M | 14 | N | N | 855 |
| aquatic-thermal springs-hot spring fesi sediment (3300010938\|Ga0137716_10003017) | 3300010938\|Ga0137716_10003017_32\|P | 14 | N | N | 803 |
| aquatic-thermal springs-hot spring sediment (3300006865\|Ga0073934_10000021) | 3300006865\|Ga0073934_10000021_236\|M | 2 | N | N | 830 |
| aquatic-thermal springs-hot spring sediment (3300006945\|Ga0073933_1000004) | 3300006945\|Ga0073933_100004_588\|P | 12 | N | N | 767 |
| aquatic-thermal springs-hot spring sediment (3300007071\|Ga0073930_1000342) | 3300007071\|Ga0073930_100342_16\|M | 12 | N | N | 767 |
| aquatic-thermal springs-hot spring sediment (3300022554\|Ga0212093_1000011) | 3300022554\|Ga0212093_100011_56\|M | 12 | N | N | 767 |
| aquatic-thermal springs-hot spring sediment (3300025094\|Ga0209478_1000005) | 3300025094\|Ga0209478_100005_814\|P | 12 | N | N | 767 |
| aquatic-thermal springs-hot spring sediment (3300025105\|Ga0209479_1000006) | 3300025105\|Ga0209479_100006_88\|P | 12 | N | N | 767 |

TABLE 3-continued

Representative CLUST.019143 (Type V-G) Effector Proteins

| Source | Effector accession | # spacers | cas 1 | cas 2 | effector size |
|---|---|---|---|---|---|
| aquatic-thermal springs-hot spring sediment (3300025310\|Ga0209172_10000050) | 3300025310\|Ga0209172_10000050_165\|P | 2 | N | N | 830 |
| aquatic-thermal springs-sediment (3300019846\|Ga0197078_1002) | 3300019846\|Ga0197078_1002_15\|M | 4 | N | N | 853 |
| bioreactor-anaerobic-anaerobic digester digestate (3300023207\|Ga0255811_11223672) | 3300023207\|Ga0255811_11223672_52\|P | 4 | N | N | 772 |
| candidate division Zixibacteria bacterium Bacteria. (QNAH01000034) | RKX31836.1 | 11 | N | N | 769 |
| hot springs metagenome (FLYL01000025) | FLYL01000025_159\|P | 13 | N | N | 767 |
| sediment metagenome (ORFD01000444) | ORFD01000444_4\|P | 12 | N | N | 767 |
| sediment metagenome (ORXB01000005) | ORXB01000005_848\|P | 12 | N | N | 767 |
| terrestrial-deep subsurface (3300027640\|Ga0209347_1003758) | 3300027640\|Ga0209347_1003758_14\|P | 10 | N | N | 774 |
| terrestrial-deep subsurface (3300027640\|Ga0209347_1003758) | 3300027640\|Ga0209347_1003758_16\|M | 10 | N | N | 763 |
| terrestrial-soil (3300027657\|Ga0256865_1003050) | 3300027657\|Ga0256865_1003050_2\|M | 3 | N | N | 752 |

TABLE 4

Amino Acid Sequences of Representative
CLUST.019143 (Type V-G) Effector Proteins

```
>RIK66295.1
[Planctomycetes bacterium]
MGLRKRYVELCDNSGLRADLSSFGTLGNFLLEPSLDGSEADERERDRWRLAVFDIVAGFRADIQLDGRTLPNELRQ
AITDAADQMRNTIADGKKKTGLRRLFQRLGDLEEAHRLVLLKSAAEWIVARYLRSVENWVRQHTEWEKEKQQWESH
KDNKTDHTLLTPDIREKYTAVFKLLVWDKDKPPGVRNKRPRICPYDRLKQNIDNCCYAGQKGHGPLCWKYNEFVKA
RKARNPSFNDKKFAEDVAKYLPPRAKGEQRHLILKAIFPNKQQDQQRFSDNWTAYLSAMKLNEQTLVQHQQLPHCL
KIGETFEKSACVWNPHTDLCGQYHRALVNPNNGFDDAMLSLEPLYRAWRRNYLAGPRKPSFRYPASRDLPMPKIFG
DGFHEVDFENSIVRLRLDDMPRGQWLDLGFTPWPRGYKPSRAEISEPGRVTSVHVHFVGVRARIGFRFEVAHAPSR
FGCTQDEIDELRSRHYPRQAQDQEFLEAARKCLLDSMTEGSENDLRIMAVDLGEKGACAAVYRGRTREMDIPLAIV
KINKLYEKPPKTLEPDRHSRPEESKRKFEEADPRGVRKEHVGRHLERVAAMSQEIAKHRQPAVATTVTVSVNDLRG
LKRHVAWMIRDWARHNASQIVKAAEEHQCDVIVFESLRGFRPPGYDKLDEMSAKKKRWLAMFAYGRVRRKVIEKAV
ERGMRVVTVPYFKSSQVCSDCGREQVNVGLLRKNKLSKGQFVCENCKVTLTSDANAARVLARVFRGEIMLPKARPG
A (SEQ ID NO: 15)

>JRYK01000049_75|P
[activated sludge metagenome]
MLPTRYKPARTLVRPLGRLPHEPRKEFVEKCRRVRMHFEQFNIDVADLCQWLMSLRPNTRIGDAQSTVFWDFFLNP
SILTVEADEKERDRWRLAAFDELLQIRFGHDPNAPPWSEEFRSAIRHVAQRPKSATAQRLFDRLRSLTAPHRLVLL
KSAAEWIIARYQRGMENWQRQFAEWQREKEEWEAAHPNLTPEVRDAFTRVFKNLFENPDGDGKIGVRRKNPRICSW
ERLKLNKDNCVYAGQKGHGPLCWEFSKFVKAQKNAGTIKTFFVDVANKYLHVRRNLSKPGVKLKKSPRQEAFKRLY
NQKGMEKARNWFTDAWSGYLTALNLNEKTILDHGCLKHCGAIGAEFEKSLCQFNPHTHLCVQYRNALESLEPAIRE
LEGDYREWRRLFLAPPRKPSFRYPSSRRLPMPKIFGEHFHQIDFDQSILRLRLEDMAEGEWIEFGFKPWPKDYRPG
KDEVRVTSVHVNFHGNRMRAGFHFEAPAKPSRFACTQDELDDLRSKQFPRQSQDRQLLEVARRRLLESFDGMLESD
LRILAVDLGEKGAAAAVYQGHGHEADVAIPIVKIDRLYDHVPDVLDVESARVPPPKFDDSRDPRGVRKEHVGRHLG
QLQRGAQTLAQHRQQDESAPAALRRHDFRSLTRHIRWMIRDWTRHNAAQITAAAETHRCHLIVFESLRGFKPRGYD
QMDFAQKARLAFFAYGRVRRKVVEKAVERGLRVVTVPYGFTSQICSECGHRQRNKGRLRKNKYQRRFVCECGEPKK
SANKTAAPDRSATVSPCTCRLQLGSDVNAARVLARVFWDEIVLPTREEMREPAVDSAPPSK (SEQ ID NO: 2)
```

TABLE 4-continued

Amino Acid Sequences of Representative
CLUST.019143 (Type V-G) Effector Proteins >JRYK01000049_79|M
[activated sludge metagenome]
MHFEQFNIDVADLCQWLMSLRPNTRIGDAQSTVFWDFFLNPSILTVEADEKERDRWRLAAFDELLQIRFGHDPNAP
PWSEEFRSAIRHVAQRPKSATAQRLFDRLRSLTAPHRLVLLKSAAEWIIARYQRGMENWQRQFAEWQREKEEWEAA
HPNLTPEVRDAFTRVFKNLFENPDGDGKIGVRRKNPRICSWERLKLNKDNCVYAGQKGHGPLCWEFSKFVKAQKNA
GTIKTFFVDVANKYLHVRRNLSKPGVKLKKSPRQEAFKRLYNQKGMEKARNWFTDAWSGYLTALNLNEKTILDHGC
LKHCGAIGAEFEKSLCQFNPHTHLCVQYRNALESLEPAIRELEGDYREWRRLFLAPPRKPSFRYPSSRRLPMPKIF
GEHFHQIDFDQSILRLRLEDMAEGEWIEFGFKPWPKDYRPGKDEVRVTSVHVNFHGNRMRAGFHFEAPAKPSRFAC
TQDELDDLRSKQFPRQSQDRQLLEVARRRLLESFDGMLESDLRILAVDLGEKGAAAAVYQGHGHEADVAIPIVKID
RLYDHVPDVLDVESARVPPPKFDDSRDPRGVRKEHVGRHLGQLQRGAQTLAQHRQQDESAPAALRRHDFRSLTRHI
RWMIRDWTRHNAAQITAAAETHRCHLIVFESLRGFKPRGYDQMDFAQKARLAFFAYGRVRRKVVEKAVERGLRVVT
VPYGFTSQICSECGHRQRNKGRLRKNKYQRRFVCECGEPKKSANKTAAPDRSATVSPCTCRLQLGSDVNAARVLAR
VFWDEIVLPTREEMREPAVDSAPPSK (SEQ ID NO: 3)

>UOQF01000587_2|M
[anaerobic digester metagenome]
MTRTKYREERTLVRGLQRLPNQDKTEFNKNVLRLRRHFEQFNLNVAELCQWLISFKPENPNSVCETKLFWEFMLEP
ENFCPDTYDRGSDWLRHEIFLLVAGWQTFEDMKAYNIRESLLTSAKMASSRPRSKTAEVLFIRLKSLEASHVMVLL
KSASEWLSTRYIRQSENWKRHVQEWQKEKAAWEDKHPKLTPAIRDKYNAIFVELGISEKRSRVCSWKKLSENKDNC
DWAGERKNIGDKWVSHSALCSKFNEFHRSLKGSPRKYFVTNANQYLELRRKNPQWTRDMAMQGLFRNVPGAQNWFP
NAWTNYLNALNILETTILKDYNGHLPHCNKLSDECLFNQHTFNCRQYKRLLVGKLSSQERDLEETYREWRREYLAP
PDKPFLRYPSAQKLPTPKLFGRGYYDLDFTRHVVKLRLDDMPAENFVSFGFKPWPRDYDKKPGEINITSVHVHFIG
TRARVGFRFAVPHSYSRFSVSQDKIDELRSRVFPRKSQDLEFLNEARLRLLDGMNENQKSALRIMAVDLGTHRAAA
AFFTGRIFDKPKLIKLKKIDLLTESITDTTQPEKHSANEKKIQREKGLTQHHVGKHLDTLETRTKEIISKRQNIKI
TPSDDTLGTLGDHDLRHLTSHIQRMIRDWVRLNAQQITELAEKEKVDLIVFESLRGFRAHAYDKLDLEQKRRLAFF
AYGRIRRKVAEKAVERGMRVLTVPYFESSQICAQCGRSQNDKNKLRDNKRKQSFQCEFSDCNYKTHSDENAARVLG
RVFWGEITLPTD (SEQ ID NO: 16)

>UOQK01013695_2|M
[anaerobic digester metagenome]
MTRTKYREERTLVRGLQRLPNQDKTEFNKNVLRLRRHFEQFNLNVAELCQWLISFKPENPNSVCETKLFWEFMLEP
ENFCPDTYDRGSDWLRHEIFLLVAGWQTFEDMKAYNIRESLLTSAKMASSRPRSKTAEVLFIRLKSLEASHVMVLL
KSASEWLSTRYIRQSENWKRHVQEWQKEKAAWEDKHPKLTPAIRDKYNAIFVELGISEKRSRVCSWKKLSENKDNC
DWAGERKNIGDKWVSHSALCSKFNEFHRSLKGSPRKYFVTNANQYLELRRKNPQWTRDMAMQGLFRNVPGAQNWFP
NAWTNYLNALNILETTILKDYNGHLPHCNKLSDECLFNQHTFNCRQYKRLLVGKLSSQERDLEETYREWRREYLAP
PDKPFLRYPSAQKLPTPKLFGRGYYDLDFTRHVVKLRLDDMPAENFVSFGFKPWPRDYDKKPGEINITSVHVHFIG
TRARVGFRFAVPHSYSRFSVSQDKIDELRSRVFPRKSQDLEFLNEARLRLLDGMNENQKSALRIMAVDLGTHRAAA
AFFTGRIFDKPKLIKLKKIDLLTESITDTTQPEKHSANEKKIQREKGLTQHHVGKHLDTLETRTKEIISKRQNIKI
TPSDDTLGTLGDHDLRHLTSHIQRMIRDWVRLNAQQITELAEKEKVDLIVFESLRGFRAHAYDKLDLEQKRRLAFF
AYGRIRRKVAEKAVERGMRVLTVPYFESSQICAQCGRSQNDKNKLRDNKRKQSFQCEFSDCNYKTHSDENAARVLG
RVFWGEITLPTD (SEQ ID NO: 16)

>3300028920|Ga0272441_10052198_2|M
[aquatic-marine-marine sediment]
MLEPERFCARNDPGDPRGDWIRHAVFEVVAGWKLSDNLDQYNLNEELTASIEAAMDKTRTATAEALFERLMRREAS
NVMVLLKVAAEWIAAKYVHQMENWKRQKEEWEKEKAEWENSHTELTEQVRDKYNRIFKELDIKNKRPRVCTWKRLS
ENKDNCDWAGKRKLIGKSWVNHAALCYKYHEYSEAPKVKHRDHFIANANKYIKIRREYPQWSRDQAMKTLFKNEPR
ASYWFPKEWKMYLGALGIEENTIIGNYTGCLPHCLKITHKCRFNKHTNECRRYKDLMHERLTNEERQLEELYREWR
RNYLIAPGKPALRYPSARTLPTPKIFGSGYYRLDFERNQVHLRLDDMSQGDFISFGIKAWPRKYDYQPDTIDITSV
QVHFVGTRARIGFRFKVPHRESIFTIRQDDIDELRSRKYPRESQDQKFLEEVRKILNGFSEDQIAKLKIMAVDLG
SDEGGVAFFKGHVFEKGESLKIIKIDELFESKKNEEAEKAKGLNVHHVGRHLDVLQKKSQEIALLRQGMTNAPSND
MVQSLYPNDMRRLTSHIRRMIRDWVRLNSSQIIKLAEREQVELIVFESMRGFLAPGYDKIDPDKKRRLAFFAFGS1
RRRKVAEKAVERGMRVVTVPYHCSSQVCAKCGKEQEDKKRFRKNKEKREFVCEDKKCNHKTNSDINAAHVCGRVFWG
EINLLGKKIKIK (SEQ ID NO: 17)

>3300028920|Ga0272441_10052198_4|P
[aquatic-marine-marine sediment]
MTRTKYREERTLVRSINRLPKQDKAEFKKNVLRLRRYFEQYNLDVSETCQWLISYRGLNLDEICKTQLFWEFMLEP
ERFCARNDPGDPRGDWIRHAVFEVVAGWKLSDNLDQYNLNEELTASIEAAMDKTRTATAEALFERLMRREASNVMV
LLKVAAEWIAAKYVHQMENWKRQKEEWEKEKAEWENSHTELTEQVRDKYNRIFKELDIKNKRPRVCTWKRLSENKD
NCDWAGKRKLIGKSWVNHAALCYKYHEYSEAPKVKHRDHFIANANKYIKIRREYPQWSRDQAMKTLFKNEPRASYW
FPKEWKMYLGALGIEENTIIGNYTGCLPHCLKITHKCRFNKHTNECRRYKDLMHERLTNEERQLEELYREWRRNYL
IAPGKPALRYPSARTLPTPKIFGSGYYRLDFERNQVHLRLDDMSQGDFISFGIKAWPRKYDYQPDTIDITSVQVHF
VGTRARIGFRFKVPHRESIFTIRQDDIDELRSRKYPRESQDQKFLEEVRKILNGFSEDQIAKLKIMAVDLGSDEG
GVAFFKGHVFEKGESLKIIKIDELFESKKNEEAEKAKGLNVHHVGRHLDVLQKKSQEIALLRQGMTNAPSNDMVQS
LYPNDMRRLTSHIRRMIRDWVRLNSSQIIKLAEREQVELIVFESMRGFLAPGYDKIDPDKKRRLAFFAFGSIRRKV
AEKAVERGMRVVTVPYHCSSQVCAKCGKEQEDKKRFRKNKEKREFVCEDKKCNHKTNSDINAAHVCGRVFWGEINL
LGKKIKIK (SEQ ID NO: 18)

>3300016590|Ga0186947_1003_42|P
[aquatic-sediment-hot spring sediment]
MDNNRTRYREERTLVRSLRPLDGENRNAFKNRVNRLRIHFKNFNLDVSEICQWLMSIRPDAKKPDKETKSFWDFFL
NPESFFDPTINNVDIIRLNLFKVITGRESEANLIRYNLPLLLYESIILLKKQEPSDTARRLFARLKKMEPVHVMIL
LKAAAEWVYARYQRLMDNHEYQYKVWHDEKSAWENKHPELTPEIREKYNSIFKELGRKQGVTIRKNPRICNWEKLE
ENKDNCGYNGKRIQFGDKWKAHSMLCIEYRNFLRDNKITGKRIGFFATHAYNNYLKLRAHQPRLTKDEAFKRIFKSA
PNGIYWFPKAWKNYLQFMNLNELNLIRKYNANLPHCLEFKGDKDCQYNKHTELCQEYKTLLLEKFTEDELKLEGLY TABLE 4-continued Amino Acid Sequences of Representative
CLUST.019143 (Type V-G) Effector Proteins REWRKQYLSGPSKPAFRYPSCSKLPTPKIFGKRFHEIDFENSIVRLRLDDMPDGEYLTFKFKPWPNDYQPQPEEAE
ISSVHVHFVGTRARVGFRFKIAHKQSRFKTSQDEIDELRSRKYPRQAQDADFLKAAREKLLQSFKGENPTKEIKIM
AVDLGEYRGYISVYKGENIEISEPLSILKIDKLYDSLESAGVDKTDLAKYIKDHKGLIKEHVDSHLKVISEKANEI
TKHRPAGKKTGASNLKDYDLRSLTAHTGWMIRDWVRLNVSQIIRIAEKHEVDLIVLESLRGWKAPGYDEFDLRKKR
WLAFFSYGRIRHKLKEKAVERGMMVVTVPYYKSSQICSKCGKEQENKGLWKKNKNERLFICDYPGCGHRDNSDANA
AKVLAKIFWGEIVL (SEQ ID NO: 8)

>3300016590|Ga0186947_1003_42|M
[aquatic-sediment-hot spring sediment]
MSIRPDAKKPDKETKSFWDFFLNPESFFDPTINNVDIIRLNLFKVITGRESEANLIRYNLPLLLYESIILLKKQEP
SDTARRLFARLKKMEPVHVMILLKAAAEWVYARYQRLMDNHEYQYKVWHDEKSAWENKHPELTPEIREKYNSIFKE
LGRKQGVTIRKNPRICNWEKLEENKDNCGYNGKRIQFGDKWKAHSMLCIEYRNFLRDNKITGKRIGFFATHAYNYL
KLRAHQPRLTKDEAFKRIFKSAPNGIYWFPKAWKNYLQFMNLNELNLIRKYNANLPHCLEFKGDKDCQYNKHTELC
QEYKTLLLEKFTEDELKLEGLYREWRKQYLSGPSKPAFRYPSCSKLPTPKIFGKRFHEIDFENSIVRLRLDDMPDG
EYLTFKFKPWPNDYQPQPEEAEISSVHVHFVGTRARVGFRFKIAHKQSRFKTSQDEIDELRSRKYPRQAQDADFLK
AAREKLLQSFKGENPTKEIKIMAVDLGEYRGYISVYKGENIEISEPLSILKIDKLYDSLESAGVDKTDLAKYIKDH
KGLIKEHVDSHLKVISEKANEITKHRPAGKKTGASNLKDYDLRSLTAHTGWMIRDWVRLNVSQIIRIAEKHEVDLI
VLESLRGWKAPGYDEFDLRKKRWLAFFSYGRIRHKLKEKAVERGMMVVTVPYYKSSQICSKCGKEQENKGLWKKNK
NERLFICDYPGCGHRDNSDANAAKVLAKIFWGEIVL (SEQ ID NO: 7)

>3300010938|Ga0137716_10003017_35|M
[aquatic-thermal springs-hot spring fe si sediment]
MVASRYREARTLVRRLGRLPGEGEASFRAKLARLRKHFERFNVDVSELCQWLMGLRKQHCHKAGTASFGVLGDFLL
HPESSNVAPGEAEADRWRLLVFDAVAGICPAKQLTNAPMPRGLPEAMEREAKRLADLEWRRRNTTQSKLIDRLAIL
EPAHRLVLLKAAAEWVVSRYQRGLENWAARRGEWEKERHAWEKRHPALSEEVRQRFTEVFKSLNDPERTDKPGVRR
KNPRICPYERLRANIDNCIYAGEKGHGALCWKYAEFVKARKTRQPQFNDKRFAEDAEKVLPLLKQGMKRHQALQRL
FPRDRPHGQLAQQRFNENWTAYLQALGLKEERVVNRGRLPHCLKIGETHEKSKCAWNPHTELCKQYKRALDQFDEE
TLKLEPLYREWRRDYLAGPGKPQFRYPSSRELPMPKIFGAGFHEIDFDRSILRLRLEDMPEGEWIEFGFAPWPRGY
RPSKEEVKVKGAISSVHVNFVGVRARAGFRFDVRHRASRFQCTQDELDQLRSRAYPRRAQDREYLDAARKRLLESF
AEGEEAAKRELRLLAVDLGETGACAAVYHGHAHQKDVQLAILKINRLYTQLPEALEPDPHGRPEEGKRKYERDDPR
GVRKEHMGRHLKRMADGAASIAARRQGTMPATVTMAGHDFRGLKRHVTWMIRDWARHNAARIVAAAEEHGCDLIVF
ESLRGQKVPGYHELSSEKERDKRQLAMLSYGRIRHKVREKAVERGMRVVMVPDYRSSRLCSSCGHEQCAEKWQERR
WRENKKKRLFKCVCGEPAPTEKPHHGGSAPDRQRAARRDGPGPGKRPGMAADQAKQRCRCGAEMNSDANAARVLAR
VFWGEITPPASERSFAGSA (SEQ ID NO: 19)

>3300010938|Ga0137716_10003017_32|P
[aquatic-thermal springs-hot spring fe si sediment]
MGLRKQHCHKAGTASFGVLGDFLLHPESSNVAPGEAEADRWRLLVFDAVAGICPAKQLTNAPMPRGLPEAMEREAK
RLADLEWRRRNTTQSKLIDRLAILEPAHRLVLLKAAAEWVVSRYQRGLENWAARRGEWEKERHAWEKRHPALSEEV
RQRFTEVFKSLNDPERTDKPGVRRKNPRICPYERLRANIDNCIYAGEKGHGALCWKYAEFVKARKTRQPQFNDKRF
AEDAEKVLPLLKQGMKRHQALQRLFPRDRPHGQLAQQRFNENWTAYLQALGLKEERVVNRGRLPHCLKIGETHEKS
KCAWNPHTELCKQYKRALDQFDEETLKLEPLYREWRRDYLAGPGKPQFRYPSSRELPMPKIFGAGFHEIDFDRSIL
RLRLEDMPEGEWIEFGFAPWPRGYRPSKEEVKVKGAISSVHVNFVGVRARAGFRFDVRHRASRFQCTQDELDQLRS
RAYPRRAQDREYLDAARKRLLESFAEGEEAAKRELRLLAVDLGETGACAAVYHGHAHQKDVQLAILKINRLYTQLP
EALEPDPHGRPEEGKRKYERDDPRGVRKEHMGRHLKRMADGAASIAARRQGTMPATVTMAGHDFRGLKRHVTWMIR
DWARHNAARIVAAAEEHGCDLIVFESLRGQKVPGYHELSSEKERDKRQLAMLSYGRIRHKVREKAVERGMRVVMVP
DYRSSRLCSSCGHEQCAEKWQERRWRENKKKRLFKCVCGEPAPTEKPHHGGSAPDRQRAARRDGPGPGKRPGMAAD
QAKQRCRCGAEMNSDANAARVLARVFWGEITPPASERSFAGSA (SEQ ID NO: 20)

>3300006865|Ga0073934_10000021_236|M
[aquatic-thermal springs-hot spring sediment]
MHPSRYKTARTLVRRLCRLPGEDRSAFRSKVGLLRGHFEQFNVDVSELCQWLMSLRKRNKVPENPATFGALGDFLL
QPGLPGEETDEKEADRLRLAVFDAVAGFRMLEDRLAASIPASLSDAIRDEAVFLAGVRAAGKPSGLARVLARLEAC
APAQRLVLLKSAAEWIVARFLRGTENWMRQRAEWEKEKAAWEAAHPHLTPEVRAQFNKIFESLHDPENSGKPGVSR
KNPRICPWDRLKQNLDNCCYGEKGHSALCWRYQDFLKQRMGENRRDLKKNFSATAMDLAQICREWKIQHSRNALNNP
RVLDRLFAEHERRKQDKTKKESRSPKPRQGGYKANPKADYLRSFKAHWKAYLEHMKLNDTTVLERGCLPHCLSIKK
NGKESTCKWNKHTELCLEYKRSLAPLPDSVLELEPEYREWRRLYLHGPGRPHFRYPSAGELPLPKVFGEGFHQVDL
DRSIVRLRLEGAAEGEWLEFGFIPWPRGYQPSRREVLITSVQVHFVGTRPRAGFRFDVSHRTSRFGCSQDELDELR
SRRYPRQAQDKEFLAAARAQLIQTFEGGEAARQQMRVMSVDLGEGGACASIYEGRTHQKDESLKVIKIDRRYDQH
PEVLEKDVGAAKPQKFEKSDPRGVRKEHVARHLNRIAAGASAIAEHRRKERSDAECSVGELQEHDFRSLKRHIAWM
IRDWVRLNAAQIIDVAKQHCCDLIVFESQRGFRLPGYDELDRGKKQFRAILAFGRIRRKVVEKAVEHGMRVVTVPY
FASSQVCSACKRVQENRGSWRENKKKRVFACEFCKLKLNSDANASRVLARVFWGEIELPEPTRAHLPSKA (SEQ
ID NO: 5)

>3300006945|Ga0073933_1000004_588|P
[aquatic-thermal springs-hot spring sediment]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPNRYPGPGETEISSVHLHFVGTRPGRFRV
PHKRSRFDCTQEELDELRSRTFPRKAQDQKFLEAARKRLLETFPGNAEQELRLLAVDLGTDSARAAFFIGKTFQQA
FPPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

TABLE 4-continued

Amino Acid Sequences of Representative
CLUST.019143 (Type V-G) Effector Proteins >3300007071|Ga0073930_1000342_16|M
[aquatic-thermal springs-hot spring sediment]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>3300022554|Ga0212093_1000011_56|M
[aquatic-thermal springs-hot spring sediment]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>3300025094|Ga0209478_1000005_814|P
[aquatic-thermal springs-hot spring sediment]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>3300025105|Ga0209479_1000006_88|P
[aquatic-thermal springs-hot spring sediment]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>3300025310|Ga0209172_10000050_165|P
[aquatic-thermal springs-hot spring sediment]
MHPSRYKTARTLVRRLCRLPGEDRSAFRSKVGLLRGHFEQFNVDVSELCQWLMSLRKRNKVPENPATFGALGDFLL
QPGLPGEETDEKEADRLRLAVFDAVAGFRMLEDRLAASIPASLSDAIRDEAVFLAGVRAAGKPSGLARVLARLEAC
APAQRLVLLKSAAEWIVARFLRGTENWMRQRAEWEKEKAAWEAAHPHLTPEVRAQFNKIFESLHDPENSGKPGVSR
KNPRICPWDRLKQNLDNCCYGEKGHSALCWRYQDFLKQRMGENRRDKKNFSATAMDLAQICREWKIQHSRNALNNP
RVLDRLFAEHERRKQDKTKKESRSPKPRQGGYKANPKADYLRFKAHWKAYLEHMKLNDTTVLERGCLPHCLSIKK
NGKESTCKWNKHTELCLEYKRSLAPLPDSVLELEPEYREWRRLYLHGPGRPHFRYPSAGELPLPKVFGEGFHQVDL
DRSIVRLRLEGAAEGEWLEFGFIPWPRGYQPSRREVLITSVQVHFVGTRPRAGFRFDVSHRTSRFGCSQDELDELR
SRRYPRQAQDKEFLAAARAQLIQTFEGGEGAARQQMRVMSVDLGEGGACASIYEGRTHQKDESLKVIKIDRRYDOH
PEVLEKDVGAAKPQKFEKSDPRGVRKEHVARHLNRIAAGASAIAEHRRKERSDAECSVGELQEHDFRSLKRHIAWM
IRDWVRLNAAQIIDVAKQHCCDLIVFESQRGFRLPGYDELDRGKKQRFAILAFGRIRRKVVEKAVEHGMRVVTVPY
FASSQVCSACKRVQENRGSWRENKKKRVFACEFCKLKLNSDANASRVLARVFWGEIELPEPTRAHLPSKA (SEQ
ID NO: 5)

>3300019846|Ga0197078_1002_15|M
[aquatic-thermal springs-sediment]
MKNPKYREERTLTMGIRSFPLEDKSHFKEKVRKLRKFFEIFNKDVADLCQWLIVFRKGGKSENIPIWEFFINPLES
IKDISEDQADELKRKVLDVIIGNESINNIRNEKLPTEVLKYLENLDDNWNQSVQELFKRMKDKKPSHRQILLKAAS
NLIYSRYYKTLENREKQKEEWKKERDTWQRKNPDLKEDIRTKYTEVYKQLGIKRKAPRICEWEKLKNWKHNCTYSS TABLE 4-continued Amino Acid Sequences of Representative
CLUST.019143 (Type V-G) Effector Proteins NKQHTERCFDFNKLFSSADNKKKRKWFIDNAHLYLQYLSKSNQKDALKQLYHKKKGSEKWFGRLWNDYLKLMKISE
QDILTKYHCILPHCISENLGSAKYREYFDNSEYGFARSEFGKCANTYLGSRKKGSNKADSLQMVYGKHKSNIDERF
EEIWNDYLKFIKKTEEEAIIEYNHSLPVYLKSDYCQFRPHGDKCKQYRDLLADFTEVEKSLEKKYREWRKSYLSGP
GKPQFRYPSAKTIAIPKLFGSGYFRIDFEESILNLKLENDEWLSLGFKPWPKRKDYDIHYSDIEIPSVSIHFVGTR
AKVGFRFKVKHKESRFKVAQEEIDKLRSQKYPRQYQDNDFLKEARELLLKDPDKKNEMKILAFDWGETGAYAALF
TGEKYEKGFQLPVLKFEKLYCSDKFKEAWDQKKKEQKWSKDESKAKLKEYKLKGLTKGHVGKHLENISEKAVKIAE
IRGEKKDEKLLRPSDLRRLFSHSAWMIRDWVRLNTKQLIKIAEKNEVDLIVFESMRGSAPPSYDKLEEITEKIKWA
FFSLGRIRHKVTEKAVERGMRTITVPYVKSSQVCFDCGKEAEDKKKWQHHKTELTKFICEHCPADLNSDENAARVL
CKVFWGDITLPSTEWEK (SEQ ID NO: 21)

>3300023207|Ga0255811_11223672_52|P
[bioreactor-anaerobic-anaerobic digester digestate]
MTRIKYRQERTLVRGLQRLPNQDKAEFNKNVLGLRRHFEQFNLNVAELCQWLISFKPENPGSVCETKLFWEFMLEP
ENFCPDTYDRGPDWLRHEIFVLAAGWRTFEDIKAHNMPESLFESIKIASSKPRSKTAEALFIRLKSLEASHVMVLL
KSASEWLSTRYVRQSENWKQNEQEWQKKKAAWEDKHPELTPAIRDKYNAIFVELGISEKRPHVCSWKKLSENKDNC
DWAGERKNIGDKWISHSDLCIKYHEFARKLRSKQRQHFVDNANQYLELRRRYPQWTRDMAMNGLFKNVPLARNWFR
NAWTNYLNALNILETTILENYSGHLPHCEKLSDECVFKKHTDNCRRYKLLLGEKLSNQERELEETYREWRREFLAP
PNKPFLRYPSAQKLPTPKLFGRGYYDLDFTRHVVKLRLDDMPADNFVSFGFKPWPRGYDKKPGEINITSVHVHFIG
TRARVGFRFAVPHSDSRFSVSQDKIDELRSGGFPGKSQDQEFLNEARQRLLDGMNENQKSALRIMAVDLGTHRAAA
AFFTGCIFNKAKLLLKKKIDLLTEPKTDTTKPEKLSADEKKIQREKGLTQHHVGKHFETLEARTKEIISKRQNMKM
APSDDTPDIVGDHDLRHLTSHIRRMIRDWVRLNARQITELAEEENVDLIVFESMRGFRAPGYDKLDLKKKRRLAFF
AYGQIRRKVAEKAVERGMRVITVPYFKSSQICAQCGRSQNDKNKLRDNKWKQSFQCEFSDCNYKTHSDENAARVLG
RVFWGEITLPTD (SEQ ID NO: 1)

>RKX31836.1
[candidate division Zixibacteria bacterium Bacteria.]
MNRTRYREERTITRGMRRLPGEERKSFKAKVITLRRNFEQFNTDVSEICQWLMSIRPNGKHNIPNTEPFWDFILEP
HNFVVNQEETNIDSVRLVVFEMAVGWRQVTDVANFELERQLLMSLESIQSVPRTIAAKRMLQRIKNYEFQHKMVLL
RSAVEWINTRFIRTYKNWEMNIKEFLEKKKVWENDHPKLTEEIRNTFNKVFDELEISKKNPNICRWSHLKKNRDNC
NYAGVRIKVGGEYNNHSEKCKRYQDFLKKHSAHKKYFAANAMMYINIRKKRRDLTKREAIKVLLDKIPQARSWFPQ
AWDNYLEYLGLNEISLINKFDGQLPHCLRLDTECIYNVHTQSCRKYYVLLKDLPDKYLSLEETYREWRKYFLREPR
KPVFAYPSTRQRTVSKIFGRDYFEADYDNSIIKLRLDDMAEGQFLSFGFKPWPVDYDVQPIDTEITSVLVHFIGTR
ARVGFRFKMPHRPSRINIKQDELDELRSRSRLIQEKDQALLEKVRLRLDGFIGIFDKELRVLAVDLGTSSCATAF
FVGRQFQESSRLQIVKYDRVYKSNYEIKKRRNNKGIDKQKQLLFKEKGLNQYHIKVHLDKLAEQNKQIIKKREASG
NPTPTEQDMRRLSLHIGWMHRDWVRINASQIIKSAKKLRADLIVFESLRDFRPMMFNEFDIDKKRRLAFFPFGLIR
HKVIEKAVESGMRVVTVPYMFSSQFCGACGRQQNDKKRLQKNKTDKRGACFICEYNDCAFEGDPDENAARVLGGVF
WGNIGLPLS (SEQ ID NO: 4)

>FLYL01000025_159|P
[hot springs metagenome]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>ORFD01000444_4|P
[sediment metagenome]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEEENQVDLIVLESLRGFRPPGYENLDQEKKRRVAFFAHGRI
RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>ORXB01000005_848|P
[sediment metagenome]
MAQASSTPAVSPRPRPRYREERTLVRKLLPRPGQSKQEFRENVKKLRKAFLQFNADVSGVCQWAIQFRPRYGKPAE
PTETFWKFFLEPETSLPPNDSRSPEFRRLQAFEAAAGINGAAALDDPAFTNELRDSILAVASRPKTKEAQRLFSRL
KDYQPAHRMILAKVAAEWIESRYRRAHQNWERNYEEWKKEKQEWEQNHPELTPEIREAFNQIFQQLEVKEKRVRIC
PAARLLQNKDNCQYAGKNKHSVLCNQFNEFKKNHLQGKAIKFFYKDAEKYLRCGLQSLKPNVQGPFREDWNKYLRY
MNLKEETLRGKNGGRLPHCKNLGQECEFNPHTALCKQYQQQLSSRPDLVQHDELYRKWRREYWREPRKPVFRYPSV
KRHSIAKIFGENYFQADFKNSVVGLRLDSMPAGQYLEFAFAPWPRNYRPQPGETEISSVHLHFVGTRPRIGFRFRV
PHKRSRFDCTQEELDELRSRTFPPRKAQDQKFLEAARKRLLETFPGNAEQELRLLAVDLGTDSARAAFFIGKTFQQA
FPLKIVKIEKLYEQWPNQKQAGDRRDASSKQPRPGLSRDHVGRHLQKMRAQASEIAQKRQELTGTPAPETTTDQAA
KKATLQPFDLRGLTVHTARMIRDWARLNARQIIQLAEEENQVDLIVLESLRGFRPPGYENLDQEKKRRVAFFAHGRI TABLE 4-continued Amino Acid Sequences of Representative
CLUST.019143 (Type V-G) Effector Proteins RRKVTEKAVERGMRVVTVPYLASSKVCAECRKKQKDNKQWEKNKKRGLFKCEGCGSQAQVDENAARVLGRVFWGEI
ELPTAIP (SEQ ID NO: 6)

>3300027640|Ga0209347_1003758_14|P
[terrestrial-deep subsurface]
MSNTRYSESRTLVRRLRRLPGESREEFRGKVRRLRKQFAQFNVNASELCQWLMSLRPGGKKASDRTKEFWEFFLEP
ERFLENQDDDRCDACRLAVFDVAAGLAPADRLGDYGVSQALAESVHVIGQISLTPTAAKLFTRLCGFEASHRQVLL
KAAAEWIVAHYLRGYENWVRRHEEWEKEKARWEASHPELTQAARDDFNRIFKDLGIERKRPRVCTGERLKANKDDC
DWAGERIPVGGTWRNHSSLCVKYWRFLKEYPRKARVPRQFREFFVTNAKTYMDLRRTSRGDRSVTMAAFLRKQRNA
QWFPQAWEAYLKALEVNEQTVLAAGYGLPHCTEIGPDADCQFNKHTADCEKYRRALDARPDLLPLEKLYRHWRREY
LSGPGKPCFQYPSQRKLPMPKIFGRGYFRVDLASSIIELRMEGGRDFERFRIAAWPSDYTPSAQEAQITSVHVSFV
GTRALAGFRFEVPHKASRFAAGQDQIDELRSRKYPRRAQDAEFLVAARKRLLESFAGGAEHDVRILAVDLGTSNGA
VAVFRGRSLEKAMPLDVIKLEKLHSSSPKENRGAGPEPSEEERKKARARGLRPSHVGRHLENWALAAREIANQRGN
EADGPATLGDHDLRRFSLHIRWMIRDWVRLNVSQIIEAAEGNHVDLIVFESMRGWRAPGYDTVDDEKKRRLAFFAH
GRIRHKIREKAVERGMRVVTVPYFMSSQFCGSCGTQQQDTRKLKTNKRERTSFTCENCGHRANSDENAAQVLAKVF
WGDVVLPEDPDDCS (SEQ ID NO: 22)

>3300027640|Ga0209347_1003758_16|M
[terrestrial-deep subsurface]
MVRRLRRLPGESREEFRGKVRRLRKQFAQFNVNASELCQWLMSLRPGGKKASDRTKEFWEFFLEPERFLENQDDDR
CDACRLAVFDVAAGLAPADRLGDYGVSQALAESVHVIGQISLTPTAAKLFTRLCGFEASHRQVLLKAAAEWIVAHY
LRGYENWVRRHEEWEKEKARWEASHPELTQAARDDFNRIFKDLGIERKRPRVCTGERLKANKDDCDWAGERIPVGG
TWRNHSSLCVKYWRFLKEYPRKARVPRQFREFFVTNAKTYMDLRRTSRGDRSVTMAAFLRKQRNAQWFPQAWEAYL
KALEVNEQTVLAAGYGLPHCTEIGPDADCQFNKHTADCEKYRRALDARPDLLPLEKLYRHWRREYLSGPGKPCFQY
PSQRKLPMPKIFGRGYFRVDLASSIIELRMEGGRDFERFRIAAWPSDYTPSAQEAQITSVHVSFVGTRALAGFRFE
VPHKASRFAAGQDQIDELRSRKYPRRAQDAEFLVAARKRLLESFAGGAEHDVRILAVDLGTSNGAVAVFRGRSLEK
AMPLDVIKLEKLHSSSPKENRGAGPEPSEEERKKARARGLRPSHVGRHLENWALAAREIANQRGNEADGPATLGDH
DLRRFSLHIRWMIRDWVRLNVSQIIEAAEGNHVDLIVFESMRGWRAPGYDTVDDEKKRRLAFFAHGRIRHKIREKA
VERGMRVVTVPYFMSSQFCGSCGTQQQDTRKLKTNKRERTSFTCENCGHRANSDENAAQVLAKVFWGDVVLPEDPD
DCS (SEQ ID NO: 23)

>3300027657|Ga0256865_1003050_2 M
[terrestrial-soil]
MAVTRYREERTLVRGLRRLPGQSREQFRKNVLLLRRHFERFNVDVSDICQWMMGLRPKDGEVTPATQPLWDFMLEP
SDGQGNAQGDPDRMRLLAFRVATGVEHSQSGVRLPLHVQESLRHVAALTSTESARRLILRFQQLEQSHQMILLKSA
SEWVRTRYSNANENWQRNRPLWEKEKAEWEKEHPALTPDACRKFSDIFKELGIKDKRPRICGWNRLKLPKDNCDYA
GERVGGGRHAPLCKFYREFQAGLRREYKKQFPDNALKYLALRKQKGHTQAVVLQQFCAKDRRKSGWFPKAWMTYLQ
KLNVTEETLIQRYQGQLPHCVKIDNKTGCSFNPHTNDCLEYKKRILKLPESDRELETQYREWRRDYLSGPRKPSFR
YPSSRNLPTPKIFGAGYYEADFTRSMLRLRLDDMPRGRFIEFGFKPWPSDYDIQPVSTQITSAHIHFIGTRARVGF
RFAVAARPSRLRISQDEIDALRRQYPRAAQDQQFLDHVRPLILDSFAGNPKQELRILTIDLGTSGGAAAAFCGVTL
VKSEVLKVIKLDLLDREDKRSPTSGLGEGHVGRHLEALSKEAAKIAQHRTTWKNPGLRPFDERQLTSHIRWM
IRDWVRLNAQQIIEIAERENADLILFESMRGYYPKARDKYDSAQKVRLGFFSYGAIRRKVAEKAVERGMRILTLPY
KFSSQICSKCGRKQENRGLKTKKAKRLFKCEHTGCGTELNSDENAARVLAGVFWGTIKLPEKAVVSHT (SEQ ID
NO: 24)

TABLE 5A

Representative CLUST.019143 (Type V-G) Effectors and Direct Repeats

| Effector Accession | Direct Repeat Nucleotide Sequence |
| --- | --- |
| RIK66295.1 (SEQ ID NO: 15) | GGTGCGACCGGCCGTCGATTGACCGGTTTCGACACC (SEQ ID NO: 25) |
| JRYK01000049_75\|P (SEQ ID NO: 2) | GGTGCGGCAGCCGGTAGAACTGCGGCTTCCGACACC (SEQ ID NO: 10) |
| JRYK01000049_79\|M (SEQ ID NO: 3) | GGTGCGGCAGCCGGTAGAACTGCGGCTTCCGACACC (SEQ ID NO: 10) |
| UOQF01000587_2\|M (SEQ ID NO: 16) | GTTGTAGCGCCCCCTGAATTAGCGGTTTCCGACACC (SEQ ID NO: 26) |
| UOQK01013695_2\|M (SEQ ID NO: 16) | GTTGTAGCGCCCCCTGAATTAGCGGTTTCCGACACC (SEQ ID NO: 26) |
| 3300028920\|Ga0272441_10052198_2\|M (SEQ ID NO: 17) | GGTGTAAGTCCGACTGAATGCGAGGTTTCCGACACC (SEQ ID NO: 27) |
| 3300028920\|Ga0272441_10052198_4\|P (SEQ ID NO: 18) | GGTGTAAGTCCGACTGAATGCGAGGTTTCCGACACC (SEQ ID NO: 27) |
| 3300016590\|Ga0186947_1003_42\|P (SEQ ID NO: 8) | GCTGTGACTCACCGGCATTTGCGGGGTTCTTACACC (SEQ ID NO: 28) |

TABLE 5A-continued

Representative CLUST.019143 (Type V-G) Effectors and Direct Repeats

| Effector Accession | Direct Repeat Nucleotide Sequence |
| --- | --- |
| 3300016590\|Ga0186947_1003_42\|M (SEQ ID NO: 7) | GCTGTGACTCACCGGCATTTGCGGGGTTCTTACACC (SEQ ID NO: 28) |
| 3300010938\|Ga0137716_10003017_35\|M (SEQ ID NO: 19) | GTTGTGACCGCCCCCGGAATCACGGTTTGCGACACC (SEQ ID NO: 29) |
| 3300010938\|Ga0137716_10003017_32\|P (SEQ ID NO: 20) | GTTGTGACCGCCCCCGGAATCACGGTTTGCGACACC (SEQ ID NO: 29) |
| 3300006865\|Ga0073934_10000021_236\|M (SEQ ID NO: 5) | GGTGTAGCGGGCCTCAAAAACACGGCATCCGACACC (SEQ ID NO: 30) |
| 3300006945\|Ga0073933_1000004_588\|P (SEQ ID NO: 6) | GGTGGAAAGGGCCGGAGATTTACCGGCTCTGACACC (SEQ ID NO: 13) |
| 3300007071\|Ga0073930_1000342_16\|M (SEQ ID NO: 6) | GGTGGAAAGGGCCGGAGATTTACCGGCTCTGACACC (SEQ ID NO: 13) |
| 3300022554\|Ga0212093_1000011_56\|M (SEQ ID NO: 6) | GGTGGAAAGGGCCGGAGATTTACCGGCTCTGACACC (SEQ ID NO: 13) |
| 3300025094\|Ga0209478_1000005_814\|P (SEQ ID NO: 6) | GGTGGAAAGGGCCGGAGATTTACCGGCTCTGACACC (SEQ ID NO: 13) |
| 3300025105\|Ga0209479_1000006_88\|P (SEQ ID NO: 6) | GGTGGAAAGGGCCGGAGATTTACCGGCTCTGACACC (SEQ ID NO: 13) |
| 3300025310\|Ga0209172_10000050_165\|P (SEQ ID NO: 5) | GGTGTAGCGGGCCTCAAAAACACGGCATCCGACACC (SEQ ID NO: 30) |
| 3300019846\|Ga0197078_1002_15\|M (SEQ ID NO: 21) | GGTTTGCAAACAGCGAGAACATCTGTGTTTTGGTGGTAGTTACAAC (SEQ ID NO: 31) |
| 3300019846\|Ga0197078_1002_15\|M (SEQ ID NO: 21) | GTTTGCAAACAGCGAGAACATCTGTGTTTTGGTGGT (SEQ ID NO: 32) |
| 3300023207\|Ga0255811_11223672_52\|P (SEQ ID NO: 1) | GTTGTAGCGGCCCCTGAATTAGCGGTTTCCGACACC (SEQ ID NO: 9) |
| RKX31836.1 (SEQ ID NO: 4) | GTTGGAGTCAGCAAGGAATCAACGGTTTTGGACACC (SEQ ID NO: 11) |
| FLYL01000025_159\|P (SEQ ID NO: 6) | GGTGGAAAGGGCCGGAGATTTACCGGCTCTGACACC (SEQ ID NO: 13) |
| ORFD01000444_4\|P (SEQ ID NO: 6) | GGTGGAAAGGGCCGGAGATTTACCGGCTCTGACACC (SEQ ID NO: 13) |
| ORXB01000005_848\|P (SEQ ID NO: 6) | GGTGGAAAGGGCCGGAGATTTACCGGCTCTGACACC (SEQ ID NO: 13) |
| 3300027640\|Ga0209347_1003758_14\|P (SEQ ID NO: 22) | GGTGGAGCCGGCCGTGAATTAGGGGGTTTCGACACC (SEQ ID NO: 33) |
| 3300027640\|Ga0209347_1003758_16\|M (SEQ ID NO: 23) | GGTGGAGCCGGCCGTGAATTAGGGGGTTTCGACACC (SEQ ID NO: 33) |
| 3300027657\|Ga0256865_1003050_2\|M (SEQ ID NO: 24) | GGTGTTGTGAACCCTGAAAGAACGGATTCCGACACC (SEQ ID NO: 34) |

TABLE 5B

Example CLUST.019143 (Type V-G) pre-crRNA sequences

| Effector Accession | Example pre-crRNA sequence | Spacer Lens |
| --- | --- | --- |
| UOQK01013695_2\|M (SEQ ID NO: 16) | GUUGUAGCGCCCCCUGAAUUAGCGGUUUCCGACACCNNNNNNNNNNNNNNNNNNNNNNNNNNGUUGUAGCGCCCCCUGAAUUAGCGGUUUCCGACACC (SEQ ID NO: 150) | 27-28 |

TABLE 5B-continued

Example CLUST.019143 (Type V-G) pre-crRNA sequences

| Effector Accession | Example pre-crRNA sequence | Spacer Lens |
|---|---|---|
| JRYK01000049_75\|P (SEQ ID NO: 2) | GGUGCGGCAGCCGGUAGAACUGCGGCUUCCGACACCNNNNNNNNNNNNNN NNNNNNNNNNNNNNNNGGUGCGGCAGCCGGUAGAACUGCGGCUUCCGACAC C (SEQ ID NO: 151) | 29-30 |
| 3300028920\|Ga0272441_ 10052198_2\|M (SEQ ID NO: 17) | GGUGUAAGUCCGACUGAAUGCGAGGUUUCCGACACCNNNNNNNNNNNNNN NNNNNNNNNNNNNNNNGGUGUAAGUCCGACUGAAUGCGAGGUUUCCGACAC C (SEQ ID NO: 152) | 29-30 |
| 3300019846\|Ga0197078_ 1002_15\|M (SEQ ID NO: 21) | GGUUUGCAAACAGCGAGAACAUCUGUGUUUUGGUGGUAGUUACAACNNNN NNNNNNNNNNNNNNNNNNNNNNNGGUUUGCAAACAGCGAGAACAUCUG UGUUUUGGUGGUAGUUACAAC (SEQ ID NO: 153) | 29-30 |
| 3300019846\|Ga0197078_ 1002_15\|M (SEQ ID NO: 21) | GUUUGCAAACAGCGAGAACAUCUGUGUUUUGGUGGUNNNNNNNNNNNNNN NNNNNNNNNNNNNNNNGUUUGCAAACAGCGAGAACAUCUGUGUUUUGGUGG U (SEQ ID NO: 154) | 29-30 |
| 3300025105\|Ga0209479_ 1000006_88\|P (SEQ ID NO: 6) | GGUGGAAAGGGCCGGAGAUUUACCGGCUCUGACACCNNNNNNNNNNNNNN NNNNNNNNNNNNNNNNGGUGGAAAGGGCCGGAGAUUUACCGGCUCUGACA CC (SEQ ID NO: 155) | 29-30 |
| FLYL01000025_159\|P (SEQ ID NO: 6) | GGUGGAAAGGGCCGGAGAUUUACCGGCUCUGACACCNNNNNNNNNNNNNN NNNNNNNNNNNNNNNNGGUGGAAAGGGCCGGAGAUUUACCGGCUCUGACA CC (SEQ ID NO: 156) | 29-30 |
| 3300027640\|Ga0209347_ 1003758_14\|P (SEQ ID NO: 22) | GGUGGAGCCGGCCGUGAAUUAGGGGGUUUCGACACCNNNNNNNNNNNNNN NNNNNNNNNNNNNNNNGGUGGAGCCGGCCGUGAAUUAGGGGGUUUCGACA CC (SEQ ID NO: 157) | 27-30 |
| 3300027640\|Ga0209347_ 1003758_16\|M (SEQ ID NO: 23) | GGUGGAGCCGGCCGUGAAUUAGGGGGUUUCGACACCNNNNNNNNNNNNNN NNNNNNNNNNNNNNNNGGUGGAGCCGGCCGUGAAUUAGGGGGUUUCGACA CC (SEQ ID NO: 158) | 27-30 |
| 3300027657\|Ga0256865_ 1003050_2 M (SEQ ID NO: 24) | GGUGUUGUGAACCCUGAAAGAACGGAUUCCGACACCNNNNNNNNNNNNNN NNNNNNNNNNNNNNNNGGUGUUGUGAACCCUGAAAGAACGGAUUCCGACA CC (SEQ ID NO: 159) | 29-30 |
| UOQF01000587_2\|M (SEQ ID NO: 16) | GUUGUAGCGCCCCCUGAAUUAGCGGUUUCCGACACCNNNNNNNNNNNNNN NNNNNNNNNNNNNNNNGUUGUAGCGCCCCCUGAAUUAGCGGUUUCCGACA CC (SEQ ID NO: 160) | 29-31 |
| 3300023207\|Ga0255811_ 11223672_52\|P (SEQ ID NO: 1) | GUUGUAGCGGCCCCUGAAUUAGCGGUUUCCGACACCNNNNNNNNNNNNNN NNNNNNNNNNNNNNNNGUUGUAGCGGCCCCUGAAUUAGCGGUUUCCGACA CC (SEQ ID NO: 161) | 29-31 |
| 3300010938\|Ga0137716_ 10003017_35\|M (SEQ ID NO: 19) | GUUGUGACCGCCCCCGGAAUCACGGUUUGCGACACCNNNNNNNNNNNNNN NNNNNNNNNNNNNNNNGUUGUGACCGCCCCCGGAAUCACGGUUUGCGACA CC (SEQ ID NO: 162) | 29-33 |
| 3300010938\|Ga0137716_ 10003017_32\|P (SEQ ID NO: 20) | GUUGUGACCGCCCCCGGAAUCACGGUUUGCGACACCNNNNNNNNNNNNNN NNNNNNNNNNNNNNNNGUUGUGACCGCCCCCGGAAUCACGGUUUGCGACA CC (SEQ ID NO: 163) | 29-33 |
| 3300006865\|Ga0073934_ 10000021_236\|M (SEQ ID NO: 5) | GGUGUAGCGGGCCUCAAAAACACGGCAUCCGACACCNNNNNNNNNNNNNN NNNNNNNNNNNNNNNNGGUGUAGCGGGCCUCAAAAACACGGCAUCCGA CACC (SEQ ID NO: 164) | 31-33 |
| 3300025310\|Ga0209172_ 10000050_165\|P (SEQ ID NO: 5) | GGUGUAGCGGGCCUCAAAAACACGGCAUCCGACACCNNNNNNNNNNNNNN NNNNNNNNNNNNNNNNGGUGUAGCGGGCCUCAAAAACACGGCAUCCGA CACC (SEQ ID NO: 165) | 31-33 |
| 3300016590\|Ga0186947_ 1003_42\|P (SEQ ID NO: 8) | GCUGUGACUCACCGGCAUUUGCGGGGUUCUUACACCNNNNNNNNNNNNNN NNNNNNNNNNNNNNNNNNGCUGUGACUCACCGGCAUUUGCGGGG UUCUUACACC (SEQ ID NO: 166) | 37-39 |
| 3300016590\|Ga0186947_ 1003_42\|M (SEQ ID NO: 7) | GCUGUGACUCACCGGCAUUUGCGGGGUUCUUACACCNNNNNNNNNNNNNN NNNNNNNNNNNNNNNNNNGCUGUGACUCACCGGCAUUUGCGGGG UUCUUACACC (SEQ ID NO: 167) | 37-39 |

Example 2. Identification of Transactivating RNA Elements

In addition to an effector protein and an RNA guide (e.g., a crRNA), some CRISPR systems also include an additional small RNA that activates robust enzymatic activity referred to as a transactivating RNA (tracrRNA). Such tracrRNAs typically include a complementary region that hybridizes to the crRNA. The crRNA-tracrRNA hybrid forms a complex with an effector resulting in the activation of programmable enzymatic activity.

tracrRNA sequences can be identified by searching genomic sequences flanking CRISPR arrays for short sequence motifs that are complementary to the direct repeat portion of the crRNA. Search methods include exact or degenerate sequence matching for the complete direct repeat (DR) or DR subsequences. For example, a DR of length n nucleotides can be decomposed into a set of overlapping 6-10 nt kmers. These kmers can be aligned to sequences flanking a CRISPR locus, and regions of homology with 1 or more kmer alignments can be identified as DR homology regions for experimental validation as tracrRNAs. Alternatively, RNA cofold free energy can be calculated for the complete DR or DR subsequences and short kmer sequences from the genomic sequence flanking the elements of a CRISPR system. Flanking sequence elements with low minimum free energy structures can be identified as DR homology regions for experimental validation as tracrRNAs.

tracrRNA elements frequently occur within close proximity to CRISPR associated genes or a CRISPR array. As an alternative to searching for DR homology regions to identify tracrRNA elements, non-coding sequences flanking CRISPR associated proteins or the CRISPR array can be isolated by cloning or gene synthesis for direct experimental validation of tracrRNAs.

Experimental validation of tracrRNA elements can be performed using small RNA sequencing of the host organism for a CRISPR system or synthetic sequences expressed heterologously in non-native species. Alignment of small RNA sequences from the originating genomic locus can be used to identify expressed RNA products containing DR homology regions and stereotyped processing typical of complete tracrRNA elements.

Complete tracrRNA candidates identified by RNA sequencing can be validated in vitro or in vivo by expressing the crRNA and effector in combination with or without the tracrRNA candidate, and monitoring the activation of effector enzymatic activity.

In engineered constructs, the expression of tracrRNAs can be driven by promoters including, but not limited to U6, U1, and H1 promoters for expression in mammalian cells or J23119 promoter for expression in bacteria.

In some instances, a tracrRNA can be fused with a crRNA and expressed as a single RNA guide.

In some instances, the CLUST.019143 (Type V-G CRISPR-Cas effector protein) system includes a tracrRNA that includes a direct repeat homology sequence listed in TABLE 6.

In some instances, the CLUST.019143 (Type V-G CRISPR-Cas effector protein) system includes a tracrRNA encoded by a non-coding sequence (or fragment thereof) listed in TABLE 7. Note that in (SEQ ID NO: 131), the Cas12g1 tracrRNA sequence is indicated in bold font.

TABLE 6

Direct Repeat Homology-containing Regions of Representative CLUST.019143 (Type V-G) Systems

| Effector accession | Homologous Region |
| --- | --- |
| 3300027657Ga0256865_1003050_2\|M | TCCGTTCTT (SEQ ID NO: 100) |
| 3300027640\|Ga0209347_1003758_16\|M | AAACCCC (SEQ ID NO: 101) |
| 3300027640Ga0209347_1003758_16\|M | CCTAATT (SEQ ID NO: 102) |
| 3300028920\|Ga0272441_10052198_2\|M | GGTGTCGGAA (SEQ ID NO: 103) |
| JRYK01000049_79\|M | CGGCTGCCG (SEQ ID NO: 104) |
| RIK66295.1 | TCGACGG (SEQ ID NO: 105) |
| RIK66295.1 | GGTGTCG (SEQ ID NO: 106) |
| RIK66295.1 | TCGACGG (SEQ ID NO: 105) |
| RIK66295.1 | CGACGGC (SEQ ID NO: 107) |
| 3300006865\|Ga0073934_10000021_236\|M | GTGTTTTTG (SEQ ID NO: 108) |
| 3300010938\|Ga0137716_10003017_35\|M | TTCCGGGG (SEQ ID NO: 109) |
| 3300023207\|Ga0255811_11223672_52\|P | GGAAACCG (SEQ ID NO: 110) |
| 3300023207\|Ga0255811_11223672_52\|P | GGGGCCGC (SEQ ID NO: 111) |
| 3300023207\|Ga0255811_11223672_52\|P | GAAACCGC (SEQ ID NO: 112) |
| 3300006945\|Ga0073933_1000004_588\|P | GAGCCGGTAAAT (SEQ ID NO: 113) |
| 3300016590\|Ga0186947_1003_42\|M | AATGCCG (SEQ ID NO: 114) |
| 3300019846\|Ga0197078_1002_15\|M | TGTAACT (SEQ ID NO: 115) |
| UOQF01000587_2\|M | GCTAATT (SEQ ID NO: 116) |

TABLE 7

Direct Repeat Homology-containing Sequences of Representative CLUST.019143 (Type V-G) CRISPR-Cas Systems >3300027657|Ga0256865_1003050_2|M
TCCGTTCTTCTTTGTAGGGTGTTGTGAACCCTGAAAGAACGGCGGGTGGCCCGGACCTTGGGGCGTGTTGAAAAA
CCCGTTTGTCGTCAGTTGATCGGTGAAGGTTATCAAGCGATGGCGATCCTGTAGTTGAGATCGACGGGGTTGGTG
TCAGACCGA (SEQ ID NO: 117)

TABLE 7-continued

Direct Repeat Homology-containing Sequences
of Representative CLUST.019143 (Type V-G) CRISPR-Cas Systems >3300027640|Ga0209347_1003758_16|M
AACAGCGACGAAAACGCCGCACAGGTGCTGGCGAAGGTGTTCTGGGGCGACGTCGTTCTACCCGAGGATCCGGAC
GATTGCTCTTGACGAAGATATCGAAGGTGGTATAGTGCCCTTGTGTCCTCGTCGTGAGTCGATAATGGCTCGGAC
AAACCCCGGCGGAGCCTTCGGTGCCAACGGGAGGAACCTGAGCCCGGAGGATACAAACTCTCTAATTCGTGGTTG
ATATGGCGATCAAGAATGCGGTTTCTTTCAGGCAATTGTGTCGCAACTCTTTGTCGATCCAGGGATTACGACGGG
ACA (SEQ ID NO: 118)

>3300027640|Ga0209347_1003758_16|M
CCAGACAGCGAAAATGCTGAATAATCCCGGGACGGCATACCTAATTGGGTTCCAGATTGCCCAGCAGGCAGAAG
AGAGCGTTTATCGCATTTGGGGTGCCGGCGGAGAGGGGGCGGGCCAAGGGTGTCACTGGATGTCTCCGCTGGTAC
CCGGCAAAGCGTCAAACGCAATCAATCCCGGCCGAAGGCCTTCCGCT (SEQ ID NO: 119)

>3300028920|Ga0272441_10052198_2|M
AGTACGCGGGCACGCGGGGGCGTGTTTAGTACGCAGGCACGCGGGGGCGTGTTTAGTACGCGGGGGCGTGATTAG
TACAAAGGGGCAAGTCAGGTATACATCATTAAAGATGTCGAAACCGCAGGGGTTTCGACCTACTCGAAGAAGAA
GGTGTCGGAACGGCCTGCATCATGGGGTTTGGGAGGGGGATTGGGGGCTATTTGAATCGAAACAAAGTTGATATT
GTCCCTATGCGGGGGATTGTTTGTAGTGTTGTTCGAGTAAGACCAGGTTTTCATCGGGGATGCGGCCTTTTTCAA
AAGAGTCGAC (SEQ ID NO: 120)

>JRYK01000049_79|M
CGAGCGCGCGCTTCAGCACGAAGCACGAGGTGCGGCTGCCGGTTGCATTGCGGCAGAATGATTGGCCCGCCTGTT
CACGCTTTCCCGACCGGCAGTGGAAAACAAACGTCCCGCACGTCGCAGTTCGTGGCTTAGTTGATGCGTGCGCGT
GGGCCGATTGACGGGCGCGCTCGGCTCCGCCTCGCGGCTAA (SEQ ID NO: 121)

>RIK66295.1
TTTCGACACCTGCGCACCGACTTCAAAGCACCATCGGTTGGGTGCGACCGGCCGTCGATTGACCGGTTTCGACAC
CCCGCTTTGCACAGCGGCAGCAGACAAGGATGGTGCGACCGGCCGTCGATTGACCGGTTTCGACACCACTCCGCC
TCGACGGTCTTAACCAGTTCTGGGTGCGACCGGCCGTCGATTGACCGGTTTCGACACCCCTGGACGTGTCGGGCAA
TACTTCTGTCGGAGGTGCGACCGGCCGTCGATTGACCGGTTTCGACACCTACGCCACGGCAAAGCACCTGATCAG
CTCGGGT (SEQ ID NO: 122)

>RIK66295.1
TGCTCCACTGGGCGATGTATGCCTGCACCACTGGGGGTGCTGCACGCGGCGGCGCAGCGCCTACAATGGCGCCGC
GGAAGGGGAGCGCGGCGCGGTCATGGAACCCACGACGATTGAGATCAGGAACGCGCGGGAGCATAACCTGCGGTC
GGTGTCGCTTTCGTTGCCGCGGGGGAAGCTGATTGTCTTCACCGGGGTTTCGGGCAGCGGGAAGAGTTCGCTGGC
GTTTGACACGCTCTATGCCGAGGGGCAGCGGCGGTATATCGAGTCGTTGTCGTCGTATGCCCGACAGTTCATGGG
GCAGATG (SEQ ID NO: 123)

>RIK66295.1
TATGCCGAGGGGCAGCGGCGGTATATCGAGTCGTTGTCGTCGTATGCCCGACAGTTCATGGGGCAGATGGCCAAG
CCGGACTGCGATCAGATCACGGGGCTTTCGCCATCGATCGCGATTCAGCAGAAGACGACGGGATGGAATCCGCGG
TCGACGGTGGGGACGACGACGGCGATCTATGACTTTCTGCGCGTGCTGTACGCGCGGATCGGGACGCAGCATTGC
ACGCAGTGTGGGCGGGCGATCACGGCGCAGTCTCGCGAGCAGATCGCGGCGGGGATCTTGAGCGCGTTTAATCCG
CGCCGCG (SEQ ID NO: 124)

>RIK66295.1
GGCGGTATATCGAGTCGTTGTCGTCGTATGCCCGACAGTTCATGGGGCAGATGGCCAAGCCGGACTGCGATCAGA
TCACGGGGCTTTCGCCATCGATCGCGATTCAGCAGAAGACGACGGGATGGAATCCGCGGTCGACGGTGGGGACGA
CGACGGCGATCTATGACTTTCTGCGCGTGCTGTACGCGCGGATCGGGACGCAGCATTGCACGCAGTGTGGGCGGG
CGATCACGGCGCAGTCTCGCGAGCAGATCGCGGCGGGGATCTTGAGCGCGTTTAATCCGCGCCGCGATCCCACCT
ATCAGAG (SEQ ID NO: 125)

>3300006865|Ga0073934_10000021_236|M
AGCCGACGAGAGCGCATTTGCCCTCCAAGGCTTGACTCTTTTTCCAGCCGTTGGCTACGCTGTTAATGCCCTTCGA
GTCGCATTGTCCTGCATACGCCCGGCGGAACTTCGGTACCAACGGGACGGACCCCGGACACGAAAGGCAAATGCT
GTGTTTTTGTGGCCTGCCGGTTTGGAACGTCACGGTTTTGTGGGCGGTTTTTTTTGACGCAAGTCCTTGTCAGAA
GCGAATTTGCAGACGAGAC (SEQ ID NO: 126)

>3300010938|Ga0137716_10003017_35|M
TTCGAGTCATTTGCCTGGAATACGCCCTGCGGACGTTTTCGACCAACGGGATGGACCCCTGGCGCTGAAGGCAGA
ATCGGTTTTTCCCGGGCGGTTTCGGGAGGCGAACGAGCGGTTTTTTCGAGGTGGAACTGGCGCAAGTCGTGTCCG
TTCCGGGGCTTGTTTGCCAAGAG (SEQ ID NO: 127)

>3300023207|Ga0255811_11223672_52|P
AATTACTCTCCCCACCGATTGATAGTTGAAAAAACTTGACAGACAGCTTAATTTAAGTTATGTATAATCAGTTGC
TTCGTGGTCCCTCTGGCCGGAAAAACCTCTGGCGGAGCGCAAGCACCAATAGAGAGGAACTCGGCCCAGAAGCGA
GGAAACCGACAATTAGGGGTTTAATTATTGAAGGAACTTTAAAGATTTTGTGACGGACGGAATAAATTAAGTTCA
AATCGCGTATGATTATATGAATGATGA (SEQ ID NO: 128)

>3300023207|Ga0255811_11223672_52|P
AAGGTCGACAAAGATTTCGGTTGGTTATAAATGAACGAGGAGGGGCAGATGTGGACATCTGCCGCCCACTTGAGT
CTGGGGCGATAAGCTGATTGTCGGGGGAGGTTTCACCACCGCTGGGGGGATCGATGTGAATCGTATTGCCGCCTG
GGGGCCGCAATAATAAATTAAACGGCGTCAGGAAGAGGTTCCAGATGCCGCTCAATACCCATAGCACTTAGCCCT
TGCCTTAACAATGAATTGTGTCTATTTTGAGGGCTGTCTTATAAATAGAAAAGATATCAAGATAAGTTGTCGAAA
CCGCAGGG (SEQ ID NO: 129)

TABLE 7-continued

Direct Repeat Homology-containing Sequences
of Representative CLUST.019143 (Type V-G) CRISPR-Cas Systems >3300023207|Ga0255811_11223672_52|P
CCTGGGGGCCGCAATAATAAATTAAACGGCGTCAGGAAGAGGTTCCAGATGCCGCTCAATACCCATAGCACTTAG
CCCTTGCCTTAACAATGAATTGTGTCTATTTTGAGGGCTGTCTTATAAATAGAAAAGATATCAAGATAAGTTGTC
GAAACCGCAGGGGTTTCGACCTAAAAGAATTATGTCTGACGAAGAAAAAAAAGAGAAGACCAAATCCGAGATGCC
GTTTCTGGATCATATCGAGGAACTGCGCTGGCGGTTGATCAAGTCCATTTTATCGGTTGCCGTGATGGCCATCCT
GGCCTTTA (SEQ ID NO: 130)

>3300006945|Ga0073933_1000004_588|P
CGAAATCGAGCTGCCGACCGCAATCCCCTGACGACCCTTGACGGAACTGGCCGATTTGCTAAAATATTTTT**GATG
CTTACTTAGTCATCTGGTTGGCAAACCTCCGCGGACCTTCGGGACCAATGGAGAGGAACCCAGCCGAGAAGCATC
GAGCCGGTAAATGCCGGAAA**TTTTTGAGTCAGGAGAAGCTAACTTCTTCAAACTCAGGCCCTTGGAGCCGGTCA
(SEQ ID NO: 131)

>3300016590|Ga0186947_1003_42|M
CTGTCCTACTGTTTTGACTTACCGATGTGTTACTCCAATACGGGCGGACTGAAGTCCGCCCTCCAGGTGATAATG
ATGGAGTTTACGTCTGCGTCACATAAGGACTTGTGACGCCAAATAGCTGTGATTCTACATCACGACGGCAGCCGG
AATGCCGCCGCTCCCATGTTGTAATTCACTGGTGTTTGTGATTGGAGCTCACGAATAAGAGGTGGGAGAATAAAA
AAAACTGCCACTTGCGGACAGGTGGCAGAACAAAATTCTCCGAAACGCATGGGTTAAGGCTACCTGCCTGAGGGA
ACAGAGA (SEQ ID NO: 132)

>3300019846|Ga0197078_1002_15|M
AGTTTTGACTGGAAAATCTCCCTTTGGACGTTTGACCTAGGGGAGGGAACCCCGTCTGAAGATGGATAATTACCG
TCAAAATTTGGATAAACTTGGAGAAAATTAGACAAAAGAGTCGGTTTTTTTGATGTTACTGATCGGCGTAACTGA
TGTAACTGTCGTTAGATACAGCGAGTCG (SEQ ID NO: 133)

>UOQF01000587_2|M
AATAAGAGGAAACAATCCTTTCAATGTGAGTTTAGTGACTGTAATTATAAAACCCATAGCGATGAGAATGCGGCC
CGTGTCCTCGGACGGGTATTTTGGGGTGAAATTACCCTCCCCACCGATTGAGTGTTGAAAATTCTTGACATATAG
GCTAATTTAAGATATGTATAATTAGTCGCTTCGTGGTCCATCTGGCCGGAAAAACCTCTGGCGGGCGCAAGCACC
AATAGAGAGGAACTCGGCCCAGAAGCGAAGAAACCAATAATTAGGGGTTTAATTATTGAAGGAACTTTAAAGATT
TTGCGAC (SEQ ID NO: 134)

Example 3: Comprehensive and Scalable In Vivo Screening of Synthetic CRISPR-Cas Systems To comprehensively evaluate the functionality of the computationally identified type V systems, we added several key attributes to the E. coli-based in vivo negative selection screen of synthetic CRISPR-Cas systems previously described for the discovery of the type VI-D subtype (Yan et al., 2018). In particular, these key features were the inclusion of non-coding sequences into the synthetic CRISPR-Cas screening system, targeting of spacers sequences derived from both pACYC184 plasmid and E. coli essential genes in the screening library of minimal CRISPR arrays, and finally, the inclusion of unique molecular identifiers (UMIs) on screening constructs. Together, this enabled a greater ability to systematically and quantitatively interrogate CRISPR-Cas systems.

As an overview of the in vivo negative selection screen, we first synthesized a plasmid containing E. coli codon-optimized sequences encoding putative effectors and accessory proteins under the control of lac and IPTG-inducible T7 promoters (Effector Plasmid, FIG. 4A). To capture the required non-coding sequences for each system, such as the tracrRNA, we concatenated non-coding sequences flanking the CRISPR array, putative effector or accessory open reading frames, and predicted anti-repeats indicative of tracrRNA elements. Non-coding sequences were cloned into pACYC184 and expressed by lac and IPTG-inducible T7 promoters (Non-coding Plasmid, FIG. 4A). For the minimal CRISPR array, we designed oligonucleotide library synthesis (OLS) pools comprising two direct repeats flanking natural-length spacer sequences targeting the pACYC184 plasmid, select E. coli essential genes, and non-targeting negative control spacers for a total of 8900 elements in the array library. These sequences were placed under the control of a J23119 promoter and cloned into the Effector Plasmid in both the forward and reverse orientations for a total library of ~18,000 plasmid elements (FIG. 4A).

The CRISPR Effector Plasmid library and/or the separate Non-coding Plasmid were then co-transformed into electro-competent E. coli, followed by 11 hours of outgrowth. During outgrowth, RNA-programmable CRISPR-Cas interference would result in loss of plasmid-based antibiotic resistance or self-targeting of essential genes, leading to depletion of bacteria containing functioning CRISPR-Cas systems. Next generation sequencing of CRISPR array elements in the Effector Plasmid library and comparison of the frequency of individual elements in the pre-transformation and post-outgrowth samples were used to identify strongly depleted CRISPR arrays conferring interference activity. Simultaneous small RNA sequencing of the surviving cells enabled the identification of required non-coding elements for activity, such as the mature crRNA and tracrRNA (FIG. 4B). The pipeline for systematic discovery, reconstruction, and evaluation of the different components of putative CRISPR-Cas systems is a generalizable method for the efficient and comprehensive search for novel CRISPR-Cas systems with in vivo interference activity. Using this approach, we identified robust activity for the subtype V-G discovered in this work.

Gene Synthesis and Oligonucleotide Library Cloning

The E. coli codon-optimized protein sequences for CRISPR effector[?] accessory proteins were cloned into pET-28a(+) (EMD-Millipore) to create the Effector Plasmid. Noncoding sequences flanking Cas genes (including 150 nt of terminal CDS coding sequence) or the CRISPR array were synthesized (Genscript) into pACYC184 (New England Biolabs) to create the Non-coding Plasmid (FIG. 4A). Effector mutants (e.g., D513A or A513D) plasmids were cloned by site directed mutagenesis using the indicated primers in the sequence table: sequence changes were first introduced into PCR fragments, which were then re-assembled into a plasmid using NEBuilder HiFi DNA Assembly Master Mix or NEB Gibson Assembly Master Mix (New England Biolabs) following the manufacturer's instructions.

For the pooled spacer library, we first computationally designed an oligonucleotide library synthesis (OLS) pool (Agilent) to express a minimal CRISPR array of "repeat-spacer-repeat" sequences. The "repeat" elements were derived from the consensus direct repeat sequence found in the CRISPR array associated with the effector, and "spacer" represents ~8,900 sequences targeting the pACYC184 plasmid and *E. coli* essential genes, or negative control non-targeting sequences. The spacer length was determined by the mode of the spacer lengths found in the endogenous CRISPR array. Flanking the minimal CRISPR array were unique PCR priming sites that enabled amplification of a specific library from a larger pool of oligo synthesis.

We next cloned the minimal CRISPR array library into the Effector Plasmid to create an Effector Plasmid library. We appended flanking restriction sites, a unique molecular identifier, and a J23119 promoter for array expression onto the oligo library using PCR (NEBNext High-Fidelity 2×PCR Master Mix), and then used NEB Golden Gate Assembly Master Mix (New England Biolabs) to assemble the full plasmid library of effectors with their targeting arrays. This represented the "input library" for the screen.

In Vivo *E. coli* Screen

The in vivo screen was performed as previously described (Yan et al., Mol Cell. 2018 Apr. 19; 70(2):327-339) with the following modifications: we performed the screen using electrocompetent E. cloni EXPRESS® BL21(DE3) *E. coli* cells (Lucigen) unless otherwise indicated. Competent cells were co-transformed with the Effector Plasmid and/or Non-coding (FIG. 4B). The cells were electroporated with the "input library" according to the manufacturer's protocols using a Gene Pulser Xcell (Bio-rad) with a 1.0 mm cuvette. The cells were plated onto bioassay plates containing both Chloramphenicol (Fisher) and Kanamycin (Alfa Aesar), and grown for 11 hours, after which we estimated the approximate colony count to ensure sufficient library representation and harvested the cells.

Plasmid DNA fractions were extracted from the harvested cells to create the 'output library' using a QIAprep Spin Miniprep Kit (Qiagen), while total RNA ≥17 nt was harvested by lysing the harvested cells in Direct-zol (Zymo Research), followed by extraction using the Direct-zol RNA miniprep kit (Zymo Research).

To identify specific parameters resulting in enzymatic activity and bacterial cell death, we used next generation sequencing (NGS) to quantify and compare the representation of individual CRISPR arrays (i.e., repeat-spacer-repeat) in the PCR product of the input and output plasmid libraries. We defined the fold depletion for each CRISPR array as the normalized input read count divided by the normalized output read count (with 1 added to avoid division by zero). An array was considered to be "strongly depleted" if the fold depletion was greater than 3. When calculating the array fold depletion across biological replicates, we took the maximum fold depletion value for a given CRISPR array across all experiments (i.e. a strongly depleted array must be strongly depleted in all biological replicates). We generated a matrix including array fold depletion and the following features for each spacer target: target strand, transcript targeting, ORI targeting, target sequence motifs, flanking sequence motifs, and target secondary structure. We investigated the degree to which different features in this matrix explained target depletion for Type V-G systems, thereby yielding a broad survey of functional parameters within a single screen. Furthermore, the RNA fractions were prepared for small RNA library preparation and sequencing as described previously (Yan et al., 2018).

Example 4. Transcription-Dependent Interference Activity of Cas12g

We first investigated the function of the CRSPR-Cas subtype V-G effector, Cas12g, which ranges in size from 696 aa-853 aa. Our initial subtype V-G in vivo screening system, including an Cas12g1 Effector Plasmid library and Non-coding Plasmid, displayed interference activity that specifically targeted the non-template, sense DNA strand of actively transcribed regions of pACYC184 (FIG. 5A) or *E. coli* essential gene substrates (FIG. 5B). This pattern of interference activity is strikingly similar to that observed for the RNA-targeting subtype VI-D CRISPR-Cas system when evaluated using a comparable screening strategy (Yan et al., 2018). Additional analysis of target flanking sequences of strongly depleted CRISPR arrays revealed no protospacer adjacent motif (PAM) or protospacer flanking sequence (PFS) requirements for Cas12g1 interference (FIGS. 6A-B).

This pattern of interference implies either transcription-dependent DNA targeting or RNA targeting, which would be surprising given that Cas12g contains a highly conserved C-terminal RuvC nuclease domain (FIG. 7) previously known to cleave only DNA. To test the requirement of the RuvC domain for this unexpected pattern of effector targeting by Cas12g, we mutated the conserved aspartate residue in the RuvC-I motif of Cas12g1 to alanine (D513A) and found that interference was abolished (FIG. 7, FIG. 8). Subsequent reversion of the mutated dCas12g1(D513A) Effector Plasmid to the Cas12g1 wild-type sequence restored the original interference pattern, demonstrating the requirement of an intact RuvC domain for Cas12g1 in vivo interference (FIG. 7, FIG. 9). In an effort to identify the minimal in vivo screening system producing the observed interference pattern, we removed the Non-coding Plasmid and observed a substantial decrease in activity, indicative of a tracrRNA requirement for the RuvC-dependent Cas12g1 interference (FIG. 7, FIG. 10).

RNA sequencing of samples from in vivo screens containing the Non-coding Plasmid revealed a highly expressed tracrRNA element in the non-coding sequence of the Cas12g1 locus containing an anti-repeat with 11 nt of complementarity to the direct repeat (FIGS. 11-13). Alignment of the RNA sequencing reads to the CRISPR array library showed that the type V-G pre-crRNA is processed in vivo, yielding a distribution of spacer lengths ranging from 18-23 nt and a 5' direct repeat that is truncated 18-nt from the terminus (FIG. 11).

Having identified a putative minimal type V-G CRISPR-Cas system, we purified a recombinant stock of the Cas12g1 effector (FIG. 14) and in vitro transcribed the mature crRNA and tracrRNA to reconstitute the complete system for in vitro analysis of the interference mechanism. We first explored the biogenesis of the activated CRISPR complex. Incubation of Cas12g1 with a pre-crRNA containing a DR-spacer-DR-spacer-DR structure resulted in no observable pre-crRNA processing by Cas12g1, in the presence or absence of the tracrRNA (FIGS. 15A-B, TABLE 8-9). Given that mature crRNA and tracrRNA were identified by RNA sequencing of the Cas12g1 system expressed in vivo, these findings suggest that biogenesis of the subtype V-G crRNA requires an endogenous nuclease(s) absent from our in vitro reaction.

To explore the mechanism of Cas12g interference further, we first assessed the cleavage of ssDNA and dsDNA in the presence of the mature crRNA and tracrRNA. Cas12g1 surveillance complexes were constructed containing the Cas12g1 effector, tracrRNA, and mature crRNAs derived from highly depleted CRISPR arrays from the in vivo screen. Cas12g1 surveillance complexes showed no cleavage of the cognate ssDNA or dsDNA substrates at 37° C. (FIG. 17A, FIG. 18A, and TABLES 9-11). Given that the Cas12g1 locus originates from a hot spring metagenome, we used a thermal melt assay to assess the stability of this protein and its complexes with RNA at temperatures above 37° C. The thermal melt results show that, in the absence of crRNA or tracrRNA, Cas12g1 is thermostable with a melting temperature ($T_m$) of 64° C. (FIGS. 16A-B). Furthermore, when complexed with the crRNA and tracrRNA, the Cas12g1 surveillance complex showed increased thermostability with a $T_m$ of 74° C. (FIGS. 16A-B). However, despite this, we observed no ssDNA or dsDNA cleavage by the Cas12g1 surveillance complex at 42° C., 50° C., or 60° C. (FIGS. 17B-D, FIGS. 18B-D).

Given the observed strong bias of in vivo interference by Cas12g towards targeting the non-template DNA strand, we studied the effect of RNA transcripts on Cas12g1 effector activity. To this end, ssDNA and ssRNA substrates were generated with either sense (containing crRNA spacer-complementary target) or antisense sequences. We tested the cleavage of ssDNA for each of the four substrate combinations (sense ssDNA:sense ssRNA; sense ssDNA:antisense ssRNA; antisense ssDNA:sense ssRNA; antisense ssDNA: antisense ssRNA). For the sense-antisense pairings of ssDNA and ssRNA, the substrates were pre-annealed, creating a DNA-RNA hybrid. We observed that, at 50° C., the Cas12g1 surveillance complex cleaves sense ssDNA in the presence of a sense RNA transcript in an efficient and dose-dependent manner (FIG. 19).

We then investigated whether this interference activity depended on the target sequence present in the ssDNA substrate and found that ssDNA containing no target sequence or complementarity to the crRNA spacer ("collateral ssDNA") was efficiently cleaved into shorter fragments at 50° C. in the presence of a sense ssRNA with crRNA spacer complementarity (FIGS. 23A-B, FIG. 33). No ssDNA cleavage was observed for any other DNA-RNA substrate combination (FIGS. 20-22). These results demonstrate that ssDNA cleavage by Cas12g1 surveillance complex is activated by an RNA transcript containing a target complementary to the crRNA spacer, hereafter referred to as the target RNA. Cleavage of ssDNA into multiple products of decreasing size by the target RNA-activated Cas12g1 complex is indicative of non-specific collateral (trans) ssDNA cleavage activity.

Cas12g1 target RNA activated collateral ssDNA cleavage presents a potential mechanism underlying in vivo interference observed for the subtype V-G CRISPR system, whereby binding of a target RNA transcript would result in cleavage of unprotected ssDNA strands at the transcriptional fork. However, target RNA-dependent ssDNA cleavage by the Cas12g1 surveillance complex was not evident at 37° C. (FIGS. 24-27). The lack of robust in vitro ssDNA cleavage by the Cas12g1 surveillance complex in the presence of a target RNA transcript at 37° C. is at odds with the strong interference observed in the in vivo screens performed at the same temperature, suggesting that the collateral ssDNA cleavage is likely not the only mode of interference for the subtype V-G system.

Purification of Effector Proteins

Effector vectors were transformed into E. coli NiCo21 (DE3) (New England BioLabs) and expressed under a T7 promoter. Transformed cells were initially grown overnight in 3 mL Luria Broth (Sigma)+50 ug/mL kanamycin, followed by inoculation of 1 L of Terrific Broth media (Sigma)+50 ug/mL kanamycin with 1 mL of overnight culture. Cells were grown at 37° C. until an OD600 of 1-1.5, then protein expression was induced with 0.2 mM IPTG. Cultures were then grown at 20° C. for an additional 14-18 hours. Cultures were harvested and pelleted via centrifugation, then resuspended in 80 mL of lysis buffer (50 mM HEPES pH 7.6, 0.5M NaCl, 10 mM imidazole, 14 mM 2-mercaptoethanol, and 5% glycerol)+protease inhibitors (Sigma). Cells were lysed via cell disruptor (Constant System Limited), then centrifuged twice at 28,000×g for 20 minutes at 4 C in order to clarify the lysate. The lysate was loaded onto a 5 mL HisTrap® FF column (GE Life Sciences), then purified via FPLC (AKTA Pure, GE Life Sciences) over an imidazole gradient from 10 mM to 250 mM. Cas12g1 was purified in low salt buffer (50 mM HEPES-KOH pH 7.8, 500 mM KCl, 10 mM $MgCl_2$, 14 mM 2-mercaptoethanol, and 5% glycerol) and high salt buffer (50 mM HEPES-KOH pH 7.8, 1M $NH_4Cl$, 10 mM $MgCl_2$, 14 mM 2-mercaptoethanol, and 5% glycerol), respectively. After purification, fractions were run on SDS-PAGE gels and fractions containing protein of the appropriate size were pooled and concentrated using 10 kD Amicon Ultra-15 Centrifugal Units. Cas12g1 was further dialyzed into a buffer without imidazole (25 mM HEPES-KOH pH 7.8, 1 M $NH_4Cl$, 10 mM $MgCl_2$, 1 mM DTT, 7 mM 2-mercaptoethanol, and 30% glycerol). Protein concentration was determined by Qubit protein assay (Thermo Fisher).

crRNA, tracrRNA and Substrate RNA Preparation

Single-stranded DNA oligo templates for crRNA, tracrRNA, and substrate RNA were ordered from Integrated DNA Technologies, Inc. (Coralville, Iowa) (IDT). Substrate RNA and pre-crRNA templates were PCR amplified to generate a double stranded in vitro transcription (IVT) template DNA using NEBNEXT Hifi 2x master mix (New England Biolabs). Double stranded DNA templates for mature cr-RNA and tracrRNA were generated by annealing T7 primer with templates followed by extension using DNA Polymerase I, Large (Klenow) Fragment (New England Biolabs). Annealing was performed by incubating for 5 min at 95° C. followed by a −5° C./min ramp down to 4° C. In vitro transcription was performed by incubating the dsDNA templates with T7 RNA polymerase at 37° C. for 3 hours using HiScribe® T7 Quick High Yield RNA kit (New England Biolabs). After incubation, IVT samples were treated with Turbo DNase (Thermo Scientific) and then purified using RNA Clean & Concentrator kit (Zymo Research). For Cas12g1, equimolar amounts of mature cr-RNA containing 5' hydroxyl and 5' monophosphate end group were used. Mature cr-RNA generated from IVT was treated with Calf Intestinal Alkaline Phosphatase (Thermo Fisher) or RNA 5'-polyphoshpatase (Lucigen) for 2 hours at 37° C. to generate 5'-hydroxyl or 5'-monophosphate, respectively, followed by clean up with RNA Clean & Concentrator kit (Zymo Research). Concentrations were measured via Nanodrop 2000 (Thermo Fisher). Pre-crRNA, tracrRNA, and mature-crRNA sequences used in biochemical characterization of Cas12g is included in TABLE 8, TABLE 9, and TABLE 10, respectively. Oligonucleotide templates and primers for preparation of crRNAs are included in TABLE 14.

Preparation of IR-800 Labeled Substrate RNA and DNA

RNA substrates from IVT were treated with Calf Intestinal Alkaline Phosphatase (Thermo Fisher) for 30 minutes at 37° C. to convert the 5'-triphosphate to 5' terminal hydroxyl group and purified using RNA Clean & Concentrator kit (Zymo Research). A thiol end group was added to the 5' terminal hydroxyl group of the DNA and RNA substrates via 5' EndTag Labeling Kit (Vector Labs), then substrates were labeled with IRDye 800CW Maleimide (LI-COR Biosciences). Substrates were purified using DNA Clean & Concentrator kit or RNA Clean & Concentrator kit (Zymo Research). Labeled dsDNA substrates were generated by labeling the non-spacer complementary ssDNA strand, annealing with a primer, then extending with DNA Polymerase I, Large (Klenow) Fragment (New England Biolabs) for 15 minutes at 25° C. These substrates were purified with DNA Clean & Concentrator kit (Zymo Research). Concentrations were measured via Nanodrop 2000 (Thermo Fisher).

RNA and DNA substrate sequences used in biochemical characterization of Cas12g are included in TABLE 11-13. Oligonucleotide templates and primers for preparation of RNA substrates are included in TABLE 15.

Cas12g1 Pre-Cr-RNA Processing Assay

Pre-cr-RNA processing assays for Cas12g1 were performed at 37° C. for 1 hour in cleavage buffer at a final pre-cr-RNA concentration of 25 nM. For Cas12g, pre-crRNA processing was performed with 5' IR800-labeled pre-crRNA to distinguish from the tracr-RNA. The tracrRNA was added at equimolar concentrations to Cas12g1. Reactions were quenched with the addition of 1 ug/uL of proteinase K (Ambion) and incubated at 37° C. for 15 minutes. 50 mM EDTA was added to the reactions before mixing with equal volume of 2×TBE-Urea sample buffer (Invitrogen) and denaturing at 65° C. for 3 minutes. Samples were analyzed on 15% TBE-Urea gels (Invitrogen). Gels were stained for 5 minutes with SYBR Gold nucleic acid stain (Invitrogen) and imaged on Gel Doc EZ (Biorad). Gels containing labeled pre-crRNA were first imaged on Odyssey CLx scanner (LI-COR Biosciences) prior to SYBR staining.

Target Cleavage Assays with Cas12g ssRNA, ssDNA and dsDNA substrates: Cas12g target cleavage assays were performed for 1 hour at the specified temperature in cleavage buffer. Cas12g surveillance complex was formed by incubating a 1:2:0.5 molar ratio of Cas12g:mature crRNA:tracrRNA for 10 minutes at 37° C. followed by transfer to ice. Since mature cr-RNA generated from processing of pre-crRNA is expected to contain a mix of 5' hydroxyl and monophosphate end groups, mature cr-RNA for the assay was prepared by mixing equimolar amounts of hydroxyl end group and monophosphate end group mature cr-RNAs. Cas12g surveillance complex was further diluted on ice keeping the molar ratio of protein to RNA fixed. The complex was then added to IR800 labeled substrates and incubated for 1 hour at the specified temperature. The final concentration of all labeled substrates was 100 nM. For collateral activity assays, the final concentration of both labeled and unlabeled substrates was 100 nM each unless otherwise specified. Reactions were treated with RNAse cocktail (Thermo Scientific) or Turbo DNase Thermo Scientific) to visualize DNA and RNA substrates respectively. Reactions were quenched by adding 1 ug/uL of proteinase K (Ambion) and incubating for 15 minutes at 37° C., followed by adding 50 mM EDTA. Samples were then mixed with equal volume of 2×TBE-Urea sample buffer and denatured at 65° C. for 3 minutes for RNA samples and 95° C. for 3 minutes for DNA samples.

Samples were analyzed on denaturing gel electrophoresis on 15% TBE-Urea gel (Invitrogen). Gels were first imaged on Odyssey CLx scanner (LI-COR Biosciences) followed by a 5 minute stain with SYBR Gold nucleic acid stain (Invitrogen) and imaged on Gel Doc EZ (Biorad). RNA:DNA hybrid substrates: Cleavage assays for RNA:DNA hybrid substrates were performed as described above using unlabeled RNA and 5'-IR800 labeled DNA. All RNA:DNA hybrid substrates were mixed at a 1:2 ratio of RNA:DNA and annealed in hybridization buffer (50 mM Tris pH 8.0 and 100 mM NaCl) by incubating at 70° C. for 2 minutes followed by a 5° C./min ramp down to 4° C. Final concentration of the labeled DNA was 100 nM. Reactions were treated with RNAse cocktail prior to the Proteinase K addition.

Thermal Melt Assays for Cas12g

Melting curves of effector proteins were determined through differential scanning fluorimetry (DSF). All reactions took place at effector concentration of 0.62 uM in DSF buffer (50 mM Tris-HCl pH 7.9, 100 mM NaCl, 1 mM DTT) with the addition of 5×SYPRO orange dye (Sigma). Binary (effector+m-crRNA) and ternary (effector+m-crRNA+tracrRNA) complexes were formed at a 2.5:1 ratio of RNA to protein. Apo and effector complexes were incubated at 37° C. for 10 minutes prior to melting to assure complex formation. The reactions were then split into four 5 uL technical replicates. Protein melting was performed in the Lightcycler 480 (Roche) over a temperature range from 20° C. to 80° C., at a rate of 0.06° C./sec, with 10 acquisitions/sec. The first derivative of the raw fluorescence data was taken in order to determine the $T_m$ of the effector.

Example 5. Cas12g1 has a RuvC-Dependent ssRNase Activity

To assess additional Cas12g1 enzymatic activities that might enable the interference activity at 37° C., we tested whether, in addition to the ssDNA cleavage activation by the target RNA binding, the Cas12g1 surveillance complex cleaves RNA directly. We IR800 dye-labeled target RNA transcripts shown to activate Cas12g1 ssDNA cleavage and incubated these substrates with the Cas12g1 surveillance complex at 37° C. and 50° C. (FIGS. 28A-B, FIGS. 29A-B, TABLES 7-9). Under these conditions, Cas12g1 showed robust, target-specific and tracrRNA-dependent RNA cleavage at 37° C. (FIGS. 28A-B). RNA cleavage by the Cas12g1 surveillance complex was further enhanced at 50° C., and we observed complete degradation of the target RNA substrate to single nucleotides at complex concentrations as low as 31 nM (FIGS. 29A-B) and detectable cleavage at complex concentrations as low as 125 pM (FIG. 30A). Cas12g1 appears to be highly specific, and no cleavage of non-target RNA was observed with the highest dose of surveillance complex tested (250 nM), over 1000-fold higher than the concentrations sufficient to observe detectable cleavage of target-containing RNAs (FIG. 30B). The high efficiency of the target RNA cleavage at 37° C. suggests that transcript targeting is the primary source of the observed in vivo interference activity by the subtype V-G CRISPR Cas system.

Having observed efficient cleavage of target transcripts to small fragments or single nucleotides, we next investigated whether the Cas12g RNA cleavage of target ssRNA substrates is accompanied by trans cleavage of collateral RNA transcripts containing no sequence similarity to the crRNA spacer. To distinguish the target and collateral RNA species, ssRNA cleavage reactions were prepared with IR800 dye-labeled collateral substrates mixed with unlabeled target transcripts. We observed robust collateral RNA cleavage by the Cas12g1 complex at 50° C. at concentrations of target RNA as low as 125 pM (FIG. 31A), demonstrating that the standalone RNA detection sensitivity of Cas12g1 is comparable to the highest performing Cas13 variants (Gootenberg et al., 2018). Finally, we observed that both target and collateral cleavage by the Cas12g1 is inhibited by an excess of EDTA, establishing the divalent cation dependency of RNA cleavage by Cas12g1 (FIG. 32).

We additionally purified the dCas12g1 (D513A) protein with the RuvC domain point mutation that lacked interference activity on the in vivo screen (FIG. 14). The dCas12g1 (D513A) mutant showed neither target RNA cleavage nor collateral cleavage of ssDNA, suggesting that an intact RuvC domain is necessary for the cleavage of both RNA and ssDNA (FIGS. 35-36). Thus, the compact Cas12g1 effector demonstrates target and collateral RNA cleavage as well as temperature-dependent RNA-activated collateral ssDNA cleavage activity, all dependent on a single, intact RuvC domain.

The Cas12g effector is a particularly remarkable case of convergent functional evolution that could help in understanding the origin and evolution of Class 2 CRISPR-Cas effectors. Cas12g contains a C-terminal RuvC-like domain characteristic of Cas12 nucleases and clearly is a derivative of TnpB (FIG. 1, FIGS. 2A-B). However, the activity of Cas12g1 dramatically differs from those of all known type V systems in its ability to target RNA, in both the RNA guide-dependent and the guide-independent, collateral modes (FIGS. 37A-B). In fact, the RNA targeting and the ensuing collateral RNA cleavage by Cas12g are closely analogous to the properties of the unrelated, HEPN-domain containing Cas13 effectors of the type VI CRISPR-Cas systems (Abudayyeh et al., 2016; East-Seletsky et al., 2016; Shmakov et al., 2015).

Although PAM-independent RNA targeting has recently been demonstrated for the Type II Cas9 nucleases from *Campylobacter jejuni* (CjCas9) and *Neisseria meningitidis* (NmeCas9), the cleavage in these cases is guide-dependent and site-specific (Dugar et al., 2018; Rousseau et al., 2018) as opposed to the collateral RNA cleavage observed with Cas12g1. While mutational analysis implicates the HNH domain as the nuclease responsible for the RNA cleavage by NmeCas9 and CjCas9 (Dugar et al., 2018; Rousseau et al., 2018), the results presented here demonstrate the requirement of an intact RuvC domain for the RNA cleavage by Cas12g1. To our knowledge, this is the first reported instance of RNA cleavage by the RuvC domain, one heretofore associated only with DNA cleavage.

In addition to the targeted and collateral RNA cleavage, we found that Cas12g1 catalyzes collateral cleavage of ssDNA (FIG. 35), resembling Cas12a in that respect (FIGS. 37A-B). In the native environment, CLUST.019143 (Type V-G) interference activities are likely to include cleavage of genomic RNA, RNA transcripts, or ssDNA of invading species. Additionally, Cas12g might be capable of PAM-independent dsDNA cleavage via transcript-activated ssDNA cleavage at the transcriptional fork, somewhat analogously to the interference by type III CRISPR-Cas systems (FIG. 37C) (Samai et al., 2015). These multiple modes of efficient interference suggest that Cas12g may not be a nascent intermediate in the convergent evolution from TnpB to large CRISPR effectors, but a stable state along one particular path from TnpB to functional CRISPR systems. Comparative structural and biochemical studies of Cas12g as well as further investigation of additional subtype V-U systems is of great interest to further elucidate the evolution of TnpB into functional type V effectors.

The efficiency and specificity, combined with the differential of temperature control of RNA and ssDNA cleavage and stability of the thermophilic Cas12g1 surveillance complex, present potential opportunities for a range of applications. Perhaps, most importantly, Cas12g1 is the smallest active RNA editing CRISPR effector identified to date and, at 768aa, is 160aa smaller than the 928aa median size of the recently discovered Cas13d family proteins (Konermann et al., 2018; Yan et al., 2018). This compactness of Cas12g1 has the advantage of being readily packaged into various delivery vehicles. Additional applications of Cas12g could involve both efficient inactivation of target RNAs, and enhanced RNA and DNA sensing (Chen et al., 2018; East-Seletsky et al., 2016; Gootenberg et al., 2017, 2018; Li et al., 2018).

TABLE 8

Pre-crRNAs used for CLUST.019143 (Type V-G) in vitro biochemistry

| Name | Sequence | DR | Spacer1 | Spacer2 | Target | Fig |
|---|---|---|---|---|---|---|
| Cas12g1 pre-crRNA 1 | gggGGUGGAAAGGGCCGGAGA UUUACCGGCUCUGACACCCCA UUCAUCCGCUUAUUAUCACUU AUUCAGGGUGGAAAGGGCCGG AGAUUUACCGGCUCUGACACC GCUUGGAGGAGCGCAGUCACC AAAACUUGUGGUGGAAAGGGC CGGAGAUUUACCGGCUCUGAC ACC (SEQ ID NO: 400) | GGUGGAAAGGG CCGGAGAUUUA CCGGCUCUGAC ACC (SEQ ID NO: 401) | CCAUUCAU CCGCUUAU UAUCACUU AUUCAG (SEQ ID NO: 402) | GCUUGGAG GAGCGCAG UCACCAAA ACUUGU (SEQ ID NO: 403) | Cas12g1 Target 1 | FIGS. 15A-15B |

TABLE 9 tracrRNAs used for CLUST.019143 (Type V-G) in vitro biochemistry

| Name | Sequence | Fig |
|---|---|---|
| Cas12g1 tracr 1 | gggGAUGCUUACUUAGUCAUCUGGUUGGCAAACCUCCGCGACCUUCGGGACCAA UGGAGAGGAACCCAGCCGAGAAGCAUCGAGCCGGUAAAUGCCGGAAAUUUUU (SEQ ID NO: 404) | FIGS. 15A-15B |
| Cas12g1 tracr 2 | gggGAUGCUUACUUAGUCAUCUGGUUGGCAAACCUCCGCGACCUUCGGGACCAA UGGAGAGGAACCCAGCCGAGAAGCAUCGAGCCGGUAAAUGCCGGAAA (SEQ ID NO: 405) | FIG. 7, FIGS. 17A-36 |
| Cas12g1 tracr 3 | gggGAUGCUUACUUAGUCAUCUGGUUGGCAAACCUCCGCGACCUUCGGGACCAA UGGAGAGGAACCCAGCCGAGAAGCAUCGAGCCGGUAAAU (SEQ ID NO: 406) | FIGS. 16A-16B |

TABLE 10

Mature-crRNAs used for CLUST.019143 (Type V-G) in vitro biochemistry

| Name | Sequence | Processed DR | Processed Spacer | Target | Fig |
|---|---|---|---|---|---|
| Cas12g1 mcrRNA 1 | gggUUUACCGGCUCUGAC ACCGCUUGGAGGAGCGCA GUCACCAAA (SEQ ID NO: 407) | UUUACCGGCUCU GACACC (SEQ ID NO: 408) | GCUUGGAGGAGCG CAGUCACCAAA (SEQ ID NO: 409) | Cas12g1 ssRNA 1 | FIGS. 16A-16B |
| Cas12g1 mcrRNA 2 | gggUUUACCGGCUCUGAC ACCAACUGUGAUAAACUA CCGCAUUAA (SEQ ID NO: 410) | UUUACCGGCUCU GACACC (SEQ ID NO: 411) | AACUGUGAUAAAC UACCGCAUUAA (SEQ ID NO: 412) | Cas12g1 ssRNA 2 | FIGS. 19-36 |
| Cas12g1 mcrRNA 3 | gggUUUACCGGCUCUGAC ACCCUUCCUUAGCUCCUG AAAAUCUCG (SEQ ID NO: 413) | UUUACCGGCUCU GACACC (SEQ ID NO: 414) | CUUCCUUAGCUCC UGAAAAUCUCG (SEQ ID NO: 415) | Cas12g1 ssRNA 3 | FIGS. 30A-31B |
| Cas12g1 mcrRNA 4 | gggUUUACCGGCUCUGAC ACCCAUCUUGCGAAUAUA UGUGUAGAA (SEQ ID NO: 416) | UUUACCGGCUCU GACACC (SEQ ID NO: 417) | CAUCUUGCGAAUA UAUGUGUAGAA (SEQ ID NO: 418) | Cas12g1 ssDNA 4 | FIGS. 17A-18D |

TABLE 11

Target substrates used for CLUST.019143 (Type V-G) in vitro biochemistry

| Name | Sequence | Nucleic acid | Fig |
|---|---|---|---|
| Cas12g1 ssRNA 2 | CAACGAGGUAUUUAUCCGAUUAAUUCUCAUGUUUGACAGCUUAU CAUCGAUAAGCUUUAAUGCGGUAGUUUAUCACAGUUAAAUUGCU AACGCAGUCAGGCACCGUGUAUUUGUAGCCCGGGGACUGUUU (SEQ ID NO: 419) | RNA | FIGS. 19-36 |
| Cas12g1 SSRNA 3 | CAACGAGGUAUUUAUCCGAUAAAUAAGAUCACUACCGGGCGUAU UUUUGAGUUAUCGAGAUUUUCAGGAGCUAAGGAAGCUAAAAUG GAGAAAAAAAUCACUGGAUAUAUUGUAGCCCGGGGACUGUUU (SEQ ID NO: 420) | RNA | FIGS. 30A-31B |
| Cas12g1 sense RNA 2 | CAACGAGGUAUUUAUCCGAUUAAUUCUCAUGUUUGACAGCUUAU CAUCGAUAAGCUUUAAUGCGGUAGUUUAUCACAGUUAAAUUGCU AACGCAGUCAGGCACCGUGUAUUUGUAGCCCGGGGACUGUUU (SEQ ID NO: 421) | RNA | FIGS. 19-22, FIGS. 24-27 |
| Cas12g1 sense DNA 2 | CAACGAGGTATTTATCCGATTAATTCTCATGTTTGACAGCTTAT CATCGATAAGCTTTAATGCGGTAGTTTATCACAGTTAAATTGCT AACGCAGTCAGGCACCGTGTATTTGTAGCCCGGGGACTGTTT (SEQ ID NO: 422) | DNA | FIGS. 19-22, FIGS. 24-27 |

TABLE 11-continued

Target substrates used for CLUST.019143 (Type V-G) in vitro biochemistry

| Name | Sequence | Nucleic acid | Fig |
|---|---|---|---|
| Cas12g1 antisense RNA 2 | AAACAGUCCCCGGGCUACAAAUACACGGUGCCUGACUGCGUUAG CAAUUUAACUGUGAUAAACUACCGCAUUAAAGCUUAUCGAUGAU AAGCUGUCAAACAUGAGAAUUAAUCGGAUAAAUACCUCGUUG (SEQ ID NO: 423) | RNA | FIGS. 19-22, FIGS. 24-27 |
| Cas12g1 antisense DNA 2 | AAACAGTCCCCGGGCTACAAATACACGGTGCCTGACTGCGTTAG CAATTTAACTGTGATAAACTACCGCATTAAAGCTTATCGATGAT AAGCTGTCAAACATGAGAATTAATCGGATAAATACCTCGTTG (SEQ ID NO: 424) | DNA | FIGS. 19-22, FIGS. 24-27 |
| Cas12g1 ssDNA 4, dsDNA 4 | CAACGAGGTATTTATCCGATCGCTCTGGAGTGAATACCACGACG ATTTCCGGCAGTTTCTACACATATATTCGCAAGATGTGGCGTGT TACGGTGAAAACCTGGCCTATTTTGTAGCCCGGGGACTGTTT (SEQ ID NO: 425) | DNA | FIGS. 17A-18D |

TABLE 12

Non-target substrates used for CLUST.019143 (Type V-G) in vitro biochemistry

| Name | Sequence | Nucleic acid | Fig |
|---|---|---|---|
| Cas12g1 SSRNA 2_RC | AAACAGUCCCCGGGCUACAAA UACACGGUGCCUGACUGCGUU AGCAAUUUAACUGUGAUAAAC UACCGCAUUAAAGCUUAUCGA UGAUAAGCUGUCAAACAUGAG AAUUAAUCGGAUAAAUACCUC GUUG (SEQ ID NO: 426) | RNA | FIGS. 23A-B, 28A-B, 29A-B, 31B, 33-34 |
| Cas12g1 SSRNA 3_RC | AAACAGUCCCCGGGCUACAAU AUAUCCAGUGAUUUUUUUCUC CAUUUUAGCUUCCUUAGCUCC UGAAAAUCUCGAUAACUCAAA AAAUACGCCGGUAGUGAUCU UAUUAUCGGAUAAAUACCUC GUUG (SEQ ID NO: 427) | RNA | FIG 30B |

TABLE 13

Collateral substrates used in this study for in vitro biochemistry

| Name | Sequence | Nucleic acid | Fig |
|---|---|---|---|
| Cas12g1 SSRNA 5_RC | AAACAGUCCCCGGGCUACAAU CUCGCCGAAACGUUUGGUGGC GGGACCAGUGACGAAGGCUUG AGCGAGGGCGUGCAAGAUUCC GAAUACCGCAAGCGACAGGCC GAUCAAUCGGAUAAAUACCUC GUUG (SEQ ID NO: 428) | RNA | FIGS. 30A-B, 31A-B, 34 |
| Cas12g1 ssDNA 4_RC | AAACAGTCCCCGGGCTACAAA ATAGGCCAGGTTTTCACCGTA ACACGCCACATCTTGCGAATA TATGTGTAGAAACTGCCGGAA ATCGTCGTGGTATTCACTCCA GAGCGATCGGATAAATACCTC GTTG (SEQ ID NO: 429) | DNA | FIGS. 23A-B, 33, 35 |

TABLE 14

IDT Template oligos and primers for crRNAs used

| Name | Template Sequence | T7 fwd primer | Rev primer |
|---|---|---|---|
| Cas12g1 pre-crRNA 1 | GGTGTCAGAGCCGGTAAATCTCCGGCCCTTTTCCA CCACAAGTTTTGGTGACTGCGCTCCTCCAAGCGG TGTCAGAGCCGGTAAATCTCCGGCCCTTTTCCACC CTGAATAAGTGATAATAAGCGGATGAATGGGGTG TCAGAGCCGGTAAATCTCCGGCCCTTTCCACCcc ctatagtgagtcgtatta (SEQ ID NO: 430) | TAATACGACTC ACTATAG (SEQ ID NO: 431) | GGTGTCAGAGCCGGTAAATC TCCGGCCCTTTCCACCACAA GTTTTGGTGACTGCGCTCCT CCAAGC (SEQ ID NO: 432) |
| Cas12g1 mcrRNA 2 | TTAATGCGGTAGTTTATCACAGTTGGTGTCAGAG CCGGTAAAcccctatagtgagtcgtattaTTAATG CGGTAGTTTATCACAGTTGGTGTCAGAGCCGGTA AAccctatagtgagtcgtatta (SEQ ID NO: 433) | TAATACGACTC ACTATAGTAAT ACGACTCACTA TAG (SEQ ID NO: 434) | |
| Cas12g1 mcrRNA 3 | CGAGATTTTCAGGAGCTAAGGAAGGGTGTCAGAG CCGGTAAAcccctatagtgagtcgtattacGAGAT TTTCAGGAGCTAAGGAAGGGTGTCAGAGCCGGTA AAccctatagtgagtcgtatta (SEQ ID NO: 435) | TAATACGACTC ACTATAGTAAT ACGACTCACTA TAG (SEQ ID NO: 436) | |

TABLE 14-continued

IDT Template oligos and primers for crRNAs used

| Name | Template Sequence | T7 fwd primer | Rev primer |
|---|---|---|---|
| Cas12g1 mcrRNA 4 | TTCTACACATATATTCGCAAGATGGGTGTCAGAG CCGGTAAAcccCTATAGTGAGTCGTATTATTCTAC ACATATATTCGCAAGATGGGTGTCAGAGCCGGTA AAccctatagtgagtcgtatta (SEQ ID NO: 437) | TAATACGACTC ACTATAGTAAT AGGACTCACTA TAG (SEQ ID NO: 438) | |
| Cas12g1 tracr 1 | AAAAATTTCCGGCATTTACCGGCTCGATGCTTCT CGGCTGGGTTCCTCTCCATTGGTCCCGAAGGTCC GCGGAGGTTTGCCAACCAGATGACTAAGTAAGCA TCccctatagtgagtcgtattaAAAAATTTCCGG CATTTACCGGCTCGATGCTTCTCGGCTGGGTTCC TCTCCATTGGTCCCGAAGGTCCGCGGAGGTTTGC CAACCAGATGACTAAGTAAGCATCccctatagtg agtcgtatta (SEQ ID NO: 439) | TAATACGACTC ACTATAGTAAT AGGACTCACTA TAG (SEQ ID NO: 440) | |
| Cas12g1 tracr 2 | TTTCCGGCATTTACCGGCTCGATGCTTCTCGGCT GGGTTCCTCTCCATTGGTCCCGAAGGTCCGCGGA GGTTTGCCAACCAGATGACTAAGTAAGCATCccc tatagtgagtcgtattaTTTCCGGCATTTACCGG CTCGATGCTTCTCGGCTGGGTTCCTCTCCATTGG TCCCGAAGGTCCGCGGAGGTTTGCCAACCAGATG ACTAAGTAAGCATCccctatagtgagtcgtatta (SEQ ID NO: 441) | TAATACGACTC ACTATAGTAAT AGGACTCACTA TAG (SEQ ID NO: 442) | |
| Cas12g1 tracr 3 | ATTTACCGGCTCGATGCTTCTCGGCTGGGTTCCT CTCCATTGGTCCCGAAGGTCCGCGGAGGTTTGCC AACCAGATGACTAAGTAAGCATCccctatagtga gtcgtattaATTTACCGGCTCGATGCTTCTCGGC TGGGTTCCTCTCCATTGGTCCCGAAGGTCCGCGG AGGTTTGCCAACCAGATGACTAAGTAAGCATCcc ctatagtgagtcgtatta (SEQ ID NO: 443) | TAATACGACTC ACTATAGTAAT AGGACTCACTA TAG (SEQ ID NO: 444) | |

TABLE 15

IDT template oligos and primers for ssRNA substrates used in this study for in vitro biochemistry

| Name | Template Sequence | -sense RNA fwd primer | -sense RNA rev primer | + sense RNA fwd primer | + sense RNA rev primer |
|---|---|---|---|---|---|
| Cas12g1 SSRNA 1 | Cas12g1 | | | | |
| Cas12g1 ssRNA 2 | ssRNA 1 AAACAGTC CCCGGGCT ACAAAGCT ACCAACTC TTTGAACC GAGGTAAC TGGCTTGG AGGAGCGC AGTCACCA AAACTTGT CCTTTCAG TTTAGCCT TAACCGGC GCATGAAT CGGATAAA TACCTCGT TG (SEQ ID NO: 445) | AAACAGTC CCCGGGCT ACAA (SEQ ID NO: 446) | AAATGTAATAA ggatccctcga gtaatacgact cactatagggC AACGAGGTATT ATCCGAT (SEQ ID NO: 447) | AAATGTAATAA ggatccctcga gtaatacgact cactatagggA AACAGTCCCCG GGCTACAA (SEQ ID NO: 448) |
| Cas12g1 ssRNA 3 | Cas12g1 | | | | |
| Cas12g1 SSRNA 4 | ssRNA 2 AAACAGTC CCCGGGCT ACAAATAC | AAACAGTC CCCGGGCT ACAA (SEQ ID NO: | AAATGTAATAA ggatccctcga gtaatacgact | AAATGTAATAA ggatccctcga gtaatacgact |

TABLE 15-continued

IDT template oligos and primers for ssRNA substrates used in this study for in vitro biochemistry

| Name | Template Sequence | -sense RNA fwd primer | -sense RNA rev primer | + sense RNA fwd primer | + sense RNA rev primer |
|---|---|---|---|---|---|
| Cas12g1 ssRNA 5 | Cas12g1 | ACGGTGCCTGACTGGGTTAGCAATTTAACTGTGATAAACTACCGGATTAAAGCTTATCGATGATAAGCTGTCAAACATGAGAATTAATCGGATAAATACCTCGTTG (SEQ ID NO: 450) | 451) | cactatagggCAACGAGGTATTTATCCGAT (SEQ ID NO: 452) | cactatagggAAACAGTCCCCGGGCTACAA (SEQ ID NO: 453) |

Example 6. CLUST.019143 (Type V-G) CRISPR-Cas Systems can be Used with a Fluorescent Reporter for the Specific Detection of Nucleic Acid Species The nuclease activities of Cas112g proteins (i.e., non-specific collateral RNase and DNase activities activated by a target RNA substrate complementary to the crRNA spacer) make these effectors promising candidates for use in the detection of nucleic acid species. Some of these methods have been previously described (see, e.g., East-Seletsky et al. (2016), Gootenberg et al. (2017), and Gootenberg et al. (2018) "Multiplexed and portable nucleic acid detection platform with Cas13, Cas12a, and Csm6" Science 15 Feb. 2018: eaaq0179), describing the general principle of RNA detection using Cas13a (East-Seletsky et al. (2016)), supplemented by amplification to increase the detection sensitivity and optimization of additional Cas13a enzymes (Gootenberg et al. (2017)), and most recently, the inclusion of additional RNA targets, orthologous and paralogous enzymes, and Csm6 activator to enable multiplexed detection of nucleic acids along with an increase in detection sensitivity (Gootenberg et al. (2018)). The addition of Cas12g to this toolkit provides an additional channel of orthogonal activity for nucleic acid detection.

The in vitro biochemical activity of Cas12g1 suggests that it may have promise in applications for sensitive nucleic acid detection, given that a dye-labeled, collateral RNA was efficiently cleaved at low target RNA concentrations (FIG. 31A) and background nuclease activity was limited with a non-targeting substrate over a wide range of Cas12g1 complex (FIG. 30B) and substrate concentrations (FIG. 31B). Adapting Cas12g1 towards sensitive nucleic acid detection application requires several steps, including, but not limited to, engineering a single RNA guide from the crRNA and tracrRNA for enhanced enzyme activity, optimizing the substrate for sensitive readout of the collateral activity and identifying per-base mismatch tolerance between the spacer and the target substrate.

Identification of the optimal substrate for nucleic acid detection can be informed by performing next generation sequencing (NGS) on the cleavage products of Cas12g collateral activity on both ssDNA and ssRNA substrates. The enzyme concentration may have to be titrated or incubation time adjusted in order to yield cleavage fragments that are still of a sufficient size to be prepared into a next generation sequencing library. The NGS data reveal the enzyme cleavage sites and the adjacent base preferences. It has been demonstrated that the individual effectors within the Cas13a and Cas13b families have different dinucleotide base preferences for RNA cleavage, yielding markedly different cleavage magnitudes and signal to noise ratios (Gootenberg et al. (2018)). The collateral NGS data thus enable better insight into the preferences for Cas12g. A separate experimental approach to identifying the dinucleotide preference of Cas12g collateral cleavage is to create a collateral RNA or DNA substrate with degenerate N's in sequential positions so as to have a broader sequence space than a defined collateral nucleic sequence. The library prep and analysis of the NGS data would proceed similarly to identify base preferences for cleavage. To verify the preference, collateral substrates containing synthesized short DNA/RNAs with a fluorophore/quencher pair on the 5' and 3' ends can be introduced into a cleavage reaction to assess the signal to noise ratio. Further optimization can be done on the length of the collateral DNA/RNA substrate to determine whether Cas12g1 has a length preference.

Having identified the collateral nuclease substrate preferences, another important parameter to determine is the mismatch tolerance of the Cas12g system, as it has implications for guide design that affects the ability of the enzyme to distinguish single base pair mismatches. The mismatch tolerance can be determined by designing a panel of targets bearing different positions and types of mismatches (for example, insertion/deletions, single base pair mismatches, adjacent double mismatches, separated double mismatches, triple mismatches, and more). Mismatch tolerance can be measured by assessing the amount of cleavage of collateral DNA for targets containing varying amounts of mismatches. As an example, the collateral RNA substrate could be a short ssRNA probe containing a fluorophore and quencher on opposite sides. For reactions containing the Cas12g effector, an RNA guide, and a target substrate containing different numbers of mismatches, insertions and deletions in the target sequence, successful activation of the Cas12g system by targeting of altered target RNA sequence will result in collateral cleavage of the fluorescent probe. Resulting fluorescent measurements denoting cleaved collateral substrate can be background subtracted using negative control samples and normalized to the signal from perfectly matching targets to estimate the impact of target alterations on the efficiency of collateral cleavage by Cas12g. Resulting maps of mismatch, insertion, and deletion tolerance by the Cas12g enzyme over the target length relative to the PAM can be used to design optimal RNA guides to distinguish between different RNA sequences or genotypes for specific detection or distinction between different Nucleic Acid Species. The lack of PAM or PFS of Cas12g1 makes it position the a target sequence over a site of genotypic variation to optimize the specificity of discrimination between the two genotypes given the Cas12g mismatch tolerance map.

The optimization process can be furthermore applied to other Cas12g orthologs to yield other systems that may have different properties. For example, orthogonal dinucleotide preferences of collateral cleavage would be helpful in generating separate channels of detection.

For nucleic acid detection applications, the unique properties of Cas12g1 may provide advantages. In some embodiments, the dual ssDNA and ssRNA collateral cleavage may serve to distinguish target-activated cleavage from background nuclease contamination. In such an application, ssDNA and ssRNA collateral substrates are labeled with fluorophores on separate channels and are both introduced into a detection reaction. Fluorescence in both ssDNA and ssRNA channels are required to be considered as a positive signal, thus potentially reducing the number of false positives especially since RNase contamination is widespread. The thermostability of Cas12g1, as evidenced by its high melting temperature and ssDNA/ssRNA cleavage activity at 50 C (FIGS. 16B, 19, 29A) may provide additional robustness in the assay. Thermostable Cas proteins have been demonstrated to be more resistant to inactivation in plasma (Harrington et al. (2017)), and the thermostability of Cas12g1 may enable it to be used directly in collected samples without the need for extensive processing. Furthermore, increased thermostability often confers robustness to environmental degradation or denaturation. Particularly since such nucleic acid detection assays such as SHERLOCK have been engineered into more portable formats for point of care applications (such as paper detection strips) (Gootenberg, et al. (2018), Myhrvold et al. (2018)), a prolonged shelf life enabled by the increased protein stability from Cas12g1 may provide greater versatility and utility.

Example 7. CLUST.019143 (Type V-G) CRISPR-Cas Systems can be Used to Provide Genotype-Gated Control of Cell Death or Dormancy Hybridization of the CLUST.019143 (Type V-G) CRISPR-Cas effector protein and crRNA with an RNA target complementary to the crRNA spacer forms an active complex that may exhibit nonspecific, "collateral" RNase activity. Such collateral RNAse activity can be used to provide genotype-gated control of cell death or dormancy. The dependence of such activity on the presence of a specific RNA target in a cell is valuable since it enables targeting of specific cell populations based on specific underlying transcriptional states or genotypes. Numerous applications exist in both eukaryotic and prokaryotic settings for such control of cell death or dormancy.

For prokaryotic applications, a CLUST.019143 (Type V-G) CRISPR-Cas system (e.g., including a Cas12g and RNA guide) is delivered (e.g., in vitro or in vivo) in order to induce cell death or dormancy of specific prokaryote populations (e.g., bacterial populations) in a genotype and transcriptome-specific way. For instance, the CLUST.019143 (Type V-G) CRISPR-Cas system includes one or more crRNAs that specifically target a particular prokaryotic genus, species, or strain. This specific targeting has many therapeutic benefits as it may be used to induce death or dormancy of undesirable bacteria (e.g., pathogenic bacteria such as *Clostridium difficile*) while protecting an individual's microbiome. In addition, the CLUST.019143 (Type V-G) systems provided herein are used to target prokaryotic cells having specific genotypes or transcriptional states. Within the microbial diversity that colonizes humans, only a small number of bacterial strains can induce pathogenesis. Further, even within pathogenic strains such as *Clostridium difficile*, not all members of the bacterial population exist continuously in active, disease-causing states. Thus, using RNA-targeting to control the activity of a Cas12g based on the genotype and transcriptional state of a prokaryotic cell allows for specific control of which cells are targeted without disrupting the entire microbiome.

Additionally, bacterial strains are readily engineered with genetic circuits or environmentally-controlled expression elements to generate genetic kill switches that limit the growth, colonization, and/or shedding of the engineered bacterial strains. For example, the expression of a Cas12g proteins, specific crRNA, or specific target RNA, is controlled using promoters derived from the regulatory regions of genes encoding proteins expressed in response to external stimuli, such as cold sensitive proteins (PcspA), heat shock proteins (Hsp), chemically inducible systems (Tet, Lac, AraC). The controlled expression of one or more elements of the CLUST.019143 (Type V-G) system allows for the full functional system to be expressed only upon exposure to an environmental stimulus, which in turn activates the nonspecific RNase activity of the system and thereby induces cell death or dormancy. Kill switches including Cas12g proteins as those described herein may be advantageous over traditional kill switch designs such as toxin/antitoxin systems (e.g., CcdB/CcdA Type II toxin/antitoxin systems), since they are not dependent on relative protein expression ratios which may be affected by leaky expression from a promoter (e.g., an environmental-stimulus dependent promoter), and thus allow for more precise control of the kill-switch.

To assess the ability of Cas12g to induce the dormancy or death of bacteria cells directly upon recognition of a target RNA, a variation of the in vivo functional screening was performed, in which the antibiotic tetracycline was removed from the culture plate. Removing tetracycline selection meant that the survival of the host *E. coli* was no longer dependent on the successful natural expression of the tetracycline resistance protein by pACYC184. However, the targeting library still contained crRNAs with spacers to the tetracycline resistance gene, $Tc^R$. When the dependence of *E. coli* survival on successful $Tc^R$ expression is removed, one would expect that there would be no impact on *E. coli* survival if the Cas12g directly cleaved $Tc^R$ mRNA, and thus no $Tc^R$ targeting spacers should register as a strong depletion event on the in vivo screen. Nevertheless, the screening data without tetracycline selection still showed strongly depleted spacers on the $Tc^R$ gene (FIGS. 6A-B), suggesting that the effect of Cas12g targeting RNA alone can mediate a growth disadvantage or cell death, even without antibiotic selection.

For eukaryotic applications, many diseases result from specific genotypes or transcriptional states in the diseased cells that distinguish them from healthy cells. Disease related genotypes are often contained in regions of the genome that are expressed, generating transcripts that can be targeted by a Cas12g using a crRNA that specifically targets the genotype. Such targeting provides cell dormancy or cell death in a population of cells with a specific disease related mutations. An example of an application is the targeted depletion of cancer cells containing specific mutations, such as driver mutations that occur spontaneously in the tumor microenvironment. In addition, the CLUST.019143 (Type V-G) CRISPR-Cas systems described herein are as kill-switch mechanisms to induce the death or dormancy of recombinant eukaryotic cells, such as chimeric antigen receptor-expressing T-cells, to limit their activity in inappropriate environments or when no longer desired.

Additionally, in a therapeutic context, numerous disease processes often involve dysregulation of cellular pathways that result in transcriptional states that are different from the normal baseline. A CLUST.019143 (Type V-G) CRISPR-Cas system can be used to specifically induce the death or dormancy of cells that have an altered transcriptome. For example, the system can be used to induce the death or dormancy of cells having a temporally altered transcriptome, such as cells involved in an anti-inflammatory response during an autoimmune disease flare that are differentiated from normal cells.

In some embodiments, the expression of the CLUST.019143 (Type V-G) CRISPR-Cas systems described herein can be controlled using synthetic biology to induce or trigger cell death or dormancy. For example, the expression of genes encoding each of the components of the CLUST.019143 (Type V-G) CRISPR-Cas systems can be controlled using genetic elements including, but are not limited to, promoters that are regulated by environmental stimuli, such as hypoxia (hif), neuronal activity (fos, arc), heat-shock (HSF-1), or exogenous controls such as light (FixJ), steroids (LexA), alcohol (AlcA), tetracycline (Tet). These promoters are used to control the expression of components of the CLUST.019143 (Type V-G) CRISPR-Cas system and/or of a specific RNA target to activate the system, thereby inducing the death or dormancy of targeted cells in response to the particular environmental stimuli to which the promoters respond.

Example 8. Adaptation of Type V-G CRISPR Cas Effector Protein Systems for Eukaryotic and Mammalian Activity Beyond the biochemical and diagnostic applications described herein, programmable RNA-modifying CRISPR-Cas systems such as CLUST.019143 (Type V-G), e.g., Cas12g, systems described herein have important applications in eukaryotic cells. Therapeutic applications include but are not limited to: genotype correction, insertion of a protective genotype, transcriptome engineering (for example, splicing modification), RNA knockdown and gene expression modulation, base editing, cellular engineering, to research and development advances, such as for RNA visualization, nucleic acid detection, and RNA knockdown screening.

To develop CLUST.019143 (Type V-G) CRISPR Cas systems for eukaryotic applications, the constructs encoding the Type V-G CRISPR-Cas effector proteins are first codon-optimized for expression in mammalian cells, and specific localization tags are optionally appended to either or both the N-terminus or C-terminus of the effector protein. These localization tags include sequences such as nuclear localization signal (NLS) sequences, which localize the effector to the nucleus for modification of nascent RNAs, as well as nuclear export signal (NES) sequences, which target the effector to the cytoplasm in order to modify mature RNAs. These sequences are described above in the "Functional Mutations" section. Other accessory proteins, such as fluorescent proteins, may be further appended. It has been demonstrated that the addition of robust, "superfolding" proteins such as superfolding green fluorescent protein (GFP) can increase the activity of CLUST.019143 (Type V-G) enzymes in mammalian cells when appended to the effector (Abudayyeh et al. (2017) *Nature* 550(7675): 280-4, and Cox et al. (2017) *Science* 358(6366): 1019-27).

Further engineering to modify the crRNA and/or tracrRNA is used to optimize activity specifically in eukaryotic and/or mammalian cells. To simplify the expression and complexing of the dual crRNA and tracrRNA required for Cas12g activity, a single RNA guide sequence is engineered. In some embodiments, the crRNA and tracrRNA are engineered by using a short linker sequence connecting the 3' end of the tracrRNA with the 5' end of the crRNA. A key feature to preserve is the overall secondary structure of the co-folded RNAs. Furthermore, the length and composition of the linker as well as the sequence of the direct repeat adjacent to the linker are optimized to design a most effective single RNA guide. Additionally, chemical modifications (Hendel et. al. *Nat Biotechnol.* 2015 September; 33(9):985-989, Yin, et. al. *Nat Biotechnol.* 2017 December; 35(12):1179-1187) can be used to enhance the in vivo editing efficiency by conferring properties such as greater resistance to nuclease degradation and enhanced secondary structure formation. In one instance, the effect of these modifications are compared in their RNA knockdown ability against the composition in which the pre-crRNA and tracrRNA are expressed as separate RNAs. Together these engineered modifications provide greater nuclease activity in eukaryotic cells and increase the flexibility of usage in genome editing applications.

The codon-optimized sequence coding for the Cas12g and appended accessory proteins and localization signals is then cloned into a eukaryotic expression vector with the appropriate 5' Kozak eukaryotic translation initiation sequence, eukaryotic promoters, and polyadenylation signals. In one embodiment, the expression of the effector is driven by a constitutive promoter, the elongation factor 1alpha short (EFS) promoter, and terminated by a bGH poly(A) signal. Expression of the RNA guide is driven by U6, a Polymerase III promoter; or if the crRNA and tracrRNA are expressed separately, by the Polymerase III promoters U6 and H1, respectively.

Depending on the application and mode of packaging, the eukaryotic expression vector can be a lentiviral plasmid backbone, adeno-associated viral (AAV) plasmid backbone. Notably, the small size of CLUST.019143 (Type V-G) CRISPR Cas effector proteins, e.g., Cas12g proteins, make them ideally suited for packaging along with its crRNA and appropriate control sequences into a single adeno-associated virus particle; the packaging size limit of 4.7 kb for AAV may preclude the use of larger effectors.

Additionally, multiplexing of Cas12g with multiple RNA guides targeting different sequences enables the manipulation of multiple RNA species for therapeutic applications requiring manipulation of multiple transcripts simultaneously.

After adapting the sequences, delivery vectors, and methods for mammalian use, the Cas12g constructs described herein are characterized for performance. For efficient testing of the mammalian activity levels of various constructs, we use a dual-luciferase reporter expressing both *Gaussia* luciferase (Glue) and *Cypridinia* luciferase (Clue) (Abudayyeh et al. 2017). The dual-luciferase reporter construct along with plasmids expressing the CLUST.019143 (Type V-G) CRISPR-Cas system and cognate RNA guides are delivered using transient transfection (e.g., Lipofectamine® 2000) into model cell lines such as HEK 293T cells. Targeting the Glue transcript and comparing the relative activity versus the internal control of the Clue activity enables an estimation of Cas12g effectiveness in a mammalian context. This activity is then corroborated on the reporter through knockdown of endogenous transcripts, such as from the well-characterized KRAS genetic locus.

In addition to testing various construct configurations and accessory sequences on individual targets, pooled library-based approaches are used to determine 1) any targeting dependency of specific Cas12g proteins in mammalian cells, as well as 2) the effect of mismatch locations and combinations along the length of the targeting crRNA. Briefly, the pooled library includes a plasmid that expresses a target RNA containing different flanking sequences as well as mismatches to the guide or guides used in the screening experiment, such that the successful target recognition and cleavage results in depletion of the sequence from the library. Furthermore, mRNA sequencing is used to determine the off-target RNA cleavage effects of the CLUST.019143 (Type V-G) CRISPR-Cas system.

Complementary possibilities to transcriptome modification using the RNA cleavage activity of Cas12g are engineered applications using catalytically-inactive Cas12g proteins in which the conserved residues of the RuvC domain are mutated to alanine (such as the inactivating D513A mutation for Cas12g1). Catalytically inactive Cas12g retains its programmable RNA binding activity, though it will no longer be able to cleave target or collateral RNA.

In addition to direct uses of dCas12g such as in RNA immunoprecipitation, transcript labeling (when dCas12g is fused with fluorescent protein), and translation modification through site-specific targeted disruption of native translational machinery, other domains can be appended onto the dCas12g protein to provide further functionality. Activities of these domains include RNA base modification (ADAR1, ADAR2, APOBEC), RNA methylation ($m^6A$ methyltransferases and demethylases), splicing modifiers (hnRNPA1), localization factors (KDEL retention sequence, mitochondrial targeting signal, peroxisomal targeting signal), translation modification factors (EIF4G translation initiation factor, GLD2 poly(A) polymerase, transcriptional repressors). Additionally, additional control is provided by further appending domains, such as light-gated control (cryptochromes) and chemically inducible components (FKBP-FRB chemically inducible dimerization).

Optimizing the activity of such fusion proteins requires a systematic way of comparing linkers that connect the dCas12g with the appended domain. These linkers include flexible glycine-serine (GS) linkers in various combinations and lengths, rigid linkers such as the alpha-helix forming EAAAK sequence, XTEN linker (Schellenberger V, et al. *Nat. Biotechnol.* 2009; 27:1186-1190), as well as different combinations thereof (see TABLE 16). The various designs are then assayed in parallel over the same RNA guide/target complex and functional readout to determine which one yields the desired properties.

For adapting Cas12g for use in targeted RNA base modification (see, e.g., Cox DBT et al., *Science* 2017 10.1126/science.aaq0180), we begin with the Cas12g ortholog and NES combination that yielded the highest endogenous mammalian RNA knockdown activity and mutate the conserved residues of the RuvC domain to create a catalytically inactive enzyme. Next, a linker is used to create the fusion protein between Cas12g-NES and the base editing domain. Initially, this domain will consist of the $ADAR2_{DD}$(E488Q/T375G) mutant engineered previously for hyperactivity and greater specificity when used with Cas13b in REPAIRv2, but alternate deaminases such as ADAR1 and APOBEC1, among others, can be engineered and assayed in parallel (TABLE 16). Given the likely structural differences between the smaller Cas12g versus the previously characterized Cas13 effectors, alternate linker designs and lengths may yield the optimal design of the base editing fusion protein.

To evaluate the activity of the dCas12g-derived base editors, the HEK 293T cells are transiently transfected with the dCas12g-ADAR construct, a plasmid expressing the RNA guide, and optionally, a reporter plasmid if the base editor is targeting the reporter and not an endogenous locus. The cells are harvested 48 hours after transient transfection, the RNA is extracted and reverse-transcribed to yield a cDNA library that is prepared for next generation sequencing. Analysis of the base composition of loci of samples containing the targeting vs. negative control non-targeting crRNAs provide information about the editing efficiency, and analysis of broader changes to the transcriptome will yield information about the off-target activity.

One particular advantage of developing an RNA base editing system using Cas12g is that the small size, smaller than the existing Cas13a-d effectors, enables more ready packaging in AAV of dCas12g-ADAR along with its RNA guide and control elements without the need for protein truncations. This all-in-one AAV vector enables greater efficacy of in vivo base editing in tissues, which is particularly relevant as a path towards therapeutic applications of Cas12g. In base editing and other applications, the small size, the lack of a biochemical PFS, and robust activity of Cas12g proteins make it a valuable addition to the toolbox of programmable RNA modifying enzymes.

TABLE 16

Amino Acid Sequences of Motifs and Functional Domains in Engineered Variants of CLUST.019143 (Type V-G) CRISPR-Cas Effector Proteins

```
>LINKER_1
GS

>LINKER_2
GSGGGGS

>LINKER_3
GGGGSGGGGSGGGGS
```

TABLE 16-continued

Amino Acid Sequences of Motifs and Functional Domains in Engineered
Variants of CLUST.019143 (Type V-G) CRISPR-Cas Effector Proteins

>LINKER_4
GGSGGSGGSGGSGGSGGS

[ADAR1, ADAR2: C-term fusion (or optionally N-term)]
>ADAR1DD-WT
SLGTGNRCVKGDSLSLKGETVNDCHAEIISRRGFIRFLYSELMKYNSQTAKDSIFEPAKGGEKLQIKKTVSFHLYI
STAPCGDGALFDKSCSDRAMESTESRHYPVFENPKQGKLRTKVENGEGTIPVESSDIVPTWDGIRLGERLRTMSCS
DKILRWNVLGLQGALLTHFLQPIYLKSVTLGYLFSQGHLTRAICCRVTRDGSAFEDGLRHPFIVNHPKVGRVSIYD
SKRQSGKTKETSVNWCLADGYDLEILDGTRGTVDGPRNELSRVSKKNIFLLFKKLCSFRYRRDLLRLSYGEAKKAA
RDYETAKNYFKKGLKDMGYGNWISKPQEEKNF >ADAR1DD-E1008Q (Cox et al., 2017)
SLGTGNRCVKGDSLSLKGETVNDCHAEIISRRGFIRFLYSELMKYNSQTAKDSIFEPAKGGEKLQIKKTVSFHLYI
STAPCGDGALFDKSCSDRAMESTESRHYPVFENPKQGKLRTKVENGQGTIPVESSDIVPTWDGIRLGERLRTMSCS
DKILRWNVLGLQGALLTHFLQPIYLKSVTLGYLFSQGHLTRAICCRVTRDGSAFEDGLRHPFIVNHPKVGRVSIYD
SKRQSGKTKETSVNWCLADGYDLEILDGTRGTVDGPRNELSRVSKKNIFLLFKKLCSFRYRRDLLRLSYGEAKKAA
RDYETAKNYFKKGLKDMGYGNWISKPQEEKNF >ADAR2DD-WT
QLHLPQVLADAVSRLVLGKFGDLTDNFSSPHARRKVLAGVVMTTGTDVKDAKVISVSTGTKCINGEYMSDRGLALN
DCHAEIISRRSLLRFLYTQLELYLNNKDDQKRSIFQKSERGGFRLKENVQFHLYISTSPCGDARIFSPHEPILEEP
ADRHPNRKARGQLRTKIESGEGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNWTVGDSAIEVINATTGKD
ELGRASRLCKHALYCRWMRVHGKVPSHLLRSKITKPNVYHESKLAAKEYQAAKARLFTAFIKAGLGAWVEKPTEQD
QFSLT ADAR2DD-E4880 (Cox et al., 2017)
QLHLPQVLADAVSRLVLGKFGDLTDNFSSPHARRKVLAGVVMTTGTDVKDAKVISVSTGTKCINGEYMSDRGLALN
DCHAEIISRRSLLRFLYTQLELYLNNKDDQKRSIFQKSERGGFRLKENVQFHLYISTSPCGDARIFSPHEPILEEP
ADRHPNRKARGQLRTKIESGQGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNWTVGDSAIEVINATTGKD
ELGRASRLCKHALYCRWMRVHGKVPSHLLRSKITKPNVYHESKLAAKEYQAAKARLFTAFIKAGLGAWVEKPTEQD
QFSLT

[Cytidine deaminase, AID, APOBEC1: N-term fusion (or optionally C-term)]
>AID-APOBEC1 (Dickerson et al., 2003, Komor et al., 2017)
MDSLLMNRRKFLYQFKNVRWAKGRRETYLCYVVKRRDSATSFSLDFGYLRNKNGCHVELLFLRYISDWDLDPGRCY
RVTWFTSWSPCYDCARHVADFLRGNPNLSLRIFTARLYFCEDRKAEPEGLRRLHRAGVQIAIMTFKDYFYCWNTFV
ENHERTFKAWEGLHENSVRLSRQLRRILLPLYEVDDLRDAFRTLGL >Lamprey_AID-APOBEC1 (Rogozin et al., 2007, Komor et al., 2017)
MTDAEYVRIHEKLDIYTFKKQFFNNKKSVSHRCYVLFELKRRGERRACFWGYAVNKPQSGTERGIHAEIFSIRKVE
EYLRDNPGQFTINWYSSWSPCADCAEKILEWYNQELRGNGHTLKIWACKLYYEKNARNQIGLWNLRDNGVGLNVMV
SEHYQCCRKIFIQSSHNQLNENRWLEKTLKRAEKRRSELSIMIQVKILHTTKSPAV >APOBEC1_BE1 (Komor et al., 2016)
MSSETGPVAVDPTLRRRIEPHEFEVFFDPRELRKETCLLYEINWGGRHSIWRHTSQNTNKHVEVNFIEKFTTERYF
CPNTRCSITWFLSWSPCGECSRAITEFLSRYPHVTLFIYIARLYHHADPRNRQGLRDLISSGVTIQIMTEQESGYC
WRNFVNYSPSNEAHWPRYPHLWVRLYVLELYCIILGLPPCLNILRRKQPQLTFFTIALQSCHYQRLPPHILWATGL
K

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)-associated (Cas) system comprising:
   an RNA guide or a nucleic acid encoding an RNA guide, wherein the RNA guide comprises a direct repeat sequence, a spacer sequence capable of hybridizing to a target nucleic acid in a eukaryotic cell, and a tracrRNA; and
   a RuvC nuclease domain-containing CRISPR-Cas effector protein or a nucleic acid encoding the RuvC nuclease domain-containing CRISPR-Cas effector protein, wherein the RuvC nuclease domain-containing CRISPR-Cas effector protein is capable of binding to the RNA guide and of targeting the target nucleic acid complementary to the spacer sequence;
   wherein the CRISPR-Cas effector protein comprises an amino acid sequence that is at least 80% identical to the amino acid sequence of SEQ ID NO: 6.

2. The system of claim 1, wherein:
   (i) the CRISPR-Cas effector protein comprises the amino acid sequence of SEQ ID NO: 6;
   (ii) the spacer sequence comprises 15 to 30 nucleotides; or
   (iii) the direct repeat sequence comprises a nucleotide sequence of SEQ ID NO: 401 or SEQ ID NO: 202.

3. The system of claim 1, wherein:
   (i) the target nucleic acid is a single-stranded RNA;
   (ii) the target nucleic acid is an RNA selected from the group consisting of an mRNA, a tRNA, a ribosomal RNA, a non-coding RNA, a lncRNA, or a nuclear RNA; or
   iii) the target nucleic acid is a DNA selected from the group consisting of chromosomal DNA, mitochondrial DNA, single-stranded DNA, or plasmid DNA.

4. The system of claim 1, wherein the targeting of the target nucleic acid by the CRISPR-Cas effector protein and the RNA guide results in a modification of the target nucleic acid, wherein:
   (i) the modification in the target nucleic acid is a cleavage event;
   (ii) the modification in the target nucleic acid is a nicking event; or
   (iii) the target nucleic is comprised in a eukaryotic cell and the modification results in cell toxicity.

5. The system of claim 4, wherein:
   (i) the CRISPR-Cas effector protein comprises at least one nuclear localization signal (NLS); or
   (ii) the CRISPR-Cas effector protein comprises at least one nuclear export signal (NES).

6. The system of claim 1, wherein the CRISPR-Cas effector protein includes one or more amino acid substitutions within the RuvC domain relative to SEQ ID NO: 6.

7. The system of claim 6, wherein the one or more amino acid substitutions within the RuvC domain include an alanine substitution at an amino residue corresponding to D513, E655, or D745 of SEQ ID NO: 6.

8. The system of claim 1, wherein the RuvC domain is catalytically inactivated.

9. The system of claim 1, wherein the CRISPR-Cas effector protein is fused to a base-editing domain, an RNA methyltransferase, an RNA demethylase, a splicing modifier, a localization factor, or a translation modification factor.

10. The system of claim 9, wherein the base-editing domain comprises Adenosine Deaminase Acting on RNA 1 (ADAR1), ADAR2, apolipoprotein B mRNA editing enzyme, catalytic polypeptide-like (APOBEC), or activation-induced cytidine deaminase (AID).

11. The system of claim 1, wherein the tracrRNA sequence comprises (SEQ ID NO: 250)
GAUGCUUACUUAGUCAUCUGGUUGGCAAACCUCCGCGGACCUUCGGGACC
AAUGGAGAGGAACCCAGCCGAGAAGCAUCGAGCCGGUAAAUGCCGGAAA.

12. An activated CRISPR complex comprising:
   a CRISPR-Cas system of claim 1; and
   a target nucleic acid bound to the RNA guide of the CRISPR-Cas system.

13. A method of modifying a collateral nucleic acid, the method comprising contacting the collateral nucleic acid with an activated CRISPR complex of claim 12, wherein the collateral nucleic acid comprises a nucleic acid sequence that does not have sequence similarity to the target nucleic acid or a fragment thereof.

14. A method of non-specifically cleaving a collateral nucleic acid, the method comprising contacting the collateral nucleic acid with an activated CRISPR complex of claim 12, wherein the collateral nucleic is a single-stranded DNA, single-stranded RNA, or double-stranded RNA, and wherein the collateral nucleic acid comprises a nucleic acid sequence that does not have sequence similarity to the target nucleic acid.

15. A eukaryotic cell comprising the system of claim 1.

16. A method of targeting and editing a target nucleic acid, the method comprising contacting the target nucleic acid with a system of claim 1.

17. A method of cleaving a single-stranded DNA substrate, a single-stranded RNA substrate, or a double-stranded RNA substrate with the CRISPR-Cas system of claim 1, the method comprising contacting the single-stranded DNA substrate, single-stranded RNA substrate, or double-stranded RNA substrate with the CRISPR-Cas system, optionally wherein the single-stranded DNA substrate, single-stranded RNA substrate, or double-stranded RNA substrate lacks a protospacer adjacent motif (PAM) sequence protospacer flanking sequence (PFS) with a target nucleic acid.

18. A method of detecting a target RNA in a sample, the method comprising:
   (a) contacting the sample with the CRISPR-Cas system of claim 1 and a labeled detector RNA, wherein hybridization of the RNA guide to the target RNA causes cleavage of the labeled detector RNA; and
   (b) measuring a detectable signal produced by cleavage of the labeled detector RNA, thereby detecting the target RNA in the sample.

19. The system of claim 1, wherein the CRISPR-Cas effector protein comprises an amino acid sequence that is at least 95% identical to the amino acid sequence of SEQ ID NO: 6.

20. The system of claim 1, wherein the CRISPR-Cas effector protein comprises an amino acid sequence that is at least 98% identical to the amino acid sequence of SEQ ID NO: 6.

* * * * *

UNITED STATES PATENT AND TRADEMARK OFFICE
CERTIFICATE OF CORRECTION

| | |
|---|---|
| PATENT NO. | : 12,195,770 B2 |
| APPLICATION NO. | : 16/980246 |
| DATED | : January 14, 2025 |
| INVENTOR(S) | : Keston-Smith et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1157 days.

Signed and Sealed this
Twenty-fourth Day of June, 2025

Coke Morgan Stewart
*Acting Director of the United States Patent and Trademark Office*

SEQUENCE LISTING

<160> NUMBER OF SEQ ID NOS: 493

<210> SEQ ID NO 1
<211> LENGTH: 772
<212> TYPE: PRT
<213> ORGANISM: Unknown
<220> FEATURE:

<223> OTHER INFORMATION: Description of Unknown:
      bioreactor-anaerobic-anaerobic digester digestate sequence

<400> SEQUENCE: 1

```
Met Thr Arg Ile Lys Tyr Arg Gln Glu Arg Thr Leu Val Arg Gly Leu
1               5                   10                  15

Gln Arg Leu Pro Asn Gln Asp Lys Ala Glu Phe Asn Lys Asn Val Leu
            20                  25                  30

Gly Leu Arg Arg His Phe Glu Gln Phe Asn Leu Asn Val Ala Glu Leu
        35                  40                  45

Cys Gln Trp Leu Ile Ser Phe Lys Pro Glu Asn Pro Gly Ser Val Cys
    50                  55                  60

Glu Thr Lys Leu Phe Trp Glu Phe Met Leu Glu Pro Glu Asn Phe Cys
65                  70                  75                  80

Pro Asp Thr Tyr Asp Arg Gly Pro Asp Trp Leu Arg His Glu Ile Phe
                85                  90                  95

Val Leu Ala Ala Gly Trp Arg Thr Phe Glu Asp Ile Lys Ala His Asn
            100                 105                 110

Met Pro Glu Ser Leu Phe Glu Ser Ile Lys Ile Ala Ser Ser Lys Pro
        115                 120                 125

Arg Ser Lys Thr Ala Glu Ala Leu Phe Ile Arg Leu Lys Ser Leu Glu
    130                 135                 140

Ala Ser His Val Met Val Leu Leu Lys Ser Ala Ser Glu Trp Leu Ser
145                 150                 155                 160

Thr Arg Tyr Val Arg Gln Ser Glu Asn Trp Lys Gln Asn Glu Gln Glu
                165                 170                 175

Trp Gln Lys Lys Lys Ala Ala Trp Glu Asp Lys His Pro Glu Leu Thr
            180                 185                 190

Pro Ala Ile Arg Asp Lys Tyr Asn Ala Ile Phe Val Glu Leu Gly Ile
        195                 200                 205

Ser Glu Lys Arg Pro His Val Cys Ser Trp Lys Lys Leu Ser Glu Asn
    210                 215                 220

Lys Asp Asn Cys Asp Trp Ala Gly Glu Arg Lys Asn Ile Gly Asp Lys
225                 230                 235                 240

Trp Ile Ser His Ser Asp Leu Cys Ile Lys Tyr His Glu Phe Ala Arg
                245                 250                 255

Lys Leu Arg Ser Lys Gln Arg Gln His Phe Val Asp Asn Ala Asn Gln
            260                 265                 270

Tyr Leu Glu Leu Arg Arg Arg Tyr Pro Gln Trp Thr Arg Asp Met Ala
        275                 280                 285

Met Asn Gly Leu Phe Lys Asn Val Pro Leu Ala Arg Asn Trp Phe Arg
    290                 295                 300

Asn Ala Trp Thr Asn Tyr Leu Asn Ala Leu Asn Ile Leu Glu Thr Thr
305                 310                 315                 320

Ile Leu Glu Asn Tyr Ser Gly His Leu Pro His Cys Glu Lys Leu Ser
                325                 330                 335

Asp Glu Cys Val Phe Lys Lys His Thr Asp Asn Cys Arg Arg Tyr Lys
            340                 345                 350

Leu Leu Leu Gly Glu Lys Leu Ser Asn Gln Arg Glu Leu Glu Glu
        355                 360                 365

Thr Tyr Arg Glu Trp Arg Glu Phe Leu Ala Pro Pro Asn Lys Pro
    370                 375                 380

Phe Leu Arg Tyr Pro Ser Ala Gln Lys Leu Pro Thr Pro Lys Leu Phe
385                 390                 395                 400
```

Gly Arg Gly Tyr Tyr Asp Leu Asp Phe Thr Arg His Val Val Lys Leu
            405                 410                 415

Arg Leu Asp Asp Met Pro Ala Asp Asn Phe Val Ser Phe Gly Phe Lys
        420                 425                 430

Pro Trp Pro Arg Gly Tyr Asp Lys Lys Pro Gly Glu Ile Asn Ile Thr
    435                 440                 445

Ser Val His Val His Phe Ile Gly Thr Arg Ala Arg Val Gly Phe Arg
450                 455                 460

Phe Ala Val Pro His Ser Asp Ser Arg Phe Ser Val Ser Gln Asp Lys
465                 470                 475                 480

Ile Asp Glu Leu Arg Ser Gly Gly Phe Pro Gly Lys Ser Gln Asp Gln
                485                 490                 495

Glu Phe Leu Asn Glu Ala Arg Gln Arg Leu Leu Asp Gly Met Asn Glu
            500                 505                 510

Asn Gln Lys Ser Ala Leu Arg Ile Met Ala Val Asp Leu Gly Thr His
        515                 520                 525

Arg Ala Ala Ala Ala Phe Phe Thr Gly Cys Ile Phe Asn Lys Ala Lys
    530                 535                 540

Leu Leu Lys Leu Lys Lys Ile Asp Leu Leu Thr Glu Pro Lys Thr Asp
545                 550                 555                 560

Thr Thr Lys Pro Glu Lys Leu Ser Ala Asp Glu Lys Lys Ile Gln Arg
                565                 570                 575

Glu Lys Gly Leu Thr Gln His His Val Gly Lys His Phe Glu Thr Leu
            580                 585                 590

Glu Ala Arg Thr Lys Glu Ile Ile Ser Lys Arg Gln Asn Met Lys Met
        595                 600                 605

Ala Pro Ser Asp Thr Pro Asp Ile Val Gly Asp His Asp Leu Arg
    610                 615                 620

His Leu Thr Ser His Ile Arg Arg Met Ile Arg Asp Trp Val Arg Leu
625                 630                 635                 640

Asn Ala Arg Gln Ile Thr Glu Leu Ala Glu Glu Asn Val Asp Leu
                645                 650                 655

Ile Val Phe Glu Ser Met Arg Gly Phe Arg Ala Pro Gly Tyr Asp Lys
            660                 665                 670

Leu Asp Leu Lys Lys Lys Arg Leu Ala Phe Phe Ala Tyr Gly Gln
        675                 680                 685

Ile Arg Arg Lys Val Ala Glu Lys Ala Val Glu Arg Gly Met Arg Val
    690                 695                 700

Ile Thr Val Pro Tyr Phe Lys Ser Ser Gln Ile Cys Ala Gln Cys Gly
705                 710                 715                 720

Arg Ser Gln Asn Asp Lys Asn Lys Leu Arg Asp Asn Lys Trp Lys Gln
                725                 730                 735

Ser Phe Gln Cys Glu Phe Ser Asp Cys Asn Tyr Lys Thr His Ser Asp
            740                 745                 750

Glu Asn Ala Ala Arg Val Leu Gly Arg Val Phe Trp Gly Glu Ile Thr
        755                 760                 765

Leu Pro Thr Asp
    770

<210> SEQ ID NO 2
<211> LENGTH: 821
<212> TYPE: PRT
<213> ORGANISM: Unknown
<220> FEATURE:

<223> OTHER INFORMATION: Description of Unknown:
activated sludge metagenome sequence

<400> SEQUENCE: 2

```
Met Leu Pro Thr Arg Tyr Lys Pro Ala Arg Thr Leu Val Arg Pro Leu
1               5                   10                  15

Gly Arg Leu Pro His Glu Pro Arg Lys Glu Phe Val Glu Lys Cys Arg
            20                  25                  30

Arg Val Arg Met His Phe Glu Gln Phe Asn Ile Asp Val Ala Asp Leu
        35                  40                  45

Cys Gln Trp Leu Met Ser Leu Arg Pro Asn Thr Arg Ile Gly Asp Ala
    50                  55                  60

Gln Ser Thr Val Phe Trp Asp Phe Phe Leu Asn Pro Ser Ile Leu Thr
65                  70                  75                  80

Val Glu Ala Asp Glu Lys Glu Arg Asp Arg Trp Arg Leu Ala Ala Phe
                85                  90                  95

Asp Glu Leu Leu Gln Ile Arg Phe Gly His Asp Pro Asn Ala Pro Pro
            100                 105                 110

Trp Ser Glu Glu Phe Arg Ser Ala Ile Arg His Val Ala Gln Arg Pro
        115                 120                 125

Lys Ser Ala Thr Ala Gln Arg Leu Phe Asp Arg Leu Arg Ser Leu Thr
130                 135                 140

Ala Pro His Arg Leu Val Leu Leu Lys Ser Ala Ala Glu Trp Ile Ile
145                 150                 155                 160

Ala Arg Tyr Gln Arg Gly Met Glu Asn Trp Gln Arg Gln Phe Ala Glu
                165                 170                 175

Trp Gln Arg Glu Lys Glu Glu Trp Glu Ala Ala His Pro Asn Leu Thr
            180                 185                 190

Pro Glu Val Arg Asp Ala Phe Thr Arg Val Phe Lys Asn Leu Phe Glu
        195                 200                 205

Asn Pro Asp Gly Asp Gly Lys Ile Gly Val Arg Lys Asn Pro Arg
210                 215                 220

Ile Cys Ser Trp Glu Arg Leu Lys Leu Asn Lys Asp Asn Cys Val Tyr
225                 230                 235                 240

Ala Gly Gln Lys Gly His Gly Pro Leu Cys Trp Glu Phe Ser Lys Phe
                245                 250                 255

Val Lys Ala Gln Lys Asn Ala Gly Thr Ile Lys Thr Phe Phe Val Asp
            260                 265                 270

Val Ala Asn Lys Tyr Leu His Val Arg Arg Asn Leu Ser Lys Pro Gly
        275                 280                 285

Val Lys Leu Lys Lys Ser Pro Arg Gln Glu Ala Phe Lys Arg Leu Tyr
290                 295                 300

Asn Gln Lys Gly Met Glu Lys Ala Arg Asn Trp Phe Thr Asp Ala Trp
305                 310                 315                 320

Ser Gly Tyr Leu Thr Ala Leu Asn Leu Asn Glu Lys Thr Ile Leu Asp
                325                 330                 335

His Gly Cys Leu Lys His Cys Gly Ala Ile Gly Ala Glu Phe Glu Lys
            340                 345                 350

Ser Leu Cys Gln Phe Asn Pro His Thr His Leu Cys Val Gln Tyr Arg
        355                 360                 365

Asn Ala Leu Glu Ser Leu Glu Pro Ala Ile Arg Glu Leu Glu Gly Asp
370                 375                 380

Tyr Arg Glu Trp Arg Arg Leu Phe Leu Ala Pro Pro Arg Lys Pro Ser
385                 390                 395                 400
```

```
Phe Arg Tyr Pro Ser Ser Arg Arg Leu Pro Met Pro Lys Ile Phe Gly
            405                 410                 415
Glu His Phe His Gln Ile Asp Phe Asp Gln Ser Ile Leu Arg Leu Arg
                420                 425                 430
Leu Glu Asp Met Ala Glu Gly Glu Trp Ile Glu Phe Gly Phe Lys Pro
            435                 440                 445
Trp Pro Lys Asp Tyr Arg Pro Gly Lys Asp Glu Val Arg Val Thr Ser
    450                 455                 460
Val His Val Asn Phe His Gly Asn Arg Met Arg Ala Gly Phe His Phe
465                 470                 475                 480
Glu Ala Pro Ala Lys Pro Ser Arg Phe Ala Cys Thr Gln Asp Glu Leu
                485                 490                 495
Asp Asp Leu Arg Ser Lys Gln Phe Pro Arg Gln Ser Gln Asp Arg Gln
            500                 505                 510
Leu Leu Glu Val Ala Arg Arg Leu Leu Glu Ser Phe Asp Gly Met
        515                 520                 525
Leu Glu Ser Asp Leu Arg Ile Leu Ala Val Asp Leu Gly Glu Lys Gly
    530                 535                 540
Ala Ala Ala Ala Val Tyr Gln Gly His Gly His Glu Ala Asp Val Ala
545                 550                 555                 560
Ile Pro Ile Val Lys Ile Asp Arg Leu Tyr Asp His Val Pro Asp Val
                565                 570                 575
Leu Asp Val Glu Ser Ala Arg Val Pro Pro Lys Phe Asp Asp Ser
            580                 585                 590
Arg Asp Pro Arg Gly Val Arg Lys Glu His Val Gly Arg His Leu Gly
            595                 600                 605
Gln Leu Gln Arg Gly Ala Gln Thr Leu Ala Gln His Arg Gln Asp
    610                 615                 620
Glu Ser Ala Pro Ala Ala Leu Arg Arg His Asp Phe Arg Ser Leu Thr
625                 630                 635                 640
Arg His Ile Arg Trp Met Ile Arg Asp Trp Thr Arg His Asn Ala Ala
                645                 650                 655
Gln Ile Thr Ala Ala Ala Glu Thr His Arg Cys His Leu Ile Val Phe
                660                 665                 670
Glu Ser Leu Arg Gly Phe Lys Pro Arg Gly Tyr Asp Gln Met Asp Phe
            675                 680                 685
Ala Gln Lys Ala Arg Leu Ala Phe Phe Ala Tyr Gly Arg Val Arg Arg
    690                 695                 700
Lys Val Val Glu Lys Ala Val Glu Arg Gly Leu Arg Val Val Thr Val
705                 710                 715                 720
Pro Tyr Gly Phe Thr Ser Gln Ile Cys Ser Glu Cys Gly His Arg Gln
                725                 730                 735
Arg Asn Lys Gly Arg Leu Arg Lys Asn Lys Tyr Gln Arg Arg Phe Val
            740                 745                 750
Cys Glu Cys Gly Glu Pro Lys Lys Ser Ala Asn Lys Thr Ala Ala Pro
            755                 760                 765
Asp Arg Ser Ala Thr Val Ser Pro Cys Thr Cys Arg Leu Gln Leu Gly
    770                 775                 780
Ser Asp Val Asn Ala Ala Arg Val Leu Ala Arg Val Phe Trp Asp Glu
785                 790                 795                 800
Ile Val Leu Pro Thr Arg Glu Glu Met Arg Glu Pro Ala Val Asp Ser
                805                 810                 815
```

Ala Pro Pro Ser Lys
            820

<210> SEQ ID NO 3
<211> LENGTH: 786
<212> TYPE: PRT
<213> ORGANISM: Unknown
<220> FEATURE:
<223> OTHER INFORMATION: Description of Unknown:
      activated sludge metagenome sequence

<400> SEQUENCE: 3

Met His Phe Glu Gln Phe Asn Ile Asp Val Ala Asp Leu Cys Gln Trp
1               5                   10                  15

Leu Met Ser Leu Arg Pro Asn Thr Arg Ile Gly Asp Ala Gln Ser Thr
            20                  25                  30

Val Phe Trp Asp Phe Phe Leu Asn Pro Ser Ile Leu Thr Val Glu Ala
        35                  40                  45

Asp Glu Lys Glu Arg Asp Arg Trp Arg Leu Ala Ala Phe Asp Glu Leu
    50                  55                  60

Leu Gln Ile Arg Phe Gly His Asp Pro Asn Ala Pro Pro Trp Ser Glu
65                  70                  75                  80

Glu Phe Arg Ser Ala Ile Arg His Val Ala Gln Arg Pro Lys Ser Ala
                85                  90                  95

Thr Ala Gln Arg Leu Phe Asp Arg Leu Arg Ser Leu Thr Ala Pro His
            100                 105                 110

Arg Leu Val Leu Leu Lys Ser Ala Ala Glu Trp Ile Ile Ala Arg Tyr
        115                 120                 125

Gln Arg Gly Met Glu Asn Trp Gln Arg Gln Phe Ala Glu Trp Gln Arg
    130                 135                 140

Glu Lys Glu Glu Trp Glu Ala Ala His Pro Asn Leu Thr Pro Glu Val
145                 150                 155                 160

Arg Asp Ala Phe Thr Arg Val Phe Lys Asn Leu Phe Glu Asn Pro Asp
                165                 170                 175

Gly Asp Gly Lys Ile Gly Val Arg Arg Lys Asn Pro Arg Ile Cys Ser
            180                 185                 190

Trp Glu Arg Leu Lys Leu Asn Lys Asp Asn Cys Val Tyr Ala Gly Gln
        195                 200                 205

Lys Gly His Gly Pro Leu Cys Trp Glu Phe Ser Lys Phe Val Lys Ala
    210                 215                 220

Gln Lys Asn Ala Gly Thr Ile Lys Thr Phe Phe Val Asp Val Ala Asn
225                 230                 235                 240

Lys Tyr Leu His Val Arg Arg Asn Leu Ser Lys Pro Gly Val Lys Leu
                245                 250                 255

Lys Lys Ser Pro Arg Gln Glu Ala Phe Lys Arg Leu Tyr Asn Gln Lys
            260                 265                 270

Gly Met Glu Lys Ala Arg Asn Trp Phe Thr Asp Ala Trp Ser Gly Tyr
        275                 280                 285

Leu Thr Ala Leu Asn Leu Asn Glu Lys Thr Ile Leu Asp His Gly Cys
    290                 295                 300

Leu Lys His Cys Gly Ala Ile Gly Ala Glu Phe Glu Lys Ser Leu Cys
305                 310                 315                 320

Gln Phe Asn Pro His Thr His Leu Cys Val Gln Tyr Arg Asn Ala Leu
                325                 330                 335

Glu Ser Leu Glu Pro Ala Ile Arg Glu Leu Glu Gly Asp Tyr Arg Glu
            340                 345                 350

-continued

Trp Arg Arg Leu Phe Leu Ala Pro Pro Arg Lys Pro Ser Phe Arg Tyr
            355                 360                 365

Pro Ser Ser Arg Arg Leu Pro Met Pro Lys Ile Phe Gly Glu His Phe
    370                 375                 380

His Gln Ile Asp Phe Asp Gln Ser Ile Leu Arg Leu Arg Leu Glu Asp
385                 390                 395                 400

Met Ala Glu Gly Glu Trp Ile Glu Phe Gly Phe Lys Pro Trp Pro Lys
                405                 410                 415

Asp Tyr Arg Pro Gly Lys Asp Glu Val Arg Val Thr Ser Val His Val
                420                 425                 430

Asn Phe His Gly Asn Arg Met Arg Ala Gly Phe His Phe Glu Ala Pro
            435                 440                 445

Ala Lys Pro Ser Arg Phe Ala Cys Thr Gln Asp Glu Leu Asp Asp Leu
    450                 455                 460

Arg Ser Lys Gln Phe Pro Arg Gln Ser Gln Asp Arg Gln Leu Leu Glu
465                 470                 475                 480

Val Ala Arg Arg Leu Leu Glu Ser Phe Asp Gly Met Leu Glu Ser
                485                 490                 495

Asp Leu Arg Ile Leu Ala Val Asp Leu Gly Glu Lys Gly Ala Ala Ala
            500                 505                 510

Ala Val Tyr Gln Gly His Gly His Glu Ala Asp Val Ala Ile Pro Ile
    515                 520                 525

Val Lys Ile Asp Arg Leu Tyr Asp His Val Pro Asp Val Leu Asp Val
    530                 535                 540

Glu Ser Ala Arg Val Pro Pro Lys Phe Asp Ser Arg Asp Pro
545                 550                 555                 560

Arg Gly Val Arg Lys Glu His Val Gly Arg His Leu Gly Gln Leu Gln
                565                 570                 575

Arg Gly Ala Gln Thr Leu Ala Gln His Arg Gln Asp Glu Ser Ala
            580                 585                 590

Pro Ala Ala Leu Arg Arg His Asp Phe Arg Ser Leu Thr Arg His Ile
        595                 600                 605

Arg Trp Met Ile Arg Asp Trp Thr Arg His Asn Ala Ala Gln Ile Thr
    610                 615                 620

Ala Ala Ala Glu Thr His Arg Cys His Leu Ile Val Phe Glu Ser Leu
625                 630                 635                 640

Arg Gly Phe Lys Pro Arg Gly Tyr Asp Gln Met Asp Phe Ala Gln Lys
                645                 650                 655

Ala Arg Leu Ala Phe Phe Ala Tyr Gly Arg Val Arg Arg Lys Val Val
            660                 665                 670

Glu Lys Ala Val Glu Arg Gly Leu Arg Val Val Thr Val Pro Tyr Gly
        675                 680                 685

Phe Thr Ser Gln Ile Cys Ser Glu Cys Gly His Arg Gln Arg Asn Lys
    690                 695                 700

Gly Arg Leu Arg Lys Asn Lys Tyr Gln Arg Arg Phe Val Cys Glu Cys
705                 710                 715                 720

Gly Glu Pro Lys Lys Ser Ala Asn Lys Thr Ala Ala Pro Asp Arg Ser
                725                 730                 735

Ala Thr Val Ser Pro Cys Thr Cys Arg Leu Gln Leu Gly Ser Asp Val
            740                 745                 750

Asn Ala Ala Arg Val Leu Ala Arg Val Phe Trp Asp Glu Ile Val Leu
        755                 760                 765

```
Pro Thr Arg Glu Glu Met Arg Glu Pro Ala Val Asp Ser Ala Pro Pro
        770                 775                 780

Ser Lys
785

<210> SEQ ID NO 4
<211> LENGTH: 769
<212> TYPE: PRT
<213> ORGANISM: Unknown
<220> FEATURE:
<223> OTHER INFORMATION: Description of Unknown:
      candidate division Zixibacteria bacterium Bacteria. sequence

<400> SEQUENCE: 4

Met Asn Arg Thr Arg Tyr Arg Glu Glu Arg Thr Ile Thr Arg Gly Met
1               5                   10                  15

Arg Arg Leu Pro Gly Glu Glu Arg Lys Ser Phe Lys Ala Lys Val Ile
            20                  25                  30

Thr Leu Arg Arg Asn Phe Glu Gln Phe Asn Thr Asp Val Ser Glu Ile
        35                  40                  45

Cys Gln Trp Leu Met Ser Ile Arg Pro Asn Gly Lys His Asn Ile Pro
50                  55                  60

Asn Thr Glu Pro Phe Trp Asp Phe Ile Leu Glu Pro His Asn Phe Val
65                  70                  75                  80

Val Asn Gln Glu Glu Thr Asn Ile Asp Ser Val Arg Leu Val Val Phe
                85                  90                  95

Glu Met Ala Val Gly Trp Arg Gln Val Thr Asp Val Ala Asn Phe Glu
            100                 105                 110

Leu Glu Arg Gln Leu Leu Met Ser Leu Glu Ser Ile Gln Ser Val Pro
        115                 120                 125

Arg Thr Ile Ala Ala Lys Arg Met Leu Gln Arg Ile Lys Asn Tyr Glu
130                 135                 140

Phe Gln His Lys Met Val Leu Leu Arg Ser Ala Val Glu Trp Ile Asn
145                 150                 155                 160

Thr Arg Phe Ile Arg Thr Tyr Lys Asn Trp Glu Met Asn Ile Lys Glu
                165                 170                 175

Phe Leu Glu Lys Lys Val Trp Glu Asn Asp His Pro Lys Leu Thr
            180                 185                 190

Glu Glu Ile Arg Asn Thr Phe Asn Lys Val Phe Asp Glu Leu Glu Ile
        195                 200                 205

Ser Lys Lys Asn Pro Asn Ile Cys Arg Trp Ser His Leu Lys Lys Asn
210                 215                 220

Arg Asp Asn Cys Asn Tyr Ala Gly Val Arg Ile Lys Val Gly Gly Glu
225                 230                 235                 240

Tyr Asn Asn His Ser Glu Lys Cys Lys Arg Tyr Gln Asp Phe Leu Lys
                245                 250                 255

Lys His Ser Ala His Lys Lys Tyr Phe Ala Ala Asn Ala Met Met Tyr
            260                 265                 270

Ile Asn Ile Arg Lys Lys Arg Arg Asp Leu Thr Lys Arg Glu Ala Ile
        275                 280                 285

Lys Val Leu Leu Asp Lys Ile Pro Gln Ala Arg Ser Trp Phe Pro Gln
290                 295                 300

Ala Trp Asp Asn Tyr Leu Glu Tyr Leu Gly Leu Asn Glu Ile Ser Leu
305                 310                 315                 320

Ile Asn Lys Phe Asp Gly Gln Leu Pro His Cys Leu Arg Leu Asp Thr
                325                 330                 335
```

```
Glu Cys Ile Tyr Asn Val His Thr Gln Ser Cys Arg Lys Tyr Tyr Val
            340                 345                 350

Leu Leu Lys Asp Leu Pro Asp Lys Tyr Leu Ser Leu Glu Thr Tyr
        355                 360                 365

Arg Glu Trp Arg Lys Tyr Phe Leu Arg Glu Pro Arg Lys Pro Val Phe
    370                 375                 380

Ala Tyr Pro Ser Thr Arg Gln Arg Thr Val Ser Lys Ile Phe Gly Arg
385                 390                 395                 400

Asp Tyr Phe Glu Ala Asp Tyr Asp Asn Ser Ile Ile Lys Leu Arg Leu
                405                 410                 415

Asp Asp Met Ala Glu Gly Gln Phe Leu Ser Phe Gly Phe Lys Pro Trp
            420                 425                 430

Pro Val Asp Tyr Asp Val Gln Pro Ile Asp Thr Glu Ile Thr Ser Val
        435                 440                 445

Leu Val His Phe Ile Gly Thr Arg Ala Arg Val Gly Phe Arg Phe Lys
        450                 455                 460

Met Pro His Arg Pro Ser Arg Ile Asn Ile Lys Gln Asp Glu Leu Asp
465                 470                 475                 480

Glu Leu Arg Ser Arg Ser Arg Leu Ile Gln Glu Lys Asp Gln Ala Leu
                485                 490                 495

Leu Glu Lys Val Arg Leu Arg Leu Arg Asp Gly Phe Ile Gly Ile Phe
            500                 505                 510

Asp Lys Glu Leu Arg Val Leu Ala Val Asp Leu Gly Thr Ser Ser Cys
        515                 520                 525

Ala Thr Ala Phe Phe Val Gly Arg Gln Phe Gln Glu Ser Ser Arg Leu
        530                 535                 540

Gln Ile Val Lys Tyr Asp Arg Val Tyr Lys Ser Asn Tyr Glu Ile Lys
545                 550                 555                 560

Lys Arg Arg Asn Asn Lys Gly Ile Asp Lys Gln Lys Gln Leu Leu Phe
                565                 570                 575

Lys Glu Lys Gly Leu Asn Gln Tyr His Ile Lys Val His Leu Asp Lys
            580                 585                 590

Leu Ala Glu Gln Asn Lys Gln Ile Ile Lys Arg Glu Ala Ser Gly
        595                 600                 605

Asn Pro Thr Pro Thr Glu Gln Asp Met Arg Arg Leu Ser Leu His Ile
        610                 615                 620

Gly Trp Met His Arg Asp Trp Val Arg Ile Asn Ala Ser Gln Ile Ile
625                 630                 635                 640

Lys Ser Ala Lys Lys Leu Arg Ala Asp Leu Ile Val Phe Glu Ser Leu
                645                 650                 655

Arg Asp Phe Arg Pro Met Met Phe Asn Glu Phe Asp Ile Asp Lys Lys
            660                 665                 670

Arg Arg Leu Ala Phe Phe Pro Phe Gly Leu Ile Arg His Lys Val Ile
        675                 680                 685

Glu Lys Ala Val Glu Ser Gly Met Arg Val Val Thr Val Pro Tyr Met
        690                 695                 700

Phe Ser Ser Gln Phe Cys Gly Ala Cys Gly Arg Gln Gln Asn Asp Lys
705                 710                 715                 720

Lys Arg Leu Gln Lys Asn Lys Thr Asp Lys Arg Gly Ala Cys Phe Ile
                725                 730                 735

Cys Glu Tyr Asn Asp Cys Ala Phe Glu Gly Asp Pro Asp Glu Asn Ala
            740                 745                 750
```

-continued

```
Ala Arg Val Leu Gly Gly Val Phe Trp Gly Asn Ile Gly Leu Pro Leu
        755                 760                 765

Ser

<210> SEQ ID NO 5
<211> LENGTH: 830
<212> TYPE: PRT
<213> ORGANISM: Unknown
<220> FEATURE:
<223> OTHER INFORMATION: Description of Unknown:
      aquatic-thermal springs-hot spring sediment sequence

<400> SEQUENCE: 5

Met His Pro Ser Arg Tyr Lys Thr Ala Arg Thr Leu Val Arg Arg Leu
1                 5                  10                  15

Cys Arg Leu Pro Gly Glu Asp Arg Ser Ala Phe Arg Ser Lys Val Gly
            20                  25                  30

Leu Leu Arg Gly His Phe Glu Gln Phe Asn Val Asp Val Ser Glu Leu
        35                  40                  45

Cys Gln Trp Leu Met Ser Leu Arg Lys Arg Asn Lys Val Pro Glu Asn
    50                  55                  60

Pro Ala Thr Phe Gly Ala Leu Gly Asp Phe Leu Leu Gln Pro Gly Leu
65                  70                  75                  80

Pro Gly Glu Glu Thr Asp Glu Lys Gly Ala Asp Arg Leu Arg Leu Ala
                85                  90                  95

Val Phe Asp Ala Val Ala Gly Phe Arg Met Leu Glu Asp Arg Leu Ala
            100                 105                 110

Ala Ser Ile Pro Ala Ser Leu Ser Asp Ala Ile Arg Asp Glu Ala Val
        115                 120                 125

Phe Leu Ala Gly Val Arg Ala Ala Gly Lys Pro Ser Gly Leu Ala Arg
    130                 135                 140

Val Leu Ala Arg Leu Glu Ala Cys Ala Pro Ala Gln Arg Leu Val Leu
145                 150                 155                 160

Leu Lys Ser Ala Ala Glu Trp Ile Val Ala Arg Phe Leu Arg Gly Thr
                165                 170                 175

Glu Asn Trp Met Arg Gln Arg Ala Glu Trp Lys Glu Lys Ala Ala
            180                 185                 190

Trp Glu Ala Ala His Pro His Leu Thr Pro Glu Val Arg Ala Gln Phe
        195                 200                 205

Asn Lys Ile Phe Glu Ser Leu His Asp Pro Glu Asn Ser Gly Lys Pro
    210                 215                 220

Gly Val Ser Arg Lys Asn Pro Arg Ile Cys Pro Trp Asp Arg Leu Lys
225                 230                 235                 240

Gln Asn Leu Asp Asn Cys Cys Tyr Gly Glu Lys Gly His Ser Ala Leu
                245                 250                 255

Cys Trp Arg Tyr Gln Asp Phe Leu Lys Gln Arg Met Gly Glu Asn Arg
            260                 265                 270

Arg Asp Lys Lys Asn Phe Ser Ala Thr Ala Met Asp Leu Ala Gln Ile
        275                 280                 285

Cys Arg Glu Trp Lys Ile Gln His Ser Arg Asn Ala Leu Asn Asn Pro
    290                 295                 300

Arg Val Leu Asp Arg Leu Phe Ala Glu His Glu Arg Arg Lys Gln Asp
305                 310                 315                 320

Lys Thr Lys Lys Glu Ser Arg Ser Pro Lys Pro Arg Gln Gly Gly Tyr
                325                 330                 335
```

```
Lys Ala Asn Pro Lys Ala Asp Tyr Leu Arg Ser Phe Lys Ala His Trp
                340                 345                 350

Lys Ala Tyr Leu Glu His Met Lys Leu Asn Asp Thr Thr Val Leu Glu
            355                 360                 365

Arg Gly Cys Leu Pro His Cys Leu Ser Ile Lys Lys Asn Gly Lys Glu
        370                 375                 380

Ser Thr Cys Lys Trp Asn Lys His Thr Glu Leu Cys Leu Glu Tyr Lys
385                 390                 395                 400

Arg Ser Leu Ala Pro Leu Pro Asp Ser Val Leu Glu Leu Glu Pro Glu
                405                 410                 415

Tyr Arg Glu Trp Arg Arg Leu Tyr Leu His Gly Pro Gly Arg Pro His
            420                 425                 430

Phe Arg Tyr Pro Ser Ala Gly Glu Leu Pro Leu Pro Lys Val Phe Gly
        435                 440                 445

Glu Gly Phe His Gln Val Asp Leu Asp Arg Ser Ile Val Arg Leu Arg
        450                 455                 460

Leu Glu Gly Ala Ala Glu Gly Glu Trp Leu Glu Phe Gly Phe Ile Pro
465                 470                 475                 480

Trp Pro Arg Gly Tyr Gln Pro Ser Arg Arg Glu Val Leu Ile Thr Ser
                485                 490                 495

Val Gln Val His Phe Val Gly Thr Arg Pro Arg Ala Gly Phe Arg Phe
            500                 505                 510

Asp Val Ser His Arg Thr Ser Arg Phe Gly Cys Ser Gln Asp Glu Leu
        515                 520                 525

Asp Glu Leu Arg Ser Arg Arg Tyr Pro Arg Gln Ala Gln Asp Lys Glu
        530                 535                 540

Phe Leu Ala Ala Ala Arg Ala Gln Leu Ile Gln Thr Phe Glu Gly Gly
545                 550                 555                 560

Glu Gly Ala Ala Arg Gln Gln Met Arg Val Met Ser Val Asp Leu Gly
                565                 570                 575

Glu Gly Gly Ala Cys Ala Ser Ile Tyr Glu Gly Arg Thr His Gln Lys
            580                 585                 590

Asp Glu Ser Leu Lys Val Ile Lys Ile Asp Arg Arg Tyr Asp Gln His
        595                 600                 605

Pro Glu Val Leu Glu Lys Asp Val Gly Ala Ala Lys Pro Gln Lys Phe
        610                 615                 620

Glu Lys Ser Asp Pro Arg Gly Val Arg Lys Glu His Val Ala Arg His
625                 630                 635                 640

Leu Asn Arg Ile Ala Ala Gly Ala Ser Ala Ile Ala Glu His Arg Arg
                645                 650                 655

Lys Glu Arg Ser Asp Ala Glu Cys Ser Val Gly Glu Leu Gln Glu His
            660                 665                 670

Asp Phe Arg Ser Leu Lys Arg His Ile Ala Trp Met Ile Arg Asp Trp
        675                 680                 685

Val Arg Leu Asn Ala Ala Gln Ile Ile Asp Val Ala Lys Gln His Cys
        690                 695                 700

Cys Asp Leu Ile Val Phe Glu Ser Gln Arg Gly Phe Arg Leu Pro Gly
705                 710                 715                 720

Tyr Asp Glu Leu Asp Arg Gly Lys Lys Gln Arg Phe Ala Ile Leu Ala
                725                 730                 735

Phe Gly Arg Ile Arg Arg Lys Val Val Glu Lys Ala Val Glu His Gly
            740                 745                 750

Met Arg Val Val Thr Val Pro Tyr Phe Ala Ser Ser Gln Val Cys Ser
```

```
                    755                 760                 765
Ala Cys Lys Arg Val Gln Glu Asn Arg Gly Ser Trp Arg Glu Asn Lys
        770                 775                 780

Lys Lys Arg Val Phe Ala Cys Glu Phe Cys Lys Leu Lys Leu Asn Ser
785                 790                 795                 800

Asp Ala Asn Ala Ser Arg Val Leu Ala Arg Val Phe Trp Gly Glu Ile
                    805                 810                 815

Glu Leu Pro Glu Pro Thr Arg Ala His Leu Pro Ser Lys Ala
        820                 825                 830

<210> SEQ ID NO 6
<211> LENGTH: 767
<212> TYPE: PRT
<213> ORGANISM: Unknown
<220> FEATURE:
<223> OTHER INFORMATION: Description of Unknown:
      aquatic-thermal springs-hot spring sediment sequence

<400> SEQUENCE: 6

Met Ala Gln Ala Ser Ser Thr Pro Ala Val Ser Pro Arg Pro Arg Pro
1               5                   10                  15

Arg Tyr Arg Glu Glu Arg Thr Leu Val Arg Lys Leu Leu Pro Arg Pro
            20                  25                  30

Gly Gln Ser Lys Gln Glu Phe Arg Glu Asn Val Lys Lys Leu Arg Lys
        35                  40                  45

Ala Phe Leu Gln Phe Asn Ala Asp Val Ser Gly Val Cys Gln Trp Ala
    50                  55                  60

Ile Gln Phe Arg Pro Arg Tyr Gly Lys Pro Ala Glu Pro Thr Glu Thr
65                  70                  75                  80

Phe Trp Lys Phe Phe Leu Glu Pro Glu Thr Ser Leu Pro Pro Asn Asp
                85                  90                  95

Ser Arg Ser Pro Glu Phe Arg Arg Leu Gln Ala Phe Glu Ala Ala Ala
            100                 105                 110

Gly Ile Asn Gly Ala Ala Ala Leu Asp Asp Pro Ala Phe Thr Asn Glu
        115                 120                 125

Leu Arg Asp Ser Ile Leu Ala Val Ala Ser Arg Pro Lys Thr Lys Glu
    130                 135                 140

Ala Gln Arg Leu Phe Ser Arg Leu Lys Asp Tyr Gln Pro Ala His Arg
145                 150                 155                 160

Met Ile Leu Ala Lys Val Ala Ala Glu Trp Ile Glu Ser Arg Tyr Arg
                165                 170                 175

Arg Ala His Gln Asn Trp Glu Arg Asn Tyr Glu Glu Trp Lys Lys Glu
            180                 185                 190

Lys Gln Glu Trp Glu Gln Asn His Pro Glu Leu Thr Pro Glu Ile Arg
        195                 200                 205

Glu Ala Phe Asn Gln Ile Phe Gln Gln Leu Glu Val Lys Glu Lys Arg
    210                 215                 220

Val Arg Ile Cys Pro Ala Ala Arg Leu Leu Gln Asn Lys Asp Asn Cys
225                 230                 235                 240

Gln Tyr Ala Gly Lys Asn Lys His Ser Val Leu Cys Asn Gln Phe Asn
                245                 250                 255

Glu Phe Lys Lys Asn His Leu Gln Gly Lys Ala Ile Lys Phe Phe Tyr
            260                 265                 270

Lys Asp Ala Glu Lys Tyr Leu Arg Cys Gly Leu Gln Ser Leu Lys Pro
        275                 280                 285
```

```
Asn Val Gln Gly Pro Phe Arg Glu Asp Trp Asn Lys Tyr Leu Arg Tyr
    290                 295                 300

Met Asn Leu Lys Glu Glu Thr Leu Arg Gly Lys Asn Gly Gly Arg Leu
305                 310                 315                 320

Pro His Cys Lys Asn Leu Gly Gln Glu Cys Glu Phe Asn Pro His Thr
                325                 330                 335

Ala Leu Cys Lys Gln Tyr Gln Gln Leu Ser Ser Arg Pro Asp Leu
                340                 345                 350

Val Gln His Asp Glu Leu Tyr Arg Lys Trp Arg Arg Glu Tyr Trp Arg
            355                 360                 365

Glu Pro Arg Lys Pro Val Phe Arg Tyr Pro Ser Val Lys Arg His Ser
370                 375                 380

Ile Ala Lys Ile Phe Gly Glu Asn Tyr Phe Gln Ala Asp Phe Lys Asn
385                 390                 395                 400

Ser Val Val Gly Leu Arg Leu Asp Ser Met Pro Ala Gly Gln Tyr Leu
                405                 410                 415

Glu Phe Ala Phe Ala Pro Trp Pro Arg Asn Tyr Arg Pro Gln Pro Gly
            420                 425                 430

Glu Thr Glu Ile Ser Ser Val His Leu His Phe Val Gly Thr Arg Pro
        435                 440                 445

Arg Ile Gly Phe Arg Phe Arg Val Pro His Lys Arg Ser Arg Phe Asp
450                 455                 460

Cys Thr Gln Glu Glu Leu Asp Glu Leu Arg Ser Arg Thr Phe Pro Arg
465                 470                 475                 480

Lys Ala Gln Asp Gln Lys Phe Leu Glu Ala Ala Arg Lys Arg Leu Leu
                485                 490                 495

Glu Thr Phe Pro Gly Asn Ala Glu Gln Glu Leu Arg Leu Leu Ala Val
            500                 505                 510

Asp Leu Gly Thr Asp Ser Ala Arg Ala Ala Phe Phe Ile Gly Lys Thr
        515                 520                 525

Phe Gln Gln Ala Phe Pro Leu Lys Ile Val Lys Ile Glu Lys Leu Tyr
530                 535                 540

Glu Gln Trp Pro Asn Gln Lys Gln Ala Gly Asp Arg Arg Asp Ala Ser
545                 550                 555                 560

Ser Lys Gln Pro Arg Pro Gly Leu Ser Arg Asp His Val Gly Arg His
                565                 570                 575

Leu Gln Lys Met Arg Ala Gln Ala Ser Glu Ile Ala Gln Lys Arg Gln
            580                 585                 590

Glu Leu Thr Gly Thr Pro Ala Pro Glu Thr Thr Thr Asp Gln Ala Ala
        595                 600                 605

Lys Lys Ala Thr Leu Gln Pro Phe Asp Leu Arg Gly Leu Thr Val His
610                 615                 620

Thr Ala Arg Met Ile Arg Asp Trp Ala Arg Leu Asn Ala Arg Gln Ile
625                 630                 635                 640

Ile Gln Leu Ala Glu Glu Asn Gln Val Asp Leu Ile Val Leu Glu Ser
                645                 650                 655

Leu Arg Gly Phe Arg Pro Pro Gly Tyr Glu Asn Leu Asp Gln Glu Lys
            660                 665                 670

Lys Arg Arg Val Ala Phe Phe Ala His Gly Arg Ile Arg Arg Lys Val
        675                 680                 685

Thr Glu Lys Ala Val Glu Arg Gly Met Arg Val Thr Val Pro Tyr
690                 695                 700

Leu Ala Ser Ser Lys Val Cys Ala Glu Cys Arg Lys Lys Gln Lys Asp
```

```
                    705                 710                 715                 720
Asn Lys Gln Trp Glu Lys Asn Lys Lys Arg Gly Leu Phe Lys Cys Glu
                725                 730                 735
Gly Cys Gly Ser Gln Ala Gln Val Asp Glu Asn Ala Ala Arg Val Leu
                740                 745                 750
Gly Arg Val Phe Trp Gly Ile Glu Leu Pro Thr Ala Ile Pro
                755                 760                 765

<210> SEQ ID NO 7
<211> LENGTH: 720
<212> TYPE: PRT
<213> ORGANISM: Unknown
<220> FEATURE:
<223> OTHER INFORMATION: Description of Unknown:
      aquatic-sediment-hot spring sediment sequence

<400> SEQUENCE: 7

Met Ser Ile Arg Pro Asp Ala Lys Lys Pro Asp Lys Glu Thr Lys Ser
1               5                   10                  15
Phe Trp Asp Phe Phe Leu Asn Pro Glu Ser Phe Phe Asp Pro Thr Ile
                20                  25                  30
Asn Asn Val Asp Ile Ile Arg Leu Asn Leu Phe Lys Val Ile Thr Gly
                35                  40                  45
Arg Glu Ser Glu Ala Asn Leu Ile Arg Tyr Asn Leu Pro Leu Leu Leu
            50                  55                  60
Tyr Glu Ser Ile Ile Leu Leu Lys Lys Gln Glu Pro Ser Asp Thr Ala
65              70                  75                  80
Arg Arg Leu Phe Ala Arg Leu Lys Lys Met Glu Pro Val His Val Met
                85                  90                  95
Ile Leu Leu Lys Ala Ala Ala Glu Trp Val Tyr Ala Arg Tyr Gln Arg
                100                 105                 110
Leu Met Asp Asn His Glu Tyr Gln Tyr Lys Val Trp His Asp Glu Lys
                115                 120                 125
Ser Ala Trp Glu Asn Lys His Pro Glu Leu Thr Pro Glu Ile Arg Glu
            130                 135                 140
Lys Tyr Asn Ser Ile Phe Lys Glu Leu Gly Arg Lys Gln Gly Val Thr
145             150                 155                 160
Ile Arg Lys Asn Pro Arg Ile Cys Asn Trp Glu Lys Leu Glu Glu Asn
                165                 170                 175
Lys Asp Asn Cys Gly Tyr Asn Gly Lys Arg Ile Gln Phe Gly Asp Lys
                180                 185                 190
Trp Lys Ala His Ser Met Leu Cys Ile Glu Tyr Arg Asn Phe Leu Arg
                195                 200                 205
Asp Asn Lys Ile Thr Gly Lys Arg Ile Gly Phe Phe Ala Thr His Ala
            210                 215                 220
Tyr Asn Tyr Leu Lys Leu Arg Ala His Gln Pro Arg Leu Thr Lys Asp
225             230                 235                 240
Glu Ala Phe Lys Arg Ile Phe Lys Ser Ala Pro Asn Gly Ile Tyr Trp
                245                 250                 255
Phe Pro Lys Ala Trp Lys Asn Tyr Leu Gln Phe Met Asn Leu Asn Glu
                260                 265                 270
Leu Asn Leu Ile Arg Lys Tyr Asn Ala Asn Leu Pro His Cys Leu Glu
            275                 280                 285
Phe Lys Gly Asp Lys Asp Cys Gln Tyr Asn Lys His Thr Glu Leu Cys
            290                 295                 300
```

```
Gln Glu Tyr Lys Thr Leu Leu Glu Lys Phe Thr Glu Asp Glu Leu
305                 310                 315                 320

Lys Leu Glu Gly Leu Tyr Arg Glu Trp Arg Lys Gln Tyr Leu Ser Gly
            325                 330                 335

Pro Ser Lys Pro Ala Phe Arg Tyr Pro Ser Cys Ser Lys Leu Pro Thr
            340                 345                 350

Pro Lys Ile Phe Gly Lys Arg Phe His Glu Ile Asp Phe Glu Asn Ser
            355                 360                 365

Ile Val Arg Leu Arg Leu Asp Asp Met Pro Asp Gly Glu Tyr Leu Thr
            370                 375                 380

Phe Lys Phe Lys Pro Trp Pro Asn Asp Tyr Gln Pro Gln Pro Glu Glu
385                 390                 395                 400

Ala Glu Ile Ser Val His Val His Phe Val Gly Thr Arg Ala Arg
            405                 410                 415

Val Gly Phe Arg Phe Lys Ile Ala His Lys Gln Ser Arg Phe Lys Thr
            420                 425                 430

Ser Gln Asp Glu Ile Asp Glu Leu Arg Ser Arg Lys Tyr Pro Arg Gln
465     435                 440                 445

Ala Gln Asp Ala Asp Phe Leu Lys Ala Ala Arg Glu Lys Leu Leu Gln
450                 455                 460

Ser Phe Lys Gly Glu Asn Pro Thr Lys Glu Ile Lys Ile Met Ala Val
465                 470                 475                 480

Asp Leu Gly Glu Tyr Arg Gly Tyr Ile Ser Val Tyr Lys Gly Glu Asn
            485                 490                 495

Ile Glu Ile Ser Glu Pro Leu Ser Ile Leu Lys Ile Asp Lys Leu Tyr
            500                 505                 510

Asp Ser Leu Glu Ser Ala Gly Val Asp Lys Thr Asp Leu Ala Lys Tyr
            515                 520                 525

Ile Lys Asp His Lys Gly Leu Ile Lys Glu His Val Asp Ser His Leu
            530                 535                 540

Lys Val Ile Ser Glu Lys Ala Asn Glu Ile Thr Lys His Arg Pro Ala
545                 550                 555                 560

Gly Lys Lys Thr Gly Ala Ser Asn Leu Lys Asp Tyr Asp Leu Arg Ser
            565                 570                 575

Leu Thr Ala His Thr Gly Trp Met Ile Arg Asp Trp Val Arg Leu Asn
            580                 585                 590

Val Ser Gln Ile Ile Arg Ile Ala Glu Lys His Glu Val Asp Leu Ile
            595                 600                 605

Val Leu Glu Ser Leu Arg Gly Trp Lys Ala Pro Gly Tyr Asp Glu Phe
            610                 615                 620

Asp Leu Arg Lys Lys Arg Trp Leu Ala Phe Phe Ser Tyr Gly Arg Ile
625                 630                 635                 640

Arg His Lys Leu Lys Glu Lys Ala Val Glu Arg Gly Met Met Val Val
            645                 650                 655

Thr Val Pro Tyr Tyr Lys Ser Ser Gln Ile Cys Ser Lys Cys Gly Lys
            660                 665                 670

Glu Gln Glu Asn Lys Gly Leu Trp Lys Lys Asn Lys Asn Glu Arg Leu
            675                 680                 685

Phe Ile Cys Asp Tyr Pro Gly Cys Gly His Arg Asp Asn Ser Asp Ala
            690                 695                 700

Asn Ala Ala Lys Val Leu Ala Lys Ile Phe Trp Gly Glu Ile Val Leu
705                 710                 715                 720
```

```
<210> SEQ ID NO 8
<211> LENGTH: 774
<212> TYPE: PRT
<213> ORGANISM: Unknown
<220> FEATURE:
<223> OTHER INFORMATION: Description of Unknown:
      aquatic-sediment-hot spring sediment sequence

<400> SEQUENCE: 8

Met Asp Asn Asn Arg Thr Arg Tyr Arg Glu Glu Arg Thr Leu Val Arg
1               5                   10                  15

Ser Leu Arg Pro Leu Asp Gly Glu Asn Arg Asn Ala Phe Lys Asn Arg
            20                  25                  30

Val Asn Arg Leu Arg Ile His Phe Lys Asn Phe Asn Leu Asp Val Ser
        35                  40                  45

Glu Ile Cys Gln Trp Leu Met Ser Ile Arg Pro Asp Ala Lys Lys Pro
    50                  55                  60

Asp Lys Glu Thr Lys Ser Phe Trp Asp Phe Phe Leu Asn Pro Glu Ser
65                  70                  75                  80

Phe Phe Asp Pro Thr Ile Asn Asn Val Asp Ile Ile Arg Leu Asn Leu
                85                  90                  95

Phe Lys Val Ile Thr Gly Arg Glu Ser Glu Ala Asn Leu Ile Arg Tyr
            100                 105                 110

Asn Leu Pro Leu Leu Leu Tyr Glu Ser Ile Ile Leu Leu Lys Lys Gln
        115                 120                 125

Glu Pro Ser Asp Thr Ala Arg Arg Leu Phe Ala Arg Leu Lys Lys Met
    130                 135                 140

Glu Pro Val His Val Met Ile Leu Leu Lys Ala Ala Ala Glu Trp Val
145                 150                 155                 160

Tyr Ala Arg Tyr Gln Arg Leu Met Asp Asn His Glu Tyr Gln Tyr Lys
                165                 170                 175

Val Trp His Asp Glu Lys Ser Ala Trp Glu Asn Lys His Pro Glu Leu
            180                 185                 190

Thr Pro Glu Ile Arg Glu Lys Tyr Asn Ser Ile Phe Lys Glu Leu Gly
        195                 200                 205

Arg Lys Gln Gly Val Thr Ile Arg Lys Asn Pro Arg Ile Cys Asn Trp
    210                 215                 220

Glu Lys Leu Glu Glu Asn Lys Asp Asn Cys Gly Tyr Asn Gly Lys Arg
225                 230                 235                 240

Ile Gln Phe Gly Asp Lys Trp Lys Ala His Ser Met Leu Cys Ile Glu
                245                 250                 255

Tyr Arg Asn Phe Leu Arg Asp Asn Lys Ile Thr Gly Lys Arg Ile Gly
            260                 265                 270

Phe Phe Ala Thr His Ala Tyr Asn Tyr Leu Lys Leu Arg Ala His Gln
        275                 280                 285

Pro Arg Leu Thr Lys Asp Glu Ala Phe Lys Arg Ile Phe Lys Ser Ala
    290                 295                 300

Pro Asn Gly Ile Tyr Trp Phe Pro Lys Ala Trp Lys Asn Tyr Leu Gln
305                 310                 315                 320

Phe Met Asn Leu Asn Glu Leu Asn Leu Ile Arg Lys Tyr Asn Ala Asn
                325                 330                 335

Leu Pro His Cys Leu Glu Phe Lys Gly Asp Lys Asp Cys Gln Tyr Asn
            340                 345                 350

Lys His Thr Glu Leu Cys Gln Glu Tyr Lys Thr Leu Leu Leu Glu Lys
        355                 360                 365
```

```
Phe Thr Glu Asp Glu Leu Lys Leu Glu Gly Leu Tyr Arg Glu Trp Arg
370                 375                 380

Lys Gln Tyr Leu Ser Gly Pro Ser Lys Pro Ala Phe Arg Tyr Pro Ser
385                 390                 395                 400

Cys Ser Lys Leu Pro Thr Pro Lys Ile Phe Gly Lys Arg Phe His Glu
                405                 410                 415

Ile Asp Phe Glu Asn Ser Ile Val Arg Leu Arg Leu Asp Asp Met Pro
                420                 425                 430

Asp Gly Glu Tyr Leu Thr Phe Lys Phe Lys Pro Trp Pro Asn Asp Tyr
                435                 440                 445

Gln Pro Gln Pro Glu Glu Ala Glu Ile Ser Ser Val His Val His Phe
450                 455                 460

Val Gly Thr Arg Ala Arg Val Gly Phe Arg Phe Lys Ile Ala His Lys
465                 470                 475                 480

Gln Ser Arg Phe Lys Thr Ser Gln Asp Glu Ile Asp Glu Leu Arg Ser
                485                 490                 495

Arg Lys Tyr Pro Arg Gln Ala Gln Asp Ala Asp Phe Leu Lys Ala Ala
                500                 505                 510

Arg Glu Lys Leu Leu Gln Ser Phe Lys Gly Glu Asn Pro Thr Lys Glu
                515                 520                 525

Ile Lys Ile Met Ala Val Asp Leu Gly Glu Tyr Arg Gly Tyr Ile Ser
530                 535                 540

Val Tyr Lys Gly Glu Asn Ile Glu Ile Ser Glu Pro Leu Ser Ile Leu
545                 550                 555                 560

Lys Ile Asp Lys Leu Tyr Asp Ser Leu Glu Ser Ala Gly Val Asp Lys
                565                 570                 575

Thr Asp Leu Ala Lys Tyr Ile Lys Asp His Lys Gly Leu Ile Lys Glu
                580                 585                 590

His Val Asp Ser His Leu Lys Val Ile Ser Glu Lys Ala Asn Glu Ile
                595                 600                 605

Thr Lys His Arg Pro Ala Gly Lys Lys Thr Gly Ala Ser Asn Leu Lys
                610                 615                 620

Asp Tyr Asp Leu Arg Ser Leu Thr Ala His Thr Gly Trp Met Ile Arg
625                 630                 635                 640

Asp Trp Val Arg Leu Asn Val Ser Gln Ile Ile Arg Ile Ala Glu Lys
                645                 650                 655

His Glu Val Asp Leu Ile Val Leu Glu Ser Leu Arg Gly Trp Lys Ala
                660                 665                 670

Pro Gly Tyr Asp Glu Phe Asp Leu Arg Lys Lys Arg Trp Leu Ala Phe
                675                 680                 685

Phe Ser Tyr Gly Arg Ile Arg His Lys Leu Lys Glu Lys Ala Val Glu
690                 695                 700

Arg Gly Met Met Val Val Thr Val Pro Tyr Tyr Lys Ser Ser Gln Ile
705                 710                 715                 720

Cys Ser Lys Cys Gly Lys Glu Gln Glu Asn Lys Gly Leu Trp Lys Lys
                725                 730                 735

Asn Lys Asn Glu Arg Leu Phe Ile Cys Asp Tyr Pro Gly Cys Gly His
                740                 745                 750

Arg Asp Asn Ser Asp Ala Asn Ala Ala Lys Val Leu Ala Lys Ile Phe
                755                 760                 765

Trp Gly Glu Ile Val Leu
770
```

```
<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gttgtagcgg cccctgaatt agcggtttcc gacacc                               36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggtgcggcag ccggtagaac tgcggcttcc gacacc                               36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gttggagtca gcaaggaatc aacggttttg gacacc                               36

<210> SEQ ID NO 12

<400> SEQUENCE: 12

000

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggtggaaagg gccggagatt taccggctct gacacc                               36

<210> SEQ ID NO 14

<400> SEQUENCE: 14

000

<210> SEQ ID NO 15
<211> LENGTH: 761
<212> TYPE: PRT
<213> ORGANISM: Unknown
<220> FEATURE:
<223> OTHER INFORMATION: Description of Unknown: Planctomycetes
      bacterium sequence

<400> SEQUENCE: 15

Met Gly Leu Arg Lys Arg Tyr Val Glu Leu Cys Asp Asn Ser Gly Leu
1               5                   10                  15
```

```
Arg Ala Asp Leu Ser Ser Phe Gly Thr Leu Gly Asn Phe Leu Leu Glu
             20                  25                  30

Pro Ser Leu Asp Gly Ser Glu Ala Asp Glu Arg Glu Arg Asp Arg Trp
         35                  40                  45

Arg Leu Ala Val Phe Asp Ile Val Ala Gly Phe Arg Ala Asp Ile Gln
     50                  55                  60

Leu Asp Gly Arg Thr Leu Pro Asn Glu Leu Arg Gln Ala Ile Thr Asp
 65                  70                  75                  80

Ala Ala Asp Gln Met Arg Asn Thr Ile Ala Asp Gly Lys Lys Lys Thr
                 85                  90                  95

Gly Leu Arg Arg Leu Phe Gln Arg Leu Gly Asp Leu Glu Glu Ala His
             100                 105                 110

Arg Leu Val Leu Leu Lys Ser Ala Ala Glu Trp Ile Val Ala Arg Tyr
         115                 120                 125

Leu Arg Ser Val Glu Asn Trp Val Arg Gln His Thr Glu Trp Glu Lys
     130                 135                 140

Glu Lys Gln Gln Trp Glu Ser His Lys Asp Asn Lys Thr Asp His Thr
145                 150                 155                 160

Leu Leu Thr Pro Asp Ile Arg Glu Lys Tyr Thr Ala Val Phe Lys Leu
                 165                 170                 175

Leu Val Trp Asp Lys Asp Lys Pro Pro Gly Val Arg Asn Lys Arg Pro
             180                 185                 190

Arg Ile Cys Pro Tyr Asp Arg Leu Lys Gln Asn Ile Asp Asn Cys Cys
         195                 200                 205

Tyr Ala Gly Gln Lys Gly His Gly Pro Leu Cys Trp Lys Tyr Asn Glu
     210                 215                 220

Phe Val Lys Ala Arg Lys Ala Arg Asn Pro Ser Phe Asn Asp Lys Lys
225                 230                 235                 240

Phe Ala Glu Asp Val Ala Lys Tyr Leu Pro Pro Arg Ala Lys Gly Glu
                 245                 250                 255

Gln Arg His Leu Ile Leu Lys Ala Ile Phe Pro Asn Lys Gln Gln Asp
             260                 265                 270

Gln Gln Arg Phe Ser Asp Asn Trp Thr Ala Tyr Leu Ser Ala Met Lys
         275                 280                 285

Leu Asn Glu Gln Thr Leu Val Gln His Gln Gln Leu Pro His Cys Leu
     290                 295                 300

Lys Ile Gly Glu Thr Phe Glu Lys Ser Ala Cys Val Trp Asn Pro His
305                 310                 315                 320

Thr Asp Leu Cys Gly Gln Tyr His Arg Ala Leu Val Asn Pro Asn Asn
                 325                 330                 335

Gly Phe Asp Asp Ala Met Leu Ser Leu Glu Pro Leu Tyr Arg Ala Trp
             340                 345                 350

Arg Arg Asn Tyr Leu Ala Gly Pro Arg Lys Pro Ser Phe Arg Tyr Pro
         355                 360                 365

Ala Ser Arg Asp Leu Pro Met Pro Lys Ile Phe Gly Asp Gly Phe His
     370                 375                 380

Glu Val Asp Phe Glu Asn Ser Ile Val Arg Leu Arg Leu Asp Asp Met
385                 390                 395                 400

Pro Arg Gly Gln Trp Leu Asp Leu Gly Phe Thr Pro Trp Pro Arg Gly
                 405                 410                 415

Tyr Lys Pro Ser Arg Ala Glu Ile Ser Glu Pro Gly Arg Val Thr Ser
             420                 425                 430

Val His Val His Phe Val Gly Val Arg Ala Arg Ile Gly Phe Arg Phe
```

```
            435                 440                 445
Glu Val Ala His Ala Pro Ser Arg Phe Gly Cys Thr Gln Asp Glu Ile
    450                 455                 460

Asp Glu Leu Arg Ser Arg His Tyr Pro Arg Gln Ala Gln Asp Gln Glu
465                 470                 475                 480

Phe Leu Glu Ala Ala Arg Lys Cys Leu Leu Asp Ser Met Thr Glu Gly
                485                 490                 495

Ser Glu Asn Asp Leu Arg Ile Met Ala Val Asp Leu Gly Lys Gly
            500                 505                 510

Ala Cys Ala Ala Val Tyr Arg Gly Arg Thr Arg Glu Met Asp Ile Pro
            515                 520                 525

Leu Ala Ile Val Lys Ile Asn Lys Leu Tyr Glu Lys Pro Pro Lys Thr
    530                 535                 540

Leu Glu Pro Asp Arg His Ser Arg Pro Glu Glu Ser Lys Arg Lys Phe
545                 550                 555                 560

Glu Glu Ala Asp Pro Arg Gly Val Arg Lys Glu His Val Gly Arg His
                565                 570                 575

Leu Glu Arg Val Ala Ala Met Ser Gln Glu Ile Ala Lys His Arg Gln
            580                 585                 590

Pro Ala Val Ala Thr Thr Val Thr Val Ser Val Asn Asp Leu Arg Gly
            595                 600                 605

Leu Lys Arg His Val Ala Trp Met Ile Arg Asp Trp Ala Arg His Asn
    610                 615                 620

Ala Ser Gln Ile Val Lys Ala Ala Glu Glu His Gln Cys Asp Val Ile
625                 630                 635                 640

Val Phe Glu Ser Leu Arg Gly Phe Arg Pro Pro Gly Tyr Asp Lys Leu
                645                 650                 655

Asp Glu Met Ser Ala Lys Lys Lys Arg Trp Leu Ala Met Phe Ala Tyr
            660                 665                 670

Gly Arg Val Arg Arg Lys Val Ile Glu Lys Ala Val Glu Arg Gly Met
    675                 680                 685

Arg Val Val Thr Val Pro Tyr Phe Lys Ser Ser Gln Val Cys Ser Asp
690                 695                 700

Cys Gly Arg Glu Gln Val Asn Val Gly Leu Leu Arg Lys Asn Lys Leu
705                 710                 715                 720

Ser Lys Gly Gln Phe Val Cys Glu Asn Cys Lys Val Thr Leu Thr Ser
                725                 730                 735

Asp Ala Asn Ala Ala Arg Val Leu Ala Arg Val Phe Arg Gly Glu Ile
            740                 745                 750

Met Leu Pro Lys Ala Arg Pro Gly Ala
            755                 760
```

<210> SEQ ID NO 16
<211> LENGTH: 772
<212> TYPE: PRT
<213> ORGANISM: Unknown
<220> FEATURE:
<223> OTHER INFORMATION: Description of Unknown: anaerobic digester metagenome sequence

<400> SEQUENCE: 16

```
Met Thr Arg Thr Lys Tyr Arg Glu Glu Arg Thr Leu Val Arg Gly Leu
1               5                   10                  15

Gln Arg Leu Pro Asn Gln Asp Lys Thr Glu Phe Asn Lys Asn Val Leu
            20                  25                  30
```

-continued

Arg Leu Arg Arg His Phe Glu Gln Phe Asn Leu Asn Val Ala Glu Leu
         35                  40                  45

Cys Gln Trp Leu Ile Ser Phe Lys Pro Glu Asn Pro Asn Ser Val Cys
 50                  55                  60

Glu Thr Lys Leu Phe Trp Glu Phe Met Leu Glu Pro Glu Asn Phe Cys
 65                  70                  75                  80

Pro Asp Thr Tyr Asp Arg Gly Ser Asp Trp Leu Arg His Glu Ile Phe
                 85                  90                  95

Leu Leu Val Ala Gly Trp Gln Thr Phe Glu Asp Met Lys Ala Tyr Asn
                100                 105                 110

Ile Arg Glu Ser Leu Leu Thr Ser Ala Lys Met Ala Ser Ser Arg Pro
        115                 120                 125

Arg Ser Lys Thr Ala Glu Val Leu Phe Ile Arg Leu Lys Ser Leu Glu
        130                 135                 140

Ala Ser His Val Met Val Leu Leu Lys Ser Ala Ser Glu Trp Leu Ser
145                 150                 155                 160

Thr Arg Tyr Ile Arg Gln Ser Glu Asn Trp Lys Arg His Val Gln Glu
                165                 170                 175

Trp Gln Lys Glu Lys Ala Ala Trp Glu Asp Lys His Pro Lys Leu Thr
        180                 185                 190

Pro Ala Ile Arg Asp Lys Tyr Asn Ala Ile Phe Val Glu Leu Gly Ile
        195                 200                 205

Ser Glu Lys Arg Ser Arg Val Cys Ser Trp Lys Lys Leu Ser Glu Asn
        210                 215                 220

Lys Asp Asn Cys Asp Trp Ala Gly Glu Arg Lys Asn Ile Gly Asp Lys
225                 230                 235                 240

Trp Val Ser His Ser Ala Leu Cys Ser Lys Phe Asn Glu Phe His Arg
                245                 250                 255

Ser Leu Lys Gly Ser Pro Arg Lys Tyr Phe Val Thr Asn Ala Asn Gln
        260                 265                 270

Tyr Leu Glu Leu Arg Arg Lys Asn Pro Gln Trp Thr Arg Asp Met Ala
        275                 280                 285

Met Gln Gly Leu Phe Arg Asn Val Pro Gly Ala Gln Asn Trp Phe Pro
290                 295                 300

Asn Ala Trp Thr Asn Tyr Leu Asn Ala Leu Asn Ile Leu Glu Thr Thr
305                 310                 315                 320

Ile Leu Lys Asp Tyr Asn Gly His Leu Pro His Cys Asn Lys Leu Ser
                325                 330                 335

Asp Glu Cys Leu Phe Asn Gln His Thr Phe Asn Cys Arg Gln Tyr Lys
        340                 345                 350

Arg Leu Leu Val Gly Lys Leu Ser Ser Gln Glu Arg Asp Leu Glu Glu
        355                 360                 365

Thr Tyr Arg Glu Trp Arg Arg Glu Tyr Leu Ala Pro Pro Asp Lys Pro
        370                 375                 380

Phe Leu Arg Tyr Pro Ser Ala Gln Lys Leu Pro Thr Pro Lys Leu Phe
385                 390                 395                 400

Gly Arg Gly Tyr Tyr Asp Leu Asp Phe Thr Arg His Val Val Lys Leu
                405                 410                 415

Arg Leu Asp Asp Met Pro Ala Glu Asn Phe Val Ser Phe Gly Phe Lys
                420                 425                 430

Pro Trp Pro Arg Asp Tyr Asp Lys Lys Pro Gly Glu Ile Asn Ile Thr
        435                 440                 445

Ser Val His Val His Phe Ile Gly Thr Arg Ala Arg Val Gly Phe Arg

```
                    450                 455                 460
Phe Ala Val Pro His Ser Tyr Ser Arg Phe Ser Val Ser Gln Asp Lys
465                 470                 475                 480

Ile Asp Glu Leu Arg Ser Arg Val Phe Pro Arg Lys Ser Gln Asp Leu
                    485                 490                 495

Glu Phe Leu Asn Glu Ala Arg Leu Arg Leu Leu Asp Gly Met Asn Glu
                500                 505                 510

Asn Gln Lys Ser Ala Leu Arg Ile Met Ala Val Asp Leu Gly Thr His
            515                 520                 525

Arg Ala Ala Ala Phe Phe Thr Gly Arg Ile Phe Asp Lys Pro Lys
        530                 535                 540

Leu Ile Lys Leu Lys Lys Ile Asp Leu Leu Thr Glu Ser Ile Thr Asp
545                 550                 555                 560

Thr Thr Gln Pro Glu Lys His Ser Ala Asn Lys Lys Ile Gln Arg
                565                 570                 575

Glu Lys Gly Leu Thr Gln His Val Gly Lys His Leu Asp Thr Leu
                580                 585                 590

Glu Thr Arg Thr Lys Glu Ile Ile Ser Lys Arg Gln Asn Ile Lys Ile
                595                 600                 605

Thr Pro Ser Asp Asp Thr Leu Gly Thr Leu Gly Asp His Asp Leu Arg
                610                 615                 620

His Leu Thr Ser His Ile Gln Arg Met Ile Arg Asp Trp Val Arg Leu
625                 630                 635                 640

Asn Ala Gln Gln Ile Thr Glu Leu Ala Glu Lys Glu Val Asp Leu
                645                 650                 655

Ile Val Phe Glu Ser Leu Arg Gly Phe Arg Ala His Ala Tyr Asp Lys
                660                 665                 670

Leu Asp Leu Glu Gln Lys Arg Arg Leu Ala Phe Phe Ala Tyr Gly Arg
            675                 680                 685

Ile Arg Arg Lys Val Ala Glu Lys Ala Val Glu Arg Gly Met Arg Val
        690                 695                 700

Leu Thr Val Pro Tyr Phe Glu Ser Ser Gln Ile Cys Ala Gln Cys Gly
705                 710                 715                 720

Arg Ser Gln Asn Asp Lys Asn Lys Leu Arg Asp Asn Lys Arg Lys Gln
                725                 730                 735

Ser Phe Gln Cys Glu Phe Ser Asp Cys Asn Tyr Lys Thr His Ser Asp
                740                 745                 750

Glu Asn Ala Ala Arg Val Leu Gly Arg Val Phe Trp Gly Glu Ile Thr
            755                 760                 765

Leu Pro Thr Asp
            770

<210> SEQ ID NO 17
<211> LENGTH: 696
<212> TYPE: PRT
<213> ORGANISM: Unknown
<220> FEATURE:
<223> OTHER INFORMATION: Description of Unknown:
      aquatic-marine-marine sediment sequence

<400> SEQUENCE: 17

Met Leu Glu Pro Glu Arg Phe Cys Ala Arg Asn Asp Pro Gly Asp Pro
1               5                   10                  15

Arg Gly Asp Trp Ile Arg His Ala Val Phe Glu Val Val Ala Gly Trp
                20                  25                  30
```

-continued

Lys Leu Ser Asp Asn Leu Asp Gln Tyr Asn Leu Asn Glu Glu Leu Thr
                35                  40                  45
Ala Ser Ile Glu Ala Ala Met Asp Lys Thr Arg Thr Ala Thr Ala Glu
 50                  55                  60
Ala Leu Phe Glu Arg Leu Met Arg Arg Glu Ala Ser Asn Val Met Val
 65                  70                  75                  80
Leu Leu Lys Val Ala Ala Glu Trp Ile Ala Ala Lys Tyr Val His Gln
                 85                  90                  95
Met Glu Asn Trp Lys Arg Gln Lys Glu Trp Glu Lys Glu Lys Ala
                100                 105                 110
Glu Trp Glu Asn Ser His Thr Glu Leu Thr Glu Gln Val Arg Asp Lys
                115                 120                 125
Tyr Asn Arg Ile Phe Lys Glu Leu Asp Ile Lys Asn Lys Arg Pro Arg
130                 135                 140
Val Cys Thr Trp Lys Arg Leu Ser Glu Asn Lys Asp Asn Cys Asp Trp
145                 150                 155                 160
Ala Gly Lys Arg Lys Leu Ile Gly Lys Ser Trp Val Asn His Ala Ala
                165                 170                 175
Leu Cys Tyr Lys Tyr His Glu Tyr Ser Glu Ala Pro Lys Val Lys His
                180                 185                 190
Arg Asp His Phe Ile Ala Asn Ala Asn Lys Tyr Ile Lys Ile Arg Arg
                195                 200                 205
Glu Tyr Pro Gln Trp Ser Arg Asp Gln Ala Met Lys Thr Leu Phe Lys
                210                 215                 220
Asn Glu Pro Arg Ala Ser Tyr Trp Phe Pro Lys Glu Trp Lys Met Tyr
225                 230                 235                 240
Leu Gly Ala Leu Gly Ile Glu Glu Asn Thr Ile Ile Gly Asn Tyr Thr
                245                 250                 255
Gly Cys Leu Pro His Cys Leu Lys Ile Thr His Lys Cys Arg Phe Asn
                260                 265                 270
Lys His Thr Asn Glu Cys Arg Arg Tyr Lys Asp Leu Met His Glu Arg
                275                 280                 285
Leu Thr Asn Glu Glu Arg Gln Leu Glu Glu Leu Tyr Arg Glu Trp Arg
                290                 295                 300
Arg Asn Tyr Leu Ile Ala Pro Gly Lys Pro Ala Leu Arg Tyr Pro Ser
305                 310                 315                 320
Ala Arg Thr Leu Pro Thr Pro Lys Ile Phe Gly Ser Gly Tyr Tyr Arg
                325                 330                 335
Leu Asp Phe Glu Arg Asn Gln Val His Leu Arg Leu Asp Asp Met Ser
                340                 345                 350
Gln Gly Asp Phe Ile Ser Phe Gly Ile Lys Ala Trp Pro Arg Lys Tyr
                355                 360                 365
Asp Tyr Gln Pro Asp Thr Ile Asp Ile Thr Ser Val Gln Val His Phe
                370                 375                 380
Val Gly Thr Arg Ala Arg Ile Gly Phe Arg Phe Lys Val Pro His Arg
385                 390                 395                 400
Glu Ser Ile Phe Thr Ile Arg Gln Asp Ile Asp Glu Leu Arg Ser
                405                 410                 415
Arg Lys Tyr Pro Arg Glu Ser Gln Asp Gln Lys Phe Leu Glu Glu Val
                420                 425                 430
Arg Lys Arg Ile Leu Asn Gly Phe Ser Glu Asp Gln Ile Ala Lys Leu
                435                 440                 445
Lys Ile Met Ala Val Asp Leu Gly Ser Asp Glu Gly Gly Val Ala Phe

```
                        450                 455                 460
Phe Lys Gly His Val Phe Glu Lys Gly Glu Ser Leu Lys Ile Ile Lys
465                 470                 475                 480

Ile Asp Glu Leu Phe Glu Ser Lys Lys Asn Glu Glu Ala Glu Lys Ala
                485                 490                 495

Lys Gly Leu Asn Val His Val Gly Arg His Leu Asp Val Leu Gln
            500                 505                 510

Lys Lys Ser Gln Glu Ile Ala Leu Leu Arg Gln Gly Met Thr Asn Ala
            515                 520                 525

Pro Ser Asn Asp Met Val Gln Ser Leu Tyr Pro Asn Asp Met Arg Arg
            530                 535                 540

Leu Thr Ser His Ile Arg Arg Met Ile Arg Asp Trp Val Arg Leu Asn
545                 550                 555                 560

Ser Ser Gln Ile Ile Lys Leu Ala Glu Arg Glu Gln Val Glu Leu Ile
                565                 570                 575

Val Phe Glu Ser Met Arg Gly Phe Leu Ala Pro Gly Tyr Asp Lys Ile
            580                 585                 590

Asp Pro Asp Lys Lys Arg Arg Leu Ala Phe Phe Ala Phe Gly Ser Ile
            595                 600                 605

Arg Arg Lys Val Ala Glu Lys Ala Val Glu Arg Gly Met Arg Val Val
610                 615                 620

Thr Val Pro Tyr His Cys Ser Ser Gln Val Cys Ala Lys Cys Gly Lys
625                 630                 635                 640

Glu Gln Glu Asp Lys Lys Arg Phe Arg Lys Asn Lys Glu Lys Arg Glu
                645                 650                 655

Phe Val Cys Glu Asp Lys Lys Cys Asn His Lys Thr Asn Ser Asp Ile
            660                 665                 670

Asn Ala Ala His Val Cys Gly Arg Val Phe Trp Gly Ile Asn Leu
            675                 680                 685

Leu Gly Lys Lys Ile Lys Ile Lys
            690                 695

<210> SEQ ID NO 18
<211> LENGTH: 768
<212> TYPE: PRT
<213> ORGANISM: Unknown
<220> FEATURE:
<223> OTHER INFORMATION: Description of Unknown:
      aquatic-marine-marine sediment sequence

<400> SEQUENCE: 18

Met Thr Arg Thr Lys Tyr Arg Glu Glu Arg Thr Leu Val Arg Ser Ile
1               5                   10                  15

Asn Arg Leu Pro Lys Gln Asp Lys Ala Glu Phe Lys Lys Asn Val Leu
                20                  25                  30

Arg Leu Arg Arg Tyr Phe Glu Gln Tyr Asn Leu Asp Val Ser Glu Thr
            35                  40                  45

Cys Gln Trp Leu Ile Ser Tyr Arg Gly Leu Asn Leu Asp Glu Ile Cys
        50                  55                  60

Lys Thr Gln Leu Phe Trp Glu Phe Met Leu Glu Pro Glu Arg Phe Cys
65                  70                  75                  80

Ala Arg Asn Asp Pro Gly Asp Pro Arg Gly Asp Trp Ile Arg His Ala
                85                  90                  95

Val Phe Glu Val Val Ala Gly Trp Lys Leu Ser Asp Asn Leu Asp Gln
            100                 105                 110
```

```
Tyr Asn Leu Asn Glu Glu Leu Thr Ala Ser Ile Glu Ala Met Asp
            115                 120                 125

Lys Thr Arg Thr Ala Thr Ala Glu Ala Leu Phe Glu Arg Leu Met Arg
130                 135                 140

Arg Glu Ala Ser Asn Val Met Val Leu Leu Lys Val Ala Ala Glu Trp
145                 150                 155                 160

Ile Ala Ala Lys Tyr Val His Gln Met Glu Asn Trp Lys Arg Gln Lys
                165                 170                 175

Glu Glu Trp Glu Lys Glu Lys Ala Glu Trp Glu Asn Ser His Thr Glu
            180                 185                 190

Leu Thr Glu Gln Val Arg Asp Lys Tyr Asn Arg Ile Phe Lys Glu Leu
            195                 200                 205

Asp Ile Lys Asn Lys Arg Pro Arg Val Cys Thr Trp Lys Arg Leu Ser
    210                 215                 220

Glu Asn Lys Asp Asn Cys Asp Trp Ala Gly Lys Arg Lys Leu Ile Gly
225                 230                 235                 240

Lys Ser Trp Val Asn His Ala Ala Leu Cys Tyr Lys Tyr His Glu Tyr
                245                 250                 255

Ser Glu Ala Pro Lys Val Lys His Arg Asp His Phe Ile Ala Asn Ala
            260                 265                 270

Asn Lys Tyr Ile Lys Ile Arg Arg Glu Tyr Pro Gln Trp Ser Arg Asp
            275                 280                 285

Gln Ala Met Lys Thr Leu Phe Lys Asn Glu Pro Arg Ala Ser Tyr Trp
            290                 295                 300

Phe Pro Lys Glu Trp Lys Met Tyr Leu Gly Ala Leu Gly Ile Glu Glu
305                 310                 315                 320

Asn Thr Ile Ile Gly Asn Tyr Thr Gly Cys Leu Pro His Cys Leu Lys
                325                 330                 335

Ile Thr His Lys Cys Arg Phe Asn Lys His Thr Asn Glu Cys Arg Arg
            340                 345                 350

Tyr Lys Asp Leu Met His Glu Arg Leu Thr Asn Glu Glu Arg Gln Leu
            355                 360                 365

Glu Glu Leu Tyr Arg Glu Trp Arg Arg Asn Tyr Leu Ile Ala Pro Gly
            370                 375                 380

Lys Pro Ala Leu Arg Tyr Pro Ser Ala Arg Thr Leu Pro Thr Pro Lys
385                 390                 395                 400

Ile Phe Gly Ser Gly Tyr Tyr Arg Leu Asp Phe Glu Arg Asn Gln Val
                405                 410                 415

His Leu Arg Leu Asp Asp Met Ser Gln Gly Asp Phe Ile Ser Phe Gly
            420                 425                 430

Ile Lys Ala Trp Pro Arg Lys Tyr Asp Tyr Gln Pro Asp Thr Ile Asp
            435                 440                 445

Ile Thr Ser Val Gln Val His Phe Val Gly Thr Arg Ala Arg Ile Gly
            450                 455                 460

Phe Arg Phe Lys Val Pro His Arg Glu Ser Ile Phe Thr Ile Arg Gln
465                 470                 475                 480

Asp Asp Ile Asp Glu Leu Arg Ser Arg Lys Tyr Pro Arg Glu Ser Gln
            485                 490                 495

Asp Gln Lys Phe Leu Glu Glu Val Arg Lys Arg Ile Leu Asn Gly Phe
            500                 505                 510

Ser Glu Asp Gln Ile Ala Lys Leu Lys Ile Met Ala Val Asp Leu Gly
            515                 520                 525

Ser Asp Glu Gly Gly Val Ala Phe Phe Lys Gly His Val Phe Glu Lys
```

```
                530                 535                 540
Gly Glu Ser Leu Lys Ile Ile Lys Ile Asp Glu Leu Phe Glu Ser Lys
545                 550                 555                 560

Lys Asn Glu Glu Ala Glu Lys Ala Lys Gly Leu Asn Val His His Val
                565                 570                 575

Gly Arg His Leu Asp Val Leu Gln Lys Lys Ser Gln Glu Ile Ala Leu
                580                 585                 590

Leu Arg Gln Gly Met Thr Asn Ala Pro Ser Asn Asp Met Val Gln Ser
                595                 600                 605

Leu Tyr Pro Asn Asp Met Arg Arg Leu Thr Ser His Ile Arg Arg Met
                610                 615                 620

Ile Arg Asp Trp Val Arg Leu Asn Ser Ser Gln Ile Ile Lys Leu Ala
625                 630                 635                 640

Glu Arg Glu Gln Val Glu Leu Ile Val Phe Glu Ser Met Arg Gly Phe
                645                 650                 655

Leu Ala Pro Gly Tyr Asp Lys Ile Asp Pro Asp Lys Lys Arg Arg Leu
                660                 665                 670

Ala Phe Phe Ala Phe Gly Ser Ile Arg Arg Lys Val Ala Glu Lys Ala
                675                 680                 685

Val Glu Arg Gly Met Arg Val Val Thr Val Pro Tyr His Cys Ser Ser
                690                 695                 700

Gln Val Cys Ala Lys Cys Gly Lys Glu Gln Glu Asp Lys Lys Arg Phe
705                 710                 715                 720

Arg Lys Asn Lys Glu Lys Arg Glu Phe Val Cys Glu Asp Lys Lys Cys
                725                 730                 735

Asn His Lys Thr Asn Ser Asp Ile Asn Ala Ala His Val Cys Gly Arg
                740                 745                 750

Val Phe Trp Gly Glu Ile Asn Leu Leu Gly Lys Lys Ile Lys Ile Lys
                755                 760                 765

<210> SEQ ID NO 19
<211> LENGTH: 855
<212> TYPE: PRT
<213> ORGANISM: Unknown
<220> FEATURE:
<223> OTHER INFORMATION: Description of Unknown:
      aquatic-thermal springs-hot spring fe si sediment sequence

<400> SEQUENCE: 19

Met Val Ala Ser Arg Tyr Arg Glu Ala Arg Thr Leu Val Arg Arg Leu
1               5                   10                  15

Gly Arg Leu Pro Gly Glu Gly Glu Ala Ser Phe Arg Ala Lys Leu Ala
                20                  25                  30

Arg Leu Arg Lys His Phe Glu Arg Phe Asn Val Asp Val Ser Glu Leu
                35                  40                  45

Cys Gln Trp Leu Met Gly Leu Arg Lys Gln His Cys His Lys Ala Gly
                50                  55                  60

Thr Ala Ser Phe Gly Val Leu Gly Asp Phe Leu His Pro Glu Ser
65                  70                  75                  80

Ser Asn Val Ala Pro Gly Glu Ala Glu Ala Asp Arg Trp Arg Leu Leu
                85                  90                  95

Val Phe Asp Ala Val Ala Gly Ile Cys Pro Ala Lys Gln Leu Thr Asn
                100                 105                 110

Ala Pro Met Pro Arg Gly Leu Pro Glu Ala Met Glu Arg Glu Ala Lys
                115                 120                 125
```

```
Arg Leu Ala Asp Leu Glu Trp Arg Arg Asn Thr Thr Gln Ser Lys
    130                 135                 140

Leu Ile Asp Arg Leu Ala Ile Leu Glu Pro Ala His Arg Leu Val Leu
145                 150                 155                 160

Leu Lys Ala Ala Ala Glu Trp Val Val Ser Arg Tyr Gln Arg Gly Leu
                165                 170                 175

Glu Asn Trp Ala Ala Arg Arg Gly Glu Trp Lys Glu Arg His Ala
            180                 185                 190

Trp Glu Lys Arg His Pro Ala Leu Ser Glu Val Arg Gln Arg Phe
        195                 200                 205

Thr Glu Val Phe Lys Ser Leu Asn Asp Pro Arg Thr Asp Lys Pro
210                 215                 220

Gly Val Arg Arg Lys Asn Pro Arg Ile Cys Pro Tyr Glu Arg Leu Arg
225                 230                 235                 240

Ala Asn Ile Asp Asn Cys Ile Tyr Ala Gly Glu Lys Gly His Gly Ala
                245                 250                 255

Leu Cys Trp Lys Tyr Ala Glu Phe Val Lys Ala Arg Lys Thr Arg Gln
            260                 265                 270

Pro Gln Phe Asn Asp Lys Arg Phe Ala Glu Asp Ala Glu Lys Val Leu
        275                 280                 285

Pro Leu Leu Lys Gln Gly Met Lys Arg His Gln Ala Leu Gln Arg Leu
290                 295                 300

Phe Pro Arg Asp Arg Pro His Gly Gln Leu Ala Gln Arg Phe Asn
305                 310                 315                 320

Glu Asn Trp Thr Ala Tyr Leu Gln Ala Leu Gly Leu Lys Glu Glu Arg
                325                 330                 335

Val Val Asn Arg Gly Arg Leu Pro His Cys Leu Lys Ile Gly Glu Thr
            340                 345                 350

His Glu Lys Ser Lys Cys Ala Trp Asn Pro His Thr Glu Leu Cys Lys
        355                 360                 365

Gln Tyr Lys Arg Ala Leu Asp Gln Phe Asp Glu Thr Leu Lys Leu
370                 375                 380

Glu Pro Leu Tyr Arg Glu Trp Arg Arg Asp Tyr Leu Ala Gly Pro Gly
385                 390                 395                 400

Lys Pro Gln Phe Arg Tyr Pro Ser Ser Arg Glu Leu Pro Met Pro Lys
                405                 410                 415

Ile Phe Gly Ala Gly Phe His Glu Ile Asp Phe Asp Arg Ser Ile Leu
            420                 425                 430

Arg Leu Arg Leu Glu Asp Met Pro Glu Gly Gly Trp Ile Glu Phe Gly
        435                 440                 445

Phe Ala Pro Trp Pro Arg Gly Tyr Arg Pro Ser Lys Glu Glu Val Lys
450                 455                 460

Val Lys Gly Ala Ile Ser Ser Val His Val Asn Phe Val Gly Val Arg
465                 470                 475                 480

Ala Arg Ala Gly Phe Arg Phe Asp Val Arg His Arg Ala Ser Arg Phe
                485                 490                 495

Gln Cys Thr Gln Asp Glu Leu Asp Gln Leu Arg Ser Arg Ala Tyr Pro
            500                 505                 510

Arg Arg Ala Gln Asp Arg Glu Tyr Leu Asp Ala Ala Lys Arg Leu
        515                 520                 525

Leu Glu Ser Phe Ala Glu Gly Glu Ala Ala Lys Arg Glu Leu Arg
530                 535                 540

Leu Leu Ala Val Asp Leu Gly Glu Thr Gly Ala Cys Ala Ala Val Tyr
```

```
                545                 550                 555                 560
His Gly His Ala His Gln Lys Asp Val Gln Leu Ala Ile Leu Lys Ile
                    565                 570                 575

Asn Arg Leu Tyr Thr Gln Leu Pro Glu Ala Leu Glu Pro Asp Pro His
                580                 585                 590

Gly Arg Pro Glu Glu Gly Lys Arg Lys Tyr Glu Arg Asp Pro Arg
            595                 600                 605

Gly Val Arg Lys Glu His Met Gly Arg His Leu Lys Arg Met Ala Asp
            610                 615                 620

Gly Ala Ala Ser Ile Ala Ala Arg Arg Gln Gly Thr Met Pro Ala Thr
625                 630                 635                 640

Val Thr Met Ala Gly His Asp Phe Arg Gly Leu Lys Arg His Val Thr
                    645                 650                 655

Trp Met Ile Arg Asp Trp Ala Arg His Asn Ala Ala Arg Ile Val Ala
                660                 665                 670

Ala Ala Glu Glu His Gly Cys Asp Leu Ile Val Phe Glu Ser Leu Arg
            675                 680                 685

Gly Gln Lys Val Pro Gly Tyr His Glu Leu Ser Ser Glu Lys Glu Arg
        690                 695                 700

Asp Lys Arg Gln Leu Ala Met Leu Ser Tyr Gly Arg Ile Arg His Lys
705                 710                 715                 720

Val Arg Glu Lys Ala Val Glu Arg Gly Met Arg Val Val Met Val Pro
                    725                 730                 735

Asp Tyr Arg Ser Ser Arg Leu Cys Ser Ser Cys Gly His Glu Gln Cys
                740                 745                 750

Ala Glu Lys Trp Gln Glu Arg Arg Trp Arg Glu Asn Lys Lys Lys Arg
            755                 760                 765

Leu Phe Lys Cys Val Cys Gly Glu Pro Ala Pro Thr Glu Lys Pro His
        770                 775                 780

His Gly Gly Ser Ala Pro Asp Arg Gln Arg Ala Ala Arg Arg Asp Gly
785                 790                 795                 800

Pro Gly Pro Gly Lys Arg Pro Gly Met Ala Asp Gln Ala Lys Gln
                    805                 810                 815

Arg Cys Arg Cys Gly Ala Glu Met Asn Ser Asp Ala Asn Ala Ala Arg
                820                 825                 830

Val Leu Ala Arg Val Phe Trp Gly Glu Ile Thr Pro Pro Ala Ser Glu
            835                 840                 845

Arg Ser Phe Ala Gly Ser Ala
    850                 855

<210> SEQ ID NO 20
<211> LENGTH: 803
<212> TYPE: PRT
<213> ORGANISM: Unknown
<220> FEATURE:
<223> OTHER INFORMATION: Description of Unknown:
      aquatic-thermal springs-hot spring fe si sediment sequence

<400> SEQUENCE: 20

Met Gly Leu Arg Lys Gln His Cys His Lys Ala Gly Thr Ala Ser Phe
1               5                   10                  15

Gly Val Leu Gly Asp Phe Leu Leu His Pro Glu Ser Ser Asn Val Ala
            20                  25                  30

Pro Gly Glu Ala Glu Ala Asp Arg Trp Arg Leu Leu Val Phe Asp Ala
        35                  40                  45
```

-continued

Val Ala Gly Ile Cys Pro Ala Lys Gln Leu Thr Asn Ala Pro Met Pro
 50                  55                  60

Arg Gly Leu Pro Glu Ala Met Glu Arg Glu Ala Lys Arg Leu Ala Asp
 65                  70                  75                  80

Leu Glu Trp Arg Arg Arg Asn Thr Thr Gln Ser Lys Leu Ile Asp Arg
                 85                  90                  95

Leu Ala Ile Leu Glu Pro Ala His Arg Leu Val Leu Leu Lys Ala Ala
                100                 105                 110

Ala Glu Trp Val Val Ser Arg Tyr Gln Arg Gly Leu Glu Asn Trp Ala
                115                 120                 125

Ala Arg Arg Gly Glu Trp Glu Lys Glu Arg His Ala Trp Glu Lys Arg
                130                 135                 140

His Pro Ala Leu Ser Glu Glu Val Arg Gln Arg Phe Thr Glu Val Phe
145                 150                 155                 160

Lys Ser Leu Asn Asp Pro Glu Arg Thr Asp Lys Pro Gly Val Arg Arg
                165                 170                 175

Lys Asn Pro Arg Ile Cys Pro Tyr Glu Arg Leu Arg Ala Asn Ile Asp
                180                 185                 190

Asn Cys Ile Tyr Ala Gly Glu Lys Gly His Gly Ala Leu Cys Trp Lys
                195                 200                 205

Tyr Ala Glu Phe Val Lys Ala Arg Lys Thr Arg Gln Pro Gln Phe Asn
210                 215                 220

Asp Lys Arg Phe Ala Glu Asp Ala Glu Lys Val Leu Pro Leu Leu Lys
225                 230                 235                 240

Gln Gly Met Lys Arg His Gln Ala Leu Gln Arg Leu Phe Pro Arg Asp
                245                 250                 255

Arg Pro His Gly Gln Leu Ala Gln Gln Arg Phe Asn Glu Asn Trp Thr
                260                 265                 270

Ala Tyr Leu Gln Ala Leu Gly Leu Lys Glu Glu Arg Val Val Asn Arg
                275                 280                 285

Gly Arg Leu Pro His Cys Leu Lys Ile Gly Glu Thr His Glu Lys Ser
                290                 295                 300

Lys Cys Ala Trp Asn Pro His Thr Glu Leu Cys Lys Gln Tyr Lys Arg
305                 310                 315                 320

Ala Leu Asp Gln Phe Asp Glu Thr Leu Lys Leu Glu Pro Leu Tyr
                325                 330                 335

Arg Glu Trp Arg Arg Asp Tyr Leu Ala Gly Pro Gly Lys Pro Gln Phe
                340                 345                 350

Arg Tyr Pro Ser Ser Arg Glu Leu Pro Met Pro Lys Ile Phe Gly Ala
                355                 360                 365

Gly Phe His Glu Ile Asp Phe Asp Arg Ser Ile Leu Arg Leu Arg Leu
                370                 375                 380

Glu Asp Met Pro Glu Gly Glu Trp Ile Glu Phe Gly Phe Ala Pro Trp
385                 390                 395                 400

Pro Arg Gly Tyr Arg Pro Ser Lys Glu Glu Val Lys Val Lys Gly Ala
                405                 410                 415

Ile Ser Ser Val His Val Asn Phe Val Gly Val Arg Ala Arg Ala Gly
                420                 425                 430

Phe Arg Phe Asp Val Arg His Arg Ala Ser Arg Phe Gln Cys Thr Gln
                435                 440                 445

Asp Glu Leu Asp Gln Leu Arg Ser Arg Ala Tyr Pro Arg Arg Ala Gln
450                 455                 460

Asp Arg Glu Tyr Leu Asp Ala Ala Arg Lys Arg Leu Leu Glu Ser Phe

```
            465                 470                 475                 480
    Ala Glu Gly Glu Glu Ala Ala Lys Arg Glu Leu Arg Leu Leu Ala Val
                    485                 490                 495

Asp Leu Gly Glu Thr Gly Ala Cys Ala Ala Val Tyr His Gly His Ala
                    500                 505                 510

His Gln Lys Asp Val Gln Leu Ala Ile Leu Lys Ile Asn Arg Leu Tyr
                    515                 520                 525

Thr Gln Leu Pro Glu Ala Leu Glu Pro Asp Pro His Gly Arg Pro Glu
                    530                 535                 540

Glu Gly Lys Arg Lys Tyr Glu Arg Asp Asp Pro Arg Gly Val Arg Lys
    545                 550                 555                 560

Glu His Met Gly Arg His Leu Lys Arg Met Ala Asp Gly Ala Ala Ser
                    565                 570                 575

Ile Ala Ala Arg Arg Gln Gly Thr Met Pro Ala Thr Val Thr Met Ala
                    580                 585                 590

Gly His Asp Phe Arg Gly Leu Lys Arg His Val Thr Trp Met Ile Arg
                    595                 600                 605

Asp Trp Ala Arg His Asn Ala Ala Arg Ile Val Ala Ala Ala Glu Glu
                    610                 615                 620

His Gly Cys Asp Leu Ile Val Phe Glu Ser Leu Arg Gly Gln Lys Val
    625                 630                 635                 640

Pro Gly Tyr His Glu Leu Ser Ser Glu Lys Glu Arg Asp Lys Arg Gln
                    645                 650                 655

Leu Ala Met Leu Ser Tyr Gly Arg Ile Arg His Lys Val Arg Glu Lys
                    660                 665                 670

Ala Val Glu Arg Gly Met Arg Val Val Met Val Pro Asp Tyr Arg Ser
                    675                 680                 685

Ser Arg Leu Cys Ser Ser Cys Gly His Glu Gln Cys Ala Glu Lys Trp
                    690                 695                 700

Gln Glu Arg Arg Trp Arg Glu Asn Lys Lys Arg Leu Phe Lys Cys
    705                 710                 715                 720

Val Cys Gly Glu Pro Ala Pro Thr Glu Lys Pro His His Gly Gly Ser
                    725                 730                 735

Ala Pro Asp Arg Gln Arg Ala Ala Arg Arg Asp Gly Pro Gly Pro Gly
                    740                 745                 750

Lys Arg Pro Gly Met Ala Ala Asp Gln Ala Lys Gln Arg Cys Arg Cys
                    755                 760                 765

Gly Ala Glu Met Asn Ser Asp Ala Asn Ala Ala Arg Val Leu Ala Arg
                    770                 775                 780

Val Phe Trp Gly Glu Ile Thr Pro Pro Ala Ser Glu Arg Ser Phe Ala
    785                 790                 795                 800

Gly Ser Ala

<210> SEQ ID NO 21
<211> LENGTH: 853
<212> TYPE: PRT
<213> ORGANISM: Unknown
<220> FEATURE:
<223> OTHER INFORMATION: Description of Unknown:
      aquatic-thermal springs-sediment sequence

<400> SEQUENCE: 21

Met Lys Asn Pro Lys Tyr Arg Glu Glu Arg Thr Leu Thr Met Gly Ile
1               5                   10                  15

Arg Ser Phe Pro Leu Glu Asp Lys Ser His Phe Lys Glu Lys Val Arg
```

```
                20                  25                  30
Lys Leu Arg Lys Phe Phe Glu Ile Phe Asn Lys Asp Val Ala Asp Leu
                35                  40                  45
Cys Gln Trp Leu Ile Val Phe Arg Lys Gly Lys Ser Glu Asn Ile
    50                  55                  60
Pro Ile Trp Glu Phe Phe Ile Asn Pro Leu Glu Ser Ile Lys Asp Ile
65                  70                  75                  80
Ser Glu Asp Gln Ala Asp Glu Leu Lys Arg Lys Val Leu Asp Val Ile
                85                  90                  95
Ile Gly Asn Glu Ser Ile Asn Asn Ile Arg Asn Glu Lys Leu Pro Thr
                100                 105                 110
Glu Val Leu Lys Tyr Leu Glu Asn Leu Asp Asp Asn Trp Asn Gln Ser
            115                 120                 125
Val Gln Glu Leu Phe Lys Arg Met Lys Asp Lys Pro Ser His Arg
    130                 135                 140
Gln Ile Leu Leu Lys Ala Ala Ser Asn Leu Ile Tyr Ser Arg Tyr Tyr
145                 150                 155                 160
Lys Thr Leu Glu Asn Arg Glu Lys Gln Lys Glu Trp Lys Lys Glu
                165                 170                 175
Arg Asp Thr Trp Gln Arg Lys Asn Pro Asp Leu Lys Glu Asp Ile Arg
                180                 185                 190
Thr Lys Tyr Thr Glu Val Tyr Lys Gln Leu Gly Ile Lys Arg Lys Ala
            195                 200                 205
Pro Arg Ile Cys Glu Trp Glu Lys Leu Lys Asn Trp Lys His Asn Cys
    210                 215                 220
Thr Tyr Ser Ser Asn Lys Gln His Thr Glu Arg Cys Phe Asp Phe Asn
225                 230                 235                 240
Lys Leu Phe Ser Ser Ala Asp Asn Lys Lys Arg Lys Trp Phe Ile
                245                 250                 255
Asp Asn Ala His Leu Tyr Leu Gln Tyr Leu Ser Lys Ser Asn Gln Lys
                260                 265                 270
Asp Ala Leu Lys Gln Leu Tyr His Lys Lys Gly Ser Glu Lys Trp
            275                 280                 285
Phe Gly Arg Leu Trp Asn Asp Tyr Leu Lys Leu Met Lys Ile Ser Glu
    290                 295                 300
Gln Asp Ile Leu Thr Lys Tyr His Cys Ile Leu Pro His Cys Ile Ser
305                 310                 315                 320
Glu Asn Leu Gly Ser Ala Lys Tyr Arg Glu Tyr Phe Asp Asn Ser Glu
                325                 330                 335
Tyr Gly Phe Ala Arg Ser Glu Phe Gly Lys Cys Ala Asn Thr Tyr Leu
                340                 345                 350
Gly Ser Arg Lys Lys Gly Ser Asn Lys Ala Asp Ser Leu Gln Met Val
            355                 360                 365
Tyr Gly Lys His Lys Ser Asn Ile Asp Glu Arg Phe Glu Glu Ile Trp
    370                 375                 380
Asn Asp Tyr Leu Lys Phe Ile Lys Lys Thr Glu Glu Glu Ala Ile Ile
385                 390                 395                 400
Glu Tyr Asn His Ser Leu Pro Val Tyr Leu Lys Ser Asp Tyr Cys Gln
                405                 410                 415
Phe Arg Pro His Gly Asp Lys Cys Lys Gln Tyr Arg Asp Leu Leu Ala
                420                 425                 430
Asp Phe Thr Glu Val Glu Lys Ser Leu Glu Lys Lys Tyr Arg Glu Trp
            435                 440                 445
```

```
Arg Lys Ser Tyr Leu Ser Gly Pro Gly Lys Pro Gln Phe Arg Tyr Pro
    450                 455                 460
Ser Ala Lys Thr Ile Ala Ile Pro Lys Leu Phe Gly Ser Gly Tyr Phe
465                 470                 475                 480
Arg Ile Asp Phe Glu Glu Ser Ile Leu Asn Leu Lys Leu Glu Asn Asp
                485                 490                 495
Glu Trp Leu Ser Leu Gly Phe Lys Pro Trp Pro Lys Arg Lys Asp Tyr
            500                 505                 510
Asp Ile His Tyr Ser Asp Ile Glu Ile Pro Ser Val Ser Ile His Phe
        515                 520                 525
Val Gly Thr Arg Ala Lys Val Gly Phe Arg Phe Lys Val Lys His Lys
    530                 535                 540
Glu Ser Arg Phe Lys Val Ala Gln Glu Glu Ile Asp Lys Leu Arg Ser
545                 550                 555                 560
Gln Lys Tyr Pro Arg Gln Tyr Gln Asp Asn Asp Phe Leu Lys Glu Ala
                565                 570                 575
Arg Glu Leu Leu Leu Lys Asp Phe Asp Gly Asp Lys Asn Glu Met Lys
            580                 585                 590
Ile Leu Ala Phe Asp Trp Gly Thr Gly Ala Tyr Ala Ala Leu Phe
        595                 600                 605
Thr Gly Glu Lys Tyr Glu Lys Gly Phe Gln Leu Pro Val Leu Lys Phe
    610                 615                 620
Glu Lys Leu Tyr Cys Ser Asp Lys Phe Lys Glu Ala Trp Asp Gln Lys
625                 630                 635                 640
Lys Lys Glu Gln Lys Trp Ser Lys Asp Glu Ser Lys Ala Lys Leu Lys
                645                 650                 655
Glu Tyr Lys Leu Lys Gly Leu Thr Lys Gly His Val Gly Lys His Leu
            660                 665                 670
Glu Asn Ile Ser Glu Lys Ala Val Lys Ile Ala Glu Ile Arg Gly Glu
        675                 680                 685
Lys Lys Asp Glu Lys Leu Leu Arg Pro Ser Asp Leu Arg Arg Leu Phe
    690                 695                 700
Ser His Ser Ala Trp Met Ile Arg Asp Trp Val Arg Leu Asn Thr Lys
705                 710                 715                 720
Gln Leu Ile Lys Ile Ala Glu Lys Asn Glu Val Asp Leu Ile Val Phe
                725                 730                 735
Glu Ser Met Arg Gly Ser Ala Pro Pro Ser Tyr Asp Lys Leu Glu Glu
            740                 745                 750
Ile Thr Glu Lys Ile Lys Trp Ala Phe Phe Ser Leu Gly Arg Ile Arg
        755                 760                 765
His Lys Val Thr Glu Lys Ala Val Glu Arg Gly Met Arg Thr Ile Thr
    770                 775                 780
Val Pro Tyr Val Lys Ser Ser Gln Val Cys Phe Asp Cys Gly Lys Glu
785                 790                 795                 800
Ala Glu Asp Lys Lys Lys Trp Gln His His Lys Thr Glu Leu Thr Lys
                805                 810                 815
Phe Ile Cys Glu His Cys Pro Ala Asp Leu Asn Ser Asp Glu Asn Ala
            820                 825                 830
Ala Arg Val Leu Cys Lys Val Phe Trp Gly Asp Ile Thr Leu Pro Ser
        835                 840                 845
Thr Glu Trp Glu Lys
    850
```

<210> SEQ ID NO 22
<211> LENGTH: 774
<212> TYPE: PRT
<213> ORGANISM: Unknown
<220> FEATURE:
<223> OTHER INFORMATION: Description of Unknown:
      terrestrial-deep subsurface sequence

<400> SEQUENCE: 22

Met Ser Asn Thr Arg Tyr Ser Glu Ser Arg Thr Leu Val Arg Arg Leu
1               5                   10                  15

Arg Arg Leu Pro Gly Glu Ser Arg Glu Phe Arg Gly Lys Val Arg
            20                  25                  30

Arg Leu Arg Lys Gln Phe Ala Gln Phe Asn Val Asn Ala Ser Glu Leu
            35                  40                  45

Cys Gln Trp Leu Met Ser Leu Arg Pro Gly Gly Lys Lys Ala Ser Asp
50                  55                  60

Arg Thr Lys Glu Phe Trp Glu Phe Phe Leu Glu Pro Glu Arg Phe Leu
65                  70                  75                  80

Glu Asn Gln Asp Asp Asp Arg Cys Asp Ala Cys Arg Leu Ala Val Phe
                85                  90                  95

Asp Val Ala Ala Gly Leu Ala Pro Ala Asp Arg Leu Gly Asp Tyr Gly
            100                 105                 110

Val Ser Gln Ala Leu Ala Glu Ser Val His Val Ile Gly Gln Ile Ser
            115                 120                 125

Leu Thr Pro Thr Ala Ala Lys Leu Phe Thr Arg Leu Cys Gly Phe Glu
130                 135                 140

Ala Ser His Arg Gln Val Leu Leu Lys Ala Ala Ala Glu Trp Ile Val
145                 150                 155                 160

Ala His Tyr Leu Arg Gly Tyr Glu Asn Trp Val Arg Arg His Glu Glu
                165                 170                 175

Trp Glu Lys Glu Lys Ala Arg Trp Glu Ala Ser His Pro Glu Leu Thr
            180                 185                 190

Gln Ala Ala Arg Asp Asp Phe Asn Arg Ile Phe Lys Asp Leu Gly Ile
            195                 200                 205

Glu Arg Lys Arg Pro Arg Val Cys Thr Gly Glu Arg Leu Lys Ala Asn
210                 215                 220

Lys Asp Asp Cys Asp Trp Ala Gly Glu Arg Ile Pro Val Gly Gly Thr
225                 230                 235                 240

Trp Arg Asn His Ser Ser Leu Cys Val Lys Tyr Trp Arg Phe Leu Lys
                245                 250                 255

Glu Tyr Pro Arg Lys Ala Arg Val Pro Arg Gln Phe Arg Glu Phe Phe
            260                 265                 270

Val Thr Asn Ala Lys Thr Tyr Met Asp Leu Arg Arg Thr Ser Arg Gly
            275                 280                 285

Asp Arg Ser Val Thr Met Ala Ala Phe Leu Arg Lys Gln Arg Asn Ala
            290                 295                 300

Gln Trp Phe Pro Gln Ala Trp Glu Ala Tyr Leu Lys Ala Leu Glu Val
305                 310                 315                 320

Asn Glu Gln Thr Val Leu Ala Ala Gly Tyr Gly Leu Pro His Cys Thr
                325                 330                 335

Glu Ile Gly Pro Asp Ala Asp Cys Gln Phe Asn Lys His Thr Ala Asp
            340                 345                 350

Cys Glu Lys Tyr Arg Arg Ala Leu Asp Ala Arg Pro Asp Leu Leu Pro
            355                 360                 365

Leu Glu Lys Leu Tyr Arg His Trp Arg Glu Tyr Leu Ser Gly Pro
    370                 375                 380

Gly Lys Pro Cys Phe Gln Tyr Pro Ser Gln Arg Lys Leu Pro Met Pro
385                 390                 395                 400

Lys Ile Phe Gly Arg Gly Tyr Phe Arg Val Asp Leu Ala Ser Ser Ile
                405                 410                 415

Ile Glu Leu Arg Met Glu Gly Gly Arg Asp Phe Glu Arg Phe Arg Ile
            420                 425                 430

Ala Ala Trp Pro Ser Asp Tyr Thr Pro Ser Ala Gln Glu Ala Gln Ile
        435                 440                 445

Thr Ser Val His Val Ser Phe Val Gly Thr Arg Ala Leu Ala Gly Phe
    450                 455                 460

Arg Phe Glu Val Pro His Lys Ala Ser Arg Phe Ala Ala Gly Gln Asp
465                 470                 475                 480

Gln Ile Asp Glu Leu Arg Ser Arg Lys Tyr Pro Arg Arg Ala Gln Asp
                485                 490                 495

Ala Glu Phe Leu Val Ala Ala Arg Lys Arg Leu Leu Glu Ser Phe Ala
            500                 505                 510

Gly Gly Ala Glu His Asp Val Arg Ile Leu Ala Val Asp Leu Gly Thr
        515                 520                 525

Ser Asn Gly Ala Val Ala Val Phe Arg Gly Arg Ser Leu Glu Lys Ala
    530                 535                 540

Met Pro Leu Asp Val Ile Lys Leu Glu Lys Leu His Ser Ser Ser Pro
545                 550                 555                 560

Lys Glu Asn Arg Gly Ala Gly Pro Glu Pro Ser Glu Glu Glu Arg Lys
                565                 570                 575

Lys Ala Arg Ala Arg Gly Leu Arg Pro Ser His Val Gly Arg His Leu
            580                 585                 590

Glu Asn Trp Ala Leu Ala Ala Arg Glu Ile Ala Asn Gln Arg Gly Asn
        595                 600                 605

Glu Ala Asp Gly Pro Ala Thr Leu Gly Asp His Asp Leu Arg Arg Phe
610                 615                 620

Ser Leu His Ile Arg Trp Met Ile Arg Asp Trp Val Arg Leu Asn Val
625                 630                 635                 640

Ser Gln Ile Ile Glu Ala Ala Glu Gly Asn His Val Asp Leu Ile Val
                645                 650                 655

Phe Glu Ser Met Arg Gly Trp Arg Ala Pro Gly Tyr Asp Thr Val Asp
            660                 665                 670

Asp Glu Lys Lys Arg Arg Leu Ala Phe Phe Ala His Gly Arg Ile Arg
        675                 680                 685

His Lys Ile Arg Glu Lys Ala Val Glu Arg Gly Met Arg Val Val Thr
    690                 695                 700

Val Pro Tyr Phe Met Ser Ser Gln Phe Cys Gly Ser Cys Gly Thr Gln
705                 710                 715                 720

Gln Gln Asp Thr Arg Lys Leu Lys Thr Asn Lys Arg Glu Arg Thr Ser
                725                 730                 735

Phe Thr Cys Glu Asn Cys Gly His Arg Ala Asn Ser Asp Glu Asn Ala
            740                 745                 750

Ala Gln Val Leu Ala Lys Val Phe Trp Gly Asp Val Val Leu Pro Glu
        755                 760                 765

Asp Pro Asp Asp Cys Ser
    770

<210> SEQ ID NO 23
<211> LENGTH: 763
<212> TYPE: PRT
<213> ORGANISM: Unknown
<220> FEATURE:
<223> OTHER INFORMATION: Description of Unknown:
      terrestrial-deep subsurface sequence

<400> SEQUENCE: 23

Met Val Arg Arg Leu Arg Arg Leu Pro Gly Glu Ser Arg Glu Phe
1               5                   10                  15

Arg Gly Lys Val Arg Arg Leu Arg Lys Gln Phe Ala Gln Phe Asn Val
            20                  25                  30

Asn Ala Ser Glu Leu Cys Gln Trp Leu Met Ser Leu Arg Pro Gly Gly
        35                  40                  45

Lys Lys Ala Ser Asp Arg Thr Lys Glu Phe Trp Glu Phe Phe Leu Glu
50                  55                  60

Pro Glu Arg Phe Leu Glu Asn Gln Asp Asp Arg Cys Asp Ala Cys
65                  70                  75                  80

Arg Leu Ala Val Phe Asp Val Ala Ala Gly Leu Ala Pro Ala Asp Arg
                85                  90                  95

Leu Gly Asp Tyr Gly Val Ser Gln Ala Leu Ala Glu Ser Val His Val
            100                 105                 110

Ile Gly Gln Ile Ser Leu Thr Pro Thr Ala Ala Lys Leu Phe Thr Arg
        115                 120                 125

Leu Cys Gly Phe Glu Ala Ser His Arg Gln Val Leu Leu Lys Ala Ala
    130                 135                 140

Ala Glu Trp Ile Val Ala His Tyr Leu Arg Gly Tyr Glu Asn Trp Val
145                 150                 155                 160

Arg Arg His Glu Glu Trp Glu Lys Glu Lys Ala Arg Trp Glu Ala Ser
                165                 170                 175

His Pro Glu Leu Thr Gln Ala Ala Arg Asp Asp Phe Asn Arg Ile Phe
            180                 185                 190

Lys Asp Leu Gly Ile Glu Arg Lys Arg Pro Arg Val Cys Thr Gly Glu
        195                 200                 205

Arg Leu Lys Ala Asn Lys Asp Cys Asp Trp Ala Gly Glu Arg Ile
    210                 215                 220

Pro Val Gly Gly Thr Trp Arg Asn His Ser Ser Leu Cys Val Lys Tyr
225                 230                 235                 240

Trp Arg Phe Leu Lys Glu Tyr Pro Arg Lys Ala Arg Val Pro Arg Gln
                245                 250                 255

Phe Arg Glu Phe Phe Val Thr Asn Ala Lys Thr Tyr Met Asp Leu Arg
            260                 265                 270

Arg Thr Ser Arg Gly Asp Arg Ser Val Thr Met Ala Ala Phe Leu Arg
        275                 280                 285

Lys Gln Arg Asn Ala Gln Trp Phe Pro Gln Ala Trp Glu Ala Tyr Leu
    290                 295                 300

Lys Ala Leu Glu Val Asn Glu Gln Thr Val Leu Ala Ala Gly Tyr Gly
305                 310                 315                 320

Leu Pro His Cys Thr Glu Ile Gly Pro Asp Ala Asp Cys Gln Phe Asn
                325                 330                 335

Lys His Thr Ala Asp Cys Glu Lys Tyr Arg Arg Ala Leu Asp Ala Arg
            340                 345                 350

Pro Asp Leu Leu Pro Leu Glu Lys Leu Tyr Arg His Trp Arg Arg Glu
        355                 360                 365

Tyr Leu Ser Gly Pro Gly Lys Pro Cys Phe Gln Tyr Pro Ser Gln Arg
        370             375                 380

Lys Leu Pro Met Pro Lys Ile Phe Gly Arg Gly Tyr Phe Arg Val Asp
385             390                 395                 400

Leu Ala Ser Ser Ile Ile Glu Leu Arg Met Glu Gly Gly Arg Asp Phe
            405                 410                 415

Glu Arg Phe Arg Ile Ala Ala Trp Pro Ser Asp Tyr Thr Pro Ser Ala
            420                 425                 430

Gln Glu Ala Gln Ile Thr Ser Val His Val Ser Phe Val Gly Thr Arg
        435                 440                 445

Ala Leu Ala Gly Phe Arg Phe Glu Val Pro His Lys Ala Ser Arg Phe
450                 455                 460

Ala Ala Gly Gln Asp Gln Ile Asp Glu Leu Arg Ser Arg Lys Tyr Pro
465                 470                 475                 480

Arg Arg Ala Gln Asp Ala Glu Phe Leu Val Ala Ala Arg Lys Arg Leu
            485                 490                 495

Leu Glu Ser Phe Ala Gly Ala Glu His Asp Val Arg Ile Leu Ala
        500                 505                 510

Val Asp Leu Gly Thr Ser Asn Gly Ala Val Ala Val Phe Arg Gly Arg
    515                 520                 525

Ser Leu Glu Lys Ala Met Pro Leu Asp Val Ile Lys Leu Glu Lys Leu
    530                 535                 540

His Ser Ser Ser Pro Lys Glu Asn Arg Gly Ala Gly Pro Glu Pro Ser
545                 550                 555                 560

Glu Glu Glu Arg Lys Lys Ala Arg Ala Arg Gly Leu Arg Pro Ser His
                565                 570                 575

Val Gly Arg His Leu Glu Asn Trp Ala Leu Ala Ala Arg Glu Ile Ala
            580                 585                 590

Asn Gln Arg Gly Asn Glu Ala Asp Gly Pro Ala Thr Leu Gly Asp His
        595                 600                 605

Asp Leu Arg Arg Phe Ser Leu His Ile Arg Trp Met Ile Arg Asp Trp
    610                 615                 620

Val Arg Leu Asn Val Ser Gln Ile Ile Glu Ala Ala Glu Gly Asn His
625                 630                 635                 640

Val Asp Leu Ile Val Phe Glu Ser Met Arg Gly Trp Arg Ala Pro Gly
            645                 650                 655

Tyr Asp Thr Val Asp Asp Glu Lys Lys Arg Arg Leu Ala Phe Phe Ala
            660                 665                 670

His Gly Arg Ile Arg His Lys Ile Arg Glu Lys Ala Val Glu Arg Gly
        675                 680                 685

Met Arg Val Val Thr Val Pro Tyr Phe Met Ser Ser Gln Phe Cys Gly
690                 695                 700

Ser Cys Gly Thr Gln Gln Asp Thr Arg Lys Leu Lys Thr Asn Lys
705                 710                 715                 720

Arg Glu Arg Thr Ser Phe Thr Cys Glu Asn Cys Gly His Arg Ala Asn
                725                 730                 735

Ser Asp Glu Asn Ala Ala Gln Val Leu Ala Lys Val Phe Trp Gly Asp
            740                 745                 750

Val Val Leu Pro Glu Asp Pro Asp Cys Ser
        755                 760

<210> SEQ ID NO 24
<211> LENGTH: 752

```
<212> TYPE: PRT
<213> ORGANISM: Unknown
<220> FEATURE:
<223> OTHER INFORMATION: Description of Unknown:
      terrestrial-soil sequence

<400> SEQUENCE: 24
```

| | | | | | | | | | | | | | | | |
|---|---|---|---|---|---|---|---|---|---|---|---|---|---|---|---|
| Met | Ala | Val | Thr | Arg | Tyr | Arg | Glu | Glu | Arg | Thr | Leu | Val | Arg | Gly | Leu |
| 1 | | | | 5 | | | | | 10 | | | | | 15 | |
| Arg | Arg | Leu | Pro | Gly | Gln | Ser | Arg | Glu | Gln | Phe | Arg | Lys | Asn | Val | Leu |
| | | | 20 | | | | | 25 | | | | | 30 | | |
| Leu | Leu | Arg | Arg | His | Phe | Glu | Arg | Phe | Asn | Val | Asp | Val | Ser | Asp | Ile |
| | | | | 35 | | | | | 40 | | | | | 45 | |
| Cys | Gln | Trp | Met | Met | Gly | Leu | Arg | Pro | Lys | Asp | Gly | Glu | Val | Thr | Pro |
| | 50 | | | | | 55 | | | | | 60 | | | | |
| Ala | Thr | Gln | Pro | Leu | Trp | Asp | Phe | Met | Leu | Glu | Pro | Ser | Asp | Gly | Gln |
| 65 | | | | | 70 | | | | | 75 | | | | | 80 |
| Gly | Asn | Ala | Gln | Gly | Asp | Pro | Asp | Arg | Met | Arg | Leu | Leu | Ala | Phe | Arg |
| | | | | 85 | | | | | 90 | | | | | 95 | |
| Val | Ala | Thr | Gly | Val | Glu | His | Ser | Gln | Ser | Gly | Val | Arg | Leu | Pro | Leu |
| | | | 100 | | | | | 105 | | | | | 110 | | |
| His | Val | Gln | Glu | Ser | Leu | Arg | His | Val | Ala | Ala | Leu | Thr | Ser | Thr | Glu |
| | | | | 115 | | | | | 120 | | | | | 125 | |
| Ser | Ala | Arg | Arg | Leu | Ile | Leu | Arg | Phe | Gln | Gln | Leu | Glu | Gln | Ser | His |
| | 130 | | | | | 135 | | | | | 140 | | | | |
| Gln | Met | Ile | Leu | Leu | Lys | Ser | Ala | Ser | Glu | Trp | Val | Arg | Thr | Arg | Tyr |
| 145 | | | | | 150 | | | | | 155 | | | | | 160 |
| Ser | Asn | Ala | Asn | Glu | Asn | Trp | Gln | Arg | Asn | Arg | Pro | Leu | Trp | Glu | Lys |
| | | | | 165 | | | | | 170 | | | | | 175 | |
| Glu | Lys | Ala | Glu | Trp | Glu | Lys | Glu | His | Pro | Ala | Leu | Thr | Pro | Asp | Ala |
| | | | 180 | | | | | 185 | | | | | 190 | | |
| Cys | Arg | Lys | Phe | Ser | Asp | Ile | Phe | Lys | Glu | Leu | Gly | Ile | Lys | Asp | Lys |
| | | | | 195 | | | | | 200 | | | | | 205 | |
| Arg | Pro | Arg | Ile | Cys | Gly | Trp | Asn | Arg | Leu | Lys | Leu | Pro | Lys | Asp | Asn |
| | 210 | | | | | 215 | | | | | 220 | | | | |
| Cys | Asp | Tyr | Ala | Gly | Glu | Arg | Val | Gly | Gly | Arg | His | Ala | Pro | Leu |
| 225 | | | | | 230 | | | | | 235 | | | | | 240 |
| Cys | Lys | Phe | Tyr | Arg | Glu | Phe | Gln | Ala | Gly | Leu | Arg | Arg | Glu | Tyr | Lys |
| | | | | 245 | | | | | 250 | | | | | 255 | |
| Lys | Gln | Phe | Pro | Asp | Asn | Ala | Leu | Lys | Tyr | Leu | Ala | Leu | Arg | Lys | Gln |
| | | | 260 | | | | | 265 | | | | | 270 | | |
| Lys | Gly | His | Thr | Gln | Ala | Val | Val | Leu | Gln | Gln | Phe | Cys | Ala | Lys | Asp |
| | | | | 275 | | | | | 280 | | | | | 285 | |
| Arg | Arg | Lys | Ser | Gly | Trp | Phe | Pro | Lys | Ala | Trp | Met | Thr | Tyr | Leu | Gln |
| | 290 | | | | | 295 | | | | | 300 | | | | |
| Lys | Leu | Asn | Val | Thr | Glu | Glu | Thr | Leu | Ile | Gln | Arg | Tyr | Gln | Gly | Gln |
| 305 | | | | | 310 | | | | | 315 | | | | | 320 |
| Leu | Pro | His | Cys | Val | Lys | Ile | Asp | Asn | Lys | Thr | Gly | Cys | Ser | Phe | Asn |
| | | | | 325 | | | | | 330 | | | | | 335 | |
| Pro | His | Thr | Asn | Asp | Cys | Leu | Glu | Tyr | Lys | Lys | Arg | Ile | Leu | Lys | Leu |
| | | | 340 | | | | | 345 | | | | | 350 | | |
| Pro | Glu | Ser | Asp | Arg | Glu | Leu | Glu | Thr | Gln | Tyr | Arg | Glu | Trp | Arg | Arg |
| | | | | 355 | | | | | 360 | | | | | 365 | |
| Asp | Tyr | Leu | Ser | Gly | Pro | Arg | Lys | Pro | Ser | Phe | Arg | Tyr | Pro | Ser | Ser |
| | 370 | | | | | 375 | | | | | 380 | | | | |

Arg Asn Leu Pro Thr Pro Lys Ile Phe Gly Ala Gly Tyr Tyr Glu Ala
385                 390                 395                 400

Asp Phe Thr Arg Ser Met Leu Arg Leu Arg Leu Asp Asp Met Pro Arg
            405                 410                 415

Gly Arg Phe Ile Glu Phe Gly Phe Lys Pro Trp Pro Ser Asp Tyr Asp
            420                 425                 430

Ile Gln Pro Val Ser Thr Gln Ile Thr Ser Ala His Ile His Phe Ile
        435                 440                 445

Gly Thr Arg Ala Arg Val Gly Phe Arg Phe Ala Val Ala Ala Arg Pro
    450                 455                 460

Ser Arg Leu Arg Ile Ser Gln Asp Glu Ile Asp Ala Leu Arg Arg Gln
465                 470                 475                 480

Tyr Pro Arg Ala Ala Gln Asp Gln Gln Phe Leu Asp His Val Arg Pro
            485                 490                 495

Leu Ile Leu Asp Ser Phe Ala Gly Asn Pro Lys Gln Glu Leu Arg Ile
        500                 505                 510

Leu Thr Ile Asp Leu Gly Thr Ser Gly Gly Ala Ala Ala Ala Phe Cys
    515                 520                 525

Gly Val Thr Leu Val Lys Ser Glu Val Leu Lys Val Ile Lys Leu Asp
530                 535                 540

Lys Leu Tyr Asp Leu Leu Asp Arg Glu Asp Lys Arg Ser Pro Thr Ser
545                 550                 555                 560

Gly Leu Gly Glu Gly His Val Gly Arg His Leu Glu Ala Leu Ser Lys
            565                 570                 575

Glu Ala Ala Lys Ile Ala Gln His Arg Thr Thr Trp Lys Asn Pro Gly
        580                 585                 590

Leu Arg Pro Phe Asp Glu Arg Gln Leu Thr Ser His Ile Arg Trp Met
    595                 600                 605

Ile Arg Asp Trp Val Arg Leu Asn Ala Gln Gln Ile Ile Glu Ile Ala
610                 615                 620

Glu Arg Glu Asn Ala Asp Leu Ile Leu Phe Glu Ser Met Arg Gly Tyr
625                 630                 635                 640

Tyr Pro Lys Ala Arg Asp Lys Tyr Asp Ser Ala Gln Lys Val Arg Leu
            645                 650                 655

Gly Phe Phe Ser Tyr Gly Ala Ile Arg Arg Lys Val Ala Glu Lys Ala
        660                 665                 670

Val Glu Arg Gly Met Arg Ile Leu Thr Leu Pro Tyr Lys Phe Ser Ser
    675                 680                 685

Gln Ile Cys Ser Lys Cys Gly Arg Lys Gln Glu Asn Arg Gly Leu Lys
690                 695                 700

Thr Lys Lys Ala Lys Arg Leu Phe Lys Cys Glu His Thr Gly Cys Gly
705                 710                 715                 720

Thr Glu Leu Asn Ser Asp Glu Asn Ala Ala Arg Val Leu Ala Gly Val
            725                 730                 735

Phe Trp Gly Thr Ile Lys Leu Pro Glu Lys Ala Val Val Ser His Thr
        740                 745                 750

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
    oligonucleotide

```
<400> SEQUENCE: 25
ggtgcgaccg gccgtcgatt gaccggtttc gacacc                              36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gttgtagcgc ccctgaatt agcggtttcc gacacc                               36

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggtgtaagtc cgactgaatg cgaggtttcc gacacc                              36

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctgtgactc accggcattt gcggggttct tacacc                              36

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttgtgaccg cccccggaat cacggtttgc gacacc                              36

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtgtagcgg gcctcaaaaa cacggcatcc gacacc                              36

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
```

-continued ggtttgcaaa cagcgagaac atctgtgttt tggtggtagt tacaac 46

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtttgcaaac agcgagaaca tctgtgtttt ggtggt 36

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggtggagccg gccgtgaatt aggggggtttc gacacc 36

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggtgttgtga accctgaaag aacggattcc gacacc 36

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

```
<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51
```

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

-continued

```
<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000
```

```
<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
```

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

```
000

<210> SEQ ID NO 97
<400> SEQUENCE: 97

000

<210> SEQ ID NO 98
<400> SEQUENCE: 98

000

<210> SEQ ID NO 99
<400> SEQUENCE: 99

000

<210> SEQ ID NO 100
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100 tccgttctt                                                                9

<210> SEQ ID NO 101
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 aaacccc                                                                  7

<210> SEQ ID NO 102
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102 cctaatt                                                                  7

<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggtgtcggaa                                                              10

<210> SEQ ID NO 104
<211> LENGTH: 9
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 104 cggctgccg                                                              9

<210> SEQ ID NO 105
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105 tcgacgg                                                                7

<210> SEQ ID NO 106
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106 ggtgtcg                                                                7

<210> SEQ ID NO 107
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107 cgacggc                                                                7

<210> SEQ ID NO 108
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108 gtgttttg                                                               9

<210> SEQ ID NO 109
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 ttccgggg                                                               8

<210> SEQ ID NO 110
<211> LENGTH: 8
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 110 ggaaaccg                                                                   8

<210> SEQ ID NO 111
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111 ggggccgc                                                                   8

<210> SEQ ID NO 112
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112 gaaaccgc                                                                   8

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gagccggtaa at                                                             12

<210> SEQ ID NO 114
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114 aatgccg                                                                    7

<210> SEQ ID NO 115
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115 tgtaact                                                                    7

<210> SEQ ID NO 116
<211> LENGTH: 7
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 116 gctaatt                                                                  7

<210> SEQ ID NO 117
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
tccgttcttc tttgtagggt gttgtgaacc ctgaaagaac ggcgggtggc ccggaccttg    60
gggcgtgttg aaaaacccgt tgtcgtcag ttgatcggtg aaggttatca agcgatggcg    120
atcctgtagt tgagatcgac ggggttggtg tcagaccga                           159

<210> SEQ ID NO 118
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
aacagcgacg aaaacgccgc acaggtgctg gcgaaggtgt tctggggcga cgtcgttcta    60
cccgaggatc cggacgattg ctcttgacga agatatcgaa ggtggtatag tgcccttgtg    120
tcctcgtcgt gagtcgataa tggctcggac aaaccccggc ggagccttcg gtgccaacgg    180
gaggaacctg agcccggagg atacaaactc tctaattcgt ggttgatatg gcgatcaaga    240
atgcggtttc tttcaggcaa ttgtgtcgca actctttgtc gatccaggga ttacgacggg    300
aca                                                                  303

<210> SEQ ID NO 119
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
ccagacagcg aaaatgctga ataatcccgg ggacggcata cctaattggg ttccagattg    60
cccagcaggc agaagagagc gtttatcgca tttggggtgc cggcggagag ggggcgggcc    120
aagggtgtca ctggatgtct ccgctggtac ccggcaaagc gtcaaacgca atcaatcccg    180
gccgaaggcc ttccgct                                                   197

<210> SEQ ID NO 120
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
agtacgcggg cacgcggggg cgtgtttagt acgcaggcac gcggggcgt gtttagtacg     60

```
cgggggcgtg attagtacaa aggggcaagt caggtataca tcattaaaga tgtcgaaacc    120
gcagggtttt cgacctactc gaagaaagaa ggtgtcggaa cggcctgcat catgggtttt   180 gggagggga ttgggggcta tttgaatcga aacaaagttg atattgtccc tatgcggggg    240
attgtttgta gtgttgttcg agtaagacca ggttttcatc ggggatgcgg ccttttcaa    300 aagagtcgac                                                          310

<210> SEQ ID NO 121
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
cgagcgcgcg cttcagcacg aagcacgagg tgcggctgcc ggttgcattg cggcagaatg    60
attggcccgc ctgttcacgc tttcccgacc ggcagtggaa aacaaacgtc ccgcacgtcg   120
cagttcgtgg cttagttgat gcgtgcgcgt gggccgattg acgggcgcgc tcggctccgc   180
ctcgcggcta a                                                        191

<210> SEQ ID NO 122
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
tttcgacacc tgcgcaccga cttcaaagca ccatcggttg ggtgcgaccg gccgtcgatt    60
gaccggtttc gacaccccgc tttgcacagc ggcagcagac aaggatggtg cgaccggccg   120
tcgattgacc ggtttcgaca ccactccgcc tcgacggtct taaccagttc tgggtgcgac   180
cggccgtcga ttgaccggtt tcgacaccct ggacgtgtcg ggcaatactt ctgtcggagg   240
tgcgaccggc cgtcgattga ccggtttcga cacctacgcc acggcaaagc acctgatcag   300
ctcgggt                                                             307

<210> SEQ ID NO 123
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
tgctccactg ggcgatgtat gcctgcacca ctggggtgc tgcacgcggc ggcgcagcgc     60
ctacaatggc gccgcggaag gggagcgcgg cgcggtcatg gaacccacga cgattgagat   120
caggaacgcg cgggagcata acctgcggtc ggtgtcgctt tcgttgccgc gggggaagct   180
gattgtcttc accggggttt cgggcagcgg gaagagttcg ctggcgtttg acacgctcta   240
tgccgagggg cagcggcggt atatcgagtc gttgtcgtcg tatgcccgac agttcatggg   300
gcagatg                                                             307

<210> SEQ ID NO 124
<211> LENGTH: 307
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 124
tatgccgagg ggcagcggcg gtatatcgag tcgttgtcgt cgtatgcccg acagttcatg    60
gggcagatgg ccaagccgga ctgcgatcag atcacggggc tttcgccatc gatcgcgatt   120
cagcagaaga cgacgggatg gaatccgcgg tcgacggtgg ggacgacgac ggcgatctat   180
gactttctgc gcgtgctgta cgcgcggatc gggacgcagc attgcacgca gtgtgggcgg   240
gcgatcacgg cgcagtctcg cgagcagatc gggcggggga tcttgagcgc gtttaatccg   300
cgccgcg                                                             307

<210> SEQ ID NO 125
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
ggcggtatat cgagtcgttg tcgtcgtatg cccgacagtt catggggcag atggccaagc    60
cggactgcga tcagatcacg gggctttcgc catcgatcgc gattcagcag aagacgacgg   120
gatggaatcc gcggtcgacg gtggggacga cgacggcgat ctatgacttt ctgcgcgtgc   180
tgtacgcgcg gatcgggacg cagcattgca cgcagtgtgg gcgggcgatc acggcgcagt   240
ctcgcgagca gatcgcggcg gggatcttga gcgcgtttaa tccgcgccgc gatcccacct   300
atcagag                                                             307

<210> SEQ ID NO 126
<211> LENGTH: 244
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
agccgacgag agcgcatttg ccctccaagg cttgactctt tttccagccg tggctacgct    60
gttaatgccc ttcgagtcgc attgtcctgc atacgcccgg cggaacttcg gtaccaacgg   120
gacggacccc ggacacgaaa ggcaaatgct gtgttttgt ggcctgccgg tttggaacgt   180
cacggttttg tgggcggttt tttttgacgc aagtccttgt cagaagcgaa tttgcagacg   240
agac                                                                244

<210> SEQ ID NO 127
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
ttcgagtcat ttgcctggaa tacgccctgc ggacgttttc gaccaacggg atggacccct    60
ggcgctgaag gcagaatcgg ttttttccgg gcggtttcgg gaggcgaacg agcggttttt   120
tcgaggtgga actggcgcaa gtcgtgtccg ttccggggct tgtttgccaa gag          173

<210> SEQ ID NO 128
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
aattactctc cccaccgatt gatagttgaa aaaacttgac agacagctta atttaagtta      60
tgtataatca gttgcttcgt ggtccctctg gccggaaaaa cctctggcgg agcgcaagca     120
ccaatagaga ggaactcggc ccagaagcga ggaaaccgac aattagggt ttaattattg      180 aaggaacttt aaagattttg tgacggacgg aataaattaa gttcaaatcg cgtatgatta    240
tatgaatgat ga                                                         252

<210> SEQ ID NO 129
<211> LENGTH: 308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
aaggtcgaca aagatttcgg ttggttataa atgaacgagg aggggcagat gtggacatct     60
gccgcccact tgagtctggg gcgataagct gattgtcggg ggaggtttca ccaccgctgg    120
ggggatcgat gtgaatcgta ttgccgcctg ggggccgcaa taataaatta aacggcgtca    180
ggaagaggtt ccagatgccg ctcaataccc atagcactta gcccttgcct taacaatgaa    240
ttgtgtctat tttgagggct gtcttataaa tagaaaagat atcaagataa gttgtcgaaa    300
ccgcaggg                                                              308

<210> SEQ ID NO 130
<211> LENGTH: 308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
cctgggggcc gcaataataa attaaacggc gtcaggaaga ggttccagat gccgctcaat     60
acccatagca cttagccctt gccttaacaa tgaattgtgt ctattttgag gctgtctta    120 taaatagaaa agatatcaag ataagttgtc gaaaccgcag gggtttcgac ctaaaagaat    180
tatgtctgac gaagaaaaaa aagagaagac caaatccgag atgccgtttc tggatcatat    240
cgaggaactg cgctggcggt tgatcaagtc cattttatcg gttgccgtga tggccatcct    300
ggccttta                                                              308

<210> SEQ ID NO 131
<211> LENGTH: 224
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
cgaaatcgag ctgccgaccg caatccctg acgacccttg acggaactgg ccgatttgct      60
aaaatatttt tgatgcttac ttagtcatct ggttggcaaa cctccgcgga ccttcgggac    120
caatggagag gaacccagcc gagaagcatc gagccggtaa atgccggaaa ttttgagtc     180 aggagaagct aacttcttca aactcaggcc cttggagccg gtca                     224
```

<210> SEQ ID NO 132
<211> LENGTH: 307
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
ctgtcctact gttttgactt accgatgtgt tactccaata cgggcggact gaagtccgcc     60
ctccaggtga taatgatgga gtttacgtct gcgtcacata aggacttgtg acgccaaata   120
gctgtgattc tacatcacga cggcagccgg aatgccgccg ctcccatgtt gtaattcact   180
ggtgtttgtg attggagctc acgaataaga ggtgggagaa taaaaaaaac tgccacttgc   240
ggacaggtgg cagaacaaaa ttctccgaaa cgcatgggtt aaggctacct gcctgaggga   300
acagaga                                                              307
```

<210> SEQ ID NO 133
<211> LENGTH: 178
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
agttttgact ggaaaatctc cctttggacg tttgacctag gggagggaac cccgtctgaa     60
gatggataat taccgtcaaa atttggataa acttggagaa aattagacaa aagagtcggt   120 tttttgatg ttactgatcg gcgtaactga tgtaactgtc gttagataca gcgagtcg      178
```

<210> SEQ ID NO 134
<211> LENGTH: 307
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
aataagagga acaatccctt tcaatgtgag tttagtgact gtaattataa acccatagc      60 gatgagaatg cggcccgtgt cctcggacgg gtattttggg gtgaaattac cctccccacc   120
gattgagtgt tgaaaattct tgacatatag gctaatttaa gatatgtata attagtcgct   180
tcgtggtcca tctggccgga aaaacctctg gcgggcgcaa gcaccaatag agaggaactc   240
ggcccagaag cgaagaaacc aataattagg ggtttaatta ttgaaggaac tttaaagatt   300
ttgcgac                                                              307
```

<210> SEQ ID NO 135

<400> SEQUENCE: 135

000

```
<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
```

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(63)
<223> OTHER INFORMATION: a, c, u, g, unknown or other

<400> SEQUENCE: 150
guuguagcgc ccccugaauu agcgguuucc gacaccnnnn nnnnnnnnn nnnnnnnnn      60 nnnguuguag cgcccccuga auuagcgguu uccgacacc                          99

<210> SEQ ID NO 151
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(65)
<223> OTHER INFORMATION: a, c, u, g, unknown or other

<400> SEQUENCE: 151
ggugcggcag ccgguagaac ugcggcuucc gacaccnnnn nnnnnnnnn nnnnnnnnn      60 nnnnnggugc ggcagccggu agaacugcgg cuuccgacac c                       101

<210> SEQ ID NO 152
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(65)
<223> OTHER INFORMATION: a, c, u, g, unknown or other

<400> SEQUENCE: 152
gguguaaguc cgacugaaug cgagguuucc gacaccnnnn nnnnnnnnn nnnnnnnnn      60 nnnnnggugu aaguccgacu gaaugcgagg uuuccgacac c                       101

<210> SEQ ID NO 153
<211> LENGTH: 121
<212> TYPE: RNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (47)..(75)
<223> OTHER INFORMATION: a, c, u, g, unknown or other

<400> SEQUENCE: 153
gguuugcaaa cagcgagaac aucuguguuu uggugguagu acaacnnnn nnnnnnnnn        60 nnnnnnnnnn nnnnngguuu gcaaacagcg agaacaucug uguuuggug guaguuacaa      120 c                                                                     121

<210> SEQ ID NO 154
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(65)
<223> OTHER INFORMATION: a, c, u, g, unknown or other

<400> SEQUENCE: 154
guuugcaaac agcgagaaca ucuguguuuu ggunnnnn nnnnnnnnnn nnnnnnnnn         60 nnnnnguuug caaacagcga gaacaucugu guuuggugg u                          101

<210> SEQ ID NO 155
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 155
gguggaaagg gccggagauu uaccggcucu gacacnnnn nnnnnnnnn nnnnnnnnn         60 nnnnnnggug gaaagggccg gagauuuacc ggcucugaca cc                        102

<210> SEQ ID NO 156
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 156
gguggaaagg gccggagauu uaccggcucu gacacnnnn nnnnnnnnn nnnnnnnnn         60 nnnnnnggug gaaagggccg gagauuuacc ggcucugaca cc                        102

<210> SEQ ID NO 157
<211> LENGTH: 102
<212> TYPE: RNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 157
gguggagccg gccgugaauu aggggguuuc gacaccnnnn nnnnnnnnnn nnnnnnnnnn      60
nnnnnnggug gagccggccg ugaauuaggg gguuucgaca cc                       102

<210> SEQ ID NO 158
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 158
gguggagccg gccgugaauu aggggguuuc gacaccnnnn nnnnnnnnnn nnnnnnnnnn      60
nnnnnnggug gagccggccg ugaauuaggg gguuucgaca cc                       102

<210> SEQ ID NO 159
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 159
gguguuguga acccugaaag aacggauucc gacaccnnnn nnnnnnnnnn nnnnnnnnnn      60
nnnnnnggug uugugaaccc ugaaagaacg gauuccgaca cc                       102

<210> SEQ ID NO 160
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 160
guuguagcgc ccccugaauu agcgguuucc gacaccnnnn nnnnnnnnnn nnnnnnnnnn      60
nnnnnnguug uagcgccccc ugaauuagcg guuccgaca cc                        102

<210> SEQ ID NO 161
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: modified_base
<222> LOCATION: (37)..(66)
<223> OTHER INFORMATION: a, c, u, g, unknown or other

<400> SEQUENCE: 161
guuguagcgg ccccugaauu agcgguuucc gacaccnnnn nnnnnnnnnn nnnnnnnnnn      60
nnnnnnguug uagcggcccc ugaauuagcg guuccgaca cc                        102

<210> SEQ ID NO 162
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 162
guugugaccg cccccggaau cacgguuugc gacaccnnnn nnnnnnnnnn nnnnnnnnnn      60
nnnnnnguug ugaccgcccc cggaaucacg guuugcgaca cc                       102

<210> SEQ ID NO 163
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, u, g, unknown or other

<400> SEQUENCE: 163
guugugaccg cccccggaau cacgguuugc gacaccnnnn nnnnnnnnnn nnnnnnnnnn      60
nnnnnnguug ugaccgcccc cggaaucacg guuugcgaca cc                       102

<210> SEQ ID NO 164
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(68)
<223> OTHER INFORMATION: a, c, u, g, unknown or other

<400> SEQUENCE: 164
gguguagcgg gccucaaaaa cacggcaucc gacaccnnnn nnnnnnnnnn nnnnnnnnnn      60
nnnnnnnngg uguagcgggc cucaaaaaca cggcauccga cacc                     104

<210> SEQ ID NO 165
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(68)
```

<223> OTHER INFORMATION: a, c, u, g, unknown or other

<400> SEQUENCE: 165
gguguagcgg gccucaaaaa cacggcaucc gacaccnnnn nnnnnnnnnn nnnnnnnnnn      60
nnnnnnnngg uguagcgggc cucaaaaaca cggcauccga cacc                      104

<210> SEQ ID NO 166
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(74)
<223> OTHER INFORMATION: a, c, u, g, unknown or other

<400> SEQUENCE: 166
gcugugacuc accggcauuu gcgggguucu uacaccnnnn nnnnnnnnnn nnnnnnnnnn      60
nnnnnnnnnn nnnngcugug acucaccggc auuugcgggg uucuuacacc                110

<210> SEQ ID NO 167
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(74)
<223> OTHER INFORMATION: a, c, u, g, unknown or other

<400> SEQUENCE: 167
gcugugacuc accggcauuu gcggguuucu uacaccnnnn nnnnnnnnnn nnnnnnnnnn      60
nnnnnnnnnn nnnngcugug acucaccggc auuugcgggg uucuuacacc                110

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: a, c, t, g, u, unknown or other

<400> SEQUENCE: 200
rvsgnhtbbg acacc                                                       15

<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
sgkggtwstt acamc                                                       15

<210> SEQ ID NO 202
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uuuaccggcu cugacacc                                                    18

<210> SEQ ID NO 203
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203 kacacc                                                                  6

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Gly, Ser or Thr
<220> FEATURE:
<221> NAME/KEY: MOD_RES
<222> LOCATION: (2)..(2)
<223> OTHER INFORMATION: Cys, Phe, Ile, Leu, Met, Pro, Val,
      Trp or Tyr
<220> FEATURE:
<221> NAME/KEY: MOD_RES
<222> LOCATION: (4)..(4)
<223> OTHER INFORMATION: Cys, Phe, Ile, Leu, Met, Pro, Val,

```
                Trp or Tyr
<220> FEATURE:
<221> NAME/KEY: MOD_RES
<222> LOCATION: (5)..(5)
<223> OTHER INFORMATION: Ala, Gly, Ser or Thr

<400> SEQUENCE: 210

Xaa Xaa Asp Xaa Xaa
1               5

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Cys, Phe, Ile, Leu, Met, Pro, Val,
      Trp or Tyr

<400> SEQUENCE: 211

Xaa Xaa Xaa Xaa Glu
1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 212

Asp Xaa Asn Ala Ala
1               5

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217
```

```
<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228
```

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gaugcuuacu uagucaucug guuggcaaac cuccgcggac cuucgggacc aauggagagg    60
aacccagccg agaagcaucg agccgguaaa ugccggaaa                          99

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

-continued

```
<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 7
<212> TYPE: PRT
<213> ORGANISM: Simian virus 40

<400> SEQUENCE: 300

Pro Lys Lys Lys Arg Lys Val
1               5

<210> SEQ ID NO 301
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 301

Lys Arg Pro Ala Ala Thr Lys Lys Ala Gly Gln Ala Lys Lys Lys Lys
1               5                   10                  15

<210> SEQ ID NO 302
<211> LENGTH: 9
<212> TYPE: PRT
<213> ORGANISM: Unknown
<220> FEATURE:
<223> OTHER INFORMATION: Description of Unknown:
      c-Myc NLS sequence

<400> SEQUENCE: 302

Pro Ala Ala Lys Arg Val Lys Leu Asp
1               5

<210> SEQ ID NO 303
<211> LENGTH: 11
<212> TYPE: PRT
<213> ORGANISM: Unknown
<220> FEATURE:
<223> OTHER INFORMATION: Description of Unknown:
``` c-Myc NLS sequence

<400> SEQUENCE: 303

Arg Gln Arg Arg Asn Glu Leu Lys Arg Ser Pro
1               5                   10

<210> SEQ ID NO 304
<211> LENGTH: 38
<212> TYPE: PRT
<213> ORGANISM: Homo sapiens

<400> SEQUENCE: 304

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 305
<211> LENGTH: 42
<212> TYPE: PRT
<213> ORGANISM: Unknown
<220> FEATURE:
<223> OTHER INFORMATION: Description of Unknown:
    IBB domain from importin-alpha sequence

<400> SEQUENCE: 305

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 306
<211> LENGTH: 8
<212> TYPE: PRT
<213> ORGANISM: Unknown
<220> FEATURE:
<223> OTHER INFORMATION: Description of Unknown:
    Myoma T protein sequence

<400> SEQUENCE: 306

Val Ser Arg Lys Arg Pro Arg Pro
1               5

<210> SEQ ID NO 307
<211> LENGTH: 8
<212> TYPE: PRT
<213> ORGANISM: Unknown
<220> FEATURE:
<223> OTHER INFORMATION: Description of Unknown:
    Myoma T protein sequence

<400> SEQUENCE: 307

Pro Pro Lys Lys Ala Arg Glu Asp
1               5

<210> SEQ ID NO 308
<211> LENGTH: 8
<212> TYPE: PRT
<213> ORGANISM: Homo sapiens

<400> SEQUENCE: 308

```
Pro Gln Pro Lys Lys Lys Pro Leu
1               5
```

<210> SEQ ID NO 309
<211> LENGTH: 12
<212> TYPE: PRT
<213> ORGANISM: Mus sp.

<400> SEQUENCE: 309

```
Ser Ala Leu Ile Lys Lys Lys Lys Lys Met Ala Pro
1               5                   10
```

<210> SEQ ID NO 310
<211> LENGTH: 5
<212> TYPE: PRT
<213> ORGANISM: Influenza virus

<400> SEQUENCE: 310

```
Asp Arg Leu Arg Arg
1               5
```

<210> SEQ ID NO 311
<211> LENGTH: 7
<212> TYPE: PRT
<213> ORGANISM: Influenza virus

<400> SEQUENCE: 311

```
Pro Lys Gln Lys Lys Arg Lys
1               5
```

<210> SEQ ID NO 312
<211> LENGTH: 10
<212> TYPE: PRT
<213> ORGANISM: Mus sp.

<400> SEQUENCE: 312

```
Arg Lys Leu Lys Lys Ile Lys Lys Leu
1               5                   10
```

<210> SEQ ID NO 313
<211> LENGTH: 10
<212> TYPE: PRT
<213> ORGANISM: Mus sp.

<400> SEQUENCE: 313

```
Arg Glu Lys Lys Lys Phe Leu Lys Arg Arg
1               5                   10
```

<210> SEQ ID NO 314
<211> LENGTH: 20
<212> TYPE: PRT
<213> ORGANISM: Homo sapiens

<400> SEQUENCE: 314

```
Lys Arg Lys Gly Asp Glu Val Asp Gly Val Asp Glu Val Ala Lys Lys
1               5                   10                  15

Lys Ser Lys Lys
            20
```

<210> SEQ ID NO 315
<211> LENGTH: 17
<212> TYPE: PRT
<213> ORGANISM: Homo sapiens -continued

```
<400> SEQUENCE: 315

Arg Lys Cys Leu Gln Ala Gly Met Asn Leu Glu Ala Arg Lys Thr Lys
1               5                   10                  15

Lys

<210> SEQ ID NO 316
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 317
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
                20                  25                  30

Val Ala Ser Leu Ser Gln Ala Gly Ala Val Pro Ala Leu Glu Lys Arg
            35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125
```

Leu Asn Pro Ala Tyr
        130

<210> SEQ ID NO 318
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Val
            100                 105                 110

Gln Ala Thr Ser Glu Asp Leu Val Val Asn Leu Val Pro Leu Gly Arg
        115                 120                 125

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

```
<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400
<211> LENGTH: 171
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 400
ggggguggaa agggccggag auuuaccggc ucugacaccc cauucauccg cuuauuauca      60
cuuauucagg guggaaaggg ccggagauuu accggcucug acaccgcuug gaggagcgca     120
gucaccaaaa cuuguggugg aaagggccgg agauuuaccg gcucugacac c              171

<210> SEQ ID NO 401
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 401
gguggaaagg gccggagauu uaccggcucu gacacc            36

<210> SEQ ID NO 402
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
ccauucaucc gcuuauuauc acuauucag            30

<210> SEQ ID NO 403
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
gcuuggagga gcgcagucac caaaacuugu            30

<210> SEQ ID NO 404
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 404
ggggaugcuu acuuagucau cugguuggca aaccuccgcg gaccuucggg accaauggag            60
aggaacccag ccgagaagca ucgagccggu aaaugccgga aauuuuu            107

<210> SEQ ID NO 405
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 405
ggggaugcuu acuuagucau cugguuggca aaccuccgcg gaccuucggg accaauggag            60
aggaacccag ccgagaagca ucgagccggu aaaugccgga aa            102

<210> SEQ ID NO 406
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ggggaugcuu acuuagucau cugguuggca aaccuccgcg gaccuucggg accaauggag            60
aggaacccag ccgagaagca ucgagccggu aaau            94

<210> SEQ ID NO 407
<211> LENGTH: 45
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 407
ggguuuaccg gcucugacac cgcuuggagg agcgcaguca ccaaa              45

<210> SEQ ID NO 408
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uuuaccggcu cugacacc                                            18

<210> SEQ ID NO 409
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
gcuuggagga gcgcagucac caaa                                     24

<210> SEQ ID NO 410
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
ggguuuaccg gcucugacac caacugugau aaacuaccgc auuaa              45

<210> SEQ ID NO 411
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
uuuaccggcu cugacacc                                            18

<210> SEQ ID NO 412
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
aacugugaua aacuaccgca uuaa                                     24

<210> SEQ ID NO 413
<211> LENGTH: 45
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 413
ggguuuaccg gcucugacac ccuuccuuag cuccugaaaa ucucg            45

<210> SEQ ID NO 414
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uuuaccggcu cugacacc                                          18

<210> SEQ ID NO 415
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
cuuccuuagc uccugaaaau cucg                                   24

<210> SEQ ID NO 416
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
ggguuuaccg gcucugacac ccaucuugcg aauauaugug uagaa            45

<210> SEQ ID NO 417
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uuuaccggcu cugacacc                                          18

<210> SEQ ID NO 418
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
caucuugcga auauaugugu agaa                                   24

<210> SEQ ID NO 419
<211> LENGTH: 130
<212> TYPE: RNA
<213> ORGANISM: Artificial Sequence
<220> FEATURE:
```

<223> OTHER INFORMATION: Description of Artificial Sequence: Synthetic
      polynucleotide

<400> SEQUENCE: 419
caacgaggua uuuauccgau uaauucucau guuugacagc uuaucaucga uaagcuuuaa    60
ugcgguaguu uaucacaguu aaauugcuaa cgcagucagg caccguguau uuguagcccg   120
gggacuguuu                                                         130

<210> SEQ ID NO 420
<211> LENGTH: 130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 420
caacgaggua uuuauccgau aaauaagauc acuaccgggc guauuuuug aguuaucgag    60 auuuucagga gcuaaggaag cuaaaaugga gaaaaaauc acuggauaua uuguagcccg   120
gggacuguuu                                                         130

<210> SEQ ID NO 421
<211> LENGTH: 130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 421
caacgaggua uuuauccgau uaauucucau guuugacagc uuaucaucga uaagcuuuaa    60
ugcgguaguu uaucacaguu aaauugcuaa cgcagucagg caccguguau uuguagcccg   120
gggacuguuu                                                         130

<210> SEQ ID NO 422
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422
caacgaggta tttatccgat taattctcat gtttgacagc ttatcatcga taagctttaa    60
tgcggtagtt tatcacagtt aaattgctaa cgcagtcagg caccgtgtat ttgtagcccg   120
gggactgttt                                                         130

<210> SEQ ID NO 423
<211> LENGTH: 130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 423
aaacaguccc cgggcuacaa auacacggug ccugacugcg uuagcaauuu aacugugaua    60
aacuaccgca uuaaagcuua ucgaugauaa gcugucaaac augagaauua aucggauaaa   120
uaccucguug                                                         130

<210> SEQ ID NO 424
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424
aaacagtccc cgggctacaa atacacggtg cctgactgcg ttagcaattt aactgtgata      60
aactaccgca ttaaagctta tcgatgataa gctgtcaaac atgagaatta atcggataaa     120
tacctcgttg                                                            130

<210> SEQ ID NO 425
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 425
caacgaggta tttatccgat cgctctggag tgaataccac gacgatttcc ggcagtttct      60
acacatatat tcgcaagatg tggcgtgtta cggtgaaaac ctggcctatt ttgtagcccg     120
gggactgttt                                                            130

<210> SEQ ID NO 426
<211> LENGTH: 130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 426
aaacaguccc cgggcuacaa auacacggug ccugacugcg uuagcaauuu aacugugaua      60
aacuaccgca uuaaagcuua ucgaugauaa gcugucaaac augagaauua aucggauaaa     120
uaccucguug                                                            130

<210> SEQ ID NO 427
<211> LENGTH: 130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 427
aaacaguccc cgggcuacaa uauauccagu gauuuuuuc uccauuuuag cuuccuuagc       60
uccugaaaau cucgauaacu caaaaaauac gcccgguagu gaucuuauuu aucggauaaa     120
uaccucguug                                                            130

<210> SEQ ID NO 428
<211> LENGTH: 130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 428

```
aaacaguccc cgggcuacaa ucucgccgaa acguuuggug gcgggaccag ugacgaaggc    60
uugagcgagg gcgugcaaga uuccgaauac cgcaagcgac aggccgauca aucggauaaa   120
uaccucguug                                                         130

<210> SEQ ID NO 429
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 429
aaacagtccc cgggctacaa aataggccag gttttcaccg taacacgcca catcttgcga    60
atatatgtgt agaaactgcc ggaaatcgtc gtggtattca ctccagagcg atcggataaa   120
tacctcgttg                                                         130

<210> SEQ ID NO 430
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 430
ggtgtcagag ccggtaaatc tccggccctt tccaccacaa gttttggtga ctgcgctcct    60
ccaagcggtg tcagagccgg taaatctccg gccctttcca ccctgaataa gtgataataa   120
gcggatgaat ggggtgtcag agccggtaaa tctccggccc tttccacccc ctatagtgag   180
tcgtatta                                                           188

<210> SEQ ID NO 431
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
taatacgact cactatag                                                 18

<210> SEQ ID NO 432
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ggtgtcagag ccggtaaatc tccggccctt tccaccacaa gttttggtga ctgcgctcct    60
ccaagc                                                              66

<210> SEQ ID NO 433
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 433
ttaatgcggt agtttatcac agttggtgtc agagccggta aaccctatag tgagtcgtat    60
tattaatgcg gtagtttatc acagttggtg tcagagccgg taaaccctat agtgagtcgt   120
atta                                                                124

<210> SEQ ID NO 434
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
taatacgact cactatagta atacgactca ctatag                              36

<210> SEQ ID NO 435
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 435
cgagattttc aggagctaag gaagggtgtc agagccggta aaccctatag tgagtcgtat    60
tacgagattt tcaggagcta aggaagggtg tcagagccgg taaaccctat agtgagtcgt   120
atta                                                                124

<210> SEQ ID NO 436
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
taatacgact cactatagta atacgactca ctatag                              36

<210> SEQ ID NO 437
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 437
ttctacacat atattcgcaa gatgggtgtc agagccggta aaccctatag tgagtcgtat    60
tattctacac atatattcgc aagatgggtg tcagagccgg taaaccctat agtgagtcgt   120
atta                                                                124

<210> SEQ ID NO 438
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
taatacgact cactatagta atacgactca ctatag                36

<210> SEQ ID NO 439
<211> LENGTH: 248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 439
aaaaatttcc ggcatttacc ggctcgatgc ttctcggctg ggttcctctc cattggtccc        60
gaaggtccgc ggaggtttgc caaccagatg actaagtaag catccctat agtgagtcgt        120 attaaaaaat tccggcatt taccggctcg atgcttctcg gctgggttcc tctccattgg        180
tcccgaaggt ccgcggaggt ttgccaacca gatgactaag taagcatccc ctatagtgag       240
tcgtatta                                                                248

<210> SEQ ID NO 440
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
taatacgact cactatagta atacgactca ctatag                36

<210> SEQ ID NO 441
<211> LENGTH: 238
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 441
tttccggcat ttaccggctc gatgcttctc ggctgggttc ctctccattg gtcccgaagg        60
tccgcggagg tttgccaacc agatgactaa gtaagcatcc ctatagtga gtcgtattat       120 tccggcatt taccggctcg atgcttctcg gctgggttcc tctccattgg tcccgaaggt       180
ccgcggaggt ttgccaacca gatgactaag taagcatccc ctatagtgag tcgtatta       238

<210> SEQ ID NO 442
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
taatacgact cactatagta atacgactca ctatag                36

<210> SEQ ID NO 443
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 443

```
atttaccggc tcgatgcttc tcggctgggt tcctctccat tggtcccgaa ggtccgcgga    60
ggtttgccaa ccagatgact aagtaagcat cccctatagt gagtcgtatt aatttaccgg   120
ctcgatgctt ctcggctggg ttcctctcca ttggtcccga aggtccgcgg aggtttgcca   180
accagatgac taagtaagca tcccctatag tgagtcgtat ta                      222
```

<210> SEQ ID NO 444
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444

```
taatacgact cactatagta atacgactca ctatag                              36
```

<210> SEQ ID NO 445
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 445

```
aaacagtccc cgggctacaa agctaccaac tctttgaacc gaggtaactg gcttggagga    60
gcgcagtcac caaaacttgt cctttcagtt tagccttaac cggcgcatga atcggataaa   120
tacctcgttg                                                          130
```

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446

```
aaacagtccc cgggctacaa                                                20
```

<210> SEQ ID NO 447
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447

```
aaatgtaata aggatccctc gagtaatacg actcactata gggcaacgag gtatttatcc    60
gat                                                                  63
```

<210> SEQ ID NO 448
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448

```
aaatgtaata aggatccctc gagtaatacg actcactata gggaaacagt ccccgggcta    60
``` caa                                                             63

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
caacgaggta tttatccgat                                           20

<210> SEQ ID NO 450
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 450
aaacagtccc cgggctacaa atacacggtg cctgactgcg ttagcaattt aactgtgata    60
aactaccgca ttaaagctta tcgatgataa gctgtcaaac atgagaatta atcggataaa   120
tacctcgttg                                                         130

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
aaacagtccc cgggctacaa                                           20

<210> SEQ ID NO 452
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
aaatgtaata aggatccctc gagtaatacg actcactata gggcaacgag gtatttatcc    60
gat                                                              63

<210> SEQ ID NO 453
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
aaatgtaata aggatccctc gagtaatacg actcactata gggaaacagt ccccgggcta    60
caa                                                              63

<210> SEQ ID NO 454
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 454
caacgaggta tttatccgat                                                    20

<210> SEQ ID NO 455
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 455
aaacagtccc cgggctacaa tatatccagt gattttttc tccattttag cttccttagc         60
tcctgaaaat ctcgataact caaaaatac gcccggtagt gatcttattt atcggataaa        120
tacctcgttg                                                              130

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
aaacagtccc cgggctacaa                                                    20

<210> SEQ ID NO 457
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
aaatgtaata aggatccctc gagtaatacg actcactata gggcaacgag gtatttatcc        60
gat                                                                      63

<210> SEQ ID NO 458
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
aaatgtaata aggatccctc gagtaatacg actcactata gggaaacagt ccccgggcta        60
caa                                                                      63

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
```

```
caacgaggta tttatccgat                                               20

<210> SEQ ID NO 460
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 460
aaacagtccc cgggctacaa aataggccag gttttcaccg taacacgcca catcttgcga    60
atatatgtgt agaaactgcc ggaaatcgtc gtggtattca ctccagagcg atcggataaa   120
tacctcgttg                                                         130

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
aaacagtccc cgggctacaa                                               20

<210> SEQ ID NO 462
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
aaatgtaata aggatccctc gagtaatacg actcactata gggcaacgag gtatttatcc    60
gat                                                                 63

<210> SEQ ID NO 463
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
aaatgtaata aggatccctc gagtaatacg actcactata gggaaacagt ccccgggcta    60
caa                                                                 63

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
caacgaggta tttatccgat                                               20

<210> SEQ ID NO 465
<211> LENGTH: 130
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 465
aaacagtccc cgggctacaa tctcgccgaa acgtttggtg gcgggaccag tgacgaaggc    60
ttgagcgagg gcgtgcaaga ttccgaatac cgcaagcgac aggccgatca atcggataaa   120
tacctcgttg                                                          130

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
aaacagtccc cgggctacaa                                                20

<210> SEQ ID NO 467
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
aaatgtaata aggatccctc gagtaatacg actcactata gggcaacgag gtatttatcc    60
gat                                                                  63

<210> SEQ ID NO 468
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
aaatgtaata aggatccctc gagtaatacg actcactata gggaaacagt ccccgggcta    60
caa                                                                  63

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
caacgaggta tttatccgat                                                20

<210> SEQ ID NO 470
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 470
guuguagcgg ccccugaauu agcgguuucc gacacc                36

<210> SEQ ID NO 471
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
ggugcggcag ccgguagaac ugcggcuucc gacacc                36

<210> SEQ ID NO 472
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
guuggaguca gcaaggaauc aacgguuuug gacacc                36

<210> SEQ ID NO 473
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
gguguagcgg gccucaaaaa cacggcaucc gaca                  34

<210> SEQ ID NO 474
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
gcugugacuc accggcauuu gcggggguu                        28

<210> SEQ ID NO 475
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(66)
<223> OTHER INFORMATION: a, c, t, g, unknown or other

<400> SEQUENCE: 475
ggtggaaagg gccggagatt taccggctct gacaccnnnn nnnnnnnnn nnnnnnnnn    60 nnnnnnggtg aaagggccg gagatttacc ggctctgaca cc                    102

<210> SEQ ID NO 476
<211> LENGTH: 39
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(39)
<223> OTHER INFORMATION: a, c, u, g, unknown or other

<400> SEQUENCE: 476
uuuaccggcu cugacaccnn nnnnnnnnnn nnnnnnnn                             39

<210> SEQ ID NO 477
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
cgataagctt taatgcggta gtttatcaca gttaaa                               36

<210> SEQ ID NO 478
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
cgauaagcuu uaaugcggua guuuaucaca guuaaa                               36

<210> SEQ ID NO 479
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
uuuaacugug auaaacuacc gcauuaaagc uuaucg                               36

<210> SEQ ID NO 480
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
tttaactgtg ataaactacc gcattaaagc ttatcg                               36

<210> SEQ ID NO 481
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Gly Gly Gly Gly Ser
1               5
```

```
<210> SEQ ID NO 482
<211> LENGTH: 4
<212> TYPE: PRT
<213> ORGANISM: Unknown
<220> FEATURE:
<223> OTHER INFORMATION: Description of Unknown:
      KDEL retention sequence

<400> SEQUENCE: 482

Lys Asp Glu Leu
1

<210> SEQ ID NO 483
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Glu Ala Ala Ala Lys
1               5

<210> SEQ ID NO 484
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Ser Gly Gly Gly Gly Ser
1               5

<210> SEQ ID NO 485
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Gly Gly Gly Gly Ser Gly Gly Gly Gly Ser Gly Gly Gly Gly Ser
1               5                   10                  15

<210> SEQ ID NO 486
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gly Gly Ser Gly Gly Ser Gly Gly Ser Gly Gly Ser Gly Gly Ser Gly
1               5                   10                  15

Gly Ser

<210> SEQ ID NO 487
<211> LENGTH: 336
<212> TYPE: PRT
<213> ORGANISM: Unknown
<220> FEATURE:
<223> OTHER INFORMATION: Description of Unknown:
```

ADAR1DD-WT sequence

<400> SEQUENCE: 487

Ser Leu Gly Thr Gly Asn Arg Cys Val Lys Gly Asp Ser Leu Ser Leu
1               5                   10                  15

Lys Gly Glu Thr Val Asn Asp Cys His Ala Glu Ile Ile Ser Arg Arg
            20                  25                  30

Gly Phe Ile Arg Phe Leu Tyr Ser Glu Leu Met Lys Tyr Asn Ser Gln
        35                  40                  45

Thr Ala Lys Asp Ser Ile Phe Glu Pro Ala Lys Gly Gly Glu Lys Leu
    50                  55                  60

Gln Ile Lys Lys Thr Val Ser Phe His Leu Tyr Ile Ser Thr Ala Pro
65                  70                  75                  80

Cys Gly Asp Gly Ala Leu Phe Asp Lys Ser Cys Ser Asp Arg Ala Met
                85                  90                  95

Glu Ser Thr Glu Ser Arg His Tyr Pro Val Phe Glu Asn Pro Lys Gln
            100                 105                 110

Gly Lys Leu Arg Thr Lys Val Glu Asn Gly Glu Gly Thr Ile Pro Val
        115                 120                 125

Glu Ser Ser Asp Ile Val Pro Thr Trp Asp Gly Ile Arg Leu Gly Glu
130                 135                 140

Arg Leu Arg Thr Met Ser Cys Ser Asp Lys Ile Leu Arg Trp Asn Val
145                 150                 155                 160

Leu Gly Leu Gln Gly Ala Leu Leu Thr His Phe Leu Gln Pro Ile Tyr
                165                 170                 175

Leu Lys Ser Val Thr Leu Gly Tyr Leu Phe Ser Gln Gly His Leu Thr
            180                 185                 190

Arg Ala Ile Cys Cys Arg Val Thr Arg Asp Gly Ser Ala Phe Glu Asp
        195                 200                 205

Gly Leu Arg His Pro Phe Ile Val Asn His Pro Lys Val Gly Arg Val
    210                 215                 220

Ser Ile Tyr Asp Ser Lys Arg Gln Ser Gly Lys Thr Lys Glu Thr Ser
225                 230                 235                 240

Val Asn Trp Cys Leu Ala Asp Gly Tyr Asp Leu Glu Ile Leu Asp Gly
                245                 250                 255

Thr Arg Gly Thr Val Asp Gly Pro Arg Asn Glu Leu Ser Arg Val Ser
            260                 265                 270

Lys Lys Asn Ile Phe Leu Leu Phe Lys Lys Leu Cys Ser Phe Arg Tyr
        275                 280                 285

Arg Arg Asp Leu Leu Arg Leu Ser Tyr Gly Glu Ala Lys Lys Ala Ala
    290                 295                 300

Arg Asp Tyr Glu Thr Ala Lys Asn Tyr Phe Lys Lys Gly Leu Lys Asp
305                 310                 315                 320

Met Gly Tyr Gly Asn Trp Ile Ser Lys Pro Gln Glu Glu Lys Asn Phe
                325                 330                 335

<210> SEQ ID NO 488
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

Ser Leu Gly Thr Gly Asn Arg Cys Val Lys Gly Asp Ser Leu Ser Leu

```
                1               5                      10                       15
            Lys Gly Glu Thr Val Asn Asp Cys His Ala Glu Ile Ile Ser Arg Arg
                            20                  25                  30
            Gly Phe Ile Arg Phe Leu Tyr Ser Glu Leu Met Lys Tyr Asn Ser Gln
                            35                  40                  45
            Thr Ala Lys Asp Ser Ile Phe Glu Pro Ala Lys Gly Gly Glu Lys Leu
                            50                  55                  60
            Gln Ile Lys Lys Thr Val Ser Phe His Leu Tyr Ile Ser Thr Ala Pro
             65                 70                  75                  80
            Cys Gly Asp Gly Ala Leu Phe Asp Lys Ser Cys Ser Asp Arg Ala Met
                            85                  90                  95
            Glu Ser Thr Glu Ser Arg His Tyr Pro Val Phe Glu Asn Pro Lys Gln
                            100                 105                 110
            Gly Lys Leu Arg Thr Lys Val Glu Asn Gly Gln Gly Thr Ile Pro Val
                            115                 120                 125
            Glu Ser Ser Asp Ile Val Pro Thr Trp Asp Gly Ile Arg Leu Gly Glu
                            130                 135                 140
            Arg Leu Arg Thr Met Ser Cys Ser Asp Lys Ile Leu Arg Trp Asn Val
            145                 150                 155                 160
            Leu Gly Leu Gln Gly Ala Leu Leu Thr His Phe Leu Gln Pro Ile Tyr
                            165                 170                 175
            Leu Lys Ser Val Thr Leu Gly Tyr Leu Phe Ser Gln Gly His Leu Thr
                            180                 185                 190
            Arg Ala Ile Cys Cys Arg Val Thr Arg Asp Gly Ser Ala Phe Glu Asp
                            195                 200                 205
            Gly Leu Arg His Pro Phe Ile Val Asn His Pro Lys Val Gly Arg Val
                            210                 215                 220
            Ser Ile Tyr Asp Ser Lys Arg Gln Ser Gly Lys Thr Lys Glu Thr Ser
            225                 230                 235                 240
            Val Asn Trp Cys Leu Ala Asp Gly Tyr Asp Leu Glu Ile Leu Asp Gly
                            245                 250                 255
            Thr Arg Gly Thr Val Asp Gly Pro Arg Asn Glu Leu Ser Arg Val Ser
                            260                 265                 270
            Lys Lys Asn Ile Phe Leu Leu Phe Lys Lys Leu Cys Ser Phe Arg Tyr
                            275                 280                 285
            Arg Arg Asp Leu Leu Arg Leu Ser Tyr Gly Glu Ala Lys Lys Ala Ala
                            290                 295                 300
            Arg Asp Tyr Glu Thr Ala Lys Asn Tyr Phe Lys Lys Gly Leu Lys Asp
            305                 310                 315                 320
            Met Gly Tyr Gly Asn Trp Ile Ser Lys Pro Gln Glu Glu Lys Asn Phe
                            325                 330                 335

<210> SEQ ID NO 489
<211> LENGTH: 385
<212> TYPE: PRT
<213> ORGANISM: Unknown
<220> FEATURE:
<223> OTHER INFORMATION: Description of Unknown:
      ADAR2DD-WT sequence

<400> SEQUENCE: 489

Gln Leu His Leu Pro Gln Val Leu Ala Asp Ala Val Ser Arg Leu Val
             1               5                  10                  15
            Leu Gly Lys Phe Gly Asp Leu Thr Asp Asn Phe Ser Ser Pro His Ala
                            20                  25                  30
```

-continued

```
Arg Arg Lys Val Leu Ala Gly Val Met Thr Thr Gly Thr Asp Val
         35                  40                  45
Lys Asp Ala Lys Val Ile Ser Val Ser Thr Gly Thr Lys Cys Ile Asn
 50                  55                  60
Gly Glu Tyr Met Ser Asp Arg Gly Leu Ala Leu Asn Asp Cys His Ala
 65                  70                  75                  80
Glu Ile Ile Ser Arg Arg Ser Leu Leu Arg Phe Leu Tyr Thr Gln Leu
                 85                  90                  95
Glu Leu Tyr Leu Asn Asn Lys Asp Asp Gln Lys Arg Ser Ile Phe Gln
            100                 105                 110
Lys Ser Glu Arg Gly Gly Phe Arg Leu Lys Glu Asn Val Gln Phe His
        115                 120                 125
Leu Tyr Ile Ser Thr Ser Pro Cys Gly Asp Ala Arg Ile Phe Ser Pro
130                 135                 140
His Glu Pro Ile Leu Glu Glu Pro Ala Asp Arg His Pro Asn Arg Lys
145                 150                 155                 160
Ala Arg Gly Gln Leu Arg Thr Lys Ile Glu Ser Gly Glu Gly Thr Ile
                165                 170                 175
Pro Val Arg Ser Asn Ala Ser Ile Gln Thr Trp Asp Gly Val Leu Gln
            180                 185                 190
Gly Glu Arg Leu Leu Thr Met Ser Cys Ser Asp Lys Ile Ala Arg Trp
        195                 200                 205
Asn Val Val Gly Ile Gln Gly Ser Leu Leu Ser Ile Phe Val Glu Pro
210                 215                 220
Ile Tyr Phe Ser Ser Ile Ile Leu Gly Ser Leu Tyr His Gly Asp His
225                 230                 235                 240
Leu Ser Arg Ala Met Tyr Gln Arg Ile Ser Asn Ile Glu Asp Leu Pro
                245                 250                 255
Pro Leu Tyr Thr Leu Asn Lys Pro Leu Leu Ser Gly Ile Ser Asn Ala
            260                 265                 270
Glu Ala Arg Gln Pro Gly Lys Ala Pro Asn Phe Ser Val Asn Trp Thr
        275                 280                 285
Val Gly Asp Ser Ala Ile Glu Val Ile Asn Ala Thr Thr Gly Lys Asp
290                 295                 300
Glu Leu Gly Arg Ala Ser Arg Leu Cys Lys His Ala Leu Tyr Cys Arg
305                 310                 315                 320
Trp Met Arg Val His Gly Lys Val Pro Ser His Leu Leu Arg Ser Lys
                325                 330                 335
Ile Thr Lys Pro Asn Val Tyr His Glu Ser Lys Leu Ala Ala Lys Glu
            340                 345                 350
Tyr Gln Ala Ala Lys Ala Arg Leu Phe Thr Ala Phe Ile Lys Ala Gly
        355                 360                 365
Leu Gly Ala Trp Val Glu Lys Pro Thr Glu Gln Asp Gln Phe Ser Leu
370                 375                 380
Thr
385

<210> SEQ ID NO 490
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490
```

```
Gln Leu His Leu Pro Gln Val Leu Ala Asp Ala Val Ser Arg Leu Val
1               5                   10                  15

Leu Gly Lys Phe Gly Asp Leu Thr Asp Asn Phe Ser Ser Pro His Ala
            20                  25                  30

Arg Arg Lys Val Leu Ala Gly Val Val Met Thr Thr Gly Thr Asp Val
            35                  40                  45

Lys Asp Ala Lys Val Ile Ser Val Ser Thr Gly Thr Lys Cys Ile Asn
            50                  55                  60

Gly Glu Tyr Met Ser Asp Arg Gly Leu Ala Leu Asn Asp Cys His Ala
65                  70                  75                  80

Glu Ile Ile Ser Arg Arg Ser Leu Leu Arg Phe Leu Tyr Thr Gln Leu
                85                  90                  95

Glu Leu Tyr Leu Asn Asn Lys Asp Asp Gln Lys Arg Ser Ile Phe Gln
            100                 105                 110

Lys Ser Glu Arg Gly Gly Phe Arg Leu Lys Glu Asn Val Gln Phe His
            115                 120                 125

Leu Tyr Ile Ser Thr Ser Pro Cys Gly Asp Ala Arg Ile Phe Ser Pro
            130                 135                 140

His Glu Pro Ile Leu Glu Glu Pro Ala Asp Arg His Pro Asn Arg Lys
145                 150                 155                 160

Ala Arg Gly Gln Leu Arg Thr Lys Ile Glu Ser Gly Gln Gly Thr Ile
                165                 170                 175

Pro Val Arg Ser Asn Ala Ser Ile Gln Thr Trp Asp Gly Val Leu Gln
            180                 185                 190

Gly Glu Arg Leu Leu Thr Met Ser Cys Ser Asp Lys Ile Ala Arg Trp
            195                 200                 205

Asn Val Val Gly Ile Gln Gly Ser Leu Leu Ser Ile Phe Val Glu Pro
210                 215                 220

Ile Tyr Phe Ser Ser Ile Ile Leu Gly Ser Leu Tyr His Gly Asp His
225                 230                 235                 240

Leu Ser Arg Ala Met Tyr Gln Arg Ile Ser Asn Ile Glu Asp Leu Pro
                245                 250                 255

Pro Leu Tyr Thr Leu Asn Lys Pro Leu Leu Ser Gly Ile Ser Asn Ala
            260                 265                 270

Glu Ala Arg Gln Pro Gly Lys Ala Pro Asn Phe Ser Val Asn Trp Thr
            275                 280                 285

Val Gly Asp Ser Ala Ile Glu Val Ile Asn Ala Thr Thr Gly Lys Asp
            290                 295                 300

Glu Leu Gly Arg Ala Ser Arg Leu Cys Lys His Ala Leu Tyr Cys Arg
305                 310                 315                 320

Trp Met Arg Val His Gly Lys Val Pro Ser His Leu Leu Arg Ser Lys
                325                 330                 335

Ile Thr Lys Pro Asn Val Tyr His Glu Ser Lys Leu Ala Ala Lys Glu
            340                 345                 350

Tyr Gln Ala Ala Lys Ala Arg Leu Phe Thr Ala Phe Ile Lys Ala Gly
            355                 360                 365

Leu Gly Ala Trp Val Glu Lys Pro Thr Glu Gln Asp Gln Phe Ser Leu
            370                 375                 380

Thr
385

<210> SEQ ID NO 491
<211> LENGTH: 198
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 492
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110
```

Arg Gly Asn Gly His Thr Leu Lys Ile Trp Ala Cys Lys Leu Tyr Tyr
            115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Ser Glu Leu Ser
            180                 185                 190

Ile Met Ile Gln Val Lys Ile Leu His Thr Thr Lys Ser Pro Ala Val
            195                 200                 205

<210> SEQ ID NO 493
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
        50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
            130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
            210                 215                 220

Ala Thr Gly Leu Lys
225